United States Patent
Cheung et al.

(10) Patent No.: US 7,612,211 B2
(45) Date of Patent: Nov. 3, 2009

(54) BENZIMIDAZOLE TRPV1 INHIBITORS

(75) Inventors: Wing S. Cheung, Plainsboro, NJ (US); Daniel J. Parks, Downingtown, PA (US); William H. Parsons, Belle Mead, NJ (US); Sharmila Patel, Jamison, PA (US); Mark R. Player, Phoenixville, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/954,647

(22) Filed: Dec. 12, 2007

(65) Prior Publication Data

US 2008/0146637 A1    Jun. 19, 2008

Related U.S. Application Data

(60) Provisional application No. 60/870,212, filed on Dec. 15, 2006.

(51) Int. Cl.
*A61K 31/4184* (2006.01)
*C07D 235/12* (2006.01)

(52) U.S. Cl. .................................. 548/310.1; 514/394
(58) Field of Classification Search ............... 548/310.1
See application file for complete search history.

(56) References Cited

U.S. PATENT DOCUMENTS 3,182,070 A * 5/1965 Moyle et al. ............. 548/310.1

2006/0160872 A1   7/2006 Norman et al.
2006/0172019 A1   8/2006 Ralston et al.
2006/0194805 A1   8/2006 Bakthavatchalam et al.

OTHER PUBLICATIONS

De Nanteuil et al., CA 134:320513, 2000.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*

* cited by examiner

*Primary Examiner*—Laura L. Stockton

(57) ABSTRACT

The invention is directed to compounds of Formula (I):

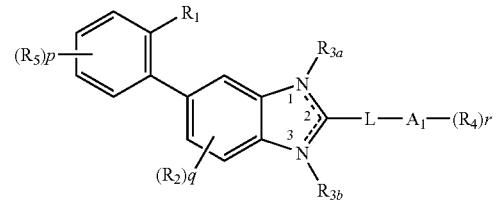

to pharmaceutical compositions containing such compounds and to methods of treatment using them.

27 Claims, No Drawings

BENZIMIDAZOLE TRPV1 INHIBITORS

CROSS REFERENCE TO RELATED APPLICATIONS

This present application claims benefit of U.S. Provisional Patent Application Ser. No. 60/870,212, filed Dec. 15, 2006, which is incorporated herein by reference in its entirety and for all purposes.

BACKGROUND OF THE INVENTION

U.S. Pat. No. 6,299,796B1 describes benzoxazolyl, benzothiazolyl and benzoimidazolyl substituted polymeric styryl compounds and their use in electroluminescent elements.

United States Patent Publication US2005/0277631 describes substituted monocyclic heteroaryl vanilloid receptor ligands and their use in various treatments.

Thus, there remains a need for potent modulators of TRPV1 and, particularly, for novel benzoimidazole compounds that exhibit potent binding affinity for the TRPV1 ion channel.

SUMMARY OF THE INVENTION

The present invention is directed to a compound of Formula (I):

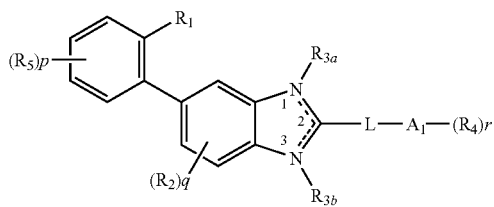

and a form thereof, wherein $R_1$, $R_2$, $R_{3a}$, $R_{3b}$, $R_4$, $R_5$, p, q, r, L and $A_1$ are as defined herein, and their use as potent modulators of TRPV1.

The present invention is also directed to a method for treating a TRPV1 mediated disease in a subject in need thereof comprising administering to the subject an effective amount of a compound of Formula I.

DETAILED DESCRIPTION OF THE INVENTION

The present invention is directed to compounds of Formula (I):

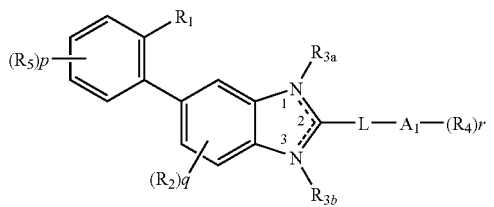

and a form thereof, wherein:
the dashed lines between positions 1, 2 and 3 in Formula (I) indicate the positions of a tautomeric double bond, wherein when a double bond is formed between positions 1 and 2, then $R_{3b}$ is present, and
wherein, when a double bond is formed between positions 2 and 3, then $R_{3a}$ is present;
p is 0, 1 or 2;
q is 0, 1 or 2;
r is 0, 1, 2 or 3;
L is —X—$C_{1-3}$alkyl- or —$C_{1-3}$alkyl-Y—, wherein each instance of alkyl is optionally perfluorinated;
X and Y are each O, S, SO, $SO_2$ or $NR_6$;
$A_1$ is selected from the group consisting of indanyl, 1,2,3,4-tetrahydro-naphthalenyl, phenyl, naphthyl, benzo[1,3]dioxolyl, pyridinyl and quinolinyl;
$R_1$ is hydrogen, hydroxy, halogen, $C_{1-6}$alkyl, $C_{1-6}$alkoxy, $C_{1-6}$alkylthio, $C_{1-6}$alkylsulfonyl, $C_{3-8}$cycloalkyl, $C_{3-8}$cycloalkyl-$C_{1-4}$alkyl, $C_{3-8}$cycloalkyl-$C_{1-4}$alkoxy, $C_{3-8}$cycloalkyl-oxy, amino, $(C_{1-6}$alkyl$)_{1-2}$amino, $(C_{3-8}$cycloalkyl$)_{1-2}$amino, $(C_{3-8}$cycloalkyl-$C_{1-4}$-alkyl$)_{1-2}$amino, cyano, $C_{1-6}$alkylcarbonyl, $C_{1-6}$alkoxycarbonyl, aminocarbonyl, $(C_{1-6}$alkyl$)_{1-2}$aminocarbonyl, $C_{1-6}$alkylcarbonylamino, aminocarbonyl-$C_{1-6}$alkyl, $(C_{1-6}$alkyl$)_{1-2}$aminocarbonyl-$C_{1-6}$alkyl, $C_{1-6}$alkoxy-aminocarbonyl-$C_{1-6}$alkyl, $C_{1-6}$alkoxycarbonylamino, aminocarbonylamino, $(C_{1-6}$alkyl$)_{1-2}$aminocarbonylamino, $C_{1-6}$alkylsulfonylamino, aminosulfonyl or $(C_{1-4}$alkyl$)_{1-2}$aminosulfonyl,
wherein each instance of alkyl is optionally substituted with one, two or three substituents independently selected from the group consisting of $C_{1-8}$alkoxy, amino, $(C_{1-4}$alkyl$)_{1-2}$amino, $C_{1-6}$alkylcarbonylamino, $C_{1-6}$alkoxycarbonylamino, aminocarbonylamino, $(C_{1-6}$alkyl$)_{1-2}$aminocarbonylamino, $C_{1-6}$alkylsulfonylamino, halogen, oxo and hydroxy, and
wherein, each instance of alkyl and alkoxy is optionally perfluorinated;
$R_2$ is each selected from the group consisting of halogen, $C_{1-4}$alkyl, $C_{1-4}$alkoxy, $C_{1-4}$alkylsulfonyl, nitro, $(C_{1-4}$alkyl$)_{1-2}$amino and cyano, wherein each instance of alkyl and alkoxy is optionally perfluorinated;
$R_{3a}$ and $R_{3b}$ are each selected from the group consisting of hydrogen and $C_{1-4}$alkyl;
$R_4$ is each halogen, nitro, cyano, $C_{1-6}$alkyl, $C_{1-6}$alkoxy, halo$C_{1-6}$alkyl, halo$C_{1-6}$alkoxy, $C_{1-6}$alkoxy-$C_{1-6}$alkyl, $C_{1-6}$alkylthio, halo$C_{1-6}$alkylthio, $C_{1-6}$alkylsulfonyl, halo$C_{1-6}$alkylsulfonyl, $C_{3-8}$cycloalkyl, $C_{3-8}$cycloalkyl-$C_{1-4}$ alkyl, $C_{3-8}$cycloalkyl-$C_{1-4}$alkoxy, $C_{3-8}$cycloalkyl-oxy, amino, $(C_{1-6}$alkyl$)_{1-2}$amino, $(C_{3-8}$cycloalkyl$)_{1-2}$amino, $(C_{3-8}$cycloalkyl-$C_{1-4}$alkyl$)_{1-2}$amino, cyano, $C_{1-6}$alkylcarbonyl, $C_{1-6}$alkoxy-carbonyl, $C_{1-6}$alkoxy-carbonyl-$C_{1-6}$alkyl, aminocarbonyl, $(C_{1-6}$alkyl$)_{1-2}$aminocarbonyl, $C_{1-6}$alkylcarbonylamino, $C_{1-6}$alkoxycarbonylamino, aminocarbonylamino, $(C_{1-6}$alkyl$)_{1-2}$aminocarbonylamino, $C_{1-6}$alkylsulfonylamino, aminosulfonyl or $(C_{1-4}$alkyl$)_{1-2}$aminosulfonyl, wherein each instance of alkyl and alkoxy is optionally perfluorinated;
$R_5$ is selected from the group consisting of halogen, hydroxy, $C_{1-4}$alkyl, halo$C_{1-4}$alkyl, hydroxy$C_{1-4}$alkyl, $C_{1-4}$alkoxy, $C_{1-4}$alkylsulfonyl, nitro, $C_{1-6}$alkylcarbonyl, $C_{1-6}$alkoxycarbonyl, amino, $(C_{1-4}$alkyl$)_{1-2}$amino, $C_{1-6}$alkylcarbonylamino, $C_{1-6}$alkylsulfonylamino, aminosulfonyl, $(C_{1-6}$alkyl$)_{1-2}$aminosulfonyl, and cyano, wherein each instance of alkyl and alkoxy is optionally perfluorinated; and
$R_6$ is one substituent selected from the group consisting of hydrogen and optionally perfluorinated $C_{1-4}$alkyl.

An example of the present invention is a compound of Formula (I) and a form thereof, wherein
a double bond is formed between positions 1 and 2 and $R_{3b}$ is present;

p is 0, 1 or 2;
q is 0;
r is 0, 1, 2 or 3;
L is —X—$C_{1-3}$alkyl- or —$C_{1-3}$alkyl-Y—, wherein each instance of alkyl is optionally perfluorinated;
X and Y are each O, S, $SO_2$ or $NR_6$;
$A_1$ is selected from the group consisting of indanyl, 1,2,3,4-tetrahydro-naphthalenyl, phenyl, naphthyl, benzo[1,3]dioxolyl, pyridinyl and quinolinyl;
$R_1$ is hydrogen, hydroxy, $C_{1-6}$alkyl, $C_{1-6}$alkylsulfonyl, amino, $C_{1-6}$alkylcarbonyl, $C_{1-6}$alkoxycarbonyl, ($C_{1-6}$alkyl)$_{1-2}$aminocarbonyl, $C_{1-6}$alkylcarbonylamino, ($C_{1-6}$alkyl)$_{1-2}$aminocarbonyl-$C_{1-6}$alkyl, $C_{1-6}$alkoxy-aminocarbonyl-$C_{1-6}$alkyl, aminocarbonylamino, $C_{1-6}$alkylsulfonylamino, aminosulfonyl or ($C_{1-4}$alkyl)$_{1-2}$aminosulfonyl,
wherein each instance of alkyl is optionally substituted with one, two or three substituents independently selected from the group consisting of halogen and hydroxy;
$R_{3b}$ is selected from the group consisting of hydrogen and $C_{1-4}$alkyl;
$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl, cyano, $C_{1-6}$alkylcarbonyl, $C_{1-6}$alkoxy-carbonyl-$C_{1-6}$alkyl and $C_{1-6}$alkylcarbonylamino;
$R_5$ is selected from the group consisting of halogen, hydroxy, $C_{1-4}$alkyl, halo$C_{1-4}$alkyl, hydroxy$C_{1-4}$alkyl, $C_{1-4}$alkylsulfonyl, $C_{1-6}$alkoxycarbonyl, amino, $C_{1-6}$alkylcarbonylamino, $C_{1-6}$alkylsulfonylamino, aminosulfonyl and ($C_{1-6}$alkyl)$_{1-2}$aminosulfonyl; and
$R_6$ is one substituent selected from the group consisting of hydrogen and $C_{1-4}$alkyl.

An example of the present invention is a compound of Formula (I) and a form thereof, wherein
a double bond is formed between positions 1 and 2 and $R_{3b}$ is present;
p is 0, 1 or 2;
q is 0;
r is 0, 1, 2 or 3;
L is —X—$C_{1-3}$alkyl- or —$C_{1-3}$alkyl-Y—, wherein each instance of alkyl is optionally perfluorinated;
X and Y are each O, S or NH;
$A_1$ is selected from the group consisting of indanyl, 1,2,3,4-tetrahydro-naphthalenyl, phenyl, naphthyl, benzo[1,3]dioxolyl and quinolinyl;
$R_1$ is $C_{1-6}$alkyl, $C_{1-6}$alkylsulfonyl, $C_{1-6}$alkylcarbonyl, $C_{1-6}$alkoxycarbonyl, ($C_{1-6}$alkyl)$_{1-2}$aminocarbonyl, $C_{1-6}$alkoxy-aminocarbonyl-$C_{1-6}$alkyl, $C_{1-6}$alkylsulfonylamino, aminosulfonyl or ($C_{1-4}$alkyl)$_{1-2}$aminosulfonyl,
wherein each instance of alkyl is optionally substituted with one, two or three substituents independently selected from the group consisting of halogen and hydroxy;
$R_{3b}$ is selected from the group consisting of hydrogen and $C_{1-4}$alkyl;
$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl, cyano or $C_{1-6}$alkylcarbonyl; and
$R_5$ is selected from the group consisting of halogen and halo$C_{1-4}$alkyl.

An example of the present invention is a compound of Formula (I) and a form thereof, wherein
a double bond is formed between positions 1 and 2 and $R_{3b}$ is present;
p is 0, 1 or 2;
q is 0;
r is 1 or 2;
L is —X—$C_{1-3}$alkyl- or —$C_{1-3}$alkyl-Y—, wherein each instance of alkyl is optionally perfluorinated;
X and Y are each O or S;
$A_1$ is selected from the group consisting of indanyl, 1,2,3,4-tetrahydro-naphthalenyl, phenyl and naphthyl;
$R_1$ is $C_{1-6}$alkyl, $C_{1-6}$alkylsulfonyl, $C_{1-6}$alkoxycarbonyl, $C_{1-6}$alkoxy-aminocarbonyl-$C_{1-6}$alkyl, $C_{1-6}$alkylsulfonylamino, aminosulfonyl or ($C_{1-4}$alkyl)$_{1-2}$aminosulfonyl,
wherein each instance of alkyl is optionally substituted with one hydroxy substituent;
$R_{3b}$ is selected from the group consisting of hydrogen and $C_{1-4}$alkyl;
$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl or $C_{1-6}$alkylcarbonyl; and
$R_5$ is halogen.

An example of the present invention is a compound of Formula (I) and a form thereof, wherein
a double bond is formed between positions 1 and 2 and $R_{3b}$ is present;
p is 0;
q is 0;
r is 1;
L is —X—$C_{1-3}$alkyl- or —$C_{1-3}$alkyl-Y—;
X and Y are each O or S;
$A_1$ is phenyl;
$R_1$ is $C_{1-6}$alkyl, $C_{1-6}$alkylsulfonyl, $C_{1-6}$alkylsulfonylamino, aminosulfonyl or ($C_{1-4}$alkyl)$_{1-2}$aminosulfonyl,
wherein each instance of alkyl is optionally substituted with one hydroxy substituent;
$R_{3b}$ is selected from the group consisting of hydrogen and $C_{1-4}$alkyl;
$R_4$ is halogen, $C_{1-6}$alkyl, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl or $C_{3-8}$cycloalkyl.

An example of the present invention is a compound of Formula (I) and a form thereof, wherein $R_4$ is cyclopropyl.

An example of the present invention is a compound of Formula (I) and a form thereof, wherein
a double bond is formed between positions 1 and 2 and $R_{3b}$ is present;
p is 0;
q is 0;
r is 1;
L is —$C_{1-3}$alkyl-O—;
$A_1$ is phenyl;
$R_1$ is $C_{1-6}$alkyl, $C_{1-6}$alkylsulfonyl, $C_{1-6}$alkylsulfonylamino, aminosulfonyl or $C_{1-4}$alkylaminosulfonyl,
wherein each instance of alkyl is optionally substituted with one hydroxy substituent;
$R_{3b}$ is hydrogen; and
$R_4$ is halo$C_{1-6}$alkyl, halo$C_{1-6}$alkoxy or halo$C_{1-6}$alkylsulfonyl.

An example of the present invention is a compound of Formula (I) and a form thereof, wherein
a double bond is formed between positions 1 and 2 and $R_{3b}$ is present;
p is 0;
q is 0;
r is 1;
L is —$CH_3$—O—;
$A_1$ is phenyl;
$R_1$ is methyl, isopropyl, methylsulfonyl, methylsulfonylamino, aminosulfonyl or methylaminosulfonyl,
wherein isopropyl is optionally substituted with one hydroxy substituent;

$R_{3b}$ is hydrogen; and
$R_4$ is trifluoromethyl, trifluoromethoxy or trifluoromethylsulfonyl.

An example of the present invention is a compound of Formula (Ia):

(Ia)

and a form thereof, wherein:
p is 0, 1 or 2;
r is 0, 1, 2 or 3;
L is —X—$C_{1-3}$alkyl- or —$C_{1-3}$alkyl-Y—, wherein each instance of alkyl is optionally perfluorinated;
X and Y are each O, S, SO, $SO_2$ or $NR_6$;
$A_1$ is selected from the group consisting of indanyl, 1,2,3,4-tetrahydro-naphthalenyl, phenyl, naphthyl, benzo[1,3]dioxolyl, pyridinyl and quinolinyl;
$R_1$ is hydrogen, hydroxy, halogen, $C_{1-6}$alkyl, $C_{1-6}$alkoxy, $C_{1-6}$alkylthio, $C_{1-6}$alkylsulfonyl, $C_{3-8}$cycloalkyl, $C_{3-8}$cycloalkyl-$C_{1-4}$alkyl, $C_{3-8}$cycloalkyl-$C_{1-4}$alkoxy, $C_{3-8}$cycloalkyl-oxy, amino, ($C_{1-6}$alkyl)$_{1-2}$amino, ($C_{3-8}$cycloalkyl)$_{1-2}$amino, ($C_{3-8}$cycloalkyl-$C_{1-4}$alkyl)$_{1-2}$amino, cyano, $C_{1-6}$alkylcarbonyl, $C_{1-6}$alkoxycarbonyl, aminocarbonyl, ($C_{1-6}$alkyl)$_{1-2}$aminocarbonyl, $C_{1-6}$alkylcarbonylamino, aminocarbonyl-$C_{1-6}$alkyl, ($C_{1-6}$alkyl)$_{1-2}$aminocarbonyl-$C_{1-6}$alkyl, $C_{1-6}$alkoxy-aminocarbonyl-$C_{1-6}$alkyl, $C_{1-6}$alkoxycarbonylamino, aminocarbonylamino, ($C_{1-6}$alkyl)$_{1-2}$aminocarbonylamino, $C_{1-6}$alkylsulfonylamino, aminosulfonyl or ($C_{1-4}$alkyl)$_{1-2}$aminosulfonyl,
wherein each instance of alkyl is optionally substituted with one, two or three substituents independently selected from the group consisting of $C_{1-8}$alkoxy, amino, ($C_{1-4}$alkyl)$_{1-2}$amino, $C_{1-6}$alkylcarbonylamino, $C_{1-6}$alkoxycarbonylamino, aminocarbonylamino, ($C_{1-6}$alkyl)$_{1-2}$aminocarbonylamino, $C_{1-6}$alkylsulfonylamino, halogen, oxo and hydroxy;
$R_{3b}$ is selected from the group consisting of hydrogen and $C_{1-4}$alkyl;
$R_4$ is each halogen, nitro, cyano, $C_{1-6}$alkyl, $C_{1-6}$alkoxy, halo$C_{1-6}$alkyl, halo$C_{1-6}$alkoxy, $C_{1-6}$alkoxy-$C_{1-6}$alkyl, $C_{1-6}$alkylthio, halo$C_{1-6}$alkylthio, $C_{1-6}$alkylsulfonyl, halo$C_{1-6}$alkylsulfonyl, $C_{3-8}$cycloalkyl, $C_{3-8}$cycloalkyl-$C_{1-4}$alkyl, $C_{3-8}$cycloalkyl-$C_{1-4}$alkoxy, $C_{3-8}$cycloalkyl-oxy, amino, ($C_{1-6}$alkyl)$_{1-2}$amino, ($C_{3-8}$cycloalkyl)$_{1-2}$amino, ($C_{3-8}$cycloalkyl-$C_{1-4}$alkyl)$_{1-2}$amino, cyano, $C_{1-6}$alkylcarbonyl, $C_{1-6}$alkoxy-carbonyl, $C_{1-6}$alkoxy-carbonyl-$C_{1-6}$alkyl, aminocarbonyl, ($C_{1-6}$alkyl)$_{1-2}$aminocarbonyl, $C_{1-6}$alkylcarbonylamino, $C_{1-6}$alkoxycarbonylamino, aminocarbonylamino, ($C_{1-6}$alkyl)$_{1-2}$aminocarbonylamino, $C_{1-6}$alkylsulfonylamino, aminosulfonyl or ($C_{1-4}$alkyl)$_{1-2}$aminosulfonyl;
$R_5$ is selected from the group consisting of halogen, hydroxy, $C_{1-4}$alkyl, halo$C_{1-4}$alkyl, hydroxy$C_{1-4}$alkyl, $C_{1-4}$alkoxy, $C_{1-4}$alkylsulfonyl, nitro, $C_{1-6}$alkylcarbonyl, $C_{1-6}$alkoxycarbonyl, amino, ($C_{1-4}$alkyl)$_{1-2}$amino, $C_{1-6}$alkylcarbonylamino, $C_{1-6}$alkylsulfonylamino, aminosulfonyl, ($C_{1-6}$alkyl)$_{1-2}$aminosulfonyl and cyano; and
$R_6$ is one substituent selected from the group consisting of hydrogen and $C_{1-4}$alkyl.

An example of the present invention is a compound of Formula (Ia) and a form thereof, wherein
p is 0, 1 or 2;
r is 0, 1, 2 or 3;
L is —X—$C_{1-3}$alkyl- or —$C_{1-3}$alkyl-Y—, wherein each instance of alkyl is optionally perfluorinated;
X and Y are each O, S, $SO_2$ or $NR_6$;
$A_1$ is selected from the group consisting of indanyl, 1,2,3,4-tetrahydro-naphthalenyl, phenyl, naphthyl, benzo[1,3]dioxolyl, pyridinyl and quinolinyl;
$R_1$ is hydrogen, hydroxy, $C_{1-6}$alkyl, $C_{1-6}$alkylsulfonyl, amino, $C_{1-6}$alkylcarbonyl, $C_{1-6}$alkoxycarbonyl, ($C_{1-6}$alkyl)$_{1-2}$aminocarbonyl, $C_{1-6}$alkylcarbonylamino, ($C_{1-6}$alkyl)$_{1-2}$aminocarbonyl-$C_{1-6}$alkyl, $C_{1-6}$alkoxy-aminocarbonyl-$C_{1-6}$alkyl, aminocarbonylamino, $C_{1-6}$alkylsulfonylamino, aminosulfonyl or ($C_{1-4}$alkyl)$_{1-2}$aminosulfonyl,
wherein each instance of alkyl is optionally substituted with one, two or three substituents independently selected from the group consisting of halogen and hydroxy;
$R_{3b}$ is selected from the group consisting of hydrogen and $C_{1-4}$alkyl;
$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl, cyano, $C_{1-6}$alkylcarbonyl, $C_{1-6}$alkoxy-carbonyl-$C_{1-6}$alkyl and $C_{1-6}$alkylcarbonylamino;
$R_5$ is selected from the group consisting of halogen, hydroxy, $C_{1-4}$alkyl, halo$C_{1-4}$alkyl, hydroxy$C_{1-4}$alkyl, $C_{1-4}$alkylsulfonyl, $C_{1-6}$alkoxycarbonyl, amino, $C_{1-6}$alkylcarbonylamino, $C_{1-6}$alkylsulfonylamino, aminosulfonyl and ($C_{1-6}$alkyl)$_{1-2}$aminosulfonyl; and
$R_6$ is one substituent selected from the group consisting of hydrogen and $C_{1-4}$alkyl.

An example of the present invention is a compound of Formula (Ia) and a form thereof, wherein
p is 0, 1 or 2;
r is 0, 1, 2 or 3;
L is —X—$C_{1-3}$alkyl- or —$C_{1-3}$alkyl-Y—, wherein each instance of alkyl is optionally perfluorinated;
X and Y are each O, S or NH;
$A_1$ is selected from the group consisting of indanyl, 1,2,3,4-tetrahydro-naphthalenyl, phenyl, naphthyl, benzo[1,3]dioxolyl and quinolinyl;
$R_1$ is $C_{1-6}$alkyl, $C_{1-6}$alkylsulfonyl, $C_{1-6}$alkylcarbonyl, $C_{1-6}$alkoxycarbonyl, ($C_{1-6}$alkyl)$_{1-2}$aminocarbonyl, $C_{1-6}$alkoxy-aminocarbonyl-$C_{1-6}$alkyl, $C_{1-6}$alkylsulfonylamino, aminosulfonyl or ($C_{1-4}$alkyl)$_{1-2}$aminosulfonyl,
wherein each instance of alkyl is optionally substituted with one, two or three substituents independently selected from the group consisting of halogen and hydroxy;
$R_{3b}$ is selected from the group consisting of hydrogen and $C_{1-4}$alkyl;
$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl, cyano or $C_{1-6}$alkylcarbonyl; and
$R_5$ is selected from the group consisting of halogen and halo$C_{1-4}$alkyl.

An example of the present invention is a compound of Formula (Ia) and a form thereof, wherein
p is 0, 1 or 2;
r is 1 or 2;
L is —X—$C_{1-3}$alkyl- or —$C_{1-3}$alkyl-Y—, wherein each instance of alkyl is optionally perfluorinated;

X and Y are each O or S;
A₁ is selected from the group consisting of indanyl, 1,2,3,4-tetrahydro-naphthalenyl, phenyl and naphthyl;
$R_1$ is $C_{1-6}$alkyl, $C_{1-6}$alkylsulfonyl, $C_{1-6}$alkoxycarbonyl, $C_{1-6}$alkoxy-aminocarbonyl-$C_{1-6}$alkyl, $C_{1-6}$alkylsulfonylamino, aminosulfonyl or $(C_{1-4}alkyl)_{1-2}$aminosulfonyl,
wherein each instance of alkyl is optionally substituted with one hydroxy substituent;
$R_{3b}$ is selected from the group consisting of hydrogen and $C_{1-4}$alkyl;
$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl or $C_{1-6}$alkylcarbonyl; and
$R_5$ is halogen.

An example of the present invention is a compound of Formula (Ia) and a form thereof, wherein
p is 0;
r is 1;
L is —X—$C_{1-3}$alkyl- or —$C_{1-3}$alkyl-Y—;
X and Y are each O or S;
A₁ is phenyl;
$R_1$ is $C_{1-6}$alkyl, $C_{1-6}$alkylsulfonyl, $C_{1-6}$alkylsulfonylamino, aminosulfonyl or $(C_{1-4}alkyl)_{1-2}$aminosulfonyl,
wherein each instance of alkyl is optionally substituted with one hydroxy substituent;
$R_{3b}$ is selected from the group consisting of hydrogen and $C_{1-4}$alkyl;
$R_4$ is halogen, $C_{1-6}$alkyl, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl or $C_{3-8}$cycloalkyl.

An example of the present invention is a compound of Formula (Ia) and a form thereof, wherein $R_4$ is cyclopropyl.

An example of the present invention is a compound of Formula (Ia) and a form thereof, wherein
p is 0;
r is 1;
L is —$C_{1-3}$alkyl-O—;
A₁ is phenyl;
$R_1$ is $C_{1-6}$alkyl, $C_{1-6}$alkylsulfonyl, $C_{1-6}$alkylsulfonylamino, aminosulfonyl or $C_{1-4}$alkylaminosulfonyl,
wherein each instance of alkyl is optionally substituted with one hydroxy substituent;
$R_{3b}$ is hydrogen; and
$R_4$ is halo$C_{1-6}$alkyl, halo$C_{1-6}$alkoxy or halo$C_{1-6}$alkylsulfonyl.

An example of the present invention is a compound of Formula (Ia) and a form thereof, wherein
p is 0;
r is 1;
L is —CH₃—O—;
A₁ is phenyl;
$R_1$ is methyl, isopropyl, methylsulfonyl, methylsulfonylamino, aminosulfonyl or methylaminosulfonyl,
wherein isopropyl is optionally substituted with one hydroxy substituent;
$R_{3b}$ is hydrogen; and
$R_4$ is trifluoromethyl, trifluoromethoxy or trifluoromethylsulfonyl.

An example of the present invention is a compound of Formula (I) selected from the group consisting of:

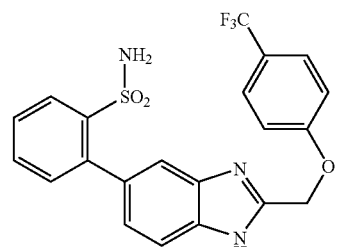

Cpd 1

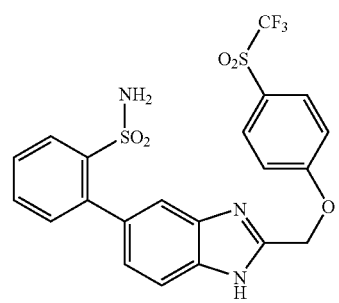

Cpd 2

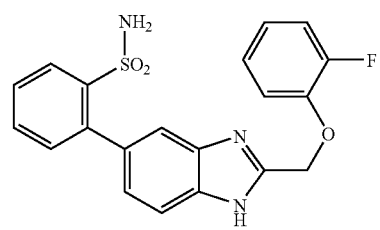

Cpd 3

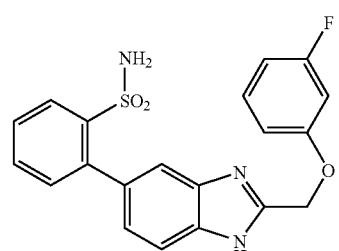

Cpd 4

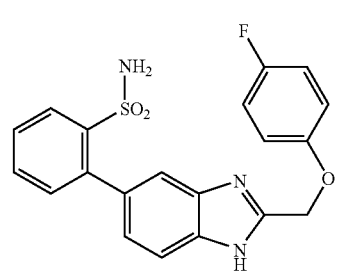

Cpd 5

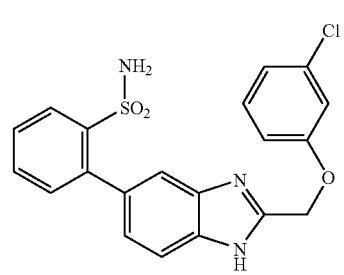

Cpd 6

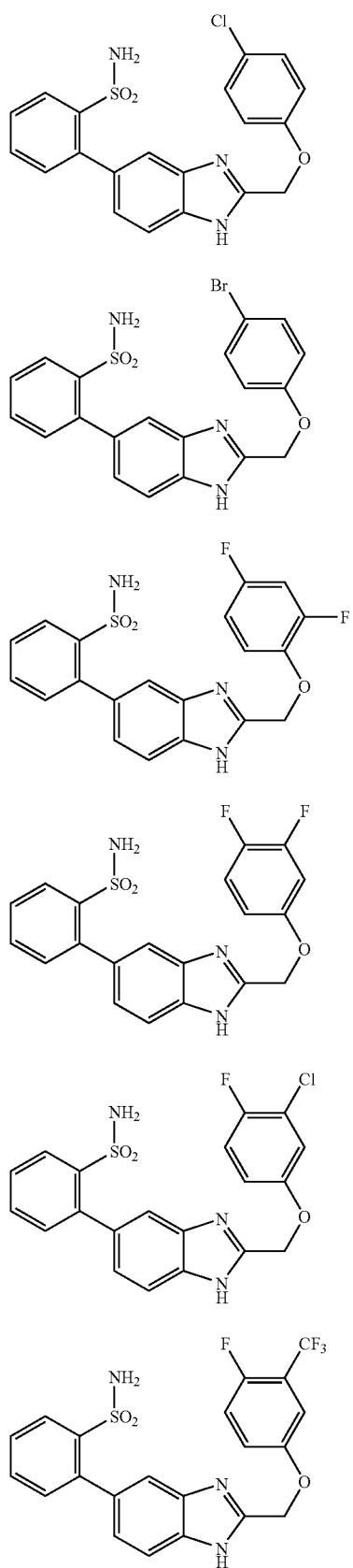
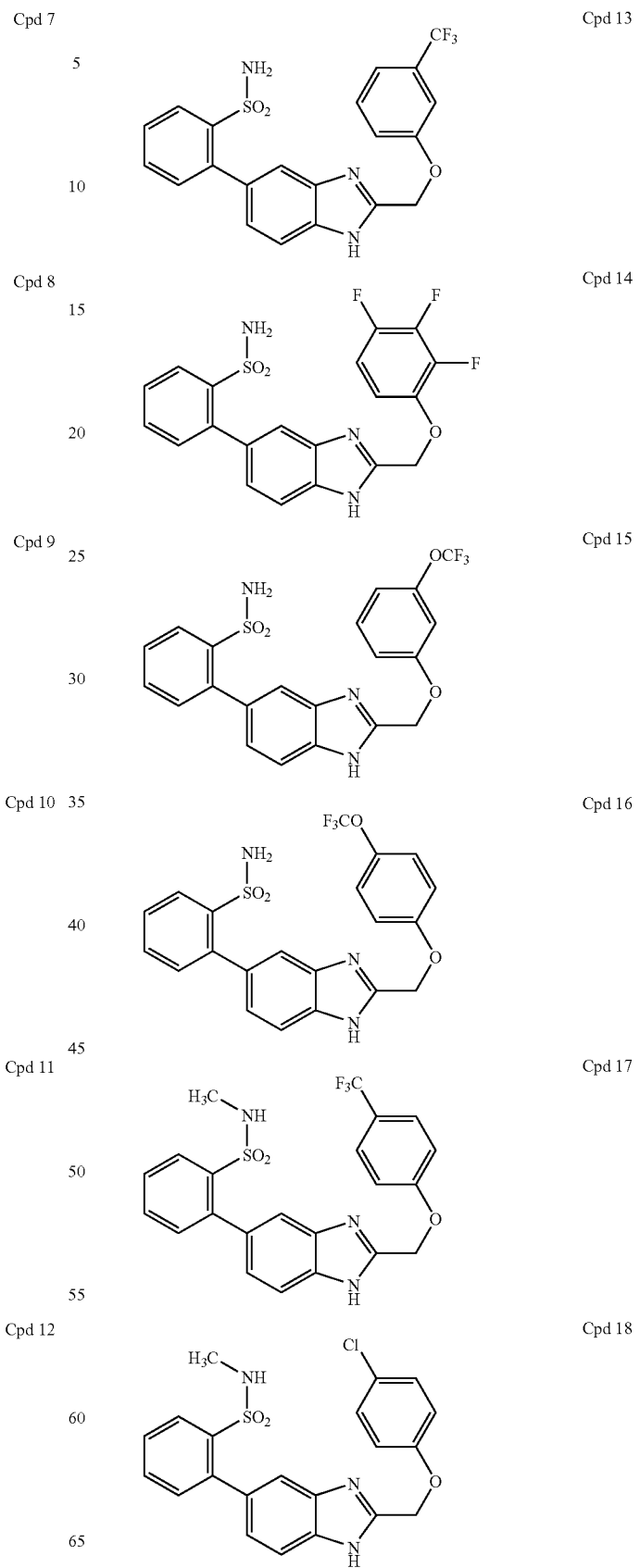

-continued
Cpd 19
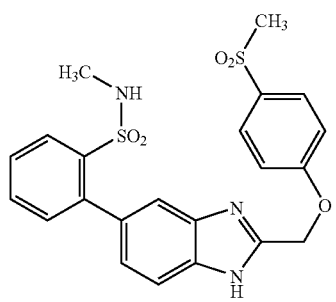
Cpd 20
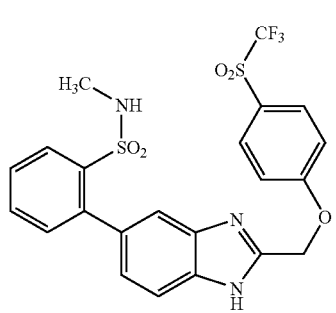
Cpd 21
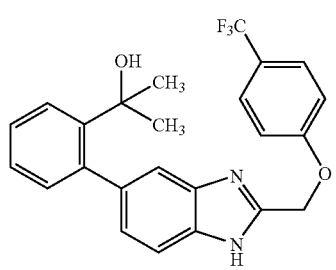
Cpd 22
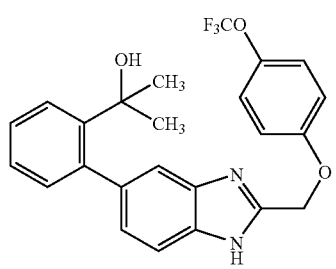
Cpd 23
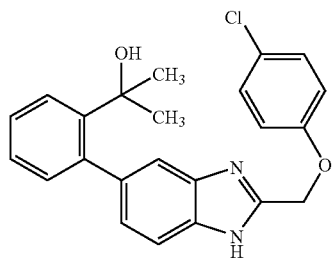
-continued
Cpd 24
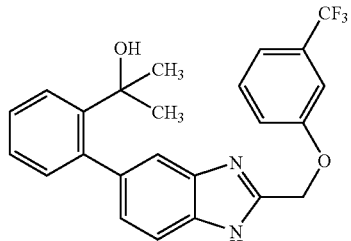
Cpd 25
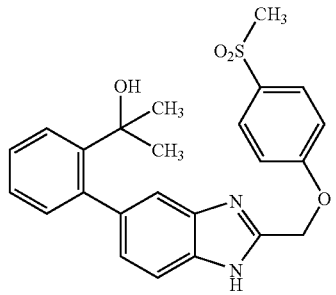
Cpd 26
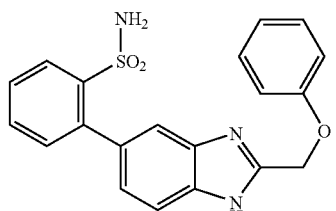
Cpd 27
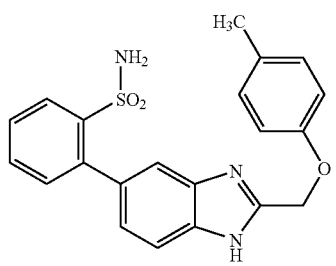
Cpd 28
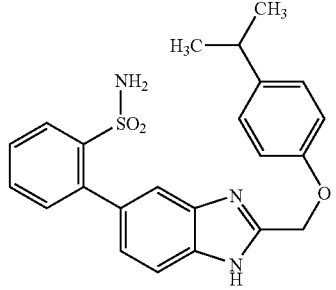
Cpd 29
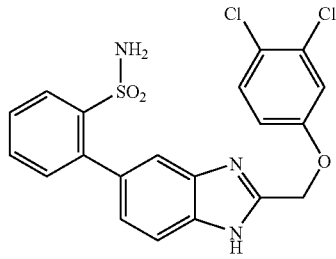

-continued
Cpd 30
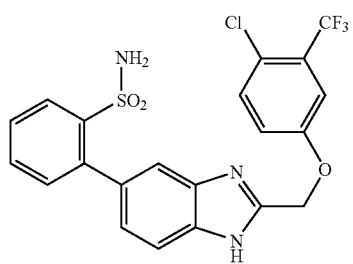
Cpd 31
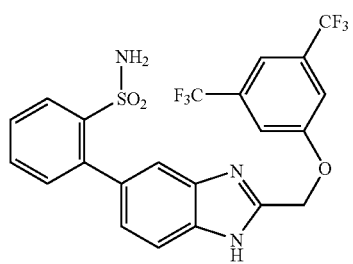
Cpd 32
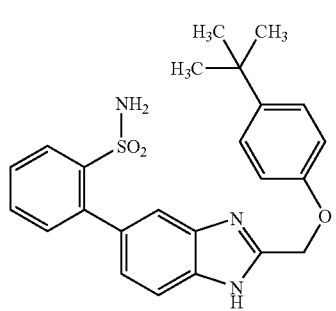
Cpd 33
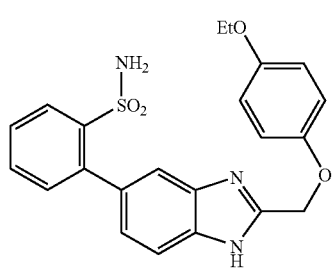
Cpd 34
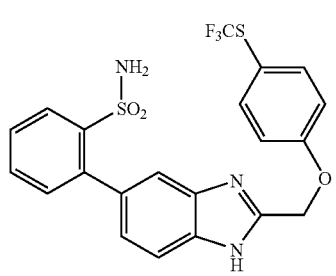
Cpd 35
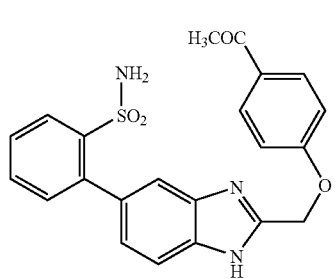
-continued
Cpd 36
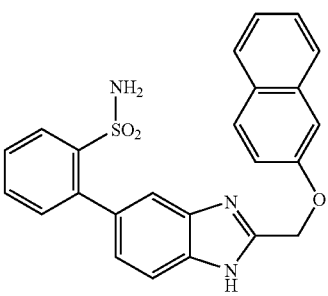
Cpd 37
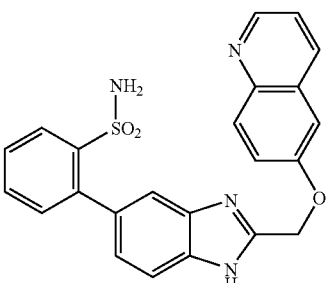
Cpd 38
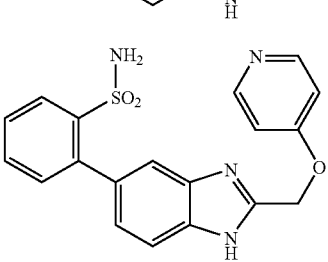
Cpd 39
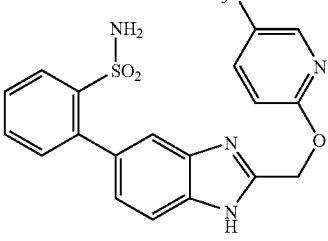
Cpd 40
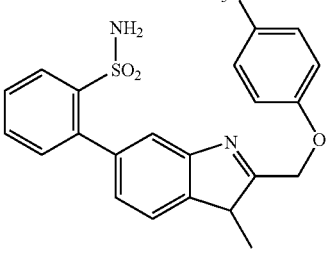
Cpd 41
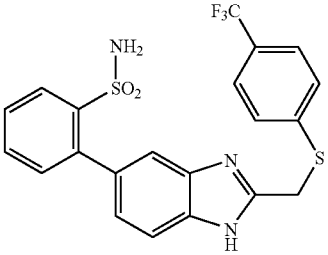

-continued
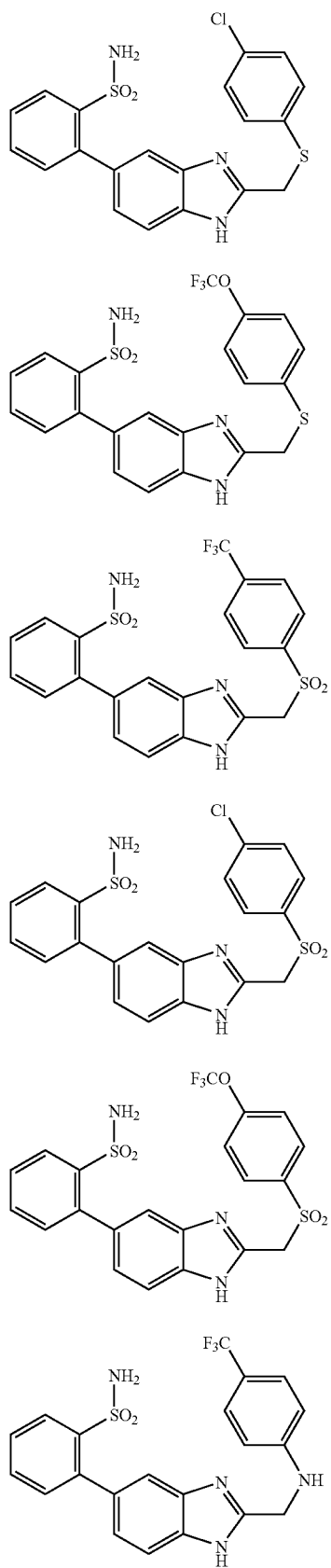
Cpd 42
Cpd 43
Cpd 44
Cpd 45
Cpd 46
Cpd 47
-continued
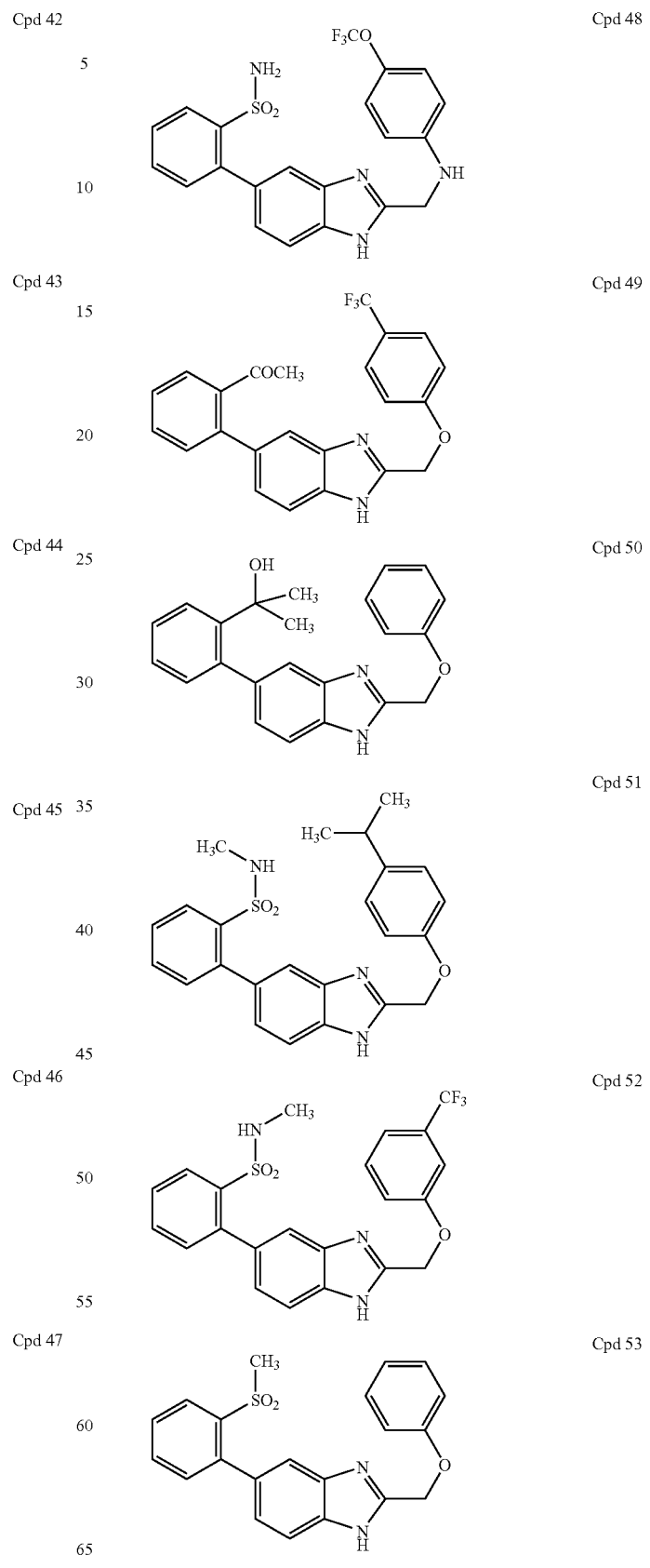
Cpd 48
Cpd 49
Cpd 50
Cpd 51
Cpd 52
Cpd 53

-continued
Cpd 54
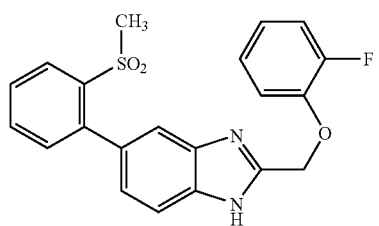
Cpd 55
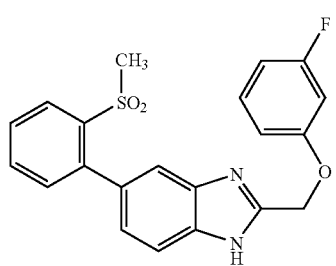
Cpd 56
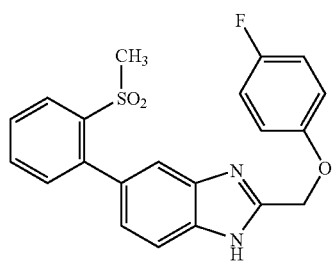
Cpd 57
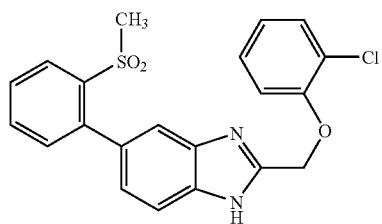
Cpd 58
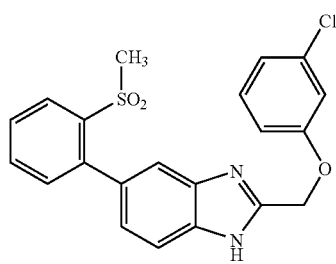
Cpd 59
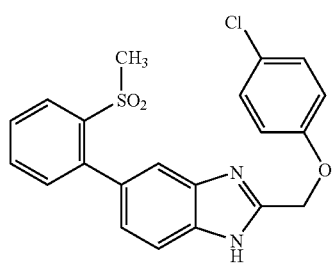
-continued
Cpd 60
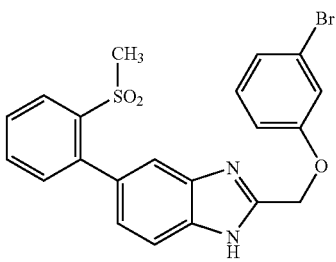
Cpd 61
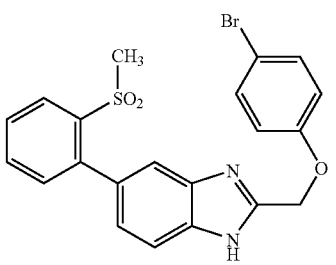
Cpd 62
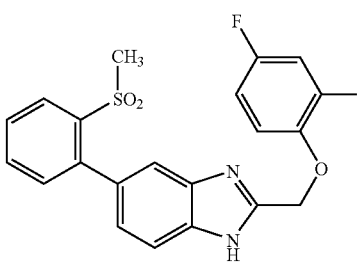
Cpd 63
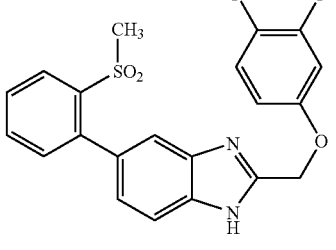
Cpd 64
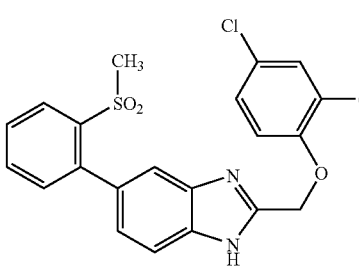
Cpd 65
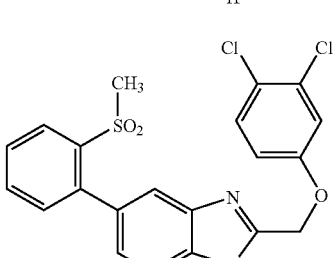

-continued
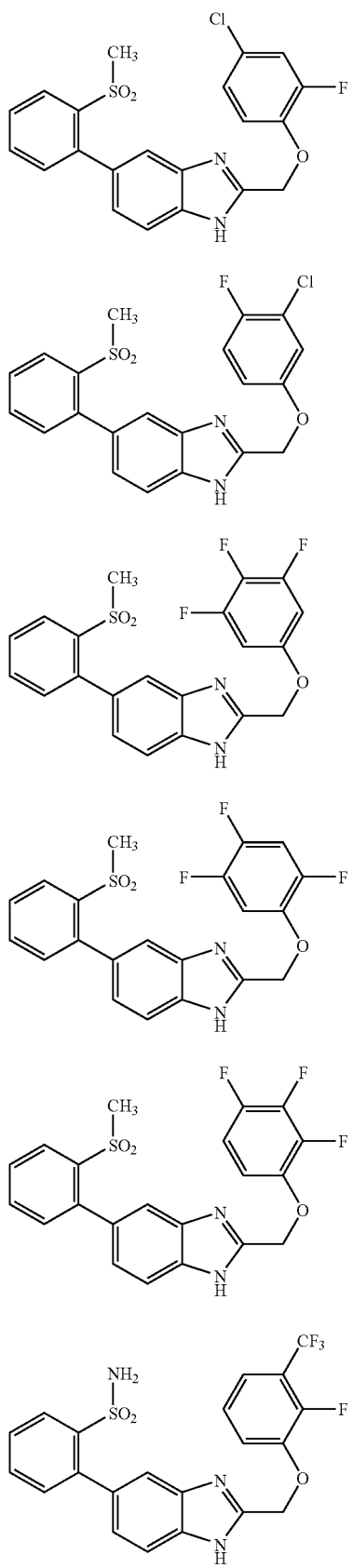
Cpd 66
Cpd 67
Cpd 68
Cpd 69
Cpd 70
Cpd 71
-continued
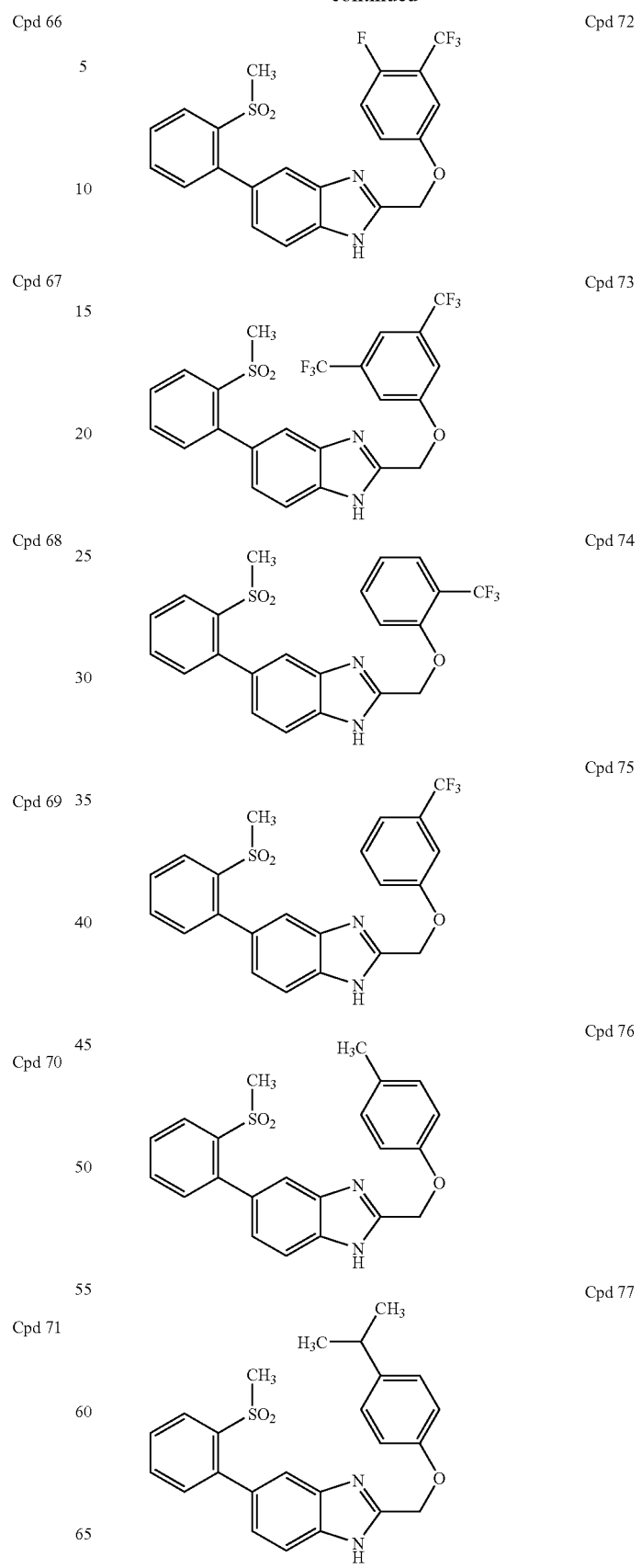
Cpd 72
Cpd 73
Cpd 74
Cpd 75
Cpd 76
Cpd 77

-continued
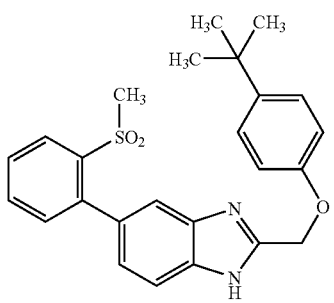
Cpd 78
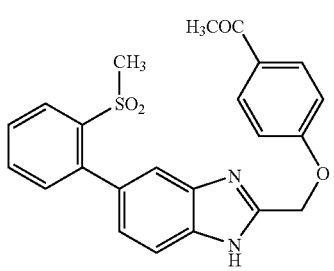
Cpd 79
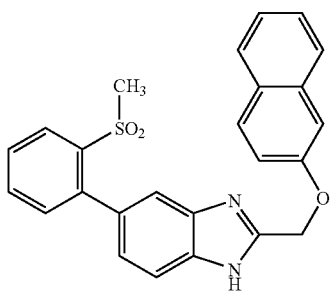
Cpd 80
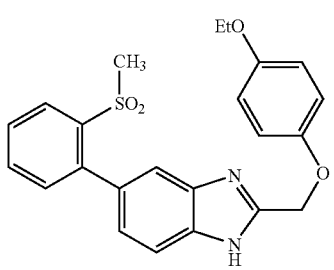
Cpd 81
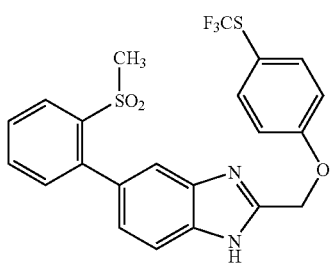
Cpd 82
-continued
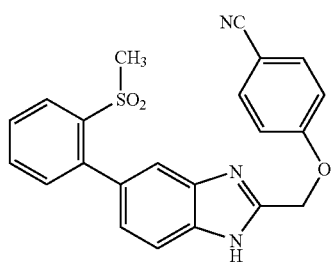
Cpd 83
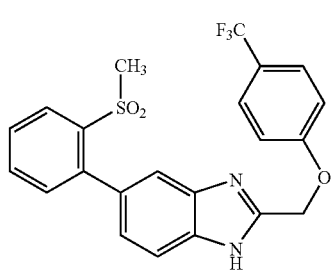
Cpd 84
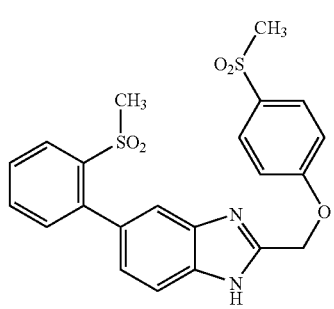
Cpd 85
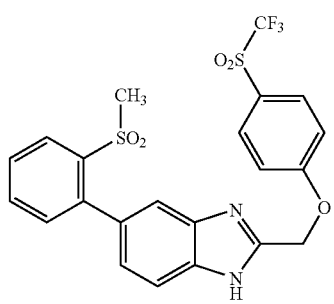
Cpd 86
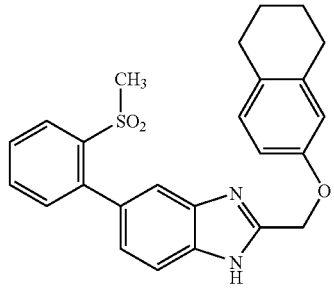
Cpd 87

-continued

Cpd 88

Cpd 89

Cpd 90

Cpd 91

Cpd 92

-continued

Cpd 93

Cpd 94

Cpd 95

Cpd 96

Cpd 97

Cpd 98

-continued
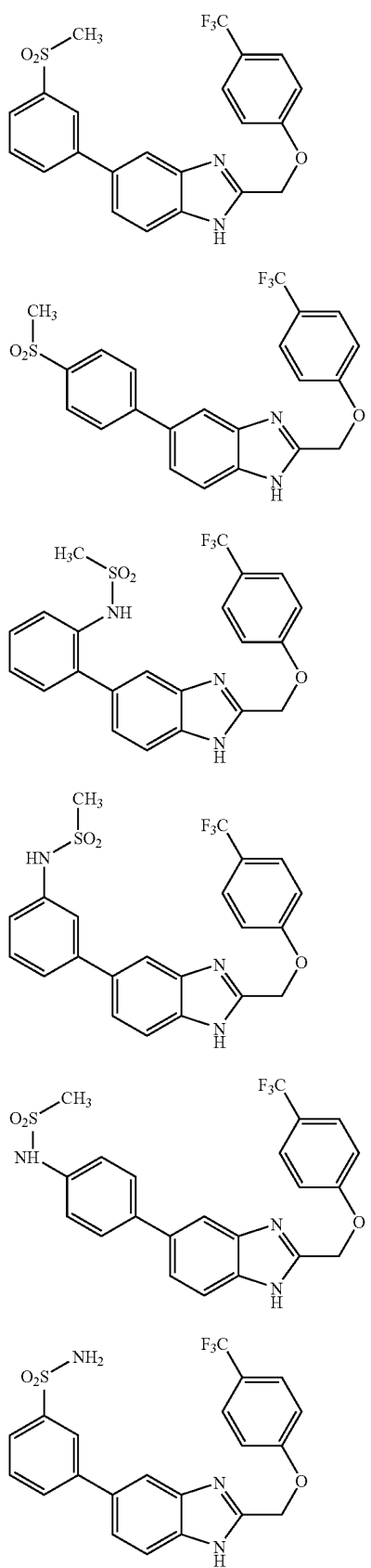
Cpd 99
Cpd 100
Cpd 101
Cpd 102
Cpd 103
Cpd 104
-continued
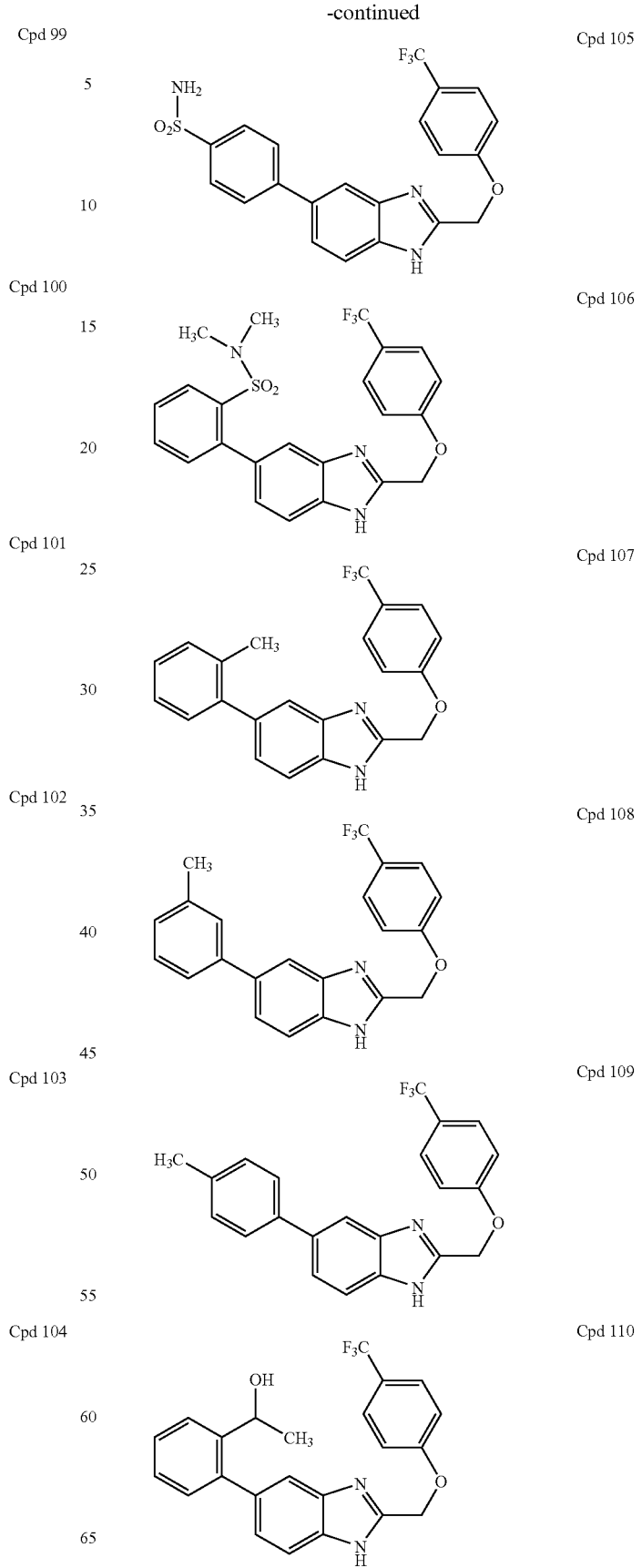
Cpd 105
Cpd 106
Cpd 107
Cpd 108
Cpd 109
Cpd 110

-continued
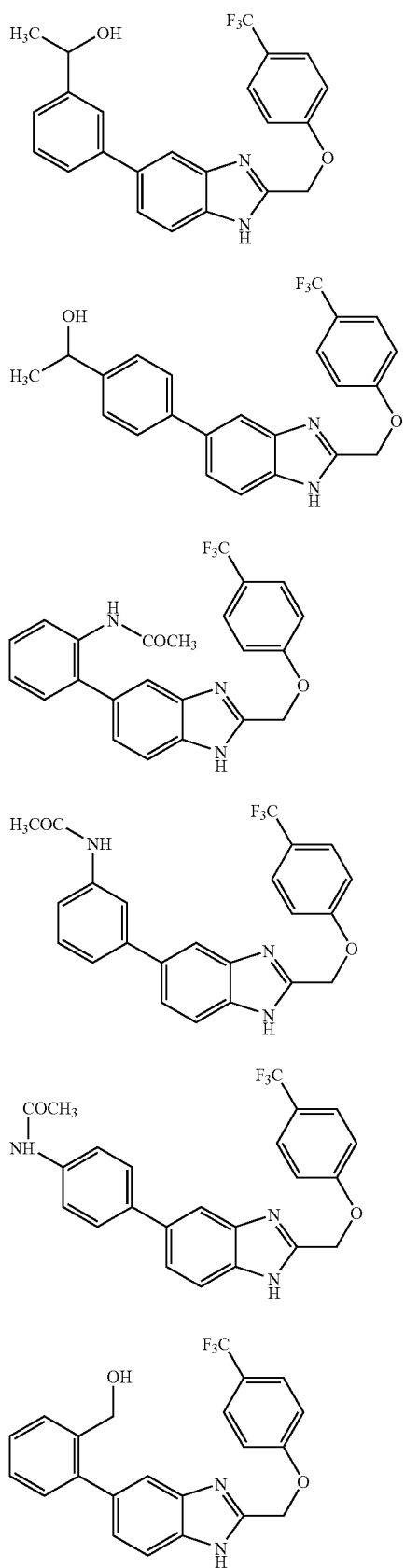
Cpd 111
Cpd 112
Cpd 113
Cpd 114
Cpd 115
Cpd 116
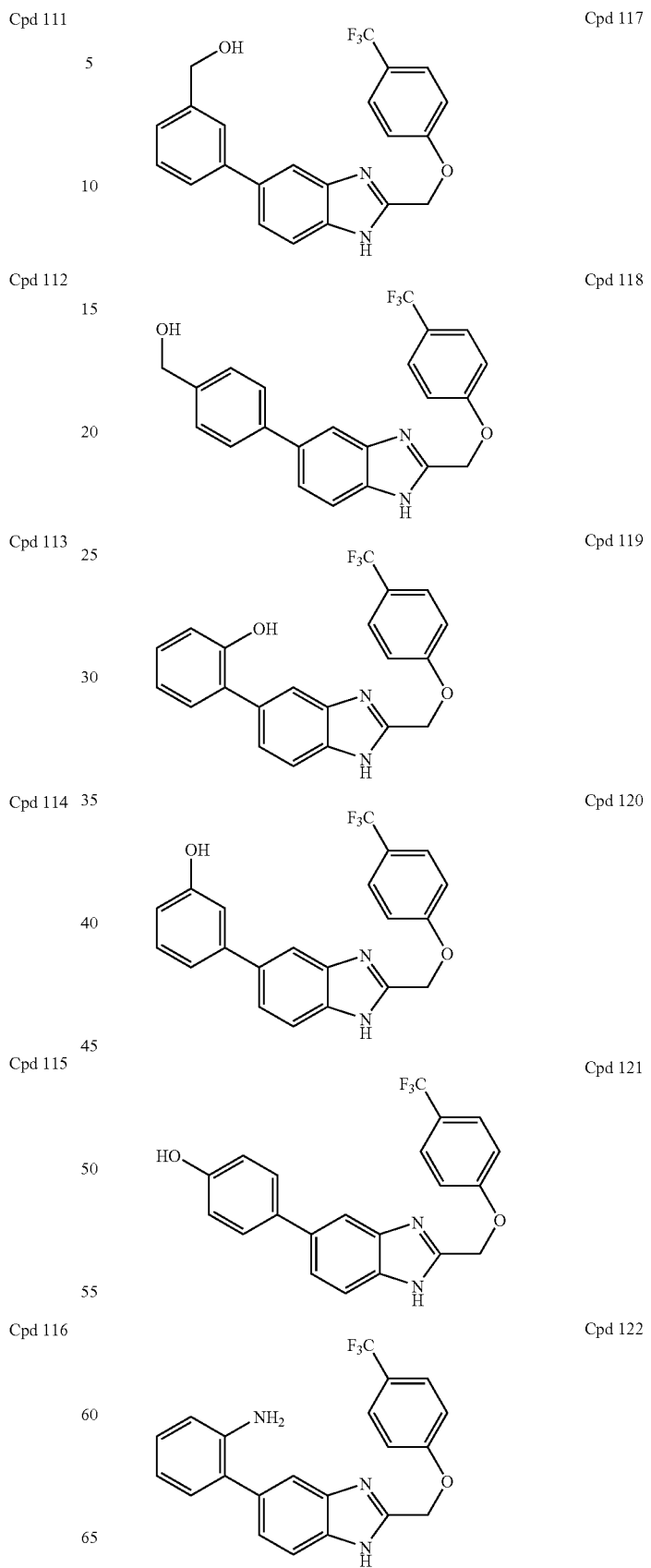
Cpd 117
Cpd 118
Cpd 119
Cpd 120
Cpd 121
Cpd 122

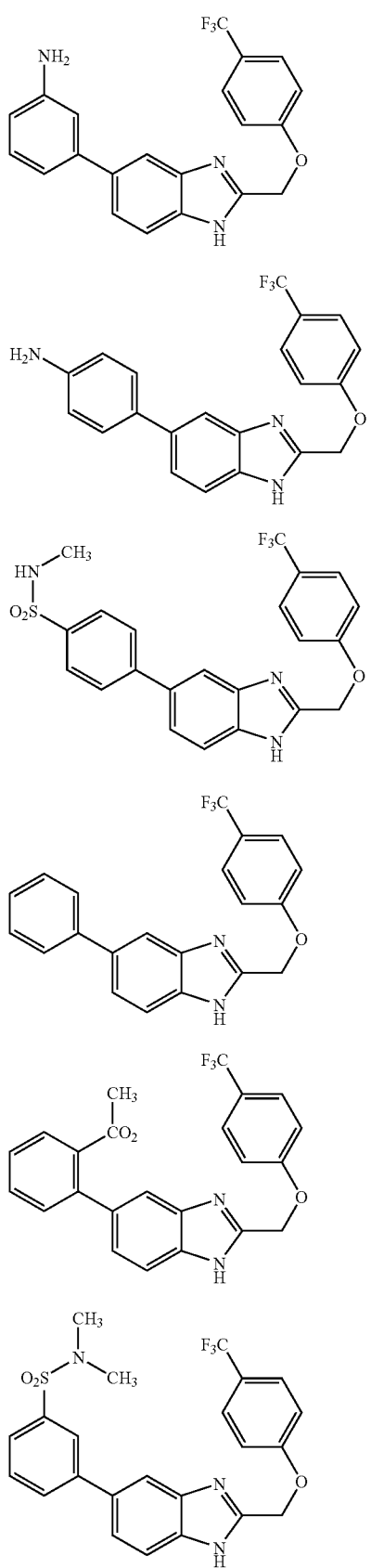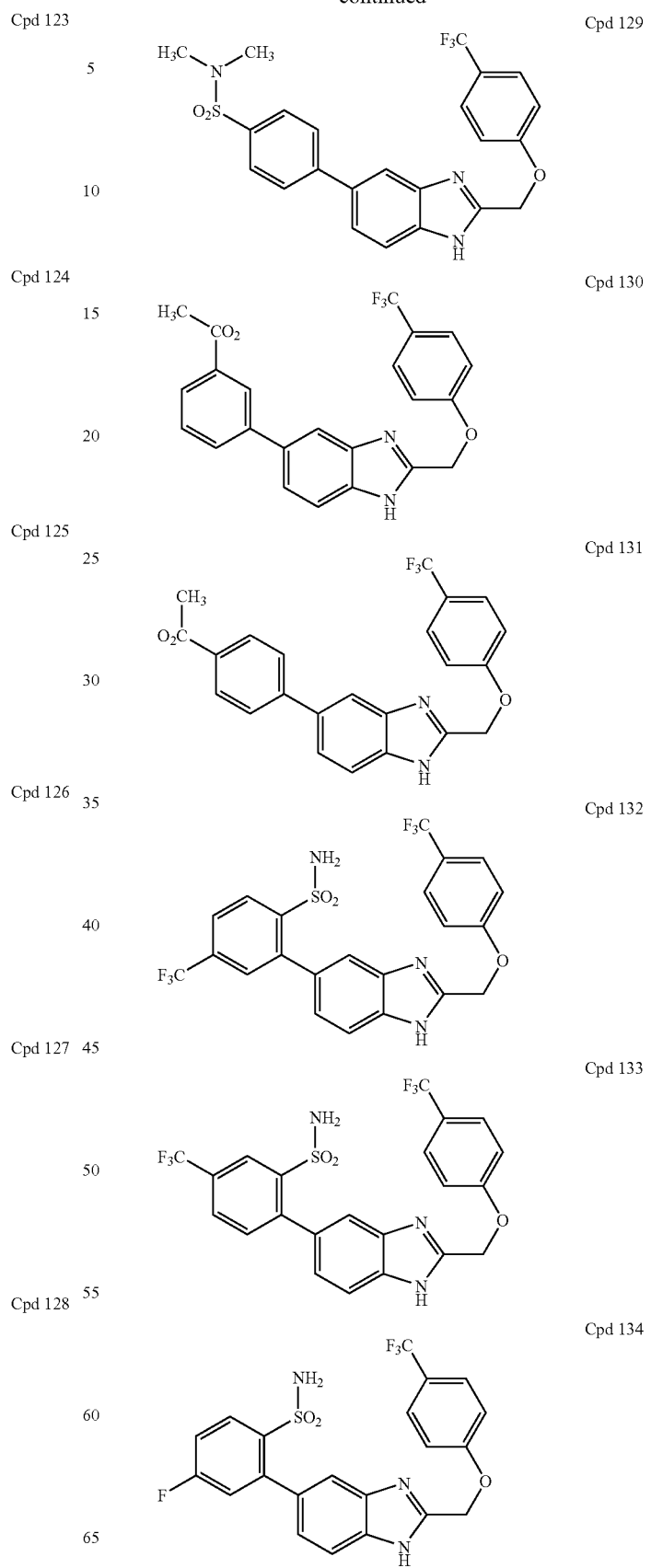

-continued
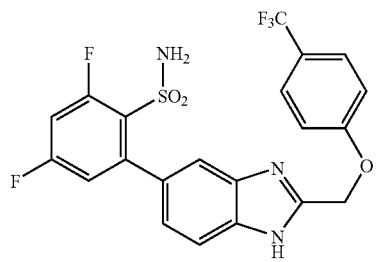
Cpd 135
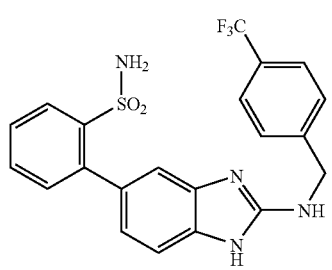
Cpd 136
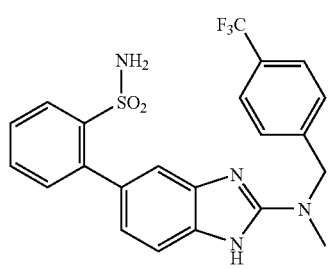
Cpd 137
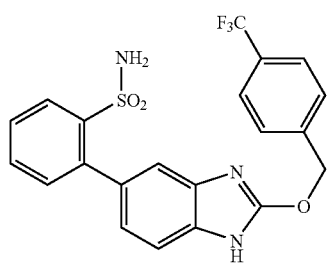
Cpd 138
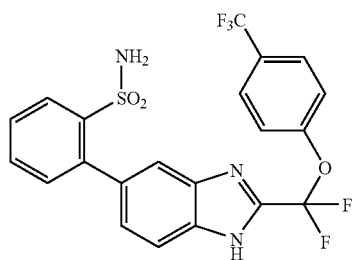
Cpd 139
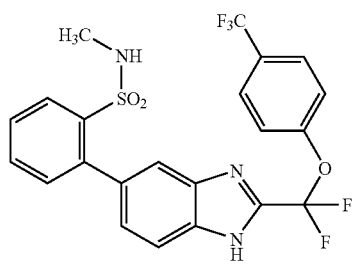
Cpd 140
-continued
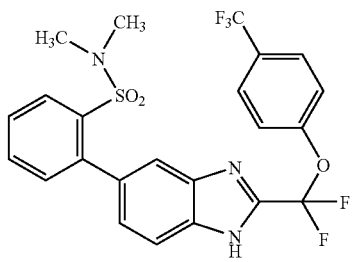
Cpd 141
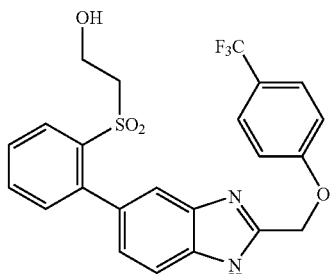
Cpd 142
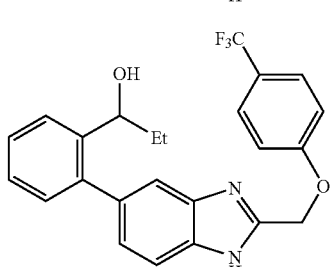
Cpd 143
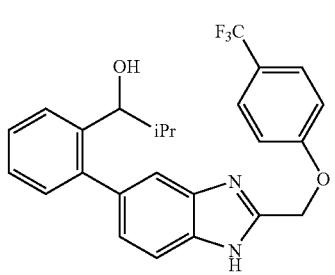
Cpd 144
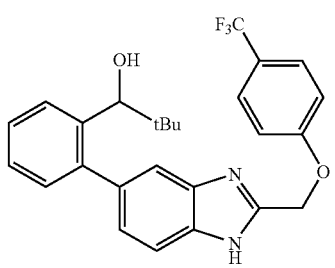
Cpd 145
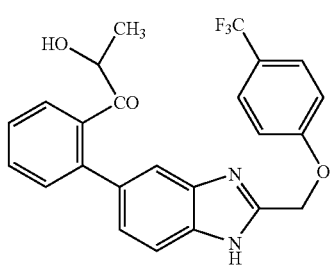
Cpd 146

Cpd 147
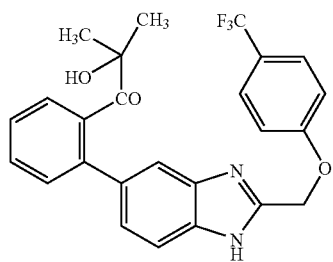
Cpd 148
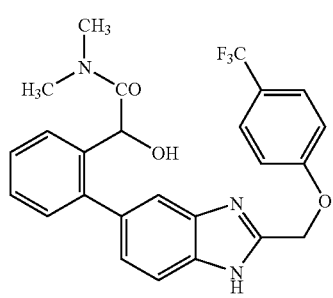
Cpd 149
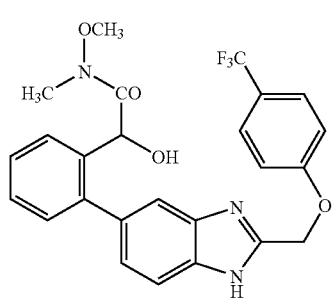
Cpd 150
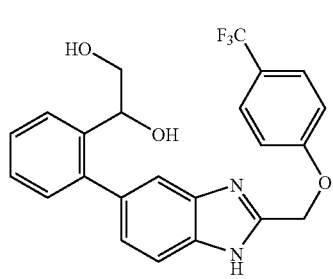
Cpd 151
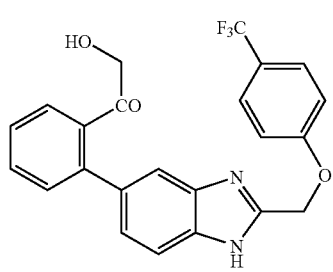
Cpd 152
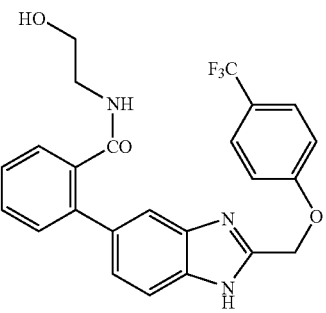
Cpd 153
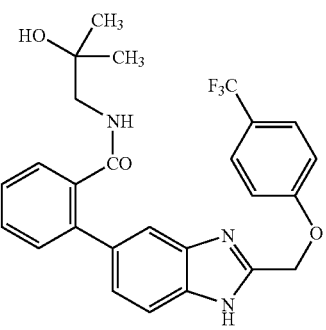
Cpd 154
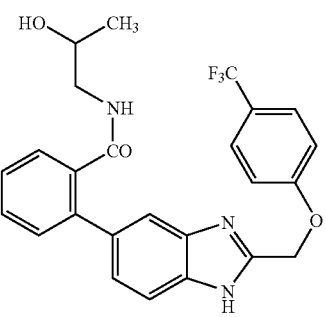
Cpd 155
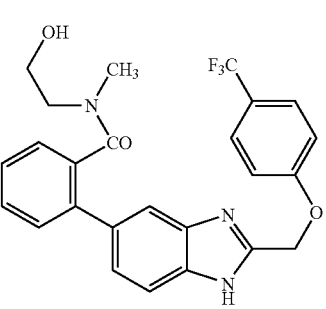
Cpd 156
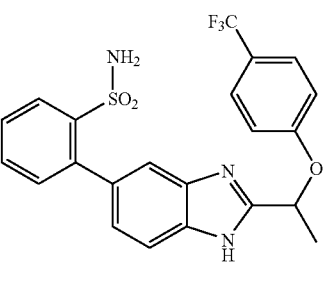

Cpd 157
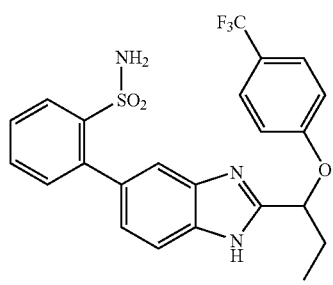
Cpd 158
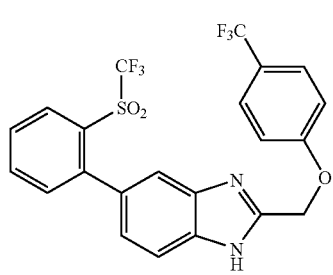
Cpd 159
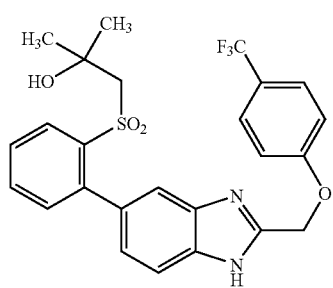
Cpd 160
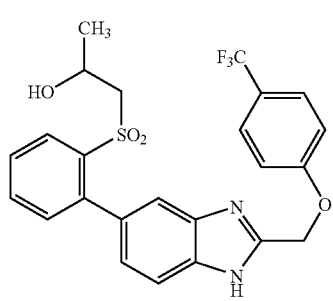
Cpd 161
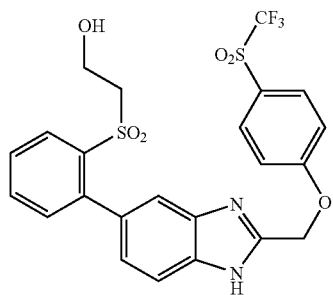
Cpd 162
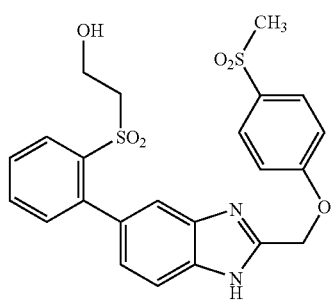
Cpd 163
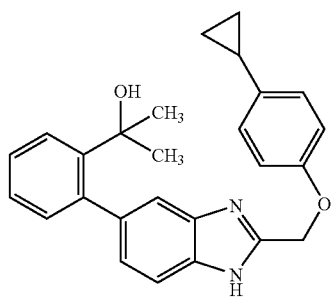
Cpd 164
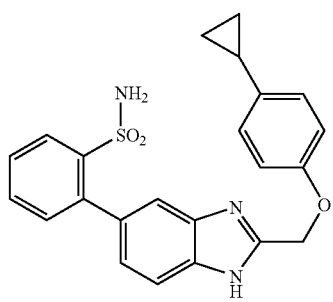
Cpd 165
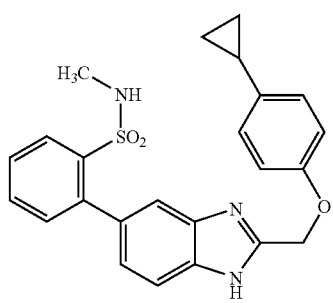
Cpd 166
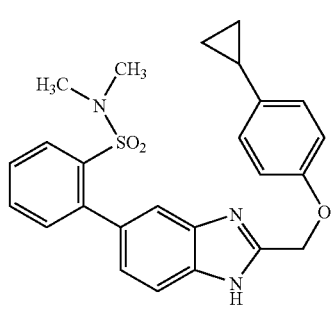

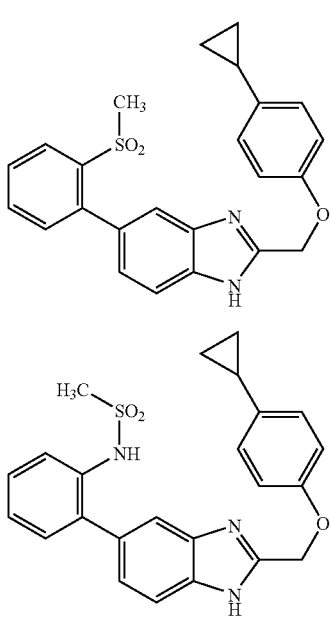

Cpd 167

Cpd 168

Compound Forms

The term "form" means, in reference to compounds of the present invention, that such may exist as, without limitation, a salt, or in a stereoisomeric, tautomeric, crystalline, polymorphic, amorphous, solvate, hydrate, ester, prodrug or metabolite form. The present invention encompasses all such compound forms and mixtures thereof.

The term "isolated form" means, in reference to compounds of the present invention, that such may exist in an essentially pure state such as, without limitation, an enantiomer, a racemic mixture, a geometric isomer (such as a cis or trans stereoisomer), a mixture of geometric isomers, and the like. The present invention encompasses all such isolated forms and mixtures thereof.

Certain compounds of Formula (I) may exist in various stereoisomeric or tautomeric forms and mixtures thereof. The invention encompasses all such compounds and mixtures thereof.

The compounds of the present invention may be present in the form of pharmaceutically acceptable salts. For use in medicines, the "pharmaceutically-acceptable" salts of the compounds of Formula (I) include the conventional non-toxic salts or the quaternary ammonium salts which are formed from inorganic or organic acids or bases. Examples of such acid salts include acetate, adipate, benzoate, benzenesulfonate, benzoate, bicarbonate, bisulfate, bitartrate, borate, bromide, calcium, camsylate (or camphorsulphonate), carbonate, chloride, choline, clavulanate, citrate, camphorate, dihydrochloride, dodecylsulfate, edetate, fumarate, gluconate, glutamate, hydrabamine, hydrochloride, hydrobromide, iodide, isothionate, lactate, malate, maleate, mandelate, mesylate, methanesulfonate, nitrate, oleate, oxalate, pamoate, palmitate, phosphate/diphosphate, pivalate, potassium/dipotassium, propionate, salicylate, stearate, succinate, sulfate, tartrate, tromethane, tosylate, trichloroacetate and trifluoroacetate. Examples of such basic salts include ammonium salts, alkali metal salts such as mono and disodium and mono and dipotassium salts, alkaline earth metal salts such as calcium and magnesium salts, salts with organic bases such as dicyclohexylamine salts and salts with amino acids such as arginine. Also, the basic nitrogen-containing groups may be quaternized with, for example, an alkyl halide.

In an example of the invention, the salt of the compound of Formula (I) is selected from the group consisting of acetate, adipate, benzenesulfonate, benzoate, bicarbonate, bisulfate, bitartrate, borate, bromide, calcium, camsylate, carbonate, chloride, choline, clavulanate, citrate, dihydrochloride, diphosphate, dipotassium, disodium, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate, potassium, salicylate, sodium, stearate, sulfate, succinate, tartrate, tromethane, tosylate, trichloroacetate and trifluoroacetate.

In another example of the invention, the salt of the compound of Formula (I) is selected from the group consisting of disodium, hydrochloride and sodium.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

Furthermore, compounds of the present invention may have at least one crystalline, polymorphic or amorphous form. The plurality of such forms is included in the scope of the invention. In addition, some of the compounds may form solvates with water (i.e., hydrates) or common organic solvents (e.g., organic esters such as ethanolate and the like). The plurality of such solvates is also intended to be encompassed within the scope of this invention.

Chemical Nomenclature and Definitions

Bond lines drawn into a ring system from a substituent variable indicate that the substituent may be attached to any of the substitutable ring atoms.

As used herein, the following terms are intended to have the following meanings (additional definitions are provided where needed throughout the Specification). The definitions herein may specify that a chemical term has an indicated formula. The particular formula provided is not intended to limit the scope of the invention, but is provided as an illustration of the term and is intended to include the plurality of variations expected to be included by one of ordinary skill in the art.

Definitions

The term "$C_{1-8}$alkyl" or "alkyl" means a straight or branched chain hydrocarbon alkyl radical or alkyldiyl linking group, comprising from 1 to 8 carbon atoms. The radical is derived by the removal of one hydrogen atom from a single carbon atom and the alkyldiyl linking group is derived by the removal of one hydrogen atom from each of two carbon atoms in the chain. Non-limiting examples include methyl, ethyl, 1-propyl, 2-propyl, 1-butyl, 2-butyl, tertiary butyl (also referred to as t-butyl or tert-butyl), 1-pentyl, 2-pentyl, 3-pentyl, 1-hexyl, 2-hexyl, 3-hexyl and the like. The term further includes alkyl groups in any combination thereof (e.g. $C_{1-2}$, $C_{1-3}$, $C_{1-4}$ and the like). An alkyl radical may be attached to a core molecule and further substituted when allowed by available valences.

The term "$C_{1-8}$alkoxy" or "alkoxy" means a straight or branched chain hydrocarbon alkyl radical or alkyldiyl linking group of the formula —O—$C_{1-8}$alkyl, comprising from 1 to 8 carbon atoms. Examples include methoxy, ethoxy, propoxy, isopropoxy, butoxy and the like. The term further includes alkoxy groups in any combination thereof (e.g. $C_{1-2}$, $C_{1-3}$, $C_{1-4}$ and the like). An alkoxy radical may be attached to a core molecule and further substituted when allowed by available valences.

The term "cycloalkyl" refers to a saturated or partially unsaturated ring composed of from 3 to 14 carbon atoms. The term includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{8-10}$cycloalkyl, $C_{9-13}$cycloalkyl, $C_{3-14}$cycloalkyl or benzofused $C_{3-14}$cycloalkyl ring system. Examples include cyclopropyl, cyclobutyl, cyclopentyl, cyclohexyl, cyclohexyl, cyclohexenyl, cycloheptyl, cyclooctyl, 1H-indenyl, indanyl, adamantanyl, 9H-fluorenyl, 1,2,3,4-tetrahydro-naphthalenyl, acenaphthenyl, bicyclo[2.2.1]heptenyl and the like. $C_{3-14}$cycloalkyl radicals may be attached to a core molecule and further substituted on any atom when allowed by available valences.

The term "$C_{3-14}$cycloalkyl" means a saturated or partially unsaturated, monocyclic, polycyclic or benzofused hydrocarbon ring system radical derived by the removal of one hydrogen atom from a single ring carbon atom. The term also includes $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-13}$cycloalkyl, $C_{5-14}$cycloalkenyl and benzofused $C_{3-14}$cycloalkyl ring systems. Examples include cyclopropyl, cyclobutyl, cyclopentyl, cyclohexyl, cyclohexyl, cyclohexenyl, cycloheptyl, cyclooctyl, 1H-indenyl, indanyl, 9H-fluorenyl, tetrahydro-naphthalenyl, acenaphthenyl, adamantanyl, bicyclo[2.2.1]heptenyl and the like. A cycloalkyl radical may be attached to a core molecule and further substituted on any atom where allowed by available valences.

The term "benzofused," used as a prefix for a ring system, means a radical formed by any ring system radical fused with a benzene ring. The benzofused radical may be attached to a core molecule via either ring of the bicyclic system and further substituted on any atom where allowed by available valences.

The term "aryl" refers to monocyclic or bicyclic aromatic ring systems containing from 6 to 12 carbons in the ring. Examples include phenyl, biphenyl, naphthalene, azulenyl, anthacenyl and the like. Aryl radicals may be attached to a core molecule and further substituted on any atom when allowed by available valences.

The term "aromatic" refers to a cycloalkylic hydrocarbon ring system having an unsaturated, conjugated π electron system.

The term "hetero," used as a prefix for a ring system, refers to the replacement of at least one ring carbon atom with one or more heteroatoms independently selected from a nitrogen, oxygen or sulfur atom, wherein the nitrogen and sulfur atoms can exist in any allowed oxidation state. Examples include rings wherein 1, 2, 3 or 4 ring members are a nitrogen atom; or, 0, 1, 2 or 3 ring members are nitrogen atoms and 1 member is an oxygen or sulfur atom. When allowed by available valences, up to two adjacent ring members may be heteroatoms; wherein one heteroatom is nitrogen and the other is one heteroatom selected from N, S or O.

The term "heterocyclyl" refers to a nonaromatic (i.e. saturated or partially unsaturated) monocyclic, polycyclic or benzofused ring system radical. Heteroatom ring members are selected from at least one of N, O, S, S(O) or $SO_2$, wherein the nitrogen and sulfur atoms can exist in any allowed oxidation state. Examples include 2H-pyrrolyl, 2-pyrrolinyl, 3-pyrrolinyl, pyrrolidinyl, 2-imidazolinyl (also referred to as 4,5-dihydro-1H-imidazolyl), imidazolidinyl, 2-pyrazolinyl, pyrazolidinyl, oxazolidinyl, tetrazolinyl, tetrazolidinyl, piperidinyl, morpholinyl, 1,4-dithianyl, thiomorpholinyl, piperazinyl, azetidinyl, azepanyl, dihydro-pyranyl, tetrahydro-furanyl, tetrahydro-thienyl, tetrahydro-pyranyl, tetrahydro-pyridazinyl, hexahydro-1,4-diazepinyl, hexahydro-1,4-oxazepanyl, 1,3-dioxolanyl, 1,4-dioxanyl, 1,3-benzodioxolyl (also referred to as benzo[1,3]dioxolyl), 2,3-dihydro-1,4-benzodioxinyl (also referred to as 2,3-dihydro-benzo[1,4]dioxinyl) and the like. Heterocyclyl radicals may be attached to a core molecule and further substituted on any atom when allowed by available valences.

The term "heteroaryl" means an aromatic monocyclic, polycyclic or benzofused ring system radical. Heteroatom ring members are selected from at least one of N, O, S, S(O) or $SO_2$, wherein the nitrogen and sulfur atoms can exist in any allowed oxidation state.

Examples include furanyl, thienyl, pyrrolyl, pyrazolyl, 1H-imidazolyl, isothiazolyl, isoxazolyl, oxazolyl, thiazolyl, oxadiazolyl, triazolyl, thiadiazolyl, 1H-tetrazolyl, 2H-tetrazolyl, 1H-[1,2,3]triazolyl, 2H-[1,2,3]triazolyl, 4H-[1,2,4]triazolyl, pyridinyl, pyrazinyl, pyrimidinyl, pyridazinyl, indolizinyl, indolyl, azaindolyl, indazolyl, azaindazolyl, isoindolyl, benzofuranyl, benzothienyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like. Heteroaryl radicals may be attached to a core molecule and further substituted on any atom when allowed by available valences.

The term "$C_{1-6}$alkoxy-$C_{1-6}$alkyl" means a radical of the formula: —$C_{1-6}$alkyl-O—$C_{1-6}$alkyl.

The term "$C_{1-6}$alkoxycarbonylamino" means a radical of the formula: —NH—C(O)—O—$C_{1-6}$alkyl. Examples include $C_{1-3}$alkylcarbonylamino.

The term "($C_{1-6}$alkyl)$_{1-2}$amino" means a radical of the formula: —NH—$C_{1-6}$alkyl or —N($C_{1-6}$alkyl)$_2$. Examples include ($C_{1-4}$alkyl)$_{1-2}$amino.

The term "($C_{1-6}$alkyl)$_{1-2}$aminocarbonyl" means a radical of the formula: —C(O)—NH—$C_{1-6}$alkyl or —C(O)—N($C_{1-6}$ alkyl)$_2$. Examples include ($C_{1-4}$alkyl)$_{1-2}$aminocarbonyl.

The term "($C_{1-6}$alkyl)$_{1-2}$aminocarbonylamino" means a radical of the formula: —NH—C(O)—NH—$C_{1-6}$alkyl or —C(O)—N($C_{1-6}$alkyl)$_2$. Examples include ($C_{1-4}$alkyl)$_{1-2}$aminocarbonylamino.

The term "($C_{1-4}$alkyl)$_{1-2}$aminosulfonyl" means a radical of the formula: —$SO_2$—NH—$C_{1-6}$alkyl or —$SO_2$—N($C_{1-6}$ alkyl)$_2$.

The term "$C_{1-6}$alkylcarbonylamino" means a radical of the formula: —NH—C(O)—$C_{1-6}$alkyl. Examples include $C_{1-3}$alkylcarbonylamino.

The term "$C_{1-6}$alkylsulfonyl" means a radical of the formula: —$SO_2$—$C_{1-6}$alkyl.

The term "$C_{1-6}$alkylsulfonylamino" means a radical of the formula: —NH—$SO_2$—$C_{1-6}$alkyl.

The term "$C_{1-6}$alkylthio" means a radical of the formula: —S—$C_{1-6}$alkyl.

The term "amino" means a radical of the formula: —$NH_2$.

The term "aminocarbonyl" means a radical of the formula: —C(O)—$NH_2$.

The term "aminocarbonylamino" means a radical of the formula: —NH—C(O)—$NH_2$.

The term "aminosulfonyl" means a radical of the formula: —$SO_2$—$NH_2$.

The term "$C_{3-8}$cycloalkyl-$C_{1-6}$alkyl" means a radical of the formula: —$C_{1-6}$alkyl-$C_{3-8}$cycloalkyl. Examples include $C_{3-8}$cycloalkyl-$C_{1-4}$alkyl.

The term "$C_{3-8}$cycloalkyl-$C_{1-6}$alkoxy" means a radical of the formula: —O—$C_{1-6}$alkyl-$C_{3-8}$cycloalkyl. Examples include $C_{3-8}$cycloalkyl-$C_{1-4}$alkoxy.

The term "$C_{3-8}$cycloalkyl-oxy" means a radical of the formula: —O—$C_{3-8}$cycloalkyl.

The term "($C_{3-8}$cycloalkyl)$_{1-2}$amino" means a radical of the formula: —NH—($C_{3-8}$cycloalkyl) or —N($C_{3-8}$cycloalkyl)$_2$.

The term "($C_{3-8}$cycloalkyl-$C_{1-4}$alkyl)$_{1-2}$amino" means a radical of the formula: —NH—$C_{1-4}$alkyl-$C_{3-8}$cycloalkyl or —N($C_{1-4}$alkyl-$C_{3-8}$cycloalkyl)$_2$.

The term "oxo" means a radical of the formula: =O.

The term "halogen" or "halo" means the group chloro, bromo, fluoro or iodo.

The term "halo-$C_{1-6}$alkyl" means a radical of the formula: —$C_{1-6}$alkyl(halo)n, wherein "n" represents that amount of available valences on $C_{1-6}$alkyl which may be substituted with one or more halogen atoms while remaining stable. Examples include difluoromethyl, trifluoromethyl, trifluoroethyl, chloromethyl and the like.

The term "halo-$C_{1-6}$alkoxy" means a radical of the formula: —O—$C_{1-6}$alkyl(halo)$_n$, wherein "n" represents that amount of available valences on $C_{1-6}$alkoxy which may be substituted with one or more halogen atoms while remaining stable. Examples include difluoromethoxy, trifluoromethoxy, trifluoroethoxy, chloromethoxy and the like.

The term "halo-$C_{1-6}$alkylsulfonyl" means a radical of the formula: —SO$_2$—$C_{1-6}$alkyl(halo)$_n$, wherein "n" represents that amount of available valences on $C_{1-6}$alkyl which may be substituted with one or more halogen atoms while remaining stable. Examples include trifluoromethylsulfonyl and the like.

The term "perfluorinated" means a radical which is substituted with fluoro atoms to the extent allowed by available valences while remaining stable.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

Therapeutic Use

Noxious chemical, thermal and mechanical stimuli excite peripheral nerve endings of small diameter sensory neurons (nociceptors), deriving from sensory ganglia (e.g., dorsal root, nodose and trigeminal ganglia), which initiate signals that are perceived as pain. Nociceptors are crucial for the detection of harmful or potentially harmful stimuli (e.g., noxious thermal, chemical, and/or mechanical) arising from changes in the extracellular environment during inflammatory, ischemic or otherwise traumatic conditions and that cause or have the potential to cause tissue damage (Wall, P. D., and Melzack, R., Textbook of Pain, 2005, New York: Churchill Livingstone).

Nociceptors transduce noxious stimuli into membrane depolarization that leads to an action potential, its subsequent conduction to the CNS, and ultimately to the perception of pain, discomfort, etc. as well as to certain responses thereto. At the molecular level, nociception is carried out by ion channels and/or receptors. Plant-derived vanilloid compounds (e.g., capsaicin and resiniferatoxin) are known to selectively depolarize nociceptors and elicit sensations of burning pain—the sensation that is typically evoked by capsaicin-containing hot chili peppers. Therefore, capsaicin mimics the action of physiological/endogenous stimuli that activate the "nociceptive pathway". Advances in pain biology have identified a vanilloid receptor, called TRPV1 (a.k.a. capsaicin receptor). Because nociceptors are drivers of unwanted pain and inflammatory conditions in human beings and animals, modulation of their function is a validated strategy for palliative and other analgesic therapies.

The compounds of the present invention demonstrate high TRPV1 affinity. Accordingly, the present invention is directed to a method for treating a TRPV1 ion channel mediated disease in a subject in need thereof comprising administering to the subject an effective amount of a compound of Formula (I).

In an example of the invention, the TRPV1 ion channel mediated disease is chronic or acute pain due to disease that causes inflammatory pain, burning pain or post-operative pain.

In an example of the invention, the effective amount of the compound of Formula (I) is in a range of from about 0.001 mg/kg/day to about 300 mg/kg/day.

In another example of the invention, the compound of Formula (I) may be used in the manufacture of a medicament for treating a TRPV1 ion channel mediated disease, wherein the TRPV1 ion channel mediated disease is chronic or acute pain due to disease that causes inflammatory pain, burning pain or post-operative pain.

In a related example of the invention, the compound of Formula (I) may also be used as a medicine for treating a TRPV1 ion channel mediated disease, wherein the TRPV1 ion channel mediated disease is chronic or acute pain due to disease that causes inflammatory pain, burning pain or post-operative pain.

The compounds of Formula (I) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

An aspect of the use for a compound of Formula (I) includes use of an instant compound as a marker, wherein the compound is labeled with a ligand such as a radioligand (selected from deuterium, tritium and the like).

A representative compound of Formula (I) or a form thereof includes a compound selected from the group consisting of:

| Cpd | Name |
|---|---|
| 1 | 2-[2-(4-trifluoromethyl-phenoxymethyl)-1H-benzoimidazol-5-yl]-benzenesulfonamide, |
| 2 | 2-[2-(4-trifluoromethanesulfonyl-phenoxymethyl)-1H-benzoimidazol-5-yl]-benzenesulfonamide, |
| 3 | 2-[2-(2-fluoro-phenoxymethyl)-1H-benzoimidazol-5-yl]-benzenesulfonamide, |
| 4 | 2-[2-(3-fluoro-phenoxymethyl)-1H-benzoimidazol-5-yl]-benzenesulfonamide, |
| 5 | 2-[2-(4-fluoro-phenoxymethyl)-1H-benzoimidazol-5-yl]-benzenesulfonamide, |
| 6 | 2-[2-(3-chloro-phenoxymethyl)-1H-benzoimidazol-5-yl]-benzenesulfonamide, |
| 7 | 2-[2-(4-chloro-phenoxymethyl)-1H-benzoimidazol-5-yl]-benzenesulfonamide, |
| 8 | 2-[2-(4-bromo-phenoxymethyl)-1H-benzoimidazol-5-yl]-benzenesulfonamide, |
| 9 | 2-[2-(2,4-difluoro-phenoxymethyl)-1H-benzoimidazol-5-yl]-benzenesulfonamide, |
| 10 | 2-[2-(3,4-difluoro-phenoxymethyl)-1H-benzoimidazol-5-yl]-benzenesulfonamide, |
| 11 | 2-[2-(3-chloro-4-fluoro-phenoxymethyl)-1H-benzoimidazol-5-yl]-benzenesulfonamide, |
| 12 | 2-[2-(4-fluoro-3-trifluoromethyl-phenoxymethyl)-1H-benzoimidazol-5-yl]-benzenesulfonamide, |
| 13 | 2-[2-(3-trifluoromethyl-phenoxymethyl)-1H-benzoimidazol-5-yl]-benzenesulfonamide, |
| 14 | 2-[2-(2,3,4-trifluoro-phenoxymethyl)-1H-benzoimidazol-5-yl]-benzenesulfonamide, |
| 15 | 2-[2-(3-trifluoromethoxy-phenoxymethyl)-1H-benzoimidazol-5-yl]-benzenesulfonamide, |
| 16 | 2-[2-(4-trifluoromethoxy-phenoxymethyl)-1H-benzoimidazol-5-yl]-benzenesulfonamide, |
| 17 | N-methyl-2-[2-(4-trifluoromethyl-phenoxymethyl)-1H-benzoimidazol-5-yl]-benzenesulfonamide, |
| 18 | 2-[2-(4-chloro-phenoxymethyl)-1H-benzoimidazol-5-yl]-N-methyl-benzenesulfonamide, |
| 19 | 2-[2-(4-methanesulfonyl-phenoxymethyl)-1H-benzoimidazol-5-yl]-N-methyl-benzenesulfonamide, |
| 20 | N-methyl-2-[2-(4-trifluoromethanesulfonyl-phenoxymethyl)-1H-benzoimidazol-5 yl]-benzenesulfonamide, |
| 21 | 2-{2-[2-(4-trifluoromethyl-phenoxymethyl)-1H-benzoimidazol-5-yl]-phenyl}-propan-2-ol, |
| 22 | 2-{2-[2-(4-trifluoromethoxy-phenoxymethyl)-1H-benzoimidazol-5-yl]-phenyl}-propan-2-ol, |
| 23 | 2-{2-[2-(4-chloro-phenoxymethyl)-1H-benzoimidazol-5-yl]-phenyl}-propan-2-ol, |
| 24 | 2-{2-[2-(3-trifluoromethyl-phenoxymethyl)-1H-benzoimidazol-5-yl]-phenyl}-propan-2-ol, |
| 25 | 2-{2-[2-(4-methanesulfonyl-phenoxymethyl)-1H-benzoimidazol-5-yl]-phenyl}-propan-2-ol, |
| 26 | 2-(2-phenoxymethyl-1H-benzoimidazol-5-yl)-benzenesulfonamide, |
| 27 | 2-(2-p-tolyloxymethyl-1H-benzoimidazol-5-yl)-benzenesulfonamide, |
| 28 | 2-[2-(4-isopropyl-phenoxymethyl)-1H-benzoimidazol-5-yl]-benzenesulfonamide, |
| 29 | 2-[2-(3,4-dichloro-phenoxymethyl)-1H-benzoimidazol-5-yl]-benzenesulfonamide, |
| 30 | 2-[2-(4-chloro-3-trifluoromethyl-phenoxymethyl)-1H-benzoimidazol-5-yl]-benzenesulfonamide, |
| 31 | 2-[2-(3,5-bis-trifluoromethyl-phenoxymethyl)-1H-benzoimidazol-5-yl]-benzenesulfonamide, |
| 32 | 2-[2-(4-tert-butyl-phenoxymethyl)-1H-benzoimidazol-5-yl]-benzenesulfonamide, |
| 33 | 2-[2-(4-ethoxy-phenoxymethyl)-1H-benzoimidazol-5-yl]-benzenesulfonamide, |
| 34 | 2-[2-(4-trifluoromethylsulfanyl-phenoxymethyl)-1H-benzoimidazol-5-yl]-benzenesulfonamide, |
| 35 | 2-[2-(4-acetyl-phenoxymethyl)-1H-benzoimidazol-5-yl]-benzenesulfonamide, |
| 36 | 2-[2-(naphthalen-2-yloxymethyl)-1H-benzoimidazol-5-yl]-benzenesulfonamide, |
| 37 | 2-[2-(quinolin-6-yloxymethyl)-1H-benzoimidazol-5-yl]-benzenesulfonamide, |
| 38 | 2-[2-(pyridin-4-yloxymethyl)-1H-benzoimidazol-5-yl]-benzenesulfonamide, |
| 39 | 2-[2-(5-trifluoromethyl-pyridin-2-yloxymethyl)-1H-benzoimidazol-5-yl]-benzenesulfonamide, |
| 40 | 2-[1-methyl-2-(4-trifluoromethyl-phenoxymethyl)-1H-benzoimidazol-5-yl]-benzenesulfonamide, |
| 41 | 2-[2-(4-trifluoromethyl-phenylsulfanylmethyl)-1H-benzoimidazol-5-yl]-benzenesulfonamide, |
| 42 | 2-[2-(4-chloro-phenylsulfanylmethyl)-1H-benzoimidazol-5-yl]-benzenesulfonamide, |
| 43 | 2-[2-(4-trifluoromethoxy-phenylsulfanylmethyl)-1H-benzoimidazol-5-yl]-benzenesulfonamide, |
| 44 | 2-[2-(4-trifluoromethyl-benzenesulfonylmethyl)-1H-benzoimidazol-5-yl]-benzenesulfonamide, |
| 45 | 2-[2-(4-chloro-benzenesulfonylmethyl)-1H-benzoimidazol-5-yl]-benzenesulfonamide, |

-continued

| Cpd | Name |
|---|---|
| 46 | 2-[2-(4-trifluoromethoxy-benzenesulfonylmethyl)-1H-benzoimidazol-5-yl]-benzenesulfonamide, |
| 47 | 2-{2-[(4-trifluoromethyl-phenylamino)-methyl]-1H-benzoimidazol-5-yl}-benzenesulfonamide, |
| 48 | 2-{2-[(4-trifluoromethoxy-phenylamino)-methyl]-1H-benzoimidazol-5-yl}-benzenesulfonamide, |
| 49 | 1-{2-[2-(4-trifluoromethyl-phenoxymethyl)-1H-benzoimidazol-5-yl]-phenyl}-ethanone, |
| 50 | 2-[2-(2-phenoxymethyl-1H-benzoimidazol-5-yl)-phenyl]-propan-2-ol, |
| 51 | 2-[2-(4-isopropyl-phenoxymethyl)-1H-benzoimidazol-5-yl]-N-methyl-benzenesulfonamide, |
| 52 | N-methyl-2-[2-(3-trifluoromethyl-phenoxymethyl)-1H-benzoimidazol-5-yl]-benzenesulfonamide, |
| 53 | 5-(2-methanesulfonyl-phenyl)-2-phenoxymethyl-1H-benzoimidazole, |
| 54 | 2-(2-fluoro-phenoxymethyl)-5-(2-methanesulfonyl-phenyl)-1H-benzoimidazole, |
| 55 | 2-(3-fluoro-phenoxymethyl)-5-(2-methanesulfonyl-phenyl)-1H-benzoimidazole, |
| 56 | 2-(4-fluoro-phenoxymethyl)-5-(2-methanesulfonyl-phenyl)-1H-benzoimidazole, |
| 57 | 2-(2-chloro-phenoxymethyl)-5-(2-methanesulfonyl-phenyl)-1H-benzoimidazole, |
| 58 | 2-(3-chloro-phenoxymethyl)-5-(2-methanesulfonyl-phenyl)-1H-benzoimidazole, |
| 59 | 2-(4-chloro-phenoxymethyl)-5-(2-methanesulfonyl-phenyl)-1H-benzoimidazole, |
| 60 | 2-(3-bromo-phenoxymethyl)-5-(2-methanesulfonyl-phenyl)-1H-benzoimidazole, |
| 61 | 2-(4-bromo-phenoxymethyl)-5-(2-methanesulfonyl-phenyl)-1H-benzoimidazole, |
| 62 | 2-(2,4-difluoro-phenoxymethyl)-5-(2-methanesulfonyl-phenyl)-1H-benzoimidazole, |
| 63 | 2-(3,4-difluoro-phenoxymethyl)-5-(2-methanesulfonyl-phenyl)-1H-benzoimidazole, |
| 64 | 2-(2,4-dichloro-phenoxymethyl)-5-(2-methanesulfonyl-phenyl)-1H-benzoimidazole, |
| 65 | 2-(3,4-dichloro-phenoxymethyl)-5-(2-methanesulfonyl-phenyl)-1H-benzoimidazole, |
| 66 | 2-(4-chloro-2-fluoro-phenoxymethyl)-5-(2-methanesulfonyl-phenyl)-1H-benzoimidazole, |
| 67 | 2-(3-chloro-4-fluoro-phenoxymethyl)-5-(2-methanesulfonyl-phenyl)-1H-benzoimidazole, |
| 68 | 5-(2-methanesulfonyl-phenyl)-2-(3,4,5-trifluoro-phenoxymethyl)-1H-benzoimidazole, |
| 69 | 5-(2-methanesulfonyl-phenyl)-2-(2,4,5-trifluoro-phenoxymethyl)-1H-benzoimidazole, |
| 70 | 5-(2-methanesulfonyl-phenyl)-2-(2,3,4-trifluoro-phenoxymethyl)-1H-benzoimidazole, |
| 71 | 2-(2-fluoro-3-trifluoromethyl-phenoxymethyl)-5-(2-methanesulfonyl-phenyl)-1H-benzoimidazole, |
| 72 | 2-(4-fluoro-3-trifluoromethyl-phenoxymethyl)-5-(2-methanesulfonyl-phenyl)-1H-benzoimidazole, |
| 73 | 2-(3,5-bis-trifluoromethyl-phenoxymethyl)-5-(2-methanesulfonyl-phenyl)-1H-benzoimidazole, |
| 74 | 5-(2-methanesulfonyl-phenyl)-2-(2-trifluoromethyl-phenoxymethyl)-1H-benzoimidazole, |
| 75 | 5-(2-methanesulfonyl-phenyl)-2-(3-trifluoromethyl-phenoxymethyl)-1H-benzoimidazole, |
| 76 | 5-(2-methanesulfonyl-phenyl)-2-p-tolyloxymethyl-1H-benzoimidazole, |
| 77 | 2-(4-isopropyl-phenoxymethyl)-5-(2-methanesulfonyl-phenyl)-1H-benzoimidazole, |
| 78 | 2-(4-tert-butyl-phenoxymethyl)-5-(2-methanesulfonyl-phenyl)-1H-benzoimidazole, |
| 79 | 1-{4-[5-(2-methanesulfonyl-phenyl)-1H-benzoimidazol-2-ylmethoxy]-phenyl}-ethanone, |
| 80 | 5-(2-methanesulfonyl-phenyl)-2-(naphthalen-2-yloxymethyl)-1H-benzoimidazole, |
| 81 | 2-(4-ethoxy-phenoxymethyl)-5-(2-methanesulfonyl-phenyl)-1H-benzoimidazole, |
| 82 | 5-(2-methanesulfonyl-phenyl)-2-(4-trifluoromethanesulfide-phenoxymethyl)-1H-benzoimidazole, |
| 83 | 4-[5-(2-methanesulfonyl-phenyl)-1H-benzoimidazol-2-ylmethoxy]-benzonitrile, |
| 84 | 5-(2-methanesulfonyl-phenyl)-2-(4-trifluoromethoxy-phenoxymethyl)-1H-benzoimidazole, |
| 85 | 2-(4-methanesulfonyl-phenoxymethyl)-5-(2-methanesulfonyl-phenyl)-1H-benzoimidazole, |
| 86 | 5-(2-methanesulfonyl-phenyl)-2-(4-trifluoromethanesulfonyl-phenoxymethyl)-1H-benzoimidazole, |
| 87 | 5-(2-methanesulfonyl-phenyl)-2-(5,6,7,8-tetrahydro-naphthalen-2-yloxymethyl)-1H-benzoimidazole, |
| 88 | 3-{4-[5-(2-methanesulfonyl-phenyl)-1H-benzoimidazol-2-ylmethoxy]-phenyl}-propionic acid methyl ester, |
| 89 | 2-(2,4-dimethyl-phenoxymethyl)-5-(2-methanesulfonyl-phenyl)-1H-benzoimidazole, |

-continued

| Cpd | Name |
|---|---|
| 90 | 2-(3,5-dimethyl-phenoxymethyl)-5-(2-methanesulfonyl-phenyl)-1H-benzoimidazole, |
| 91 | 2-(indan-5-yloxymethyl)-5-(2-methanesulfonyl-phenyl)-1H-benzoimidazole, |
| 92 | 2-(benzo[1,3]dioxol-5-yloxymethyl)-5-(2-methanesulfonyl-phenyl)-1H-benzoimidazole, |
| 93 | 2-(3,5-dichloro-phenoxymethyl)-5-(2-methanesulfonyl-phenyl)-1H-benzoimidazole, |
| 94 | N-{3-[5-(2-methanesulfonyl-phenyl)-1H-benzoimidazol-2-ylmethoxy]-phenyl}-acetamide, |
| 95 | N-{4-[5-(2-methanesulfonyl-phenyl)-1H-benzoimidazol-2-ylmethoxy]-phenyl}-acetamide, |
| 96 | 5-(2-methanesulfonyl-phenyl)-2-(4-methoxy-phenoxymethyl)-1H-benzoimidazole, |
| 97 | 5-(2-methanesulfonyl-phenyl)-2-(3-methoxy-phenoxymethyl)-1H-benzoimidazole, |
| 98 | 5-(2-methanesulfonyl-phenyl)-2-(4-trifluoromethyl-phenoxymethyl)-1H-benzoimidazole, |
| 99 | 5-(3-methanesulfonyl-phenyl)-2-(4-trifluoromethyl-phenoxymethyl)-1H-benzoimidazole, |
| 100 | 5-(4-methanesulfonyl-phenyl)-2-(4-trifluoromethyl-phenoxymethyl)-1H-benzoimidazole, |
| 101 | N-{2-[2-(4-trifluoromethyl-phenoxymethyl)-1H-benzoimidazol-5-yl]-phenyl}-methanesulfonamide, |
| 102 | N-{3-[2-(4-trifluoromethyl-phenoxymethyl)-1H-benzoimidazol-5-yl]-phenyl}-methanesulfonamide, |
| 103 | N-{4-[2-(4-trifluoromethyl-phenoxymethyl)-1H-benzoimidazol-5-yl]-phenyl}-methanesulfonamide, |
| 104 | 3-[2-(4-trifluoromethyl-phenoxymethyl)-1H-benzoimidazol-5-yl]-benzenesulfonamide, |
| 105 | 4-[2-(4-trifluoromethyl-phenoxymethyl)-1H-benzoimidazol-5-yl]-benzenesulfonamide, |
| 106 | N,N-dimethyl-2-[2-(4-trifluoromethyl-phenoxymethyl)-1H-benzoimidazol-5-yl]-benzenesulfonamide, |
| 107 | 5-o-tolyl-2-(4-trifluoromethyl-phenoxymethyl)-1H-benzoimidazole, |
| 108 | 5-m-tolyl-2-(4-trifluoromethyl-phenoxymethyl)-1H-benzoimidazole, |
| 109 | 5-p-tolyl-2-(4-trifluoromethyl-phenoxymethyl)-1H-benzoimidazole, |
| 110 | 1-{2-[2-(4-trifluoromethyl-phenoxymethyl)-1H-benzoimidazol-5-yl]-phenyl}-ethanol, |
| 111 | 1-{3-[2-(4-trifluoromethyl-phenoxymethyl)-1H-benzoimidazol-5-yl]-phenyl}-ethanol, |
| 112 | 1-{4-[2-(4-trifluoromethyl-phenoxymethyl)-1H-benzoimidazol-5-yl]-phenyl}-ethanol, |
| 113 | N-{2-[2-(4-trifluoromethyl-phenoxymethyl)-1H-benzoimidazol-5-yl]-phenyl}-acetamide, |
| 114 | N-{3-[2-(4-trifluoromethyl-phenoxymethyl)-1H-benzoimidazol-5-yl]-phenyl}-acetamide, |
| 115 | N-{4-[2-(4-trifluoromethyl-phenoxymethyl)-1H-benzoimidazol-5-yl]-phenyl}-acetamide, |
| 116 | {2-[2-(4-trifluoromethyl-phenoxymethyl)-1H-benzoimidazol-5-yl]-phenyl}-methanol, |
| 117 | {3-[2-(4-trifluoromethyl-phenoxymethyl)-1H-benzoimidazol-5-yl]-phenyl}-methanol, |
| 118 | {4-[2-(4-trifluoromethyl-phenoxymethyl)-1H-benzoimidazol-5-yl]-phenyl}-methanol, |
| 119 | 2-[2-(4-trifluoromethyl-phenoxymethyl)-1H-benzoimidazol-5-yl]-phenol, |
| 120 | 3-[2-(4-trifluoromethyl-phenoxymethyl)-1H-benzoimidazol-5-yl]-phenol, |
| 121 | 4-[2-(4-trifluoromethyl-phenoxymethyl)-1H-benzoimidazol-5-yl]-phenol, |
| 122 | 2-[2-(4-trifluoromethyl-phenoxymethyl)-1H-benzoimidazol-5-yl]-phenylamine, |
| 123 | 3-[2-(4-trifluoromethyl-phenoxymethyl)-1H-benzoimidazol-5-yl]-phenylamine, |
| 124 | 4-[2-(4-trifluoromethyl-phenoxymethyl)-1H-benzoimidazol-5-yl]-phenylamine, |
| 125 | N-methyl-4-[2-(4-trifluoromethyl-phenoxymethyl)-1H-benzoimidazol-5-yl]-benzenesulfonamide, |
| 126 | 5-phenyl-2-(4-trifluoromethyl-phenoxymethyl)-1H-benzoimidazole, |
| 127 | 2-[2-(4-trifluoromethyl-phenoxymethyl)-1H-benzoimidazol-5-yl]-benzoic acid methyl ester, |
| 128 | N,N-dimethyl-3-[2-(4-trifluoromethyl-phenoxymethyl)-1H-benzoimidazol-5-yl]-benzenesulfonamide, |
| 129 | N,N-dimethyl-4-[2-(4-trifluoromethyl-phenoxymethyl)-1H-benzoimidazol-5-yl]-benzenesulfonamide, |
| 130 | 3-[2-(4-trifluoromethyl-phenoxymethyl)-1H-benzoimidazol-5-yl]-benzoic acid methyl ester, |
| 131 | 4-[2-(4-trifluoromethyl-phenoxymethyl)-1H-benzoimidazol-5-yl]-benzoic acid methyl ester, |
| 132 | 4-trifluoromethyl-2-[2-(4-trifluoromethyl-phenoxymethyl)-1H-benzoimidazol-5-yl]-benzenesulfonamide, |
| 133 | 5-trifluoromethyl-2-[2-(4-trifluoromethyl-phenoxymethyl)-1H-benzoimidazol-5-yl]-benzenesulfonamide, |

-continued

| Cpd | Name |
|---|---|
| 134 | 4-fluoro-2-[2-(4-trifluoromethyl-phenoxymethyl)-1H-benzoimidazol-5-yl]-benzenesulfonamide, |
| 135 | 2,4-difluoro-6-[2-(4-trifluoromethyl-phenoxymethyl)-1H-benzoimidazol-5-yl]-benzenesulfonamide, |
| 136 | 2-[2-(4-trifluoromethyl-benzylamino)-1H-benzoimidazol-5-yl]-benzenesulfonamide, |
| 137 | 2-{2-[methyl-(4-trifluoromethyl-benzyl)-amino]-1H-benzoimidazol-5-yl}-benzenesulfonamide, |
| 138 | 2-[2-(4-trifluoromethyl-benzyloxy)-1H-benzoimidazol-5-yl]-benzenesulfonamide, |
| 139 | 2-{2-[difluoro-(4-trifluoromethyl-phenoxy)-methyl]-1H-benzoimidazol-5-yl}-benzenesulfonamide, |
| 140 | 2-{2-[difluoro-(4-trifluoromethyl-phenoxy)-methyl]-1H-benzoimidazol-5-yl}-N-methyl-benzenesulfonamide, |
| 141 | 2-{2-[difluoro-(4-trifluoromethyl-phenoxy)-methyl]-1H-benzoimidazol-5-yl}-N,N-dimethyl-benzenesulfonamide, |
| 142 | 2-{2-[2-(4-trifluoromethyl-phenoxymethyl)-1H-benzoimidazol-5-yl]-benzenesulfonyl}-ethanol, |
| 143 | 1-{2-[2-(4-trifluoromethyl-phenoxymethyl)-1H-benzoimidazol-5-yl]-phenyl}-ethanol, |
| 144 | 2-methyl-1-{2-[2-(4-trifluoromethyl-phenoxymethyl)-1H-benzoimidazol-5-yl]-phenyl}-propan-1-ol, |
| 145 | 2,2-dimethyl-1-{2-[2-(4-trifluoromethyl-phenoxymethyl)-1H-benzoimidazol-5-yl]-phenyl}-propan-1-ol, |
| 146 | 2-hydroxy-1-{2-[2-(4-trifluoromethyl-phenoxymethyl)-1H-benzoimidazol-5-yl]-phenyl}-propan-1-one, |
| 147 | 2-hydroxy-2-methyl-1-{2-[2-(4-trifluoromethyl-phenoxymethyl)-1H-benzoimidazol-5-yl]-phenyl}-propan-1-one, |
| 148 | N,N-dimethyl-2-hydroxy-2-{2-[2-(4-trifluoromethyl-phenoxymethyl)-1H-benzoimidazol-5-yl]-phenyl}-acetamide, |
| 149 | 2-hydroxy-N-methoxy-N-methyl-2-{2-[2-(4-trifluoromethyl-phenoxymethyl)-1H-benzoimidazol-5-yl]-phenyl}-acetamide, |
| 151 | 2-hydroxy-1-{2-[2-(4-trifluoromethyl-phenoxymethyl)-1H-benzoimidazol-5-yl]-phenyl}-ethanone, |
| 150 | 1-{2-[2-(4-trifluoromethyl-phenoxymethyl)-1H-benzoimidazol-5-yl]-phenyl}-ethane-1,2-diol, |
| 152 | N-(2-hydroxy-ethyl)-2-[2-(4-trifluoromethyl-phenoxymethyl)-1H-benzoimidazol-5-yl]-benzamide, |
| 153 | N-(2-hydroxy-2-methyl-propyl)-2-[2-(4-trifluoromethyl-phenoxymethyl)-1H-benzoimidazol-5-yl]-benzamide, |
| 154 | N-(2-hydroxy-propyl)-2-[2-(4-trifluoromethyl-phenoxymethyl)-1H-benzoimidazol-5-yl]-benzamide, |
| 155 | N-(2-hydroxy-ethyl)-N-methyl-2-[2-(4-trifluoromethyl-phenoxymethyl)-1H-benzoimidazol-5-yl]-benzamide, |
| 156 | 2-{2-[1-(4-trifluoromethyl-phenoxy)-ethyl]-1H-benzoimidazol-5-yl}-benzenesulfonamide, |
| 157 | 2-{2-[1-(4-trifluoromethyl-phenoxy)-propyl]-1H-benzoimidazol-5-yl}-benzenesulfonamide, |
| 158 | 5-(2-trifluoromethanesulfonyl-phenyl)-2-(4-trifluoromethyl-phenoxymethyl)-1H-benzoimidazole, |
| 159 | 2-methyl-1-{2-[2-(4-trifluoromethyl-phenoxymethyl)-1H-benzoimidazol-5-yl]-benzenesulfonyl}-propan-2-ol, |
| 160 | 1-{2-[2-(4-trifluoromethyl-phenoxymethyl)-1H-benzoimidazol-5-yl]-benzenesulfonyl}-propan-2-ol, |
| 161 | 2-{2-[2-(4-trifluoromethanesulfonyl-phenoxymethyl)-1H-benzoimidazol-5-yl]-benzenesulfonyl}-ethanol, |
| 162 | 2-{2-[2-(4-methanesulfonyl-phenoxymethyl)-1H-benzoimidazol-5-yl]-benzenesulfonyl}-ethanol, |
| 163 | 2-{2-[2-(4-cyclopropyl-phenoxymethyl)-1H-benzoimidazol-5-yl]-phenyl}-propan-2-ol, |
| 164 | 2-[2-(4-cyclopropyl-phenoxymethyl)-1H-benzoimidazol-5-yl]-benzenesulfonamide, |
| 165 | 2-[2-(4-cyclopropyl-phenoxymethyl)-1H-benzoimidazol-5-yl]-N-methyl-benzenesulfonamide, |
| 166 | 2-[2-(4-cyclopropyl-phenoxymethyl)-1H-benzoimidazol-5-yl]-N,N-dimethyl-benzenesulfonamide, |
| 167 | 2-(4-cyclopropyl-phenoxymethyl)-5-(2-methanesulfonyl-phenyl)-1H-benzoimidazole, and |
| 168 | N-{2-[2-(4-cyclopropyl-phenoxymethyl)-1H-benzoimidazol-5-yl]-phenyl}-methanesulfonamide. |

A representative compound of Formula (I) or a form thereof includes a compound selected from the group consisting of:

| Cpd | Name |
|---|---|
| 1 | 2-[2-(4-trifluoromethyl-phenoxymethyl)-1H-benzoimidazol-5-yl]-benzenesulfonamide, |
| 2 | 2-[2-(4-trifluoromethanesulfonyl-phenoxymethyl)-1H-benzoimidazol-5-yl]-benzenesulfonamide, |
| 4 | 2-[2-(3-fluoro-phenoxymethyl)-1H-benzoimidazol-5-yl]-benzenesulfonamide, |
| 5 | 2-[2-(4-fluoro-phenoxymethyl)-1H-benzoimidazol-5-yl]-benzenesulfonamide, |
| 6 | 2-[2-(3-chloro-phenoxymethyl)-1H-benzoimidazol-5-yl]-benzenesulfonamide, |
| 7 | 2-[2-(4-chloro-phenoxymethyl)-1H-benzoimidazol-5-yl]-benzenesulfonamide, |
| 8 | 2-[2-(4-bromo-phenoxymethyl)-1H-benzoimidazol-5-yl]-benzenesulfonamide, |
| 9 | 2-[2-(2,4-difluoro-phenoxymethyl)-1H-benzoimidazol-5-yl]-benzenesulfonamide, |
| 10 | 2-[2-(3,4-difluoro-phenoxymethyl)-1H-benzoimidazol-5-yl]-benzenesulfonamide, |
| 11 | 2-[2-(3-chloro-4-fluoro-phenoxymethyl)-1H-benzoimidazol-5-yl]-benzenesulfonamide, |
| 12 | 2-[2-(4-fluoro-3-trifluoromethyl-phenoxymethyl)-1H-benzoimidazol-5-yl]-benzenesulfonamide, |
| 13 | 2-[2-(3-trifluoromethyl-phenoxymethyl)-1H-benzoimidazol-5-yl]-benzenesulfonamide, |
| 14 | 2-[2-(2,3,4-trifluoro-phenoxymethyl)-1H-benzoimidazol-5-yl]-benzenesulfonamide, |
| 15 | 2-[2-(3-trifluoromethoxy-phenoxymethyl)-1H-benzoimidazol-5-yl]-benzenesulfonamide, |
| 16 | 2-[2-(4-trifluoromethoxy-phenoxymethyl)-1H-benzoimidazol-5-yl]-benzenesulfonamide, |
| 17 | N-methyl-2-[2-(4-trifluoromethyl-phenoxymethyl)-1H-benzoimidazol-5-yl]-benzenesulfonamide, |
| 18 | 2-[2-(4-chloro-phenoxymethyl)-1H-benzoimidazol-5-yl]-N-methyl-benzenesulfonamide, |
| 19 | 2-[2-(4-methanesulfonyl-phenoxymethyl)-1H-benzoimidazol-5-yl]-N-methyl-benzenesulfonamide, |
| 20 | N-methyl-2-[2-(4-trifluoromethanesulfonyl-phenoxymethyl)-1H-benzoimidazol-5 yl]-benzenesulfonamide, |
| 21 | 2-{2-[2-(4-trifluoromethyl-phenoxymethyl)-1H-benzoimidazol-5-yl]-phenyl}-propan-2-ol, |
| 22 | 2-{2-[2-(4-trifluoromethoxy-phenoxymethyl)-1H-benzoimidazol-5-yl]-phenyl}-propan-2-ol, |
| 23 | 2-{2-[2-(4-chloro-phenoxymethyl)-1H-benzoimidazol-5-yl]-phenyl}-propan-2-ol, |
| 24 | 2-{2-[2-(3-trifluoromethyl-phenoxymethyl)-1H-benzoimidazol-5-yl]-phenyl}-propan-2-ol, |
| 25 | 2-{2-[2-(4-methanesulfonyl-phenoxymethyl)-1H-benzoimidazol-5-yl]-phenyl}-propan-2-ol, |
| 26 | 2-(2-phenoxymethyl-1H-benzoimidazol-5-yl)-benzenesulfonamide, |
| 27 | 2-(2-p-tolyloxymethyl-1H-benzoimidazol-5-yl)-benzenesulfonamide, |
| 28 | 2-[2-(4-isopropyl-phenoxymethyl)-1H-benzoimidazol-5-yl]-benzenesulfonamide, |
| 29 | 2-[2-(3,4-dichloro-phenoxymethyl)-1H-benzoimidazol-5-yl]-benzenesulfonamide, |
| 30 | 2-[2-(4-chloro-3-trifluoromethyl-phenoxymethyl)-1H-benzoimidazol-5-yl]-benzenesulfonamide, |
| 31 | 2-[2-(3,5-bis-trifluoromethyl-phenoxymethyl)-1H-benzoimidazol-5-yl]-benzenesulfonamide, |
| 32 | 2-[2-(4-tert-butyl-phenoxymethyl)-1H-benzoimidazol-5-yl]-benzenesulfonamide, |
| 33 | 2-[2-(4-ethoxy-phenoxymethyl)-1H-benzoimidazol-5-yl]-benzenesulfonamide, |
| 34 | 2-[2-(4-trifluoromethylsulfanyl-phenoxymethyl)-1H-benzoimidazol-5-yl]-benzenesulfonamide, |
| 35 | 2-[2-(4-acetyl-phenoxymethyl)-1H-benzoimidazol-5-yl]-benzenesulfonamide, |
| 36 | 2-[2-(naphthalen-2-yloxymethyl)-1H-benzoimidazol-5-yl]-benzenesulfonamide, |
| 37 | 2-[2-(quinolin-6-yloxymethyl)-1H-benzoimidazol-5-yl]-benzenesulfonamide, |
| 40 | 2-[1-methyl-2-(4-trifluoromethyl-phenoxymethyl)-1H-benzoimidazol-5-yl]-benzenesulfonamide, |
| 41 | 2-[2-(4-trifluoromethyl-phenylsulfanylmethyl)-1H-benzoimidazol-5-yl]-benzenesulfonamide, |
| 42 | 2-[2-(4-chloro-phenylsulfanylmethyl)-1H-benzoimidazol-5-yl]-benzenesulfonamide, |
| 43 | 2-[2-(4-trifluoromethoxy-phenylsulfanylmethyl)-1H-benzoimidazol-5-yl]-benzenesulfonamide, |
| 49 | 1-{2-[2-(4-trifluoromethyl-phenoxymethyl)-1H-benzoimidazol-5-yl]-phenyl}-ethanone, |
| 50 | 2-[2-(2-phenoxymethyl-1H-benzoimidazol-5-yl)-phenyl]-propan-2-ol, |
| 51 | 2-[2-(4-isopropyl-phenoxymethyl)-1H-benzoimidazol-5-yl]-N-methyl-benzenesulfonamide, |
| 52 | N-methyl-2-[2-(3-trifluoromethyl-phenoxymethyl)-1H-benzoimidazol-5-yl]-benzenesulfonamide, |
| 59 | 2-(4-chloro-phenoxymethyl)-5-(2-methanesulfonyl-phenyl)-1H-benzoimidazole, |
| 61 | 2-(4-bromo-phenoxymethyl)-5-(2-methanesulfonyl-phenyl)-1H-benzoimidazole, |

-continued

| Cpd | Name |
|---|---|
| 64 | 2-(2,4-dichloro-phenoxymethyl)-5-(2-methanesulfonyl-phenyl)-1H-benzoimidazole, |
| 65 | 2-(3,4-dichloro-phenoxymethyl)-5-(2-methanesulfonyl-phenyl)-1H-benzoimidazole, |
| 66 | 2-(4-chloro-2-fluoro-phenoxymethyl)-5-(2-methanesulfonyl-phenyl)-1H-benzoimidazole, |
| 67 | 2-(3-chloro-4-fluoro-phenoxymethyl)-5-(2-methanesulfonyl-phenyl)-1H-benzoimidazole, |
| 68 | 5-(2-methanesulfonyl-phenyl)-2-(3,4,5-trifluoro-phenoxymethyl)-1H-benzoimidazole, |
| 72 | 2-(4-fluoro-3-trifluoromethyl-phenoxymethyl)-5-(2-methanesulfonyl-phenyl)-1H-benzoimidazole, |
| 74 | 5-(2-methanesulfonyl-phenyl)-2-(2-trifluoromethyl-phenoxymethyl)-1H-benzoimidazole, |
| 75 | 5-(2-methanesulfonyl-phenyl)-2-(3-trifluoromethyl-phenoxymethyl)-1H-benzoimidazole, |
| 76 | 5-(2-methanesulfonyl-phenyl)-2-p-tolyloxymethyl-1H-benzoimidazole, |
| 77 | 2-(4-isopropyl-phenoxymethyl)-5-(2-methanesulfonyl-phenyl)-1H-benzoimidazole, |
| 78 | 2-(4-tert-butyl-phenoxymethyl)-5-(2-methanesulfonyl-phenyl)-1H-benzoimidazole, |
| 81 | 2-(4-ethoxy-phenoxymethyl)-5-(2-methanesulfonyl-phenyl)-1H-benzoimidazole, |
| 82 | 5-(2-methanesulfonyl-phenyl)-2-(4-trifluoromethanesulfide-phenoxymethyl)-1H-benzoimidazole, |
| 83 | 4-[5-(2-methanesulfonyl-phenyl)-1H-benzoimidazol-2-ylmethoxy]-benzonitrile, |
| 84 | 5-(2-methanesulfonyl-phenyl)-2-(4-trifluoromethoxy-phenoxymethyl)-1H-benzoimidazole, |
| 86 | 5-(2-methanesulfonyl-phenyl)-2-(4-trifluoromethanesulfonyl-phenoxymethyl)-1H-benzoimidazole, |
| 87 | 5-(2-methanesulfonyl-phenyl)-2-(5,6,7,8-tetrahydro-naphthalen-2-yloxymethyl)-1H-benzoimidazole, |
| 89 | 2-(2,4-dimethyl-phenoxymethyl)-5-(2-methanesulfonyl-phenyl)-1H-benzoimidazole, |
| 91 | 2-(indan-5-yloxymethyl)-5-(2-methanesulfonyl-phenyl)-1H-benzoimidazole, |
| 92 | 2-(benzo[1,3]dioxol-5-yloxymethyl)-5-(2-methanesulfonyl-phenyl)-1H-benzoimidazole, |
| 98 | 5-(2-methanesulfonyl-phenyl)-2-(4-trifluoromethyl-phenoxymethyl)-1H-benzoimidazole, |
| 101 | N-{2-[2-(4-trifluoromethyl-phenoxymethyl)-1H-benzoimidazol-5-yl]-phenyl}-methanesulfonamide, |
| 106 | N,N-dimethyl-2-[2-(4-trifluoromethyl-phenoxymethyl)-1H-benzoimidazol-5-yl]-benzenesulfonamide, |
| 110 | 1-{2-[2-(4-trifluoromethyl-phenoxymethyl)-1H-benzoimidazol-5-yl]-phenyl}-ethanol, |
| 116 | {2-[2-(4-trifluoromethyl-phenoxymethyl)-1H-benzoimidazol-5-yl]-phenyl}-methanol, |
| 127 | 2-[2-(4-trifluoromethyl-phenoxymethyl)-1H-benzoimidazol-5-yl]-benzoic acid methyl ester, |
| 132 | 4-trifluoromethyl-2-[2-(4-trifluoromethyl-phenoxymethyl)-1H-benzoimidazol-5-yl]-benzenesulfonamide, |
| 133 | 5-trifluoromethyl-2-[2-(4-trifluoromethyl-phenoxymethyl)-1H-benzoimidazol-5-yl]-benzenesulfonamide, |
| 134 | 4-fluoro-2-[2-(4-trifluoromethyl-phenoxymethyl)-1H-benzoimidazol-5-yl]-benzenesulfonamide, |
| 135 | 2,4-difluoro-6-[2-(4-trifluoromethyl-phenoxymethyl)-1H-benzoimidazol-5-yl]-benzenesulfonamide, |
| 136 | 2-[2-(4-trifluoromethyl-benzylamino)-1H-benzoimidazol-5-yl]-benzenesulfonamide, |
| 139 | 2-{2-[difluoro-(4-trifluoromethyl-phenoxy)-methyl]-1H-benzoimidazol-5-yl}-benzenesulfonamide, |
| 140 | 2-{2-[difluoro-(4-trifluoromethyl-phenoxy)-methyl]-1H-benzoimidazol-5-yl}-N-methyl-benzenesulfonamide, |
| 141 | 2-{2-[difluoro-(4-trifluoromethyl-phenoxy)-methyl]-1H-benzoimidazol-5-yl}-N,N-dimethyl-benzenesulfonamide, |
| 142 | 2-{2-[2-(4-trifluoromethyl-phenoxymethyl)-1H-benzoimidazol-5-yl]-benzenesulfonyl}-ethanol, |
| 143 | 1-{2-[2-(4-trifluoromethyl-phenoxymethyl)-1H-benzoimidazol-5-yl]-phenyl}-ethanol, |
| 144 | 2-methyl-1-{2-[2-(4-trifluoromethyl-phenoxymethyl)-1H-benzoimidazol-5-yl]-phenyl}-propan-1-ol, |
| 146 | 2-hydroxy-1-{2-[2-(4-trifluoromethyl-phenoxymethyl)-1H-benzoimidazol-5-yl]-phenyl}-propan-1-one, |
| 147 | 2-hydroxy-2-methyl-1-{2-[2-(4-trifluoromethyl-phenoxymethyl)-1H-benzoimidazol-5-yl]-phenyl}-propan-1-one, |
| 149 | 2-hydroxy-N-methoxy-N-methyl-2-{2-[2-(4-trifluoromethyl-phenoxymethyl)-1H-benzoimidazol-5-yl]-phenyl}-acetamide, |

-continued

| Cpd | Name |
|---|---|
| 151 | 2-hydroxy-1-{2-[2-(4-trifluoromethyl-phenoxymethyl)-1H-benzoimidazol-5-yl]-phenyl}-ethanone, |
| 154 | N-(2-hydroxy-propyl)-2-[2-(4-trifluoromethyl-phenoxymethyl)-1H-benzoimidazol-5-yl]-benzamide, |
| 156 | 2-{2-[1-(4-trifluoromethyl-phenoxy)-ethyl]-1H-benzoimidazol-5-yl}-benzenesulfonamide, |
| 159 | 2-methyl-1-{2-[2-(4-trifluoromethyl-phenoxymethyl)-1H-benzoimidazol-5-yl]-benzenesulfonyl}-propan-2-ol, |
| 160 | 1-{2-[2-(4-trifluoromethyl-phenoxymethyl)-1H-benzoimidazol-5-yl]-benzenesulfonyl}-propan-2-ol, |
| 161 | 2-{2-[2-(4-trifluoromethanesulfonyl-phenoxymethyl)-1H-benzoimidazol-5-yl]-benzenesulfonyl}-ethanol, |
| 163 | 2-{2-[2-(4-cyclopropyl-phenoxymethyl)-1H-benzoimidazol-5-yl]-phenyl}-propan-2-ol, |
| 164 | 2-[2-(4-cyclopropyl-phenoxymethyl)-1H-benzoimidazol-5-yl]-benzenesulfonamide, |
| 165 | 2-[2-(4-cyclopropyl-phenoxymethyl)-1H-benzoimidazol-5-yl]-N-methyl-benzenesulfonamide, |
| 166 | 2-[2-(4-cyclopropyl-phenoxymethyl)-1H-benzoimidazol-5-yl]-N,N-dimethyl-benzenesulfonamide, |
| 167 | 2-(4-cyclopropyl-phenoxymethyl)-5-(2-methanesulfonyl-phenyl)-1H-benzoimidazole, and |
| 168 | N-{2-[2-(4-cyclopropyl-phenoxymethyl)-1H-benzoimidazol-5-yl]-phenyl}-methanesulfonamide. |

A representative compound of Formula (I) or a form thereof includes a compound selected from the group consisting of:

| Cpd | Name |
|---|---|
| 1 | 2-[2-(4-trifluoromethyl-phenoxymethyl)-1H-benzoimidazol-5-yl]-benzenesulfonamide, |
| 2 | 2-[2-(4-trifluoromethanesulfonyl-phenoxymethyl)-1H-benzoimidazol-5-yl]-benzenesulfonamide, |
| 7 | 2-[2-(4-chloro-phenoxymethyl)-1H-benzoimidazol-5-yl]-benzenesulfonamide, |
| 8 | 2-[2-(4-bromo-phenoxymethyl)-1H-benzoimidazol-5-yl]-benzenesulfonamide, |
| 11 | 2-[2-(3-chloro-4-fluoro-phenoxymethyl)-1H-benzoimidazol-5-yl]-benzenesulfonamide, |
| 12 | 2-[2-(4-fluoro-3-trifluoromethyl-phenoxymethyl)-1H-benzoimidazol-5-yl]-benzenesulfonamide, |
| 15 | 2-[2-(3-trifluoromethoxy-phenoxymethyl)-1H-benzoimidazol-5-yl]-benzenesulfonamide, |
| 16 | 2-[2-(4-trifluoromethoxy-phenoxymethyl)-1H-benzoimidazol-5-yl]-benzenesulfonamide, |
| 17 | N-methyl-2-[2-(4-trifluoromethyl-phenoxymethyl)-1H-benzoimidazol-5-yl]-benzenesulfonamide, |
| 19 | 2-[2-(4-methanesulfonyl-phenoxymethyl)-1H-benzoimidazol-5-yl]-N-methyl-benzenesulfonamide, |
| 20 | N-methyl-2-[2-(4-trifluoromethanesulfonyl-phenoxymethyl)-1H-benzoimidazol-5-yl]-benzenesulfonamide, |
| 21 | 2-{2-[2-(4-trifluoromethyl-phenoxymethyl)-1H-benzoimidazol-5-yl]-phenyl}-propan-2-ol, |
| 22 | 2-{2-[2-(4-trifluoromethoxy-phenoxymethyl)-1H-benzoimidazol-5-yl]-phenyl}-propan-2-ol, |
| 23 | 2-{2-[2-(4-chloro-phenoxymethyl)-1H-benzoimidazol-5-yl]-phenyl}-propan-2-ol, |
| 25 | 2-{2-[2-(4-methanesulfonyl-phenoxymethyl)-1H-benzoimidazol-5-yl]-phenyl}-propan-2-ol, |
| 27 | 2-(2-p-tolyloxymethyl-1H-benzoimidazol-5-yl)-benzenesulfonamide, |
| 28 | 2-[2-(4-isopropyl-phenoxymethyl)-1H-benzoimidazol-5-yl]-benzenesulfonamide, |
| 29 | 2-[2-(3,4-dichloro-phenoxymethyl)-1H-benzoimidazol-5-yl]-benzenesulfonamide, |
| 30 | 2-[2-(4-chloro-3-trifluoromethyl-phenoxymethyl)-1H-benzoimidazol-5-yl]-benzenesulfonamide, |
| 31 | 2-[2-(3,5-bis-trifluoromethyl-phenoxymethyl)-1H-benzoimidazol-5-yl]-benzenesulfonamide, |
| 32 | 2-[2-(4-tert-butyl-phenoxymethyl)-1H-benzoimidazol-5-yl]-benzenesulfonamide, |
| 33 | 2-[2-(4-ethoxy-phenoxymethyl)-1H-benzoimidazol-5-yl]-benzenesulfonamide, |
| 34 | 2-[2-(4-trifluoromethylsulfanyl-phenoxymethyl)-1H-benzoimidazol-5-yl]-benzenesulfonamide, |
| 35 | 2-[2-(4-acetyl-phenoxymethyl)-1H-benzoimidazol-5-yl]-benzenesulfonamide, |
| 36 | 2-[2-(naphthalen-2-yloxymethyl)-1H-benzoimidazol-5-yl]-benzenesulfonamide, |

-continued

| Cpd | Name |
|---|---|
| 40 | 2-[1-methyl-2-(4-trifluoromethyl-phenoxymethyl)-1H-benzoimidazol-5-yl]-benzenesulfonamide, |
| 41 | 2-[2-(4-trifluoromethyl-phenylsulfanylmethyl)-1H-benzoimidazol-5-yl]-benzenesulfonamide, |
| 51 | 2-[2-(4-isopropyl-phenoxymethyl)-1H-benzoimidazol-5-yl]-N-methyl-benzenesulfonamide, |
| 52 | N-methyl-2-[2-(3-trifluoromethyl-phenoxymethyl)-1H-benzoimidazol-5-yl]-benzenesulfonamide, |
| 59 | 2-(4-chloro-phenoxymethyl)-5-(2-methanesulfonyl-phenyl)-1H-benzoimidazole, |
| 72 | 2-(4-fluoro-3-trifluoromethyl-phenoxymethyl)-5-(2-methanesulfonyl-phenyl)-1H-benzoimidazole, |
| 76 | 5-(2-methanesulfonyl-phenyl)-2-p-tolyloxymethyl-1H-benzoimidazole, |
| 77 | 2-(4-isopropyl-phenoxymethyl)-5-(2-methanesulfonyl-phenyl)-1H-benzoimidazole, |
| 78 | 2-(4-tert-butyl-phenoxymethyl)-5-(2-methanesulfonyl-phenyl)-1H-benzoimidazole, |
| 82 | 5-(2-methanesulfonyl-phenyl)-2-(4-trifluoromethanesulfide-phenoxymethyl)-1H-benzoimidazole, |
| 86 | 5-(2-methanesulfonyl-phenyl)-2-(4-trifluoromethanesulfonyl-phenoxymethyl)-1H-benzoimidazole, |
| 87 | 5-(2-methanesulfonyl-phenyl)-2-(5,6,7,8-tetrahydro-naphthalen-2-yloxymethyl)-1H-benzoimidazole, |
| 91 | 2-(indan-5-yloxymethyl)-5-(2-methanesulfonyl-phenyl)-1H-benzoimidazole, |
| 98 | 5-(2-methanesulfonyl-phenyl)-2-(4-trifluoromethyl-phenoxymethyl)-1H-benzoimidazole, |
| 101 | N-{2-[2-(4-trifluoromethyl-phenoxymethyl)-1H-benzoimidazol-5-yl]-phenyl}-methanesulfonamide, |
| 106 | N,N-dimethyl-2-[2-(4-trifluoromethyl-phenoxymethyl)-1H-benzoimidazol-5-yl]-benzenesulfonamide, |
| 116 | {2-[2-(4-trifluoromethyl-phenoxymethyl)-1H-benzoimidazol-5-yl]-phenyl}-methanol, |
| 127 | 2-[2-(4-trifluoromethyl-phenoxymethyl)-1H-benzoimidazol-5-yl]-benzoic acid methyl ester, |
| 134 | 4-fluoro-2-[2-(4-trifluoromethyl-phenoxymethyl)-1H-benzoimidazol-5-yl]-benzenesulfonamide, |
| 135 | 2,4-difluoro-6-[2-(4-trifluoromethyl-phenoxymethyl)-1H-benzoimidazol-5-yl]-benzenesulfonamide, |
| 139 | 2-{2-[difluoro-(4-trifluoromethyl-phenoxy)-methyl]-1H-benzoimidazol-5-yl}-benzenesulfonamide, |
| 140 | 2-{2-[difluoro-(4-trifluoromethyl-phenoxy)-methyl]-1H-benzoimidazol-5-yl}-N-methyl-benzenesulfonamide, |
| 142 | 2-{2-[2-(4-trifluoromethyl-phenoxymethyl)-1H-benzoimidazol-5-yl]-benzenesulfonyl}-ethanol, |
| 143 | 1-{2-[2-(4-trifluoromethyl-phenoxymethyl)-1H-benzoimidazol-5-yl]-phenyl}-ethanol, |
| 147 | 2-hydroxy-2-methyl-1-{2-[2-(4-trifluoromethyl-phenoxymethyl)-1H-benzoimidazol-5-yl]-phenyl}-propan-1-one, |
| 149 | 2-hydroxy-N-methoxy-N-methyl-2-{2-[2-(4-trifluoromethyl-phenoxymethyl)-1H-benzoimidazol-5-yl]-phenyl}-acetamide, |
| 151 | 2-hydroxy-1-{2-[2-(4-trifluoromethyl-phenoxymethyl)-1H-benzoimidazol-5-yl]-phenyl}-ethanone, |
| 159 | 2-methyl-1-{2-[2-(4-trifluoromethyl-phenoxymethyl)-1H-benzoimidazol-5-yl]-benzenesulfonyl}-propan-2-ol, |
| 160 | 1-{2-[2-(4-trifluoromethyl-phenoxymethyl)-1H-benzoimidazol-5-yl]-benzenesulfonyl}-propan-2-ol, |
| 163 | 2-{2-[2-(4-cyclopropyl-phenoxymethyl)-1H-benzoimidazol-5-yl]-phenyl}-propan-2-ol, |
| 164 | 2-[2-(4-cyclopropyl-phenoxymethyl)-1H-benzoimidazol-5-yl]-benzenesulfonamide, |
| 165 | 2-[2-(4-cyclopropyl-phenoxymethyl)-1H-benzoimidazol-5-yl]-N-methyl-benzenesulfonamide, |
| 166 | 2-[2-(4-cyclopropyl-phenoxymethyl)-1H-benzoimidazol-5-yl]-N,N-dimethyl-benzenesulfonamide, |
| 167 | 2-(4-cyclopropyl-phenoxymethyl)-5-(2-methanesulfonyl-phenyl)-1H-benzoimidazole, and |
| 168 | N-{2-[2-(4-cyclopropyl-phenoxymethyl)-1H-benzoimidazol-5-yl]-phenyl}-methanesulfonamide. |

A representative compound of Formula (I) or a form thereof includes a compound selected from the group consisting of:

| Cpd | Name |
|---|---|
| 1 | 2-[2-(4-trifluoromethyl-phenoxymethyl)-1H-benzoimidazol-5-yl]-benzenesulfonamide, |
| 2 | 2-[2-(4-trifluoromethanesulfonyl-phenoxymethyl)-1H-benzoimidazol-5-yl]-benzenesulfonamide, |
| 8 | 2-[2-(4-bromo-phenoxymethyl)-1H-benzoimidazol-5-yl]-benzenesulfonamide, |
| 16 | 2-[2-(4-trifluoromethoxy-phenoxymethyl)-1H-benzoimidazol-5-yl]-benzenesulfonamide, |
| 17 | N-methyl-2-[2-(4-trifluoromethyl-phenoxymethyl)-1H-benzoimidazol-5-yl]-benzenesulfonamide, |
| 19 | 2-[2-(4-methanesulfonyl-phenoxymethyl)-1H-benzoimidazol-5-yl]-N-methyl-benzenesulfonamide, |
| 21 | 2-{2-[2-(4-trifluoromethyl-phenoxymethyl)-1H-benzoimidazol-5-yl]-phenyl}-propan-2-ol, |
| 22 | 2-{2-[2-(4-trifluoromethoxy-phenoxymethyl)-1H-benzoimidazol-5-yl]-phenyl}-propan-2-ol, |
| 28 | 2-[2-(4-isopropyl-phenoxymethyl)-1H-benzoimidazol-5-yl]-benzenesulfonamide, |
| 32 | 2-[2-(4-tert-butyl-phenoxymethyl)-1H-benzoimidazol-5-yl]-benzenesulfonamide, |
| 40 | 2-[1-methyl-2-(4-trifluoromethyl-phenoxymethyl)-1H-benzoimidazol-5-yl]-benzenesulfonamide, |
| 41 | 2-[2-(4-trifluoromethyl-phenylsulfanylmethyl)-1H-benzoimidazol-5-yl]-benzenesulfonamide, |
| 51 | 2-[2-(4-isopropyl-phenoxymethyl)-1H-benzoimidazol-5-yl]-N-methyl-benzenesulfonamide, |
| 77 | 2-(4-isopropyl-phenoxymethyl)-5-(2-methanesulfonyl-phenyl)-1H-benzoimidazole, |
| 78 | 2-(4-tert-butyl-phenoxymethyl)-5-(2-methanesulfonyl-phenyl)-1H-benzoimidazole, |
| 82 | 5-(2-methanesulfonyl-phenyl)-2-(4-trifluoromethanesulfide-phenoxymethyl)-1H-benzoimidazole, |
| 86 | 5-(2-methanesulfonyl-phenyl)-2-(4-trifluoromethanesulfonyl-phenoxymethyl)-1H-benzoimidazole, |
| 98 | 5-(2-methanesulfonyl-phenyl)-2-(4-trifluoromethyl-phenoxymethyl)-1H-benzoimidazole, |
| 101 | N-{2-[2-(4-trifluoromethyl-phenoxymethyl)-1H-benzoimidazol-5-yl]-phenyl}-methanesulfonamide, |
| 106 | N,N-dimethyl-2-[2-(4-trifluoromethyl-phenoxymethyl)-1H-benzoimidazol-5-yl]-benzenesulfonamide, |
| 116 | {2-[2-(4-trifluoromethyl-phenoxymethyl)-1H-benzoimidazol-5-yl]-phenyl}-methanol, |
| 142 | 2-{2-[2-(4-trifluoromethyl-phenoxymethyl)-1H-benzoimidazol-5-yl]-benzenesulfonyl}-ethanol, |
| 147 | 2-hydroxy-2-methyl-1-{2-[2-(4-trifluoromethyl-phenoxymethyl)-1H-benzoimidazol-5-yl]-phenyl}-propan-1-one, |
| 163 | 2-{2-[2-(4-cyclopropyl-phenoxymethyl)-1H-benzoimidazol-5-yl]-phenyl}-propan-2-ol, |
| 165 | 2-[2-(4-cyclopropyl-phenoxymethyl)-1H-benzoimidazol-5-yl]-N-methyl-benzenesulfonamide, |
| 166 | 2-[2-(4-cyclopropyl-phenoxymethyl)-1H-benzoimidazol-5-yl]-N,N-dimethyl-benzenesulfonamide, and |
| 167 | 2-(4-cyclopropyl-phenoxymethyl)-5-(2-methanesulfonyl-phenyl)-1H-benzoimidazole. |

A representative compound of Formula (I) or a form thereof includes a compound selected from the group consisting of:

| Cpd | Name |
|---|---|
| 1 | 2-[2-(4-trifluoromethyl-phenoxymethyl)-1H-benzoimidazol-5-yl]-benzenesulfonamide, |
| 2 | 2-[2-(4-trifluoromethanesulfonyl-phenoxymethyl)-1H-benzoimidazol-5-yl]-benzenesulfonamide, |
| 16 | 2-[2-(4-trifluoromethoxy-phenoxymethyl)-1H-benzoimidazol-5-yl]-benzenesulfonamide, |
| 17 | N-methyl-2-[2-(4-trifluoromethyl-phenoxymethyl)-1H-benzoimidazol-5-yl]-benzenesulfonamide, |

-continued

| Cpd | Name |
|---|---|
| 21 | 2-{2-[2-(4-trifluoromethyl-phenoxymethyl)-1H-benzoimidazol-5-yl]-phenyl}-propan-2-ol, |
| 86 | 5-(2-methanesulfonyl-phenyl)-2-(4-trifluoromethanesulfonyl-phenoxymethyl)-1H-benzoimidazole, |
| 98 | 5-(2-methanesulfonyl-phenyl)-2-(4-trifluoromethyl-phenoxymethyl)-1H-benzoimidazole, and |
| 101 | N-{2-[2-(4-trifluoromethyl-phenoxymethyl)-1H-benzoimidazol-5-yl]-phenyl}-methanesulfonamide. |

General Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields though routine variations in reaction times, temperatures, solvents and/or reagents.

The terms used in describing the invention are commonly used and known to those skilled in the art. As used herein, the following abbreviations and formulas have the indicated meanings:

| Abbreviation | Meaning |
|---|---|
| Cpd | compound |
| DCM | dichloromethane |
| DMF | N,N-dimethylformamide |
| DMSO | dimethyl sulfoxide |
| EtOAc | ethyl acetate |
| HOBT | 1-hydroxybenzotriazole hydrate |
| min | minute(s) |
| h | hour(s) |
| rt | room temperature |
| TEA or Et$_3$N | triethylamine |
| THF | tetrahydrofuran |

SCHEME I

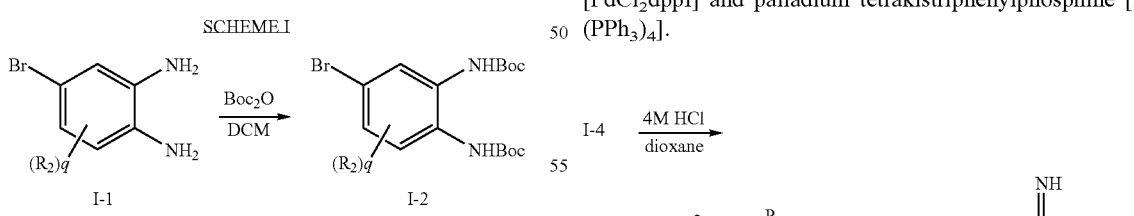

Commercially available bromo-diaminobenzene Compound I-1 is protected, in this instance with a Boc group, to provide a Compound I-2. Compound I-2 is then coupled with a suitably substituted phenyl group by a variety of coupling reactions (Suzuki, Stille) that are well known to those versed in the art. A particularly useful method is by a palladium catalyzed cross-coupling Suzuki reaction (see Huff, B. et. al. Org. Syn., 1997, 75: 53-60; and, Goodson, F. E. et. al. Org. Synth., 1997, 75: 61-68).

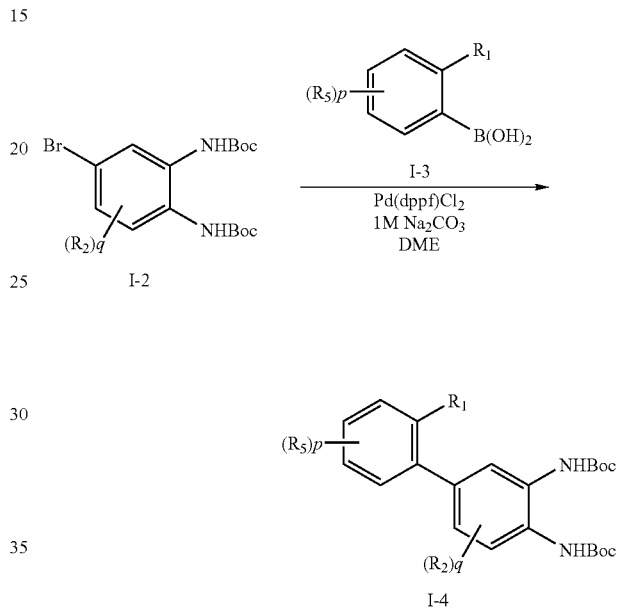

In this instance, a mixture of Compound I-2 and a boronic acid or boronate ester Compound I-3 in sodium carbonate and a catalytic amount of a palladium catalyst in a mixture of dioxane or dimethoxyethane and water or ethanol is heated to 100° C. or more to give an intermediate Compound I-4.

Suitable palladium catalysts for this reaction include, but are not limited to, a dichloro[1,1'-bis-(diphenylphosphino)ferrocene]palladium (II) dichloromethane adduct [PdCl$_2$dppf] and palladium tetrakistriphenylphosphine [Pd(PPh$_3$)$_4$].

-continued

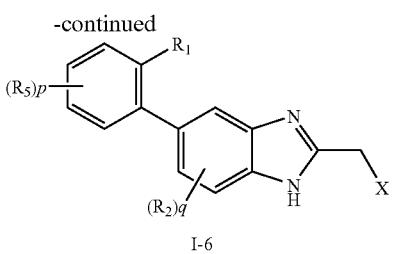
I-6

The Compound I-4 Boc protecting groups are removed under acidic conditions to give a Compound I-5, which is stirred in a solvent such as ethanol with a halogenated acetimidic acid ethyl ester hydrochloride salt (wherein X represents 2-chloro- or 2-bromo-), prepared according to the procedure described in J. Med. Chem., 1986, 29, 2280) to give a Compound I-6.

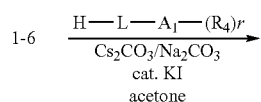

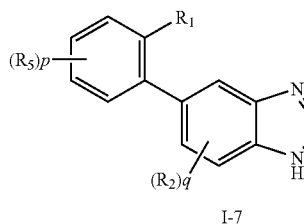
I-7

Compound I-6 is then reacted with H-L-$A_1$-$(R_4)_r$ to provide a Compound I-7 of Formula (I).

For example, to prepare compounds of the present invention wherein L is —$C_{1-3}$alkyl-Y— and Y is O, Compound I-6 is reacted with a solution of an alcohol substituted $A_1$ ring (in a solvent such as acetone) in the presence of a base (such as cesium carbonate) with heating to provide an ether analogue compound of Formula (I).

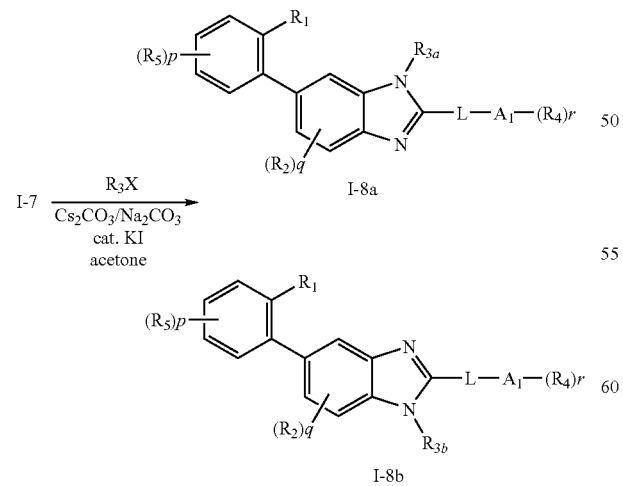

Compound I-7 can be reacted with $R_3X$ to provide a Compound I-8a and Compound I-8b as a tautomeric mixture. Each isomer may subsequently be obtained using separation techniques known to those skilled in the art.

Scheme II

Scheme II provides an alternate procedure to produce compounds of the present invention.

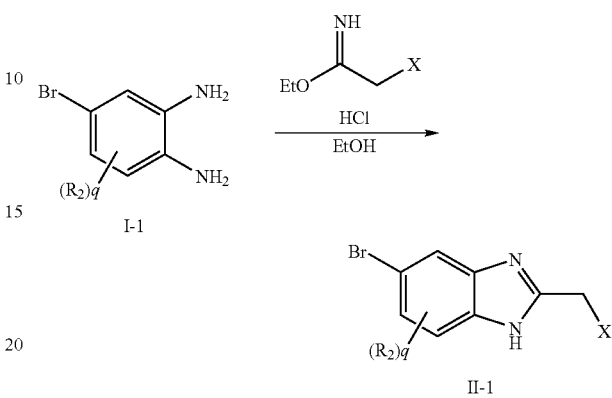

Compound I-1 is reacted with a halogenated acetimidic acid ethyl ester hydrochloride salt (wherein X represents 2-chloro- or 2-bromo-), under conditions described in Scheme I to provide Compound II-1.

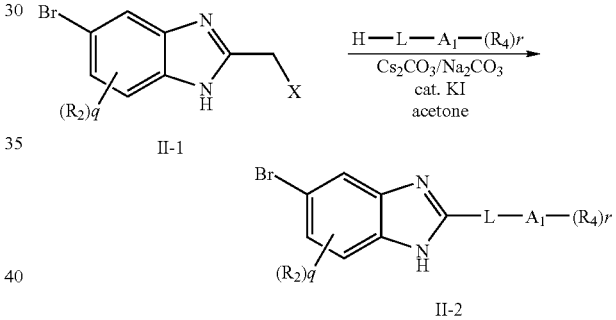

As described in Scheme I, Compound II-1 is reacted with H-L-$A_1$-$(R_4)_r$ (wherein H is a leaving group) to provide a Compound II-2, which may be carried forward using Suzuki type coupling with a Compound I-3 to provide Compound I-7 of Formula (I).

Scheme III

Scheme III provides an alternate procedure to produce ether-linked compounds of the present invention.

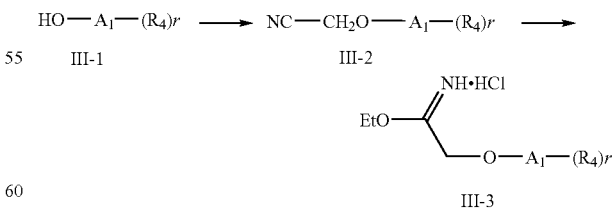

Reaction of an alcohol Compound III-1 with bromoacetonitrile in a solvent such as DMF with sodium carbonate and an equivalent of sodium iodide gives a Compound III-2. Reaction of Compound III-2 with 2N HCl and 1.1 equivalents of ethanol gives a Compound III-3.

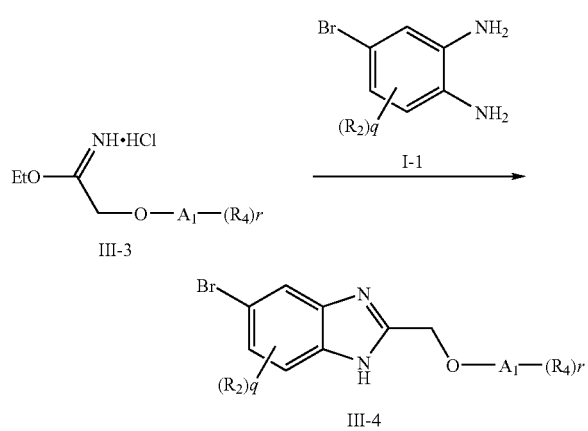

Reaction of Compound III-3 with Compound I-1 in ethanol gives a Compound III-4.

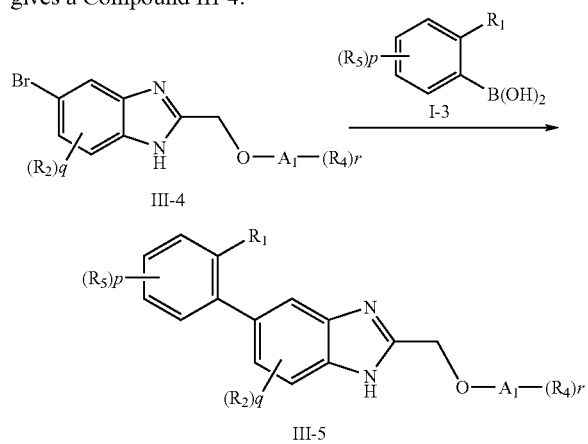

Reaction of Compound III-4 with a boronic acid or boronate ester Compound I-3 in sodium carbonate and a catalytic amount of a palladium catalyst in a solvent at a temperature of at least about 100° C. gives a Compound III-5 of Formula (I).

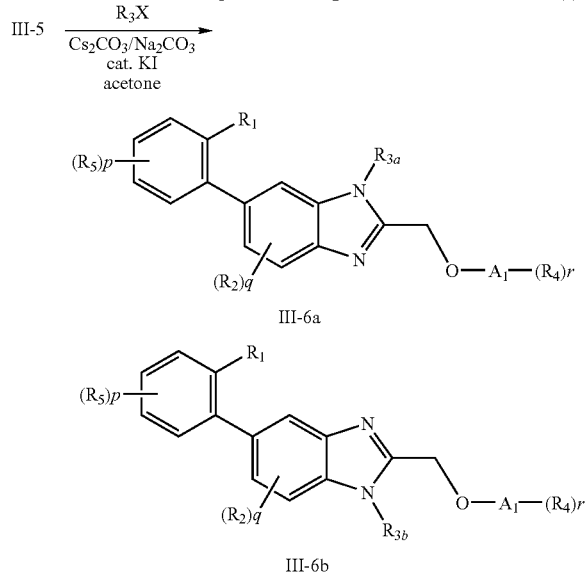

Compound III-5 can be reacted with $R_3X$ to provide a Compound III-6a and Compound III-6b as a tautomeric mixture. Each substantially pure isomer may subsequently be obtained using separation techniques known to those skilled in the art.

Suitable palladium catalysts for this reaction include, but are not limited to, a dichloro[1,1'-bis(diphenylphosphino)ferrocene]palladium (II) dichloromethane adduct ($PdCl_2$dppf), palladium tetrakistriphenylphosphine [$Pd(PPh_3)_4$] and 1,1'-[bis(di-tert-butylphosphino)ferrocene]-palladium dichloride [1,1'-di(tbpf)-palladium dichloride]. Suitable solvents include, but are not limited to, a mixture of dioxane or dimethoxyethane and water or ethanol.

Protecting groups may be needed at certain stages of the synthesis depending upon substituents and functional groups present on the reactants. Reaction time may be reduced by using a similar or lower temperature in a microwave synthesizer. Microwave accelerated reactions were performed using a Biotage Initiator Microwave Synthesizer.

The product of each process step may be separated from the reaction mixture and purified before use as a starting material in a subsequent step. Separation techniques typically include evaporation, extraction, precipitation and filtration. Purification techniques typically include column chromatography (Still, W. C. et. al., J. Org. Chem., 1978, 43, 2921), thin-layer chromatography, crystallization and distillation.

The starting materials and product of each process step may be confirmed by spectroscopic, spectrometric and analytical methods including nuclear magnetic resonance (NMR), mass spectrometry (MS) and liquid chromatography (HPLC).

For preparing compounds of the present invention, common solvents known to those skilled in the art were used such as, but not necessarily limited to: ethyl ether ($Et_2O$), tetrahydrofuran (THF), dioxane, benzene, toluene, hexanes, cyclohexane, dichloromethane (DCM) and dichloroethane (DCE). Compounds of the present invention may be isolated as the acid addition salt and may contain one or more equivalents of the acid. The free base may be obtained by techniques known to those skilled in the art.

EXAMPLE 1

2-[2-(4-trifluoromethyl-phenoxymethyl)-1H-benzoimidazol-5-yl]-benzenesulfonamide (Cpd 1)

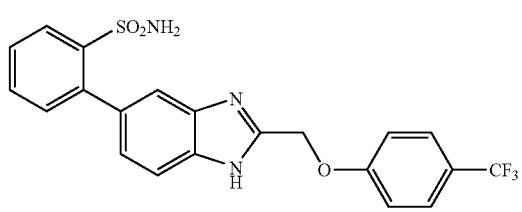

A. (5-bromo-2-tert-butoxycarbonylamino-phenyl)-carbamic acid tert-butyl ester

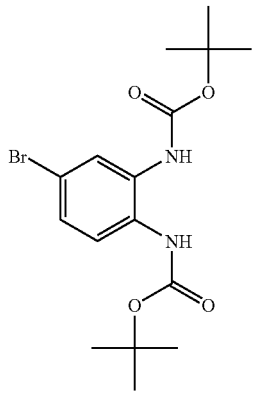

A mixture of 4-bromo-benzene-1,2-diamine (20 g, 107 mmol), di-t-butyl dicarbonate (117 g, 535 mmol) and a solution of 2N NaOH (134 mL, 267 mmol) in dichloromethane (300 mL) was stirred at room temperature for 12 h. The reaction mixture was extracted with dichloromethane (700 mL) and brine (500 mL). The organic layer was dried over $Na_2SO_4$, filtered, and the filtrate was concentrated in vacuo. The residue was purified by chromatography (silica, EtOAc: hexanes, 3:7) to afford the title compound as a brown solid (41 g, quantitative yield). $^1$H NMR (400 MHz, $CDCl_3$) δ (ppm): 7.74 (br s, 1H), 7.31 (br s, 1H) 7.19 (dd, 1H, J=8.6 Hz, J=2.2 Hz), 6.81 (br s, 1H), 6.63 (br s, 1H), 1.51 (s, 18H).). Mass Spectrum (LCMS, ESI pos.) Calcd. For $C_{16}H_{23}BrN_2O_4$: 388.27 (M+H), Found 388.4.

B. 2-tert-butoxycarbonylamino-5-(2-tert-butylamino-sulfonyl-phenyl)-phenyl carbamic acid tert-butyl ester

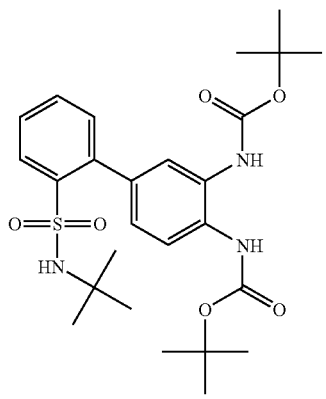

A solution of (5-bromo-2-tert-butoxycarbonylamino-phenyl)-carbamic acid tert-butyl ester (4.0 g, 10.3 mmol), 2-(tert-butylaminosulfonyl)-phenyl boronic acid (5.3 g; 20.6 mmol), $PdCl_2$ dppf (1.7 g, 0.20 mmol) and 1M $Na_2CO_3$ solution (83 mL, 82.7 mmol) in 1,2-dimethoxyethane was heated to 90° C. for 12 h under inert atmosphere. The reaction mixture was cooled to room temperature and concentrated under reduced pressure. The residue was purified by chromatography (silica, EtOAc: hexanes, 3:7) to afford the title compound as a yellow viscous oil (5.4 g, quantitative yield). $^1$H NMR (400 MHz, $CDCl_3$) δ (ppm): 8.14 (m, 1H), 7.88 (m, 1H), 7.43-7.69 (m, 6H), 7.19 (m, 1H), 7.28 (m, 1H), 1.52 (s, 9H), 1.48 (s, 9H), 1.06 (s, 9H). Mass Spectrum (LCMS, ESI pos.) Calcd. For $C_{26}H_{37}N_3O_6S$: 520.65 (M+H), Found 520.1.

C. 3',4'-diamino-biphenyl-2-sulfonic acid tert-butylamide

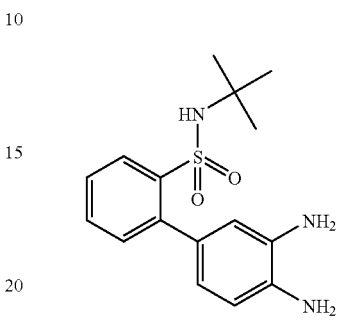

2-tert-butoxycarbonylamino-5-(2-tert-butylaminosulfonyl-phenyl)-phenyl carbamic acid tert-butyl ester (5.4 g, 10.3 mmol) in a solution of 4M HCl in 1,4-dioxane (250 mL) was stirred at room temperature for 4 h. The reaction mixture was concentrated under reduced pressure. The residue was dissolved in dichloromethane, and the solution was washed with saturated sodium bicarbonate and water (pH=7). The organic layer was dried over $Na_2SO_4$, filtered, and the filtrate was concentrated in vacuo. The residue was purified by chromatography (silica, EtOAc: hexanes, 1:1) to afford the title compound as a brown viscous oil (6.1 g, 92% yield). $^1$H NMR (400 MHz, $CDCl_3$) δ (ppm): 8.12 (dd, 1H, J=7.9, J=1.7), 7.51 (td, 1H, J=7.5 Hz, J=1.5 Hz), 7.42 (td, 1H, J=7.6 Hz, J=1.3 Hz), 7.30 (dd, 1H, J=7.8, J=1.5), 6.94 (d, 1H, J=1.9), 6.80 (m, 2H), 3.80 (s, NH), 3.50 (br s, 4H), 0.98 (s, 9H). Mass Spectrum (LCMS, ESI pos.) Calcd. For $C_{16}H_{21}N_3O_2S$: 320.42 (M+H), Found 320.9.

D. N-tert-butyl-2-(2-chloromethyl-1H-benzoimidazol-5-yl)benzenesulfonamide

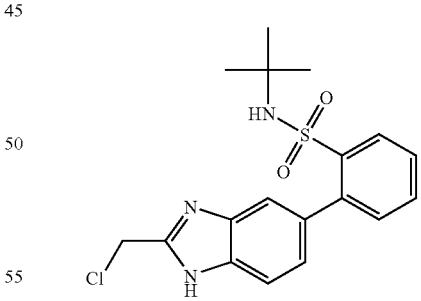

A mixture of 3',4'-diamino-biphenyl-2-sulfonic acid tert-butylamide (1.0 g, 3.13 mmol), 2-chloroacetimidic acid ethyl ester hydrochloride salt (591 mg, 3.76 mmol) (prepared according to the procedure described in J. Med. Chem., 1986, 29, 2280) in anhydrous ethanol (100%, 20 mL) was stirred at room temperature for 4 h. The reaction mixture was concentrated under reduced pressure and extracted with ethyl acetate and brine. The organic layer was dried over $Na_2SO_4$, filtered, and the filtrate was concentrated in vacuo. The residue was purified by chromatography (silica, EtOAc) to afford the title compound as an off-white solid (708 mg, 60% yield). ¹H NMR (400 MHz, CD₃OD) δ (ppm): 8.14 (dd, 1H, J=8.1 Hz, J=1.5 Hz), 7.79 (m, 1H), 7.74 (dd, 1H, J=8.5 Hz, J=1.1 Hz), 7.65 (td, 1H, J=7.5 Hz, J=1.6 Hz), 7.57 (td, 1H, J=7.8 Hz, J=1.6 Hz), 7.50 (dd, 1H, J=8.3 Hz, J=1.6 Hz), 7.39 (dd, 1H, J=7.3 Hz, J=1.2 Hz), 5.05 (s, 2H), 1.02 (s, 9H). Mass Spectrum (LCMS, ESI pos.) Calcd. For C₁₈H₂₀ClN₃O₂S: 378.89 (M+H), Found 378.1.

E. N-tert-butyl-2-[2-(4-trifluoromethyl-phenoxymethyl)-1H-benzoimidazol-5-yl]-benzenesulfonamide

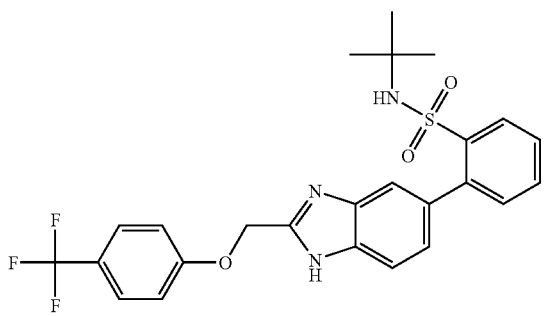

A mixture of N-tert-butyl-2-(2-chloromethyl-1H-benzoimidazol-5-yl)benzenesulfonamide (100 mg, 0.26 mmol), α,α,α-trifluoro-p-cresol (43.0 mg, 0.26 mmol), Na₂CO₃ (28.1 mg, 0.26 mmol), Cs₂CO₃ (86.5 mg, 0.26 mmol), and catalytic KI (1.5 mg, 0.009 mmol) in acetone (2 mL) was refluxed for 12 h. The reaction mixture was concentrated under reduced pressure, and the residue was purified by chromatography (silica, EtOAc: hexanes, 1:1) to afford the title compound as an off-white solid (40.1 mg, 30% yield). Calcd. For C₂₅H₂₄F₃N₃O₃S: 504.54 (M+H), Found 504.2.

F. 2-[2-(4-trifluoromethyl-phenoxymethyl)-1H-benzoimidazol-5-yl]-benzenesulfonamide A solution of N-tert-butyl-2-[2-(4-trifluoromethyl-phenoxymethyl)-1H benzoimidazol-5-yl]-benzenesulfonamide (40.0 mg, 0.80 mmol) in trifluoroacetic acid (4 mL) was heated at 75° C. for 2 h. The reaction mixture was concentrated under reduced pressure. The resulting TFA salt was diluted with methanol and passed though a sodium bicarbonate cartridge to afford the title compound as the free base (33.8 mg, 95% yield).

¹H NMR (400 MHz, CD₃OD) δ (ppm): 8.12 (dd, 1H, J=7.7 Hz, J=1.1 Hz), 7.60-7.67 (m, 5H), 7.53 (td, 1H, J=7.7 Hz, J=1.3 Hz), 7.39 (dd, 1H, J=7.3 Hz, J=1.1 Hz), 7.33 (dd, 1H, J=8.6 Hz, J=1.6 Hz), 7.24 (d, 1H, J=8.5 Hz), 5.44 (s, 2H). Calcd. For C₂₁H₁₆F₃N₃O₃S: 448.43 (M+H), Found 448.1.

EXAMPLE 1.1

2-[2-(4-trifluoromethyl-phenoxymethyl)-1H-benzoimidazol-5-yl]-benzenesulfonamide (Cpd 1)

The following example provides an alternate preparation of Compound 1.

A. (4-trifluoromethyl-phenoxy)-acetonitrile

A 5-L 3-neck round bottom flask equipped with a mechanical stirrer, reflux condenser with gas outlet adapter, a Claisen head with a thermocouple and nitrogen inlet adapter, and heating mantle was charged with 4-trifluoromethyl-phenol (225.25 g, 1.39 mol), DMF (1.91 L), followed by NaI (208.3 g, 1.39 mol), Na₂CO₃ (294.5 g, 2.78 mol), and bromoacetonitrile (214.2 g, 1.76 mol). A modest exotherm to 37° C. was noted. The reaction was warmed to 65° C. for 2 h and the brown suspension was assayed by several methods and judged not to be complete. The reaction was heated to 80° C. for 1 h, when the phenol was found to be absent by HPLC. The reaction was allowed to come to room temperature overnight (14 h). The reaction was diluted with water (2 L), transferred to a 22-L separatory funnel with additional water (6 L) and extracted with a mixture of methyl-t-butylether(MTBE)/ether (2×3 L, 2:1, then 2 L, 1:1). The combined organic layers were washed with aqueous HCl (10%, 2×700 mL), aqueous KOH (3 M, 300 mL), water (2×700 mL), and brine (2×700 mL). The organics were dried (Na₂SO₄) and filtered though silica gel (500 g), and the silica gel was washed with MTBE/ether (~1 L). The organics were concentrated in vacuo and the resulting orange oil transferred to a smaller flask with dichloromethane and MTBE. The concentration was continued under hi-vac (60 torr) at 50° C. and afforded 273.2 g (97.7% isolated yield, residual MTBE by NMR was 0.7% wt/wt) of 2 as an orange oil. ¹H-NMR (400 MHz, CD₃Cl) δ (ppm) 7.63 (d, 2H) 7.07 (d, 2H) 4.83 (s, 2H).

B. 2-(4-trifluoromethyl-phenoxy)-acetimidic acid ethyl ester hydrochloride

A 5-L 3-neck round bottom flask equipped with a mechanical stirrer, 1-L pressure-equalizing addition funnel and gas outlet adapter, Claisen head with a thermocouple and nitrogen inlet adapter, in an ice bath, was charged with HCl in ether (2 M, 815 mL) via addition funnel. The addition funnel was replaced with a clean 500-mL addition funnel, and the solution was stirred until the internal temperature was approximately 0° C. To the addition funnel was added (4-trifluoromethyl-phenoxy)-acetonitrile (neat, 273.0 g, 1.36 mol) followed by ethanol (86.9 mL, 1.49 mol). The solution of (4-trifluoromethyl-phenoxy)-acetonitrile was added dropwise over 20 min, so not to exceed 2.6° C. The stirring was continued for 20 min in the ice bath after the addition was complete. The ice bath was removed and the reaction was stirred at room temperature for 6 h. At 15° C., the orange solution became hazy, followed by sudden precipitation of a thick solid. Once room temperature was achieved, ether (800 mL) was added, a spatula was used to free the solid from the sides of the flask, and the solid was filtered with a Buchner funnel. The yellowish solid became white after washing with ether (500 mL), and the solid was air-dried for 12 h at rt. The collected solid was transferred to an amber bottle and afforded 306.0 g (79.5% isolated yield, 67% HPLC purity). ¹H-NMR (400 MHz, CD₃Cl) δ (ppm) 7.60 (d, 2H, J=8.8 Hz) 7.18 (d, 2H, J=8.4 Hz) 5.01 (s, 2H) 4.87 (q, 2H, J=7.1 Hz) 1.25 (t, 3H, J=7.0 Hz).

C. 5-bromo-2-(4-trifluoromethyl-phenoxymethyl)-1H-benzoimidazole

A 5-L 4-neck round bottom flask equipped with a thermocouple, mechanical stirrer and an argon inlet adapter was charged with 4-bromo-1,2-phenylenediamine (166.4 g, 0.863 mol), ethanol (2 L), followed by the addition of 2-(4-trifluoromethyl-phenoxy)-acetimidic acid ethyl ester hydrochloride (272.0 g, 0.959 mol) and ethanol (0.9 L). The initial solution of diamine turned to a suspension upon the addition of 2-(4-trifluoromethyl-phenoxy)-acetimidic acid ethyl ester hydrochloride, and an exotherm from 17° C. to 28° C. was noted. The reaction was assayed at 2.5 h and found to be complete. The reaction was filtered though Celite (60 g) and the gray solid was washed with ethanol (200 mL) until the filtrates were no longer colored. A clean 12-L 4-neck round bottom flask equipped with a mechanical stirrer, a 1-L addition funnel and ice bath for cooling was set-up and the ethanol filtrates were transferred into the 12-L flask. While cooling the flask, water (3.5 L) was added to the ethanol, and the resulting brown suspension was stirred for 1 h in the ice bath to enhance recovery. The brown solid was filtered evenly between two Buchner funnels, each washed with cold water (150 mL, 2×200 mL), and the brown solid was air-dried for a few hours. The brown solid was transferred to two amber bottles, dried in a hi-vac oven (60 mm) at 60° C., to a constant weight and afforded a total of 331.9 g (103% isolated yield; 97.7-98%, HPLC area %) of the title compound as a brown powder.

$^1$H-NMR (400 MHz, CD$_3$OD) δ (ppm) 7.74 (s, 1H) 7.62 (d, 2H, J=8.0 Hz) 7.50 (d, 1H, J=8.8 Hz) 7.39 (dd, 1H, J=1.6 and 8.4 Hz) 7.23 (d, 2H, J=8.4 Hz) 5.41 (s, 2H). MS (ESI, pos. ion) m/z: 372.9 (M+1).

D. N-tert-butyl-2-[2-(4-trifluoromethyl-phenoxymethyl)-1H-benzoimidazol-5-yl]-benzenesulfonamide A 12-L 4-neck round bottom flask equipped with a thermocouple, heating mantle, mechanical stirrer, reflux condenser with argon outlet to a bubbler, and an argon inlet adapter was purged with argon for 1 h. Solid Na$_2$CO$_3$ (336.8 g, 3.18 mol) and water (975 mL) were added and the contents stirred until completely dissolved. There was no attempt to control the rise in temperature to 38° C. To the solution were added 2-(tert-butylamino) sulfonylphenylboronic acid (163.4 g, 0.637 mol), 5-bromo-2-(4-trifluoromethyl-phenoxymethyl)-1H-benzoimidazole (196.6 g, 0.53 mol) and DME (2 L). The argon inlet was removed and the heterogeneous mixture was sparged as vigorously as possible with two pipette-tip argon lines for 1 h. 1,1'-Di(tbpf)-palladium dichloride (34.5 g, 0.053 mol) was added, the argon inlet replaced, and the reaction was warmed to 61° C., where it was held for 30 min. Two additional liters of sparged DME was added, and the heating resumed to 78° C. and maintained for 12 h. The heating was turned off (automatically) and the reaction was allowed to cool to room temperature overnight.

The reaction was diluted with water (1.5 L), transferred to a 22-L separatory funnel, and the layers were separated. The top layer (O1) was diluted with EtOAc (1 L), and additional separation of an aqueous bottom layer (A1) that resulted was drained with the initial bottom layer (thick with salts). The EtOAc diluted top layer (O1) was put aside. The aqueous fraction (A1) was diluted with water (1 L, to dissolve all the salts), returned to the separatory funnel, and extracted with EtOAc (1.5 L). The resulting aqueous layer (A2) was removed and saved for later. The remaining organic layer (O2) was combined with the first EtOAc diluted top layer (O1) and the combined fraction was washed with water (1.5 L). The resulting aqueous layer (A3) was drained into A2. The remaining organic layer (O3) was washed with water (1 L), and the resulting aqueous layer (A4) was drained into A2. The remaining organic layer (O4) was washed with aqueous trithiocyanuric acid, trisodium salt (5%, 1 L), and this aqueous layer (A5) was discarded. The remaining organic layer (O5) was washed with brine (2×1 L), and the resulting aqueous layer (A6) was saved in A2. The remaining washed organic layer (O6) was drained into two 4-L Erlenmeyer flasks and dried (Na$_2$SO$_4$). The combined aqueous A2 layer was returned to the separatory funnel, extracted with EtOAc (1 L) and the resulting organic layer (O7) was saved for washing the drying agent and celite later. The dried organic layer (O6) was decanted from the drying agent and transferred to a 20-L round bottom flask with Si-thiol functionalized silica gel (Silicycle, 510 g). The drying agent was filtered with Celite, and washed with the EtOAc washing (O7) and combined. The organics were swirled on the 20-L rotary evaporator at a bath temperature of 45° C. for 1 h. The silica gel was removed by filtration (sintered glass funnel—golden brown), washed ad lib with EtOAc, and treated again with Si-thiol functionalized silica gel (Silicycle, 510 g) in a 20-L round bottom flask, with swirling at 45° C. for 1 h. The silica gel was removed by filtration (sintered glass funnel—sandy brown), washed ad lib with EtOAc, and the organics were concentrated in vacuo on a large rotary evaporator. The resulting thick oil crystallized in the flask; a minimum amount of EtOAc (1.5 L) was used to redissolve the oil at room temperature. Heptane (1.5 L) was carefully added and the dark solution was transferred to a BIOTAGE column (5 kg, pre-wetted with 8 L 2:1 heptane/EtOAc). The column was eluted with 16 L 1:1 heptane/EtOAc (2-L fractions collected), 16 L 1:1 heptane/EtOAc (3-L fractions collected), and 16 L 70% EtOAc (2-L fractions collected) in heptane. After evaporation, the product fractions (B1) (147 g, HPLC: 94.2% purity at 6.853 min, 8.96 min impurity at 3.39%) and (B2) (145 g, 97.9% purity at 6.725 min, with only impurity at 5.95 min, 0.58) were treated separately for recyrstallization.

The B1 product fraction sample (previously transferred to a 3-L round bottom flask) was dissolved in boiling toluene (~210 mL) and pre-warmed heptane (180 mL) was added until just cloudy. A stir bar was added, the mixture was stirred at room temperature; and within 4-5 min, a thick solid precipitated that was not stirrable. Immediately, a portion of toluene (250 mL) was added using it to transfer the suspension to a 12-L 4-neck round bottom flask equipped with a thermocouple, heating mantle, mechanical stirrer, and reflux condenser. Additional toluene (1100 mL) was added with warming to near reflux (100° C.), enough to completely dissolve the solid. Pre-warmed heptane (1700 mL) was added, followed by the careful addition of more heptane (room temperature, 1200 mL) until the solution was permanently cloudy. The heating mantle was removed, and notice was taken of the oily black film on the bottom of the flask, and the solution was quickly decanted to a clean 12-L 4-neck round bottom flask. However, more globs formed as product oiled out again. The heating mantle was reapplied, toluene (300 mL) was added, the solution was heated to near 100° C., and most of the oil dissolved (a spatula was used to mechanically remove the oil from the sides of the flask). The mantle was removed and the hazy solution was allowed to cool to room temperature overnight (heavy precipitation was noted around 60° C.). The next day, the solid was filtered from the orange filtrate, and the solid was washed with heptane (2×100 mL) that was kept separate from the main filtrate. The product was collected in an amber jar and dried in a hi-vac oven at 55° C., to afford 90.2 g (35.7% isolated yield; 97.9%, HPLC area %) of the title compound as an off-white solid.

The B2 product fraction sample (previously transferred to a 3-L round bottom flask) was dissolved in boiling toluene (750 mL) but was not totally clear. Pre-warmed heptane (660 mL) was added, and the mixture was transferred to a 12-L 4-neck round bottom flask equipped with a thermocouple, heating mantle, mechanical stirrer, and reflux condenser. Instant crystallization occurred when stirred; heating was reapplied, and toluene (1.95 L) was added until the solution was clear at near boiling. Warming was continued and pre-warmed heptane (2 L) was added, followed by the careful addition of more heptane (room temperature, 7.7 L) until the additions caused the persistence of a cloud-point (at 93° C.). The heating mantle was removed, and the hazy solution was allowed to cool to room temperature overnight. The next day, an ice bath was applied to enhance the recovery, the solid was filtered from the nearly colorless filtrate, and the solid was washed with heptane (2×100 mL), which was kept separate from the main filtrate. The product was collected in an amber jar, dried in a hi-vacuum oven at 40° C., and afforded 125.3 g (49.5% isolated yield; 98.6%, HPLC area %) of the title compound as a light brown, dense solid. The combined yield was 215.5 g for a combined overall yield of 82%. $^1$H-NMR (400 MHz, $CD_3Cl_3$) δ (ppm) 7.13 (d, 1H, J=7.2 Hz) 7.81 (s, 1H) 7.69 (s, 1H) 7.57-7.44 (m, 4H) 7.33 (d, 2H, J=6.8 Hz) 7.03 (s, 2H) 5.43 (s, 2H) 0.95 (s, 9H). MS (ESI, pos. ion) m/z: 504.1 (M+1).

E. 2-[2-(4-trifluoromethyl-phenoxymethyl)-1H-benzoimidazol-5-yl]-benzenesulfonamide A 5-L 4-neck round bottom flask equipped with a thermocouple, heating mantle, mechanical stirrer, reflux condenser with gas outlet, and a nitrogen inlet adapter was charged with N-tert-butyl-2-[2-(4-trifluoromethyl-phenoxymethyl)-1H-benzoimidazol-5-yl]-benzenesulfonamide (150.0 g, 0.298 mol) and HCl in isopropyl alcohol (IPA) (5-6 M, 2.51 L). The reaction was warmed step-wise with stirring, first to 45° C., then 60° C., and finally 72° C. Heating was continued for 12 h, after which time the heat was turned off, and the reaction allowed to cool to room temperature. HPLC analysis showed there to be about 1.8% of N-tert-butyl-2-[2-(4-trifluoromethyl-phenoxymethyl)-1H-benzoimidazol-5-yl]-benzenesulfonamide remaining. The reaction was chilled in an ice bath to 4° C., the solid was filtered and washed with IPA (350 mL). The grayish solid (159.2 g) was air-dried for a short while. During this drying, a 22-L 4-neck round bottom flask equipped with a mechanical stirrer was assembled and charged with aqueous sodium bicarbonate (saturated, 3 L) and EtOAc (12 L). The grayish solid was added to the stirred biphasic mixture and within 5 minutes, was completely dissolved. The mixture was transferred to a 22-L separatory funnel and the layers were separated. The aqueous layer (pH 8.5) was discarded. The organic layer was washed with aqueous sodium bicarbonate (saturated, 1 L), brine (half-saturated, 1 L), dried ($Na_2SO_4$) between 4×4 L Erlenmeyer flasks, and filtered over fresh $Na_2SO_4$. The dried EtOAc layer-containing product was placed in a 22-L rotary evaporator flask with Si-thiol functionalized silica gel (Silicycle, 150 g) and swirled in a 45° C. for 1 h. The silica gel was removed by filtration (sintered glass funnel), washed with ad lib EtOAc, and evaporated on a large rotary evaporator. Towards the end of the evaporation, MeCN (1 L) was added to the suspension to assist the azeotropic distillation of residual EtOAc. Evaporation was complete when no liquid distilled at a vacuum of 65 torr. The flask containing the whitish brown solid (125.3 g) was placed in a 22-L heating mantle and carefully heated with MeCN (2200 mL) with the aid of a large paddle stirrer. The completely clear, boiling yellow solution was quickly filtered though a coarse-sintered glass funnel into a 4 L heavy-walled side arm flask. A stir bar was added, the solution was stirred while crystallization ensued and the suspension came to room temperature (approx 2.5 h). The suspension was chilled for 30 min, filtered and washed with MeCN (up to 300 mL). After 15 min air-drying there was afforded 118.0 g (88.5% isolated yield; 98.2-99.5%, HPLC area %) of the title compound as a brilliant white solid. $^1$H-NMR (400 MHz, CD3Cl) δ (ppm) 8.13 (dd, 1H, J=1.2 and 8.4 Hz) 7.77 (d, 1H, J=0.8 Hz) 7.71 (d, 1H, 7.6 Hz) 7.66-7.61 (m, 3H) 7.56 (td, 1H, J=1.2 and 8.4 Hz) 7.65 (dd, 1H, J=1.6 and 8.4 Hz) 7.39 (dd, 1H, J=1.6 and 7.6 Hz) 7.27 (d, 2H, J=8.4 Hz) 5.58 (s, 2H). MS (ESI, pos. ion) m/z: 448.1 (M+1).

EXAMPLE 1.2

2-[2-(4-trifluoromethyl-phenoxymethyl)-1H-benzoimidazol-5-yl]-benzenesulfonamide disodium salt (Cpd 1)

A 3-L 1-neck round bottom flask equipped with a wide-mouth funnel was charged with compound 2-[2-(4-trifluoromethyl-phenoxymethyl)-1H-benzoimidazol-5-yl]-benzenesulfonamide (160.1 g, 0.358 mol). Methanol (100 mL) was used to completely wash the material into the flask. A 2-L Erlenmeyer flask was tared on an open-pan balance (+/−0.1 g) and sodium methoxide in methanol (0.5 M, 1145.0 g) was weighed out, and then poured to the 3-L round bottom, washing with fresh methanol (150 mL). The flask was attached to a rotary evaporator (no vacuum) and swirled at a bath temperature of 30° C. until the solid had dissolved. The vacuum was carefully applied and the solvent removed in vacuo, with a bath temperature no higher than 38° C. High vacuum (20 torr) was applied, and drying was continued at 38° C. for 1 h. The flask was transferred to hi-vac (~20 torr) drying oven, and drying continued at 37° C. for 4 h. The flask was removed, the material was mechanically freed from the sides of the flask, the free-flowing material was poured out of the flask into a large crystallizing dish, and the small lump of MeOH-wet material that remained at the bottom was transferred to a small crystallizing dish. Drying was continued in the hi-vac oven at 43° C. for about 14 h (overnight). Analysis showed both samples in the crystallizing dishes to have the same amount of MeOH (6.3% wt/wt=1 equiv MeOH); therefore both were combined in one bottle, which afforded 181.8 g (97% isolated yield; 98.1-99.6%, HPLC area %) of the disodium salt as a slightly off-white solid. Elemental analysis calculated for $C_{21}H_{14}F_3N_3O_4SNa_2 \cdot MeOH \cdot 0.9H_2O$: C, 48.96; H, 3.70; F, 10.56; N, 7.79; Na, 8.52; S, 5.94; Found: C, 48.66; H, 3.86; F, 10.06; N, 7.78; Na, 10.43 (n=2); S, 6.32;

EXAMPLE 1.3

2-[2-(4-trifluoromethyl-phenoxymethyl)-1H-benzoimidazol-5-yl]-benzenesulfonamide hydrochloride salt (Cpd 1)

2-[2-(4-trifluoromethyl-phenoxymethyl)-1H-benzoimidazol-5-yl]-benzenesulfonamide (19 g, 42.5 mmol) was dissolved in EtOAc (1000 mL) with warming to near boiling for complete dissolution. To the stirred solution at rt (orange in color) was added aqueous HCl (1 N, 850 mL, 20 eq.) all at once. The resulting suspension was stirred for 30 min at room temperature. The solid was filtered, washed with a small amount of EtOAc and water. The solid was dried in a high vacuum (2 torr) oven at 45° C. for 16 h, to provide (15.71 g) of the title compound in 77% yield. Calculated $C_{21}H_{16}N_3O_3F_3S \times 1.0$ HCl×0.08$H_2O$: C, 51.97; H, 3.56; N, 8.66; Cl 7.30; F 11.74; S 6.61; KF 0.30 Found: C, 52.11; H, 3.38; N, 8.37; Cl 7.43; F 11.53; S 6.56; KF 0.27

Using the procedures described in Example 1, and reagents, starting materials and conditions known to those skilled in the art, the following compounds representative of the present invention were prepared:

| Cpd | Name and Data |
|---|---|
| 2 | 2-[2-(4-trifluoromethanesulfonyl-phenoxymethyl)-1H-benzoimidazol-5-yl]-benzenesulfonamide<br>$^1$H NMR (400 MHz, CD$_3$OD) δ (ppm): 8.13 (dd, 1H, J = 7.7 Hz, J = 1.2 Hz), 8.05 (d, 2H, J = 9.1 Hz), 7.68 (m, 1H), 7.63 (td, 2H, J = 8.1 Hz, J = 1.8 Hz), 7.54 (td, 1H, J = 8.2 Hz, J = 1.2 Hz), 7.45 (d, 2H, J = 9.1 Hz), 7.40 (dd, 1H, J = 7.7 Hz, J = 1.5 Hz), 7.34 (dd, 1H, J = 8.2 Hz, J = 1.7 Hz), 5.55 (s, 2H). Mass Spectrum (LCMS, ESI pos.) Calcd. For C$_{21}$H$_{16}$F$_3$N$_3$O$_5$S$_2$: 512.50 (M + H), Found 512.0. |
| 3 | 2-[2-(2-fluoro-phenoxymethyl)-1H-benzoimidazol-5-yl]-benzenesulfonamide<br>$^1$H NMR (400 MHz, CD$_3$OD) δ (ppm): 8.12 (dd, 1H, J = 7.6 Hz, J = 1.2 Hz), 7.67 (m, 1H), 7.62 (td, 2H, J = 7.5 Hz, J = 1.2 Hz), 7.54 (td, 1H, J = 7.8 Hz, J = 1.7 Hz), 7.39 (dd, 1H, J = 7.4 Hz, J = 1.1 Hz), 7.34 (dd, 1H, J = 8.3 Hz, J = 1.6 Hz), 7.21 (td, 1H, J = 8.2 Hz, J = 1.7 Hz), 7.08-7.16 (m, 2H), 6.98 (m, 1H), 5.43 (s, 2H). Mass Spectrum (LCMS, ESI pos.) Calcd. For C$_{20}$H$_{16}$FN$_3$O$_3$S: 398.42 (M + H), Found 398.1. |
| 4 | 2-[2-(3-fluoro-phenoxymethyl)-1H-benzoimidazol-5-yl]-benzenesulfonamide<br>$^1$H NMR (400 MHz, CD$_3$OD) δ (ppm): 8.12 (dd, 1H, J = 7.7 Hz, J = 1.1 Hz), 7.60-7.67 (m, 3H), 7.54 (td, 1H, J = 7.7 Hz, J = 1.6 Hz), 7.39 (dd, 1H, J = 7.3 Hz, J = 1.0 Hz), 7.28-7.34 (m, 2H), 6.85-6.92 (m, 2H), 5.37 (s, 2H). Mass Spectrum (LCMS, ESI pos.) Calcd. For C$_{20}$H$_{16}$FN$_3$O$_3$S: 398.42 (M + H), Found 398.1. |
| 5 | 2-[2-(4-fluoro-phenoxymethyl)-1H-benzoimidazol-5-yl]-benzenesulfonamide<br>$^1$H NMR (400 MHz, CD$_3$OD) δ (ppm): 8.13 (m, 1H), 7.56-7.74 (m, 4H), 7.43 (m, 2H), 7.09 (m, 4H) 5.46 (s, 2H). Mass Spectrum (LCMS, ESI pos.) Calcd. For C$_{20}$H$_{16}$FN$_3$O$_3$S: 398.42 (M + H), Found 398.0. |
| 6 | 2-[2-(3-chloro-phenoxymethyl)-1H-benzoimidazol-5-yl]-benzenesulfonamide<br>$^1$H NMR (400 MHz, CD$_3$OD) δ (ppm): 8.12 (dd, 1H, J = 8.3 Hz, J = 1.2 Hz), 7.68 (m, 1H), 7.62 (td, 2H, J = 7.7 Hz, J = 1.5 Hz), 7.54 (td, 1H, J = 8.0 Hz, J = 1.1 Hz), 7.39 (dd, 1H, J = 7.8 Hz, J = 1.3 Hz), 7.35 (dd, 1H, J = 8.5 Hz, J = 2.0 Hz), 7.29 (t, 1H, J = 8.2 Hz), 7.14 (t, 1H, J = 2.1 Hz), 6.99-7.05 (m, 2H), 5.39 (s, 2H). Mass Spectrum (LCMS, ESI pos.) Calcd. For C$_{20}$H$_{16}$ClN$_3$O$_3$S: 414.88 (M + H), Found 414.1. |
| 7 | 2-[2-(4-chloro-phenoxymethyl)-1H-benzoimidazol-5-yl]-benzenesulfonamide<br>$^1$H NMR (400 MHz, CD$_3$OD) δ (ppm): 8.14 (m, 1H), 7.81-7.86 (m, 2H), 7.61-7.67 (m, 3H), 7.36-7.42 (m, 3H), 7.11-7.16 (m, 2H), 5.66 (s, 2H). Mass Spectrum (LCMS, ESI pos.) Calcd. For C$_{20}$H$_{16}$ClN$_3$O$_3$S: 414.88 (M + H), Found 414.1. |
| 8 | 2-[2-(4-bromo-phenoxymethyl)-1H-benzoimidazol-5-yl]-benzenesulfonamide<br>$^1$H NMR (400 MHz, CD$_3$OD) δ (ppm): 8.12 (dd, 1H, J = 8.0 Hz, J = 1.4 Hz), 7.60-7.68 (m, 3H), 7.54 (td, 1H, J = 7.7 Hz, J = 1.5 Hz), 7.30-7.44 (m, 4H), 7.02 (m, 2H), 5.35 (s, 2H). Mass Spectrum (LCMS, ESI pos.) Calcd. For C$_{20}$H$_{16}$BrN$_3$O$_3$S: 458.33 (M + H), Found 458.1. |
| 9 | 2-[2-(2,4-difluoro-phenoxymethyl)-1H-benzoimidazol-5-yl]-benzenesulfonamide<br>$^1$H NMR (400 MHz, CD$_3$OD) δ (ppm): 8.15 (dd, 1H, J = 7.9 Hz, J = 1.1 Hz), 7.81-7.86 (m, 2H), 7.58-7.69 (m, 3H), 7.41 (m, 1H), 7.25-7.32 (m, 1H), 7.13-7.19 (m, 1H), 6.97 (m, 1H), 5.68 (s, 2H). Mass Spectrum (LCMS, ESI pos.) Calcd. For C$_{20}$H$_{15}$F$_2$N$_3$O$_3$S: 416.41 (M + H), Found 416.0. |
| 10 | 2-[2-(3,4-difluoro-phenoxymethyl)-1H-benzoimidazol-5-yl]-benzenesulfonamide<br>$^1$H NMR (400 MHz, CD$_3$OD) δ (ppm): 8.15 (dd, 1H, J = 7.9 Hz, J = 1.6 Hz), 7.81-7.87 (m, 2H), 7.58-7.69 (m, 3H), 7.41 (m, 1H), 7.30-7.36 (m, 1H), 7.09-7.15 (m, 1H), 6.95-6.99 (m, 1H), 5.66 (s, 2H). Mass Spectrum (LCMS, ESI pos.) Calcd. For C$_{20}$H$_{15}$F$_2$N$_3$O$_3$S: 416.41 (M + H), Found 4160. |
| 11 | 2-[2-(3-chloro-4-fluoro-phenoxymethyl)-1H-benzoimidazol-5-yl]-benzenesulfonamide<br>$^1$H NMR (400 MHz, CD$_3$OD) δ (ppm): 8.14 (dd, 1H, J = 7.9 Hz, J = 1.3 Hz), 7.77-7.82 (m, 2H), 7.55-7.67 (m, 3H), 7.41 (m, 1H), 7.31 (m, 1H), 7.25 (t, 1H, J = 8.9 Hz), 7.10-7.13 (m, 1H), 5.59 (s, 2H). Mass Spectrum (LCMS, ESI pos.) Calcd. For C$_{20}$H$_{15}$ClFN$_3$O$_3$S: 432.87 (M + H), Found 432.0. |
| 12 | 2-[2-(4-fluoro-3-trifluoromethyl-phenoxymethyl)-1H-benzoimidazol-5-yl]-benzenesulfonamide<br>$^1$H NMR (400 MHz, CD$_3$OD) δ (ppm): 8.15 (dd, 1H, J = 7.9 Hz, J = 1.4 Hz), 7.84 (m, 2H), 7.60-7.67 (m, 3H), 7.40-7.50 (m, 4H), 5.72 (s, 2H). Mass Spectrum (LCMS, ESI pos.) Calcd. For C$_{21}$H$_{15}$F$_4$N$_3$O$_3$S: 466.42 (M + H), Found 466.0. |
| 13 | 2-[2-(3-trifluoromethyl-phenoxymethyl)-1H-benzoimidazol-5-yl]-benzenesulfonamide<br>$^1$H NMR (400 MHz, CD$_3$OD) δ (ppm): 8.14 (dd, 1H, J = 7.8 Hz, J = 1.1 Hz), 7.80-7.85 (m, 2H), 7.57-7.68 (m, 4H), 7.38-7.47 (m, 4H), 5.72 (s, 2H). Mass Spectrum (LCMS, ESI pos.) Calcd. For C$_{21}$H$_{16}$F$_3$N$_3$O$_3$S: 448.43 (M + H), Found 448.0. |
| 14 | 2-[2-(2,3,4-trifluoro-phenoxymethyl)-1H-benzoimidazol-5-yl]-benzenesulfonamide<br>$^1$H NMR (400 MHz, CD$_3$OD) δ (ppm): 8.14 (dd, 1H, J = 7.8 Hz, J = 1.4 Hz), 7.79-7.84 (m, 2H), 7.58-7.66 (m, 3H), 7.41 (dd, 1H, J = 7.8 Hz, J = 1.3 Hz), 7.12 (m, 2H), 5.72 (s, 2H). Mass Spectrum (LCMS, ESI pos.) Calcd. For C$_{20}$H$_{14}$F$_3$N$_3$O$_3$S: 434.40 (M + H), Found 434.0. |
| 15 | 2-[2-(3-trifluoromethoxy-phenoxymethyl)-1H-benzoimidazol-5-yl]-benzenesulfonamide<br>$^1$H NMR (400 MHz, CD$_3$OD) δ (ppm): 8.12 (m, 1H), 7.52-7.68 (m, 4H), 7.34-7.42 (m, 3H), 6.92-7.12 (m, 3H), 5.41 (s, 2H). Mass Spectrum (LCMS, ESI pos.) Calcd. For C$_{21}$H$_{16}$F$_3$N$_3$O$_4$S: 464.43 (M + H), Found 4641. |

| Cpd | Name and Data |
|---|---|
| 16 | 2-[2-(4-trifluoromethoxy-phenoxymethyl)-1H-benzoimidazol-5-yl]-benzenesulfonamide<br>$^1$H NMR (400 MHz, CD$_3$OD) δ (ppm): 8.12 (dd, 1H, J = 7.6 Hz, J = 1.0 Hz), 7.60-7.69 (m, 3H), 7.55 (td, 1H, J = 7.8 Hz, J = 1.6 Hz), 7.40 (dd, 1H, J = 7.6 Hz, J = 1.5 Hz), 7.34 (m, 1H), 7.23 (m, 2H), 7.16 (m, 2H), 5.39 (s, 2H). Mass Spectrum (LCMS, ESI pos.) Calcd. For C$_{21}$H$_{16}$F$_3$N$_3$O$_4$S: 464.43 (M + H), Found 464.1. |
| 17 | N-methyl-2-[2-(4-trifluoromethyl-phenoxymethyl)-1H-benzoimidazol-5-yl]-benzenesulfonamide<br>$^1$H NMR (400 MHz, CDCl$_3$) δ (ppm): 8.16 (dd, 1H, J = 7.9 Hz, J = 1.4 Hz), 7.51-7.74 (m, 6H), 7.36 (m, 2H), 7.07 (d, 2H, J = 9.0 Hz), 5.38 (s, 2H), 2.36 (br s, 3H). Mass Spectrum (LCMS, ESI pos.) Calcd. For C$_{22}$H$_{18}$F$_3$N$_3$O$_3$S: 462.46 (M + H), Found 462.4. |
| 18 | 2-[2-(4-chloro-phenoxymethyl)-1H-benzoimidazol-5-yl]-N-methyl-benzenesulfonamide<br>$^1$H NMR (400 MHz, CDCl$_3$) δ (ppm): 8.16 (dd, 1H, J = 7.7 Hz, J = 1.1 Hz), 7.72 (m, 1H), 7.61 (td, 1H, J = 7.8 Hz, J = 1.3 Hz), 7.53 (td, 1H, J = 7.8 Hz, J = 1.5 Hz), 7.37 (dd, 2H, J = 7.3 Hz, J = 1.0 Hz), 7.21-7.26 (m on CDCl$_3$, 3H), 6.91 (m, 2H), 5.30 (s, 2H), 2.36 (br s, 3H). Mass Spectrum (LCMS, ESI pos.) Calcd. For C$_{21}$H$_{18}$ClN$_3$O$_3$S: 428.90 (M + H), Found 428.3. |
| 19 | 2-[2-(4-methanesulfonyl-phenoxymethyl)-1H-benzoimidazol-5-yl]-N-methyl-benzenesulfonamide<br>$^1$H NMR (400 MHz, CDCl$_3$) δ (ppm): 8.15 (dd, 1H, J = 7.7 Hz, J = 1.2 Hz), 7.72-7.81 (m, 4H), 7.51-7.63 (m, 2H), 7.32-7.45 (m, 2H), 7.07 (d, 2H, J = 9.2 Hz), 5.37 (s, 2H), 3.02 (s, 3H), 2.38 (br s, 3H). Mass Spectrum (LCMS, ESI pos.) Calcd. For C$_{22}$H$_{21}$N$_3$O$_5$S$_2$: 472.55 (M + H), Found 472.4. |
| 20 | N-methyl-2-[2-(4-trifluoromethanesulfonyl-phenoxymethyl)-1H-benzoimidazol-5-yl]-benzenesulfonamide<br>$^1$H NMR (400 MHz, CDCl$_3$) δ (ppm): 8.08 (dd, 1H, J = 8.0 Hz, J = 1.5 Hz), 7.90 (d, 2H, J = 8.9 Hz), 7.69 (m, 1H), 7.56 (td, 2H, J = 7.5 Hz, J = 1.7 Hz), 7.48 (td, 2H, J = 8.0 Hz, J = 1.8 Hz), 7.31 (dd, 1H, J = 7.2 Hz, J = 1.1 Hz), 7.16-7.19 (m on CDCl$_3$, 2H), 5.40 (s, 2H), 2.31 (br s, 3H). Mass Spectrum (LCMS, ESI pos.) Calcd. For C$_{22}$H$_{18}$F$_3$N$_3$O$_5$S$_2$: 526.52 (M + H), Found 526.4. |
| 26 | 2-(2-phenoxymethyl-1H-benzoimidazol-5-yl)-benzenesulfonamide<br>$^1$H NMR (400 MHz, CD$_3$OD) δ (ppm): 8.12 (dd, 1H, J = 8.1 Hz, J = 1.5 Hz), 7.59 (m, 3H), 7.53 (td, 1H, J = 8.0 Hz, J = 1.7 Hz), 7.39 (dd, 1H, J = 7.6 Hz, J = 1.1 Hz), 7.30 (m, 3H), 7.07 (m, 2H), 6.98 (tt, 1H, J = 7.4 Hz, J = 1.1 Hz), 5.35 (s, 2H). Mass Spectrum (LCMS, ESI pos.) Calcd. For C$_{20}$H$_{17}$N$_3$O$_3$S: 380.43 (M + H), Found 380.1. |
| 27 | 2-(2-p-tolyloxymethyl-1H-benzoimidazol-5-yl)-benzenesulfonamide<br>$^1$H NMR (400 MHz, CD$_3$OD) δ (ppm): 8.12 (dd, 1H, J = 8.0 Hz, J = 1.3 Hz), 7.62 (m, 3H), 7.53 (td, 1H, J = 8.0 Hz, J = 1.7 Hz), 7.39 (dd, 1H, J = 7.6 Hz, J = 1.3 Hz), 7.32 (dd, 1H, J = 8.4 Hz, J = 1.5 Hz), 7.10 (m, 2H), 6.96 (m, 2H), 5.31 (s, 2H), 2.26 (s, 3H). Mass Spectrum (LCMS, ESI pos.) Calcd. For C$_{21}$H$_{19}$N$_3$O$_3$S: 394.46 (M + H), Found 394.1. |
| 28 | 2-[2-(4-isopropyl-phenoxymethyl)-1H-benzoimidazol-5-yl]-benzenesulfonamide<br>$^1$H NMR (400 MHz, CD$_3$OD) δ (ppm): 8.14 (dd, 1H, J = 8.0 Hz, J = 1.0 Hz), 7.53-7.98 (m, 5H), 7.40 (d, 1H, J = 7.1 Hz), 7.22 (m, 2H), 7.07 (m, 2H), 5.51 (s, 2H), 2.87 (m, 1H), 1.21 (d, 6H, J = 6.6 Hz). Mass Spectrum (LCMS, ESI pos.) Calcd. For C$_{23}$H$_{23}$N$_3$O$_3$S: 422.51 (M + H), Found 422.1. |
| 29 | 2-[2-(3,4-dichloro-phenoxymethyl)-1H-benzoimidazol-5-yl]-benzenesulfonamide<br>$^1$H NMR (400 MHz, CD$_3$OD) δ (ppm): 8.13 (dd, 1H, J = 8.0 Hz, J = 1.4 Hz), 7.76 (s, 1H), 7.70 (d, 1H, J = 8.2 Hz), 7.63 (td, 1H, J = 7.4 Hz, J = 1.5 Hz), 7.56 (td, 1H, J = 7.8 Hz, J = 1.1 Hz), 7.46 (m, 2H), 7.39 (dd, 1H, J = 7.3 Hz, J = 0.95 Hz), 7.33 (d, 1H, J = 2.8 Hz), 7.07 (dd, 1H, J = 9.2 Hz, J = 2.7 Hz), 5.51 (s, 2H). Mass Spectrum (LCMS, ESI pos.) Calcd. For C$_{20}$H$_{15}$Cl$_2$N$_3$O$_3$S: 448.32 (M + H), Found 448.0. |
| 30 | 2-[2-(4-chloro-3-trifluoromethyl-phenoxymethyl)-1H-benzoimidazol-5-yl]-benzenesulfonamide<br>$^1$H NMR (400 MHz, CD$_3$OD) δ (ppm): 8.13 (dd, 1H, J = 8.0 Hz, J = 1.3 Hz), 7.73 (m, 2H), 7.63 (td, 1H, J = 7.4 Hz, J = 1.6 Hz), 7.54 (m, 3H), 7.45 (d, 1H, J = 8.2 Hz), 7.39 (dd, 2H, J = 7.3 Hz, J = 0.97 Hz), 5.55 (s, 2H). Mass Spectrum (LCMS, ESI pos.) Calcd. For C$_{21}$H$_{15}$ClF$_3$N$_3$O$_3$S: 482.88 (M + H), Found 482.0. |
| 31 | 2-[2-(3,5-bis-trifluoromethyl-phenoxymethyl)-1H-benzoimidazol-5-yl]-benzenesulfonamide<br>$^1$H NMR (400 MHz, CD$_3$OD) δ (ppm): 8.13 (dd, 1H, J = 7.7 Hz, J = 1.4 Hz), 7.78 (m, 4H), 7.67 (d, 1H, J = 1.1 Hz), 7.64 (dd, 1H, J = 7.4 Hz, J = 1.5 Hz), 7.58 (td, 1H, J = 7.8 Hz, J = 1.4 Hz), 7.52 (dd, 1H, J = 8.6 Hz, J = 1.5 Hz), 7.41 (dd, 1H, J = 7.6 Hz, J = 1.1 Hz), 5.73 (s, 2H). Mass Spectrum (LCMS, ESI pos.) Calcd. For C$_{22}$H$_{15}$F$_6$N$_3$O$_3$S: 516.43 (M + H), Found 516.1. |
| 32 | 2-[2-(4-tert-butyl-phenoxymethyl)-1H-benzoimidazol-5-yl]-benzenesulfonamide<br>$^1$H NMR (400 MHz, CD$_3$OD) δ (ppm): 8.12 (dd, 1H, J = 8.2 Hz, J = 1.1 Hz), 7.63 (m, 3H), 7.53 (td, 1H, J = 7.7 Hz, J = 1.5 Hz), 7.39 (dd, 1H, J = 7.6 Hz, J = 1.5 Hz), 7.33 (m, 1H), 7.00 (m, 2H), 5.34 (s, 2H), 1.28 (s, 9H). Mass Spectrum (LCMS, ESI pos.) Calcd. For C$_{24}$H$_{25}$N$_3$O$_3$S: 436.54 (M + H), Found 436.2. |
| 33 | 2-[2-(4-ethoxy-phenoxymethyl)-1H-benzoimidazol-5-yl]-benzenesulfonamide<br>$^1$H NMR (400 MHz, CD$_3$OD) δ (ppm): 8.12 (dd, 1H, J = 7.7 Hz, J = 1.1 Hz), 7.63 (m, 3H), 7.54 (td, 1H, J = 7.9 Hz, J = 1.2 Hz), 7.40 (dd, 1H, J = 7.5 Hz, J = 1.6 Hz), |

| Cpd | Name and Data |
|---|---|
| | 7.32 (dd, 1H, J = 8.3 Hz, J = 1.6 Hz), 6.99 (m, 2H), 6.85 (m, 2H), 5.29 (s, 2H), 3.96 (q, 2H, J = 7.0 Hz), 1.34 (t, 3H, J = 7. Hz). Mass Spectrum (LCMS, ESI pos.) Calcd. For $C_{22}H_{21}N_3O_4S$: 424.49 (M + H), Found 424.1. |
| 34 | 2-[2-(4-trifluoromethylsulfanyl-phenoxymethyl)-1H-benzoimidazol-5-yl]-benzenesulfonamide<br>$^1$H NMR (400 MHz, CD$_3$OD) δ (ppm): 8.12 (dd, 1H, J = 8.0 Hz, J = 1.5 Hz), 7.65 (m, 5H), 7.54 (td, 1H, J = 8.0 Hz, J = 1.5 Hz), 7.40 (dd, 1H, J = 7.3 Hz, J = 1.1 Hz), 7.34 (m, 1H), 7.21 (m, 2H), 5.43 (s, 2H). Mass Spectrum (LCMS, ESI pos.) Calcd. For $C_{21}H_{16}F_3N_3O_3S_2$: 480.50 (M + H), Found 480.0. |
| 35 | 2-[2-(4-acetyl-phenoxymethyl)-1H-benzoimidazol-5-yl]-benzenesulfonamide<br>$^1$H NMR (400 MHz, CD$_3$OD) δ (ppm): 8.12 (dd, 1H, J = 8.0 Hz, J = 1.2 Hz), 8.0 (m, 2H), 7.63 (m, 3H), 7.54 (td, 1H, J = 7.6 Hz, J = 1.5 Hz), 7.39 (dd, 1H, J = 7.6 Hz, J = 1.2 Hz), 7.33 (d, 1H, J = 7.7 Hz), 7.19 (m, 2H), 5.46 (s, 2H), 2.55 (s, 3H). Mass Spectrum (LCMS, ESI pos.) Calcd. For $C_{22}H_{19}N_3O_4S$: 422.7 (M + H), Found 422.1. |
| 36 | 2-[2-(naphthalen-2-yloxymethyl)-1H-benzoimidazol-5-yl]-benzenesulfonamide<br>$^1$H NMR (400 MHz, CD$_3$OD) δ (ppm): 8.15 (dd, 1H, J = 8.1 Hz, J = 1.6 Hz), 7.84 (m, 5H), 7.66 (td, 1H, J = 7.4 Hz, J = 1.6 Hz), 7.60 (td, 2H, J = 7.4 Hz, J = 1.6 Hz), 7.35-7.50 (m, 5H), 5.75 (s, 2H). Mass Spectrum (LCMS, ESI pos.) Calcd. For $C_{22}H_{19}N_3O_4S$: 430.47 (M + H), Found 430.0. |
| 37 | 2-[2-(quinolin-6-yloxymethyl)-1H-benzoimidazol-5-yl]-benzenesulfonamide<br>$^1$H NMR (400 MHz, CD$_3$OD) δ (ppm): 8.95 (dd, 1H, J = 5.0 Hz, J = 1.3 Hz), 8.80 (d, 1H, J = 8.1 Hz), 8.16 (m, 2H), 7.84 (m, 5H), 7.61 (m, 3H), 7.41 (dd, 1H, J = 7.5 Hz, J = 1.7 Hz), 5.83 (s, 2H). Mass Spectrum (LCMS, ESI pos.) Calcd. For $C_{23}H_{18}N_4O_3S$: 431.48 (M + H), Found 431.1. |
| 38 | 2-[2-(pyridin-4-yloxymethyl)-1H-benzoimidazol-5-yl]-benzenesulfonamide<br>$^1$H NMR (400 MHz, CD$_3$OD) δ (ppm): 8.29 (m, 2H), 8.11 (dd, 1H, J = 8.1 Hz, J = 0.8 Hz), 7.73 (m, 2H), 7.62 (td, 1H, J = 7.4 Hz, J = 1.4 Hz), 7.54 (td, 1H, J = 7.6 Hz, J = 1.0 Hz), 7.36 (m, 2H), 6.85 (m, 2H), 5.67 (s, 2H). Mass Spectrum (LCMS, ESI pos.) Calcd. For $C_{19}H_{16}N_4O_3S$: 381.42 (M + H), Found 381.0. |
| 39 | 2-[2-(5-trifluoromethyl-pyridin-2-yloxymethyl)-1H-benzoimidazol-5-yl]-benzenesulfonamide<br>$^1$H NMR (400 MHz, CD$_3$OD) δ (ppm): 8.43 (m, 1H), 8.11 (dd, 1H, J = 8.1 Hz, J = 1.4 Hz), 7.74 (dd, 1H, J = 9.4 Hz, J = 2.5 Hz), 7.57 (m, 4H), 7.37 (dd, 1H, J = 7.8 Hz, J = 1.6 Hz), 7.29 (d, 1H, J = 8.5 Hz), 6.68 (d, 1H, J = 9.5 Hz), 5.47 (s, 2H). Mass Spectrum (LCMS, ESI pos.) Calcd. For $C_{20}H_{15}F_3N_4O_3S$: 449.42 (M + H), Found 449.0. |
| 40 | 2-[1-methyl-2-(4-trifluoromethyl-phenoxymethyl)-1H-benzoimidazol-5-yl]-benzenesulfonamide<br>$^1$H NMR (400 MHz, CD$_3$OD) δ (ppm): 8.13 (m, 1H), 7.72 (m, 1H), 7.58 (m, 5H), 7.39 (m, 2H), 7.26 (d, 1H, J = 8.8 Hz), 5.50 (m, 2H), 3.92 (m, 3H). Calcd. For $C_{22}H_{18}F_3N_3O_3S$: 462.46 (M + H), Found 462.1. |
| 41 | 2-[2-(4-trifluoromethyl-phenylsulfanylmethyl)-1H-benzoimidazol-5-yl]-benzenesulfonamide<br>$^1$H NMR (400 MHz, CD$_3$OD) δ (ppm): 8.12 (d, 1H, J = 7.8 Hz), 7.55-7.72 (m, 8H), 7.48 (d, 1H, J = 8.2 Hz), 7.37 (d, 1H, J = 6.7 Hz), 4.93 (s, 2H). Calcd. For $C_{21}H_{16}F_3N_3O_2S_2$: 464.50 (M + H), Found 464.2. |
| 42 | 2-[2-(4-chloro-phenylsulfanylmethyl)-1H-benzoimidazol-5-yl]-benzenesulfonamide<br>$^1$H NMR (400 MHz, CD$_3$OD) δ (ppm): 8.12 (dd, 1H, J = 7.9 Hz, J = 1.4 Hz), 7.65 (m, 3H), 7.57 (td, 1H, J = 8.0 Hz, J = 1.7 Hz), 7.47 (dd, 1H, J = 8.7 Hz, J = 1.6 Hz), 7.38 (m, 3H), 7.31 (m, 2H), 4.54 (s, 2H). Calcd. For $C_{20}H_{16}ClN_3O_2S_2$: 430.04 (M + H), Found 430.1. |
| 43 | 2-[2-(4-trifluoromethoxy-phenylsulfanylmethyl)-1H-benzoimidazol-5-yl]-benzenesulfonamide<br>$^1$H NMR (400 MHz, CD$_3$OD) δ (ppm): 8.12 (dd, 1H, J = 8.0 Hz, J = 1.1 Hz), 7.66 (m, 3H), 7.57 (td, 1H, J = 8.0 Hz, J = 1.7 Hz), 7.50 (m, 3H), 7.37 (dd, 1H, J = 7.6 Hz, J = 1.1 Hz), 7.22 (m, 2H), 4.57 (s, 2H). Calcd. For $C_{21}H_{16}F_3N_3O_3S_2$: 480.50 (M + H), Found 480.1. |
| 44 | 2-[2-(4-trifluoromethyl-benzenesulfonylmethyl)-1H-benzoimidazol-5-yl]-benzenesulfonamide<br>$^1$H NMR (400 MHz, CD$_3$OD) δ (ppm): 8.12 (dd, 1H, J = 7.9 Hz, J = 1.2 Hz), 7.87 (d, 2H, J = 8.1 Hz), 7.72 (d, 2H, J = 8.3 Hz), 7.65 (m, 1H), 7.52 (m, 2H), 7.43 (td, 1H, J = 7.8 Hz, J = 1.2 Hz), 7.34 (dd, 1H, J = 7.6 Hz, J = 1.0 Hz), 7.22 (dd, 1H, J = 8.4 Hz, J = 1.7 Hz), 4.75 (s, 2H). Calcd. For $C_{21}H_{16}F_3N_3O_4S_2$: 496.50 (M + H), Found 496.0. |
| 45 | 2-[2-(4-chloro-benzenesulfonylmethyl)-1H-benzoimidazol-5-yl]-benzenesulfonamide<br>$^1$H NMR (400 MHz, CD$_3$OD) δ (ppm): 8.15 (dd, 1H, J = 7.9 Hz, J = 1.2 Hz), 7.74 (dt, 2H, J = 9.1 Hz, J = 2.3 Hz), 7.54-7.67 (m, 6H), 7.41 (dd, 1H, J = 7.4 Hz, J = 1.0 Hz), 7.35 (m, 1H), 4.88 (s, 2H). Calcd. For $C_{20}H_{16}ClN_3O_4S_2$: 462.03 (M + H), Found 462.0. |
| 46 | 2-[2-(4-trifluoromethoxy-benzenesulfonylmethyl)-1H-benzoimidazol-5-yl]-benzenesulfonamide<br>$^1$H NMR (400 MHz, CD$_3$OD) δ (ppm): 8.02 (dd, 1H, J = 8.2 Hz, J = 1.6 Hz), 7.95 (td, 2H, J = 9.2 Hz, J = 2.1 Hz), 7.60 (m, 3H), 7.54 (td, 1H, J = 9.2 Hz, J = 1.5 Hz), 7.47 (m, 1H), 7.42 (d, 1H, J = 8.0 Hz), 7.35 (dd, 1H, J = 7.5 Hz, J = 1.2 Hz), 7.07 (dd, 1H, |

-continued

| Cpd | Name and Data |
|---|---|
| | J = 9.0 Hz, J = 1.2 Hz), 4.595 (s, 2H). Calcd. For $C_{21}H_{16}F_3N_3O_5S_2$: 512.50 (M + H), Found 512.0. |
| 47 | 2-{2-[(4-trifluoromethyl-phenylamino)-methyl]-1H-benzoimidazol-5-yl}-benzenesulfonamide<br>$^1$H NMR (400 MHz, CD$_3$OD) δ (ppm): 8.13 (dd, 1H, J = 8.0 Hz, J = 1.4 Hz), 7.75 (m, 2H), 7.61 (m, 3H), 7.41 (m, 3H), 6.73 (m, 2H), 4.96 (s, 2H). Calcd. For $C_{21}H_{17}F_3N_4O_2S$: 447.45 (M + H), Found 447.0. |
| 48 | 2-{2-[(4-trifluoromethoxy-phenylamino)-methyl]-1H-benzoimidazol-5-yl}-benzenesulfonamide<br>$^1$H NMR (400 MHz, CD$_3$OD) δ (ppm): 8.12 (dd, 1H, J = 7.8 Hz, J = 1.1 Hz), 7.75 (s, 1H), 7.71 (d, 1H, J = 8.5 Hz), 7.64 (td, 1H, J = 7.4 Hz, J = 1.7 Hz), 7.58 (td, 1H, J = 7.7 Hz, J = 1.5 Hz), 7.52 (dd, 1H, J = 8.6 Hz, J = 1.5 Hz), 7.39 (dd, 1H, J = 7.4 Hz, J = 0.9 Hz), 7.07 (d, 2H, J = 8.6 Hz), 6.72 (m, 2H), 4.87 (s, 2H). Calcd. For $C_{21}H_{17}F_3N_4O_3S$: 463.45 (M + H), Found 463.0. |
| 51 | 2-[2-(4-isopropyl-phenoxymethyl)-1H-benzoimidazol-5-yl]-N-methyl-benzenesulfonamide<br>$^1$H NMR (400 MHz, CDCl$_3$) δ (ppm): 8.05 (dd, 1H, J = 7.9 Hz, J = 1.2 Hz), 7.74 (m, 2H), 7.68 (td, 1H, J = 7.7 Hz, J = 1.6 Hz), 7.60 (td, 1H, J = 7.9 Hz, J = 1.0 Hz), 7.45 (ddd, 2H, J = 17.0, J = 8.3 Hz, J = 1.6 Hz), 7.21 (m, 2H), 7.04 (m, 2H), 5.49 (s, 2H), 2.87 (m, 1H), 2.40 (s, 3H), 1.23 (s, 3H), 1.21 (s, 3H). Mass Spectrum (LCMS, ESI pos.) Calcd. For $C_{24}H_{25}N_3O_3S$: 436.54 (M + H), Found 436.1. |
| 52 | N-methyl-2-[2-(3-trifluoromethyl-phenoxymethyl)-1H-benzoimidazol-5-yl]-benzenesulfonamide<br>$^1$H NMR (400 MHz, CDCl$_3$) δ (ppm): 8.05 (dd, 1H, J = 7.7 Hz, J = 1.0 Hz), 7.68 (m, 3H), 7.56 (m, 2H), 7.32-7.43 (m, 5H), 5.53 (s, 2H), 2.38 (s, 3H). Mass Spectrum (LCMS, ESI pos.) Calcd. For $C_{22}H_{18}F_3N_3O_3S$: 462.46 (M + H), Found 462.1. |

EXAMPLE 2

2-{2-[2-(4-trifluoromethyl-phenoxymethyl)-1H-benzoimidazol-5-yl]-phenyl}-propan-2-ol (Cpd 21)

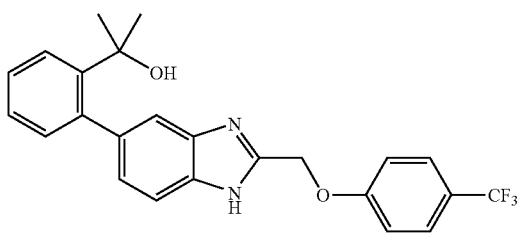

A. 5-bromo-2-chloromethyl-1H-benzimidazole

Using the procedure for Step D in Example 1 (as described in J. Med. Chem., 1986, 29, 2280), the title compound was prepared from 4-bromo-benzene-1,2-diamine (200 mg, 1.07 mmol) and 2-chloroacetimidic acid ethyl ester hydrochloride salt (168 mg, 1.07 mmol) and was obtained as an off-white solid (240.3 mg, 92% yield). $^1$H NMR (400 MHz, CD$_3$OD) δ (ppm): 7.75 (d, 1H, J=1.4 Hz), 7.47 (d, 1H, J=8.6 Hz), 7.74 (dd, 1H, J=8.6 Hz, J=1.3 Hz), 4.84 (s, 2H). Mass Spectrum (LCMS, ESI pos.) Calcd. For $C_{18}H_{20}ClN_3O_2S$: 247.50 (M+H), Found 247.0.

B. 5-bromo-2-(4-trifluoromethyl-phenoxymethyl)-1H-benzimidazole

Using the procedure for Step E in Example 1, the title compound was prepared from 5-bromo-2-chloromethyl-1H-benzimidazole (200 mg, 0.816 mmol) and α,α,α-trifluoro-p-cresol (132 mg, 0.816 mmol) and was obtained as an off-white solid (76.2 mg, 25% yield). Calcd. For $C_{21}H_{16}F_3N_3O_3S$: 371.15 (M+H), Found 371.0.

C. 3,3-dimethyl-3H-benzo[c][1,2]oxaborol-1-ol

To a solution of 2-(2-bromo-phenyl)-propan-2-ol (4.0 g, 18.6 mmol, prepared as described in Egan, W. et al. J. Am. Chem. Soc., 1971, 93, 6205) in 60 mL of anhydrous THF under argon at −78° C. was slowly added n-butyl lithium (15 mL, 2.5 M). The mixture was stirred at −78° C. for 2 h, and then triisopropylborate (5.5 mL, 24.2 mmol) was added to the mixture. The mixture was allowed to warm to room temperature and stirred at room temperature for 12 h. The mixture was then cooled to 0° C. and hydrochloric acid (10 mL, 1N) was added to the mixture until pH was <5. The mixture was then stirred at room temperature for 1 h. The two layers were separated. The aqueous layer was extracted twice with ethyl acetate. The organic layers were combined, dried with anhydrous sodium sulfate and filtered. The filtrate was concentrated under reduced pressure to afford a yellow oil. The oil was purified by chromatography (silica, EtOAc: hexanes,1:3) to afford a white solid (1.16 g, 40%). $^1$H NMR (400 MHz, CDCl$_3$) δ (ppm): 7.53 (m, 1H), 7.36 (m, 2H), 7.28 (m, 1H), 1.62 (s, 3H), 1.61 (s, 3H).

D. 2-{2-[2-(4-trifluoromethyl-phenoxymethyl)-1H-benzoimidazol-5-yl]-phenyl}-propan-2-ol A mixture of 3,3-dimethyl-3H-benzo[c][1,2]oxaborol-1-ol (66.5 mg, 0.411 mmol), 5-bromo-2-(4-trifluoromethyl-phenoxymethyl)-1H-benzimidazole (76.2 mg, 0.205 mmol), PdCl$_2$(dppf)$_2$.CH$_2$Cl$_2$ (34 mg, 0.041 mmol), and tetrabutylammonium bromide (66 mg 0.205 mmol) in 8 mL of DME and 1.64 mL of Na$_2$CO$_3$ solution (1.0 M) was degassed and purged with argon twice. The mixture was then heated to 90° C. for 12 h. The mixture was then cooled to room temperature, and filtered though a pad of Celite 545. The filtrate was concentrated under reduced pressure to yield a dark brown oil. The residue was purified by chromatography (silica, ethyl acetate:hexanes, 1:1) to afford the title compound as an off-white solid (26.8 mg, 30%). $^1$H NMR (400 MHz, CD$_3$OD) δ (ppm): 7.81 (dd, 1H, J=8.1 Hz, J=1.1 Hz), 7.63 (m, 2H), 7.56

(m, 1H), 7.45 (m, 1H), 7.34 (td, 1H, J=7.8 Hz, J=1.5 Hz), 7.16-7.26 (m, 4H), 7.05 (dd, 1H, J=7.4 Hz, J=1.7 Hz), 5.44 (s, 2H), 1.32 (s, 6H). Mass Spectrum (LCMS, ESI pos.) Calcd. For $C_{24}H_{21}F_3N_2O_2$: 427.43 (M+H), Found 427.1.

Using the procedures described in Example 2, and reagents, starting materials and conditions known to those skilled in the art, the following compounds representative of the present invention were prepared:

| Cpd | Name and Data |
|---|---|
| 22 | 2-{2-[2-(4-trifluoromethoxy-phenoxymethyl)-1H-benzoimidazol-5-yl]-phenyl}-propan-2-ol<br>$^1$H NMR (400 MHz, CD$_3$OD) δ (ppm): 7.81 (dd, 1H, J = 8.4 Hz, J = 0.7 Hz), 7.32-7.50 (m, 2H), 7.15-7.25 (m, 7H), 7.45 (m, 1H), 7.06 (dd, 1H, J = 7.5 Hz, J = 1.0 Hz), 5.38 (s, 2H), 1.32 (s, 6H). Mass Spectrum (LCMS, ESI pos.) Calcd. For $C_{24}H_{21}F_3N_2O_3$: 443.43 (M + H), Found 443.1. |
| 23 | 2-{2-[2-(4-chloro-phenoxymethyl)-1H-benzoimidazol-5-yl]-phenyl}-propan-2-ol<br>$^1$H NMR (400 MHz, CDCl$_3$) δ (ppm): 7.63-7.73 (m, 2H), 7.35-7.51 (m, 3H), 7.22-7.28 (m on CDCl$_3$, 4H), 7.11 (m, 1H), 6.95 (m, 2H), 5.37 (s, 2H), 1.47 (s, 6H). Mass Spectrum (LCMS, ESI pos.) Calcd. For $C_{23}H_{21}ClN_2O_2$: 393.88 (M + H), Found 393.4. |
| 24 | 2-{2-[2-(3-trifluoromethyl-phenoxymethyl)-1H-benzoimidazol-5-yl]-phenyl}-propan-2-ol<br>$^1$H NMR (400 MHz, CDCl$_3$) δ (ppm): 7.63-7.76 (m, 2H), 7.35-7.46 (m, 3H), 7.19-7.30 (m on CDCl$_3$, 5H), 7.11 (m, 1H), 5.42 (s, 2H), 1.47 (s, 6H). Mass Spectrum (LCMS, ESI pos.) Calcd. For $C_{24}H_{21}F_3N_2O_2$: 427.43 (M + H), Found 427.4. |
| 25 | 2-{2-[2-(4-methanesulfonyl-phenoxymethyl)-1H-benzoimidazol-5-yl]-phenyl}-propan-2-ol<br>$^1$H NMR (400 MHz, CD$_3$OD) δ (ppm): 7.92 (dd, 2H, J = 7.1 Hz, J = 2.1 Hz), 7.81 (dd, 2H, J = 8.2 Hz, J = 1.4 Hz), 7.50-7.70 (m, 2H), 7.30-7.36 (m, 3H), 7.19 (qd, 2H, J = 7.5 Hz, J = 1.4 Hz), 7.04 (dd, 1H, J = 7.8 Hz, J = 1.3 Hz), 5.48 (s, 2H), 3.08 (s, 3H), 1.32 (s, 6H). Mass Spectrum (LCMS, ESI pos.) Calcd. For $C_{24}H_{24}N_2O_4S$: 437.52 (M + H), Found 437.4. |
| 49 | 1-{2-[2-(4-trifluoromethyl-phenoxymethyl)-1H-benzoimidazol-5-yl]-phenyl}-ethanone<br>$^1$H NMR (400 MHz, CD$_3$OD) δ (ppm): 7.61 (m, 3H), 7.53 (m, 3H), 7.44 (m, 2H), 7.22 (m, 3H), 5.43 (s, 2H), 1.96 (s, 3H). Calcd. For $C_{23}H_{17}F_3N_2O_2$: 411.39 (M + H), Found 411.1. |
| 50 | 2-[2-(2-phenoxymethyl-1H-benzoimidazol-5-yl)-phenyl]-propan-2-ol<br>$^1$H NMR (400 MHz, CD$_3$OD) δ (ppm): 7.81 (dd, 1H, J = 8.3 Hz, J = 1.1 Hz), 7.55 (d, 1H, J = 8.1 Hz), 7.44 (s, 1H), 7.32 (m, 3H), 7.20 (td, 1H, J = 7.5 Hz, J = 1.5 Hz), 7.16 (dd, 1H, J = 8.1 Hz, J = 1.7 Hz), 7.06 (m, 3H), 6.98 (t, 1H, J = 7.4 Hz), 5.34 (s, 2H), 1.32 (s, 6H). Mass Spectrum (LCMS, ESI pos.) Calcd. For $C_{23}H_{22}N_2O_2$: 359.43 (M + H), Found 359.1. |

EXAMPLE 3

5-(2-methanesulfonyl-phenyl)-2-phenoxymethyl-1H-benzoimidazole (Cpd 53)

A. (3-tert-butoxycarbonylamino-2'-methanesulfonyl-biphenyl-4-yl)-carbamic acid tert-butyl ester

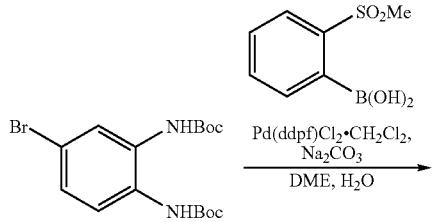

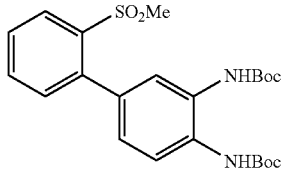

A mixture of (5-bromo-2-tert-butoxycarbonylamino-phenyl)-carbamic acid tert-butyl ester (Example 1, Step A, 8.81 g, 0.0385 mol), 2-methylsulfonylphenylboronic acid (10.00 g, 0.0500 mol), Pd(dppf)Cl$_2$·CH$_2$Cl$_2$ (4.71 g, 0.0578 mmol), and Na$_2$CO$_3$ (24.46 g, 0.116 mol) in 1,2-dimethoxyethane (200 mL) and water (50 mL) was heated 80° C. for 12 hours under inert atmosphere. The reaction mixture was cooled to room temperature and concentrated under reduced pressure.

The residue was purified by chromatography (silica, EtOAc: hexanes, 1:2) to afford the title compound as a yellow oil (15.30 g, 86%).

B. 2'-methanesulfonyl-biphenyl-3,4-diamine

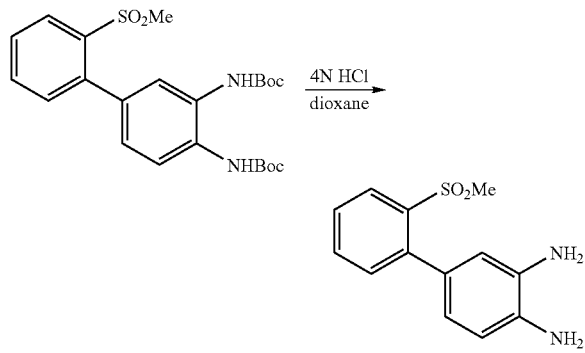

A solution of (3-tert-butoxycarbonylamino-2'-methanesulfonyl-biphenyl-4-yl)-carbamic acid tert-butyl ester (12.47 g, 0.0270 mol) in 4M HCl in dioxane (120 mL) was stirred at room temperature for 2 h. The reaction mixture was concentrated under reduced pressure. The residue was dissolved in EtOAc, and the solution was washed with saturated sodium bicarbonate and water (pH=7). The organic layer was dried over $Na_2SO_4$, filtered, and the filtrate was concentrated in vacuo to provide the title compound as a yellow oil (6.93 g, 98%).

C. 2-bromomethyl-5-(2-methanesulfonyl-phenyl)-benzoimidazole-1-carboxylic acid tert-butyl ester

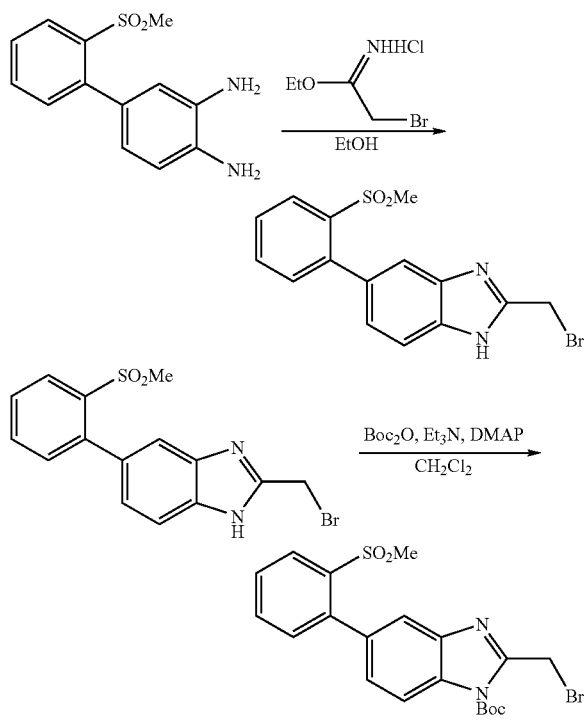

A mixture of 2'-methanesulfonyl-biphenyl-3,4-diamine (8.09 g, 0.0308 mol) and 2-bromoacetimidic acid ethyl ester hydrochloride salt (11.82 g, 0.0370 mol) in anhydrous ethanol (200 proof, 120 mL) was stirred at room temperature for 12 h. The reaction mixture was concentrated under reduced pressure and extracted with ethyl acetate and brine. The organic layer was dried over $Na_2SO_4$, filtered, and the filtrate was concentrated in vacuo to provide 2-bromomethyl-5-(2-methanesulfonyl-phenyl)-1H-benzoimidazole (10.36 g, 92%) as a yellow oil. To a solution of this material in $CH_2Cl_2$, was added $Boc_2O$ (7.39 g, 0.0339 mol), $Et_3N$ (12.9 mL, 0.0924 mol), and DMAP (0.19 g, 0.00154 mol). After stirring 1 h at room temperature, the reaction mixture was concentrated under reduced pressure and the residue was purified by chromatography (silica, EtOAc: hexanes, 1:2) to afford the title compound as a yellow oil (10.17 g, 77%).

D. 5-(2-methanesulfonyl-phenyl)-2-phenoxymethyl-1H-benzoimidazole

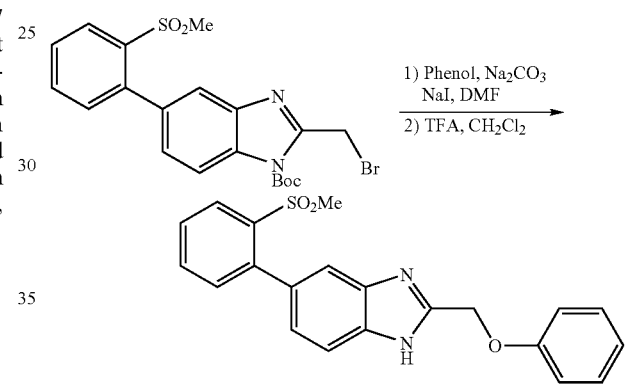

To a solution of 2-bromomethyl-5-(2-methanesulfonyl-phenyl)-benzoimidazole-1-carboxylic acid tert-butyl ester (0.050 g, 0.107 mmol) in DMF (1 mL) was added phenol (0.040 g, 0.430 mmol), $Na_2CO_3$ (0.068 g, 0.644 mmol), and NaI (0.097 g, 0.644 mmol).

After stirring 12 hours at room temperature, the reaction mixture was concentrated under reduced pressure. The residue was dissolved in $CH_2Cl_2$ (1 mL) followed by an addition of TFA (0.3 mL) and the reaction mixture was stirred for 3 hours. The reaction mixture was concentrated, and the residue was purified by chromatography (silica, EtOAc: hexanes, 2:1) to afford the title compound as a brown solid. $^1$H NMR (400 MHz, $CD_3OD$) δ (ppm): 8.21 (d, 1H, J=8.4 Hz), 7.88 (s, 1H), 7.86 (d, 1H, J=8.8 Hz), 7.88 (t, 1H, J=7.4 Hz), 7.71 (t, 1H, J=8.4 Hz), 7.63 (d, 1H, J=10 Hz), 7.49 (d, 1H, J=7.2 Hz), 7.38 (t, 2H, J=8.0 Hz), 7.16 (d, 2H, J=8.8 Hz), 7.08 (t, 1H, J=7.8 Hz), 5.66 (s, 2H), 2.77 (s, 3H). Mass Spectrum (LCMS, ESI pos.) Calcd. For $C_{21}H_{19}N_2O_3S$: 379.5 (M+H), Found 379.2.

The free base was converted to the disodium salt by adding two equivalents of a 0.5M NaOMe solution in methanol.

Using the procedures described in Example 3, and reagents, starting materials and conditions known to those skilled in the art, the following compounds representative of the present invention were prepared:

| Cpd | Name and Data |
|---|---|
| 54 | 2-(2-fluoro-phenoxymethyl)-5-(2-methanesulfonyl-phenyl)-1H-benzoimidazole<br>$^1$H NMR (400 MHz, CD$_3$OD) δ (ppm): 8.19 (dd, 1H, J = 7.6 Hz, J = 1.6 Hz), 7.73 (td, 1H, J = 7.6 Hz, J = 1.6 Hz), 7.70-7.64 (m, 2H), 7.63 (td, 1H, J = 8.0 Hz, J = 1.6 Hz), 7.48 (dd, 1H, J = 7.6 Hz, J = 1.2 Hz), 7.34 (d, 1H, J = 8.4 Hz), 7.23 (td, 1H, J = 8.4 Hz, J = 1.6 Hz), 7.17-7.08 (m, 2H), 7.02-6.96 (m, 1H), 5.42 (s, 2H), 2.65 (s, 3H). Mass Spectrum (LCMS, ESI pos.) Calcd. For C$_{21}$H$_{18}$FN$_2$O$_3$S: 397.4 (M + H), Found 397.2. |
| 55 | 2-(3-fluoro-phenoxymethyl)-5-(2-methanesulfonyl-phenyl)-1H-benzoimidazole<br>$^1$H NMR (400 MHz, CD$_3$OD) δ (ppm): 8.19 (dd, 1H, J = 8.0 Hz, J = 1.6 Hz), 7.74 (td, 1H, J = 7.6 Hz, J = 1.6 Hz), 7.73-7.67 (m, 2H), 7.64 (td, 1H, J = 8.0 Hz, J = 1.2 Hz), 7.48 (dd, 1H, J = 7.2 Hz, J = 1.2 Hz), 7.34-7.29 (m, 2H), 6.94 (dd, 1H, J = 8.4 Hz, J = 2.0 Hz), 6.88 (dt, 1H, J = 10.8 Hz, J = 2.2 Hz), 6.77-6.72 (m, 1H), 5.38 (s, 2H), 2.66 (s, 3H). Mass Spectrum (LCMS, ESI pos.) Calcd. For C$_{21}$H$_{18}$FN$_2$O$_3$S: 397.4 (M + H), Found 397.2. |
| 56 | 2-(4-fluoro-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.87 (s, 1H), 7.85 (d, 1H, J = 8.4 Hz), 7.78 (td, 1H, J = 7.2 Hz, J = 1.2 Hz), 7.71 (td, 1H, J = 7.6 Hz, J = 1.2 Hz), 7.62 (dd, 1H, J = 8.0 Hz, J = 1.2 Hz), 7.49 (dd, 1H, J = 7.6 Hz, J = 1.2 Hz), 7.18-7.09 (m, 4H), 5.62 (s, 2H), 2.77 (s, 3H). Mass Spectrum (LCMS, ESI pos.) Calcd. For C$_{21}$H$_{18}$FN$_2$O$_3$S: 397.4 (M + H), Found 397.2. |
| 57 | 2-(2-chloro-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.4 Hz, J = 1.2 Hz), 7.87 (s, 1H), 7.85 (d, 1H, J = 8.4 Hz), 7.78 (td, 1H, J = 7.2 Hz, J = 1.6 Hz), 7.70 (td, 1H, J = 7.6 Hz, J = 1.6 Hz), 7.61 (dd, 1H, J = 8.8 Hz, J = 1.6 Hz), 7.50-7.46 (m, 2H), 7.36-7.27 (m, 2H), 7.09 (td, 1H, J = 7.6 Hz, J = 1.6 Hz), 5.67 (s, 2H), 2.76 (s, 3H). Mass Spectrum (LCMS, ESI pos.) Calcd. For C$_{21}$H$_{18}$ClN$_2$O$_3$S: 413.9 (M + H), Found 413.2. |
| 58 | 2-(3-chloro-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.4 Hz, J = 1.2 Hz), 7.88 (s, 1H), 7.86 (d, 1H, J = 8.8 Hz), 7.78 (td, 1H, J = 7.2 Hz, J = 1.6 Hz), 7.71 (td, 1H, J = 7.6 Hz, J = 1.6 Hz), 7.62 (dd, 1H, J = 8.0 Hz, J = 1.2 Hz), 7.49 (dd, 1H, J = 7.2 Hz, J = 1.2 Hz), 7.37 (t, 1H, J = 8.2 Hz), 7.23 (t, 1H, J = 2.2 Hz), 7.11 (dt, 2H, J = 8.8 Hz, J = 2.0 Hz), 5.67 (s, 2H), 2.76 (s, 3H). Mass Spectrum (LCMS, ESI pos.) Calcd. For C$_{21}$H$_{18}$ClN$_2$O$_3$S: 413.9 (M + H), Found 413.2. |
| 59 | 2-(4-chloro-phenoxymethyl)-5-(2-methanesulfonyl-phenyl)-1H-benzoimidazole<br>$^1$H NMR (400 MHz, CD$_3$OD) δ (ppm): 8.19 (dd, 1H, J = 7.6 Hz, J = 1.2 Hz), 7.73 (td, 1H, J = 7.6 Hz, J = 1.6 Hz), 7.70-7.67 (m, 2H), 7.63 (td, 1H, J = 8.0 Hz, J = 1.2 Hz), 7.47 (dd, 1H, J = 8.0 Hz, J = 1.2 Hz), 7.33 (d, 1H, J = 10.0 Hz), 7.30 (dt, 2H, J = 9.2 Hz, J = 3.6 Hz), 7.08 (dt, 2H, J = 9.2 Hz, 2.8 Hz), 5.36 (s, 2H), 2.65 (s, 3H). Mass Spectrum (LCMS, ESI pos.) Calcd. For C$_{21}$H$_{18}$ClN$_2$O$_3$S: 413.9 (M + H), Found 413.2. |
| 60 | 2-(3-bromo-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.88 (d, 1H, J = 0.8 Hz), 7.86 (d, 1H, J = 8.8 Hz), 7.78 (td, 1H, J = 8.2 Hz, J = 1.6 Hz), 7.71 (td, 1H, J = 8.4 Hz, J = 1.2 Hz), 7.62 (dd, 1H, J = 8.4 Hz, J = 1.6 Hz), 7.49 (dd, 1H, J = 7.2 Hz, J = 1.2 Hz), 7.39 (t, 1H, J = 2.2 Hz), 7.33-7.24 (m, 2H), 7.15 (ddd, 1H, J = 8.2 Hz, J = 2.4 Hz, J = 1.2 Hz), 5.67 (s, 2H), 2.77 (s, 3H). Mass Spectrum (LCMS, ESI pos.) Calcd. For C$_{21}$H$_{18}$BrN$_2$O$_3$S: 398.4 (M + H), Found 398.1. |
| 61 | 2-(4-bromo-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.4 Hz, J = 1.2 Hz), 7.88 (d, 1H, J = 1.2 Hz), 7.85 (d, 1H, J = 9.2 Hz), 7.78 (td, 1H, J = 7.4 Hz, J = 1.2 Hz), 7.70 (td, 1H, J = 8.4 Hz, J = 1.2 Hz), 7.62 (dd, 1H, J = 8.0 Hz, J = 1.6 Hz), 7.52-7.48 (m, 3H), 7.10 (dt, 2H, J = 9.2 Hz, J = 2.0 Hz), 5.65 (s, 2H), 2.77 (s, 3H). Mass Spectrum (LCMS, ESI pos.) Calcd. For C$_{21}$H$_{18}$FN$_2$O$_3$S: 398.4 (M + H), Found 398.1. |
| 62 | 2-(2,4-difluoro-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.6 Hz), 7.87 (d, 1H, J = 0.8 Hz), 7.85 (d, 1H, J = 8.8 Hz), 7.78 (td, 1H, J = 8.2 Hz, J = 1.2 Hz), 7.70 (td, 1H, J = 8.4 Hz, J = 1.6 Hz), 7.61 (dd, 1H, J = 8.4 Hz, J = 1.6 Hz), 7.49 (dd, 1H, J = 7.6 Hz, J = 1.2 Hz), 7.36-7.30 (m, 1H), 7.14-7.09 (m, 1H), 6.99-6.94 (m, 1H), 5.66 (s, 2H), 2.77 (s, 3H). Mass Spectrum (LCMS, ESI pos.) Calcd. For C$_{21}$H$_{17}$F$_2$N$_2$O$_3$S: 415.4 (M + H), Found 415.2. |
| 63 | 2-(3,4-difluoro-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 9.2 Hz, J = 1.2 Hz), 7.88 (d, 1H, J = 0.8 Hz), 7.86 (d, 1H, J = 8.4 Hz), 7.79 (td, 1H, J = 8.2 Hz, J = 1.2 Hz), 7.71 (td, 1H, J = 8.4 Hz, J = 1.2 Hz), 7.63 (dd, 1H, J = 8.0 Hz, J = 1.6 Hz), 7.49 (dd, 1H, J = 7.2 Hz, J = 1.2 Hz), 7.29 (q, 1H, J = 9.5 Hz), 7.16 (ddd, 1H, J = 11.6 Hz, J = 6.4 Hz, J = 3.2 Hz), 6.99-6.95 (m, 1H), 5.65 (s, 2H), 2.77 (s, 3H). Mass Spectrum (LCMS, ESI pos.) Calcd. For C$_{21}$H$_{17}$F$_2$N$_2$O$_3$S: 415.4 (M + H), Found 415.2. |
| 64 | 2-(2,4-dichloro-phenoxymethyl)-5-(2-methanesulfonyl-phenyl)-1H-benzoimidazole<br>$^1$H NMR (400 MHz, CD$_3$OD) δ (ppm): 8.20 (dd, 1H, J = 8.0 Hz, J = 1.2 Hz), 7.88 (s, 1H), 7.86 (d, 1H, J = 8.4 Hz), 7.78 (td, 1H, J = 8.2 Hz, J = 1.6 Hz), 7.70 (td, 1H, |

| Cpd | Name and Data |
|---|---|
| | J = 8.4 Hz, J = 1.6 Hz), 7.62 (dd, 1H, J = 8.4 Hz, J = 1.2 Hz), 7.53 (d, 1H, J = 2.0 Hz), 7.49 (dd, 1H, J = 7.2 Hz, J = 1.2 Hz), 7.36 (dd, 1H, J = 8.8 Hz, J = 2.4 Hz), 7.29 (d, 1H, J = 9.2 Hz), 5.69 (s, 2H), 2.77 (s, 3H). Mass Spectrum (LCMS, ESI pos.) Calcd. For $C_{21}H_{16}Cl_2N_2O_3S$: 448.3 (M), Found 447.1. |
| 65 | 2-(3,4-dichloro-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.85 (d, 1H, J = 1.2 Hz), 7.82 (d, 1H, J = 8.8 Hz), 7.78 (td, 1H, J = 8.2 Hz, J = 1.2 Hz), 7.70 (td, 1H, J = 8.4 Hz, J = 1.2 Hz), 7.57 (dd, 1H, J = 8.4 Hz, J = 1.6 Hz), 7.52 (d, 1H, J = 9.2 Hz), 7.49 (dd, 1H, J = 7.6 Hz, J = 1.2 Hz), 7.39 (d, 1H, J = 2.8 Hz), 7.12 (dd, 1H, J = 8.4 Hz, J = 2.8 Hz), 5.62 (s, 2H), 2.75 (s, 3H). Mass Spectrum (LCMS, ESI pos.) Calcd. For $C_{21}H_{16}Cl_2N_2O_3S$: 448.3 (M), Found 447.2. |
| 66 | 2-(4-chloro-2-fluoro-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.84 (s, 1H), 7.82 (d, 1H, J = 8.4 Hz), 7.78 (td, 1H, J = 8.4 Hz, J = 1.2 Hz), 7.70 (td, 1H, J = 8.4 Hz, J = 1.6 Hz), 7.57 (dd, 1H, J = 8.4 Hz, J = 1.6 Hz), 7.49 (dd, 1H, J = 7.6 Hz, J = 1.2 Hz), 7.33 (dd, 1H, J = 10.4 Hz, J = 2.4 Hz), 7.30 (t, 1H, J = 8.4 Hz), 7.20 (ddd, 1H, J = 8.8 Hz, J = 2.4 Hz, J = 1.6 Hz), 5.64 (s, 2H), 2.75 (s, 3H). Mass Spectrum (LCMS, ESI pos.) Calcd. For $C_{21}H_{17}ClFN_2O_3S$: 431.9 (M + H), Found 431.2. |
| 67 | 2-(3-chloro-4-fluoro-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.4 Hz, J = 1.2 Hz), 7.86 (s, 1H), 7.84 (d, 1H, J = 8.0 Hz), 7.78 (td, 1H, J = 8.2 Hz, J = 1.6 Hz), 7.70 (td, 1H, J = 8.4 Hz, J = 1.6 Hz), 7.60 (dd, 1H, J = 8.8 Hz, J = 1.6 Hz), 7.49 (dd, 1H, J = 7.6 Hz, J = 1.2 Hz), 7.34 (dd, 1H, J = 6.0 Hz, J = 3.2 Hz), 7.27 (t, 1H, J = 8.8 Hz), 7.13 (dt, 1H, J = 8.4 Hz, J = 3.2 Hz), 5.63 (s, 2H), 2.76 (s, 3H). Mass Spectrum (LCMS, ESI pos.) Calcd. For $C_{21}H_{17}ClFN_2O_3S$: 431.9 (M + H), Found 431.2. |
| 68 | 5-(2-methanesulfonyl-phenyl)-2-(3,4,5-trifluoro-phenoxymethyl)-1H-benzoimidazole<br>$^1$H NMR (400 MHz, CD$_3$OD) δ (ppm): 8.21 (dd, 1H, J = 8.0 Hz, J = 1.2 Hz), 7.87 (s, 1H), 7.85 (d, 1H, J = 8.4 Hz), 7.78 (td, 1H, J = 8.2 Hz, J = 1.6 Hz), 7.70 (td, 1H, J = 8.4 Hz, J = 1.2 Hz), 7.61 (dd, 1H, J = 8.8 Hz, J = 1.2 Hz), 7.05-7.01 (m, 2H), 5.64 (s, 2H), 2.76 (s, 3H). Mass Spectrum (LCMS, ESI pos.) Calcd. For $C_{21}H_{16}F_3N_2O_3S$: 433.4 (M + H), Found 433.2. |
| 69 | 5-(2-methanesulfonyl-phenyl)-2-(2,4,5-trifluoro-phenoxymethyl)-1H-benzoimidazole<br>$^1$H NMR (400 MHz, CD$_3$OD) δ (ppm): 8.21 (dd, 1H, J = 8.0 Hz, J = 1.2 Hz), 7.86 (d, 1H, J = 1.6 Hz), 7.83 (d, 1H, J = 8.4 Hz), 7.78 (td, 1H, J = 8.4 Hz, J = 1.2 Hz), 7.70 (td, 1H, J = 7.6 Hz, J = 1.2 Hz), 7.59 (dd, 1H, J = 8.4 Hz, J = 1.2 Hz), 7.49 (dd, 1H, J = 7.6 Hz, J = 1.2 Hz), 7.49 (dt, 1H, J = 11.2 Hz, J = 7.8 Hz), 7.37-7.30 (m, 1H), 5.65 (s, 2H), 2.76 (s, 3H). Mass Spectrum (LCMS, ESI pos.) Calcd. For $C_{21}H_{16}F_3N_2O_3S$: 433.4 (M + H), Found 433.2. |
| 70 | 5-(2-methanesulfonyl-phenyl)-2-(2,3,4-trifluoro-phenoxymethyl)-1H-benzoimidazole<br>$^1$H NMR (400 MHz, CD$_3$OD) δ (ppm): 8.21 (dd, 1H, J = 8.4 Hz, J = 1.6 Hz), 7.88 (d, 1H, J = 0.8 Hz), 7.85 (d, 1H, J = 8.8 Hz), 7.78 (td, 1H, J = 8.2 Hz, J = 1.6 Hz), 7.70 (td, 1H, J = 8.4 Hz, J = 1.6 Hz), 7.62 (dd, 1H, J = 8.4 Hz, J = 1.6 Hz), 7.49 (dd, 1H, J = 8.8 Hz, J = 1.6 Hz), 7.16-7.12 (m, 2H), 5.71 (s, 2H), 2.77 (s, 3H). Mass Spectrum (LCMS, ESI pos.) Calcd. For $C_{21}H_{16}F_3N_2O_3S$: 433.4 (M + H), Found 433.2. |
| 71 | 2-(2-fluoro-3-trifluoromethyl-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz), 7.86 (s, 1H), 7.83 (d, 1H, J = 8.4 Hz), 7.78 (t, 1H, J = 7.4 Hz), 7.70 (t, 1H, J = 7.6 Hz), 7.63-7.57 (m, 2H), 7.49 (d, 1H, J = 7.2 Hz), 7.40-7.33 (m, 2H), 5.74 (s, 2H), 2.75 (s, 3H). Mass Spectrum (LCMS, ESI pos.) Calcd. For $C_{24}H_{20}F_4N_3O_3S$: 506.5 (M + MeCN + H), Found 506.2. |
| 72 | 2-(4-fluoro-3-trifluoromethyl-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.4 Hz, J = 1.2 Hz), 7.88 (d, 1H, J = 5.6 Hz), 7.87 (dd, 1H, J = 13.2 Hz, J = 0.8 Hz), 7.79 (td, 1H, J = 8.4 Hz, J = 1.6 Hz), 7.71 (td, 1H, J = 8.4 Hz, J = 1.6 Hz), 7.62 (dd, 1H, J = 8.0 Hz, J = 1.6 Hz), 7.502-7.44 (m, 3H), 7.38 (t, 1H, J = 9.2 Hz), 5.71 (s, 2H), 2.77 (s, 3H). Mass Spectrum (LCMS, ESI pos.) Calcd. For $C_{24}H_{20}F_4N_3O_3S$: 506.5 (M + MeCN + H), Found 506.2. |
| 73 | 2-(3,5-bis-trifluoromethyl-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.6 Hz), 7.88 (d, 1H, J = 0.8 Hz), 7.85 (d, 1H, J = 8.8 Hz), 7.80-7.68 (m, 3H), 7.70 (td, 2H, J = 8.4 Hz, J = 1.2 Hz), 7.60 (dd, 1H, J = 8.8 Hz, J = 1.6 Hz), 7.50 (dd, 1H, J = 7.2 Hz, J = 1.2 Hz), 5.81 (s, 2H), 2.76 (s, 3H). Mass Spectrum (LCMS, ESI pos.) Calcd. For $C_{25}H_{20}F_6N_3O_3S$: 556.6 (M + MeCN + H), Found 556.2. |
| 74 | 5-(2-methanesulfonyl-phenyl)-2-(2-trifluoromethyl-phenoxymethyl)-1H-benzoimidazole<br>$^1$H NMR (400 MHz, CD$_3$OD) δ (ppm): 8.19 (dd, 1H, J = 7.6 Hz, J = 1.2 Hz), 7.76-7.72 (m, 2H), 7.69 (d, 1H, J = 8.8 Hz), 7.66-7.59 (m, 3H), 7.48 (dd, 1H, J = 7.2 Hz, |

| Cpd | Name and Data |
|---|---|
| | J = 1.2 Hz), 7.40-7.36 (m, 2H), 7.14 (t, 1H, J = 7.6 Hz), 5.55 (s, 2H), 2.66 (s, 3H). Mass Spectrum (LCMS, ESI pos.) Calcd. For $C_{22}H_{18}F_3N_2O_3S$: 447.5 (M + H), Found 447.2. |
| 75 | 5-(2-methanesulfonyl-phenyl)-2-(3-trifluoromethyl-phenoxymethyl)-1H-benzoimidazole<br>$^1$H NMR (400 MHz, CD$_3$OD) δ (ppm): 8.21 (dd, 1H, J = 8.0 Hz, J = 1.2 Hz), 7.88 (d, 1H, J = 1.2 Hz), 7.86 (d, 1H, J = 8.8 Hz), 7.78 (td, 1H, J = 8.4 Hz, J = 1.2 Hz), 7.70 (td, 1H, J = 8.4 Hz, J = 1.6 Hz), 7.73-7.58 (m, 2H), 7.50-7.39 (m, 4H), 5.73 (s, 2H), 2.76 (s, 3H). Mass Spectrum (LCMS, ESI pos.) Calcd. For $C_{24}H_{21}F_3N_3O_3S$: 488.6 (M + MeCN + H), Found 488.2. |
| 76 | 5-(2-methanesulfonyl-phenyl)-2-p-tolyloxymethyl-1H-benzoimidazole<br>$^1$H NMR (400 MHz, CD$_3$OD) δ (ppm): 8.21 (dd, 1H, J = 8.0 Hz, J = 1.2 Hz), 7.88 (s, 1H), 7.85 (d, 1H, J = 8.0 Hz), 7.79 (td, 1H, J = 8.2 Hz, J = 1.6 Hz), 7.71 (td, 1H, J = 8.4 Hz, J = 1.2 Hz), 7.63 (dd, 1H, J = 8.0 Hz, J = 1.6 Hz), 7.49 (dd, 1H, J = 7.2 Hz, J = 1.2 Hz), 7.18 (d, 2H, J = 8.0 Hz), 7.03 (dt, 2H, J = 9.2 Hz, J = 2.4 Hz), 5.62 (s, 2H), 2.77 (s, 3H), 2.30 (s, 3H). Mass Spectrum (LCMS, ESI pos.) Calcd. For $C_{22}H_{21}N_2O_3S$: 393.5 (M + H), Found 393.2. |
| 77 | 2-(4-isopropyl-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.88 (d, 1H, J = 0.8 Hz), 7.86 (d, 1H, J = 9.2 Hz), 7.79 (td, 1H, J = 8.2 Hz, J = 1.6 Hz), 7.71 (td, 1H, J = 8.4 Hz, J = 1.2 Hz), 7.63 (dd, 1H, J = 8.4 Hz, J = 1.2 Hz), 7.49 (dd, 1H, J = 7.2 Hz, J = 1.2 Hz), 7.03 (dt, 2H, J = 8.8 Hz, J = 2.4 Hz), 7.07 (dt, 2H, J = 9.2 Hz, J = 2.8 Hz), 5.63 (s, 2H), 2.89 (m, 1H), 2.77 (s, 3H), 2.30 (s, 3H), 1.23 (d, 6H, J = 7.2 Hz). Mass Spectrum (LCMS, ESI pos.) Calcd. For $C_{26}H_{28}N_3O_3S$: 462.6 (M + MeCN + H), Found 462.2. |
| 78 | 2-(4-tert-butyl-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.4 Hz, J = 1.2 Hz), 7.88 (d, 1H, J = 0.8 Hz), 7.86 (d, 1H, J = 9.2 Hz), 7.79 (td, 1H, J = 8.2 Hz, J = 1.6 Hz), 7.71 (td, 1H, J = 8.4 Hz, J = 1.6 Hz), 7.63 (dd, 1H, J = 8.8 Hz, J = 1.2 Hz), 7.49 (dd, 1H, J = 7.6 Hz, J = 1.2 Hz), 7.41 (dt, 2H, J = 9.2 Hz, J = 2.4 Hz), 7.07 (dt, 2H, J = 8.8 Hz, J = 2.0 Hz), 5.64 (s, 2H), 2.77 (s, 3H), 1.31 (s, 9H). Mass Spectrum (LCMS, ESI pos.) Calcd. For $C_{27}H_{30}N_3O_3S$: 476.7 (M + MeCN + H), Found 476.2. |
| 79 | 1-{4-[5-(2-methanesulfonyl-phenyl)-1H-benzoimidazol-2-ylmethoxy]-phenyl}-ethanone<br>$^1$H NMR (400 MHz, CD$_3$OD) δ (ppm): 8.21 (dd, 1H, J = 8.0 Hz, J = 1.2 Hz), 8.06 (dt, 2H, J = 8.8 Hz, J = 2.4 Hz), 7.87 (d, 1H, J = 0.8 Hz), 7.84 (d, 1H, J = 8.8 Hz), 7.78 (td, 1H, J = 7.4 Hz, J = 1.6 Hz), 7.70 (td, 1H, J = 8.4 Hz, J = 1.2 Hz), 7.60 (dd, 1H, J = 8.8 Hz, J = 1.6 Hz), 7.49 (dd, 1H, J = 7.2 Hz, J = 1.2 Hz), 7.25 (dt, 2H, J = 9.2 Hz, J = 2.0 Hz), 5.73 (s, 2H), 2.76 (s, 3H), 2.58 (s, 3H). Mass Spectrum (LCMS, ESI pos.) Calcd. For $C_{23}H_{21}N_2O_4S$: 421.5 (M + H), Found 421.2. |
| 80 | 5-(2-methanesulfonyl-phenyl)-2-(naphthalen-2-yloxymethyl)-1H-benzoimidazole<br>$^1$H NMR (400 MHz, CD$_3$OD) δ (ppm): 8.21 (dd, 1H, J = 8.0 Hz, J = 1.2 Hz), 7.90 (s, 2H), 7.87 (t, 1H, J = 4.4 Hz), 7.83 (d, 2H, J = 13.6 Hz), 7.79 (td, 1H, J = 8.2 Hz, J = 1.6 Hz), 7.71 (td, 1H, J = 8.4 Hz, J = 1.2 Hz), 7.63 (dd, 1H, J = 10.0 Hz, J = 1.6 Hz), 7.50-7.46 (m, 3H), 7.41-7.37 (m, 2H), 5.78 (s, 2H), 2.78 (s, 3H). Mass Spectrum (LCMS, ESI pos.) Calcd. For $C_{25}H_{21}N_2O_3S$: 429.5 (M + H), Found 429.2. |
| 81 | 2-(4-ethoxy-phenoxymethyl)-5-(2-methanesulfonyl-phenyl)-1H-benzoimidazole<br>$^1$H NMR (400 MHz, CD$_3$OD) δ (ppm): 8.19 (dd, 1H, J = 9.2 Hz, J = 1.2 Hz), 7.32 (td, 1H, J = 8.4 Hz, J = 1.6 Hz), 7.69-7.61 (m, 3H), 7.47 (dd, 1H, J = 8.8 Hz, J = 1.2 Hz), 7.33 (dd, 1H, J = 8.8 Hz, J = 1.6 Hz), 7.00 (dt, 2H, J = 9.2 Hz, J = 2.4 Hz), 7.07 (dt, 2H, J = 9.2 Hz, J = 2.4 Hz), 5.30 (s, 2H), 3.96 (q, 1H, J = 6.9 Hz), 2.65 (s, 3H), 1.35 (t, 3H, J = 6.8 Hz). Mass Spectrum (LCMS, ESI pos.) Calcd. For $C_{23}H_{23}N_2O_4S$: 423.5 (M + H), Found 423.2. |
| 82 | 5-(2-methanesulfonyl-phenyl)-2-(4-trifluoromethanesulfide-phenoxymethyl)-1H-benzoimidazole<br>$^1$H NMR (400 MHz, CD$_3$OD) δ (ppm): 8.21 (d, 1H, J = 8.4 Hz), 7.88 (s, 1H), 7.86 (d, 1H, J = 8.8 Hz), 7.79 (t, 1H, J = 7.4 Hz), 7.74-7.69 (m, 3H), 7.62 (d, 1H, J = 8.4 Hz), 7.49 (d, 1H, J = 7.2 Hz), 7.29 (d, 2H, J = 9.2 Hz), 5.73 (s, 2H), 2.77 (s, 3H). Mass Spectrum (LCMS, ESI pos.) Calcd. For $C_{24}H_{21}F_3N_3O_3S_2$: 520.5 (M + MeCN + H), Found 520.1. |
| 83 | 4-[5-(2-methanesulfonyl-phenyl)-1H-benzoimidazol-2-ylmethoxy]-benzonitrile<br>$^1$H NMR (400 MHz, CD$_3$OD) δ (ppm): 8.21 (dd, 1H, J = 8.0 Hz, J = 1.2 Hz), 7.86 (d, 1H, J = 1.2 Hz), 7.84 (d, 1H, J = 8.8 Hz), 7.80-7.75 (m, 3H), 7.70 (td, 1H, J = 8.4 Hz, J = 1.2 Hz), 7.60 (dd, 1H, J = 8.8 Hz, J = 1.6 Hz), 7.49 (dd, 1H, J = 7.2 Hz, J = 1.2 Hz), 7.32 (dt, 2H, J = 8.8 Hz, J = 2.4 Hz), 5.73 (s, 2H), 2.76 (s, 3H). Mass Spectrum (LCMS, ESI pos.) Calcd. For $C_{22}H_{18}N_3O_3S$: 404.5 (M + H), Found 404.2. |
| 84 | 5-(2-methanesulfonyl-phenyl)-2-(4-trifluoromethoxy-phenoxymethyl)-1H-benzoimidazole<br>$^1$H NMR (400 MHz, CD$_3$OD) δ (ppm): 8.21 (dd, 1H, J = 8.0 Hz, J = 1.2 Hz), 7.86 (d, 1H, J = 1.2 Hz), 7.83 (d, 1H, J = 8.4 Hz), 7.78 (td, 1H, J = 8.2 Hz, J = 1.6 Hz), 7.70 (td, 1H, J = 8.4 Hz, J = 1.2 Hz), 7.59 (dd, 1H, J = 10.0 Hz, J = 1.6 Hz), 7.50-7.46 (m, |

| Cpd | Name and Data |
|---|---|
| | 2H), 7.17 (ddd, 1H, J = 8.8 Hz, J = 2.4 Hz, J = 0.8 Hz), 7.11 (s, 1H), 7.02 (d, 1H, J = 11.6 Hz), 5.66 (s, 2H), 2.76 (s, 3H). Mass Spectrum (LCMS, ESI pos.) Calcd. For $C_{24}H_{21}N_2F_3O_4S$: 504.5 (M + H), Found 504.2. |
| 85 | 2-(4-methanesulfonyl-phenoxymethyl)-5-(2-methanesulfonyl-phenyl)-1H-benzoimidazole<br>$^1$H NMR (400 MHz, CD$_3$OD) δ (ppm): 8.20 (d, 1H, J = 8.0 Hz), 7.98 (s, 1H), 7.94 (d, 1H, J = 8.8 Hz), 7.77-7.63 (m, 4H), 7.48 (d, 1H, J = 7.6 Hz), 7.39 (d, 1H, J = 8.4 Hz), 7.33 (d, 2H, J = 8.8 Hz), 5.55 (s, 2H), 3.09 (s, 3H), 2.67 (s, 3H). Mass Spectrum (LCMS, ESI pos.) Calcd. For $C_{24}H_{24}N_3O_5S_2$: 498.5 (M + MeCN + H), Found 498.2. |
| 86 | 5-(2-methanesulfonyl-phenyl)-2-(4-trifluoromethanesulfonyl-phenoxymethyl)-1H-benzoimidazole<br>$^1$H NMR (400 MHz, CD$_3$OD) δ (ppm): 8.21 (dd, 1H, J = 8.0 Hz, J = 1.2 Hz), 8.12 (d, 2H, J = 8.8 Hz), 7.89 (d, 1H, J = 0.8 Hz), 7.86 (d, 1H, J = 8.4 Hz), 7.78 (td, 1H, J = 8.2 Hz, J = 1.6 Hz), 7.70 (td, 1H, J = 8.4 Hz, J = 1.2 Hz), 7.61 (dd, 1H, J = 10.0 Hz, J = 1.6 Hz), 7.53 (dt, 2H, J = 9.2 Hz, J = 2.6 Hz), 7.49 (dd, 1H, J = 7.2 Hz, J = 1.2 Hz), 5.84 (s, 2H), 2.76 (s, 3H). Mass Spectrum (LCMS, ESI pos.) Calcd. For $C_{24}H_{21}F_3N_3O_5S_2$: 552.5 (M + MeCN + H), Found 552.1. |
| 87 | 5-(2-methanesulfonyl-phenyl)-2-(5,6,7,8-tetrahydro-naphthalen-2-yloxymethyl)-1H-benzoimidazole<br>$^1$H NMR (400 MHz, CD$_3$OD) δ (ppm): 8.21 (dd, 1H, J = 8.0 Hz, J = 1.2 Hz), 7.87 (s, 1H), 7.85 (d, 1H, J = 8.4 Hz), 7.78 (td, 1H, J = 8.2 Hz, J = 1.2 Hz), 7.70 (td, 1H, J = 8.6 Hz, J = 1.6 Hz), 7.62 (dd, 1H, J = 10.0 Hz, J = 1.6 Hz), 7.49 (dd, 1H, J = 8.8 Hz, J = 1.2 Hz), 7.03 (d, 1H, J = 8.4 Hz), 6.87-6.83 (m, 2H), 5.59 (s, 2H), 2.77 (s, 3H), 2.74 (d, 4H, J = 23.6 Hz), 1.79 (quin, 4H, J = 3.3 Hz). Mass Spectrum (LCMS, ESI pos.) Calcd. For $C_{27}H_{28}N_3O_3S$: 474.6 (M + MeCN + H), Found 474.3. |
| 88 | 3-{4-[5-(2-methanesulfonyl-phenyl)-1H-benzoimidazol-2-ylmethoxy]-phenyl}-propionic acid methyl ester<br>$^1$H NMR (400 MHz, CD$_3$OD) δ (ppm): 8.21 (dd, 1H, J = 8.0 Hz, J = 1.2 Hz), 7.88 (d, 1H, J = 1.2 Hz), 7.85 (d, 1H, J = 8.8 Hz), 7.79 (td, 1H, J = 8.2 Hz, J = 1.6 Hz), 7.71 (td, 1H, J = 8.4 Hz, J = 1.2 Hz), 7.63 (dd, 1H, J = 10.0 Hz, J = 1.6 Hz), 7.49 (dd, 1H, J = 7.2 Hz, J = 1.2 Hz), 7.23 (dt, 2H, J = 8.4 Hz, J = 2.0 Hz), 7.07 (dt, 2H, J = 8.8 Hz, J = 2.0 Hz), 5.63 (s, 2H), 3.62 (s, 3H), 2.89 (t, 2H, J = 7.6 Hz), 2.77 (s, 3H), 2.61 (t, 2H, J = 7.4 Hz). Mass Spectrum (LCMS, ESI pos.) Calcd. For $C_{25}H_{25}N_2O_5S$: 465.5 (M + H), Found 465.2. |
| 89 | 2-(2,4-dimethyl-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.88 (dd, 1H, J = 2.4 Hz, J = 0.8 Hz), 7.86 (d, 1H, J = 8.4 Hz), 7.78 (td, 1H, J = 8.2 Hz, J = 1.6 Hz), 7.71 (td, 1H, J = 8.4 Hz, J = 1.2 Hz), 7.63 (dd, 1H, J = 9.6 Hz, J = 1.6 Hz), 7.49 (dd, 1H, J = 7.2 Hz, J = 1.2 Hz), 7.04-6.98 (m, 2H), 6.91 (d, 1H, J = 8.0 Hz), 7.11 (s, 1H), 7.02 (d, 1H, J = 11.6 Hz), 5.59 (s, 2H), 2.77 (s, 3H), 2.31 (s, 3H), 2.26 (s, 2H). Mass Spectrum (LCMS, ESI pos.) Calcd. For $C_{23}H_{23}N_2O_3S$: 407.5 (M + H), Found 407.2. |
| 90 | 2-(3,5-dimethyl-phenoxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.89 (s, 1H), 7.86 (d, 1H, J = 8.8 Hz), 7.79 (td, 1H, J = 8.2 Hz, J = 1.2 Hz), 7.71 (td, 1H, J = 8.4 Hz, J = 1.2 Hz), 7.63 (dd, 1H, J = 10.4 Hz, J = 1.6 Hz), 7.49 (dd, 1H, J = 8.8 Hz, J = 1.2 Hz), 6.77 (s, 2H), 6.74 (s, 1H), 5.62 (s, 2H), 2.78 (s, 3H), 2.31 (s, 6H). Mass Spectrum (LCMS, ESI pos.) Calcd. For $C_{24}H_{23}N_2O_3S$: 407.5 (M + H), Found 407.2. |
| 91 | 2-(indan-5-yloxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.88 (s, 1H, J = 1.2 Hz), 7.86 (d, 1H, J = 8.8 Hz), 7.78 (td, 1H, J = 8.2 Hz, J = 1.2 Hz), 7.71 (td, 1H, J = 8.4 Hz, J = 1.6 Hz), 7.63 (dd, 1H, J = 8.4 Hz, J = 1.6 Hz), 7.49 (dd, 1H, J = 7.6 Hz, J = 1.2 Hz), 7.17 (d, 1H, J = 8.0 Hz), 7.02 (d, 1H, J = 2.4 Hz), 6.90 (dd, 1H, J = 8.4, J = 2.8 Hz), 5.62 (s, 2H), 2.88 (dt, 4H, J = 18.4 Hz, J = 7.4 Hz), 2.77 (s, 3H), 2.08 (quin, 2H, J = 7.4 Hz). Mass Spectrum (LCMS, ESI pos.) Calcd. For $C_{24}H_{23}N_2O_3S$: 419.5 (M + H), Found 419.2. |
| 92 | 2-(benzo[1,3]dioxol-5-yloxymethyl)-5-(2-methanesulfonyl-phenyl)-1H-benzoimidazole<br>$^1$H NMR (400 MHz, CD$_3$OD) δ (ppm): 8.21 (dd, 1H, J = 8.0 Hz, J = 1.2 Hz), 7.87 (d, 1H, J = 1.2 Hz), 7.85 (d, 1H, J = 8.8 Hz), 7.78 (td, 1H, J = 8.2 Hz, J = 1.2 Hz), 7.71 (td, 1H, J = 8.4 Hz, J = 1.6 Hz), 7.62 (dd, 1H, J = 8.4 Hz, J = 1.6 Hz), 7.49 (dd, 1H, J = 7.2 Hz, J = 1.2 Hz), 6.72 (d, 1H, J = 12.0 Hz), 6.76 (d, 1H, J = 6.4 Hz), 6.58 (dd, 1H, J = 8.8 Hz, J = 2.4 Hz), 5.94 (s, 2H), 5.57 (s, 2H), 2.77 (s, 3H). Mass Spectrum (LCMS, ESI pos.) Calcd. For $C_{22}H_{19}N_2O_5S$: 423.5 (M + H), Found 423.1. |
| 93 | 2-(3,5-dichloro-phenoxymethyl)-5-(2-methanesulfonyl-phenyl)-1H-benzoimidazole<br>$^1$H NMR (400 MHz, CD$_3$OD) δ (ppm): 8.21 (d, 1H, J = 8.0 Hz), 7.87 (s, 1H), 7.84 (d, 1H, J = 8.4 Hz), 7.78 (t, 1H, J = 7.6 Hz), 7.70 (t, 1H, J = 7.6 Hz), 7.60 (d, 1H, J = 8.4 Hz), 7.49 (d, 1H, J = 7.2 Hz), 7.21-7.18 (m, 3H), 5.62 (s, 2H), 2.78 (s, 3H), 2.31 (s, 6H). Mass Spectrum (LCMS, ESI pos.) Calcd. For $C_{23}H_{19}Cl_2N_3O_3S$: 488.3 (M + MeCN), Found 488.1. |

-continued

| Cpd | Name and Data |
|---|---|
| 94 | N-{3-[5-(2-methanesulfonyl-phenyl)-1H-benzoimidazol-2-ylmethoxy]-phenyl}-acetamide<br>$^1$H NMR (400 MHz, CD$_3$OD) δ (ppm): 8.19 (dd, 1H, J = 7.6 Hz, J = 1.2 Hz), 7.77 (s, 1H), 7.75-7.72 (m, 2H), 7.66 (td, 1H, J = 8.4 Hz, J = 1.6 Hz), 7.55 (t, 1H, J = 2.2 Hz), 7.46 (td, 1H, J = 9.6 Hz, J = 1.2 Hz), 7.26 (t, 1H, J = 8.2 Hz), 7.08 (dd, 1H, J = 8.0 Hz, J = 1.2 Hz), 6.47 (dd, 1H, J = 8.4 Hz, J = 2.4 Hz), 5.48 (s, 2H), 2.70 (s, 3H), 2.12 (s, 3H). Mass Spectrum (LCMS, ESI pos.) Calcd. For C$_{23}$H$_{22}$N$_3$O$_4$S: 436.5 (M + H), Found 436.2. |
| 95 | N-{4-[5-(2-methanesulfonyl-phenyl)-1H-benzoimidazol-2-ylmethoxy]-phenyl}-acetamide<br>$^1$H NMR (400 MHz, CD$_3$OD) δ (ppm): 8.21 (dd, 1H, J = 7.6 Hz, J = 1.2 Hz), 7.82 (d, 1H, J = 0.8 Hz), 7.89 (d, 1H, J = 8.4 Hz), 7.77 (td, 1H, J = 8.2 Hz, J = 1.6 Hz), 7.68 (td, 1H, J = 8.4 Hz, J = 1.2 Hz), 7.55-7.47 (m, 4H), 7.09 (dt, 2H, J = 8.8 Hz, J = 2.4 Hz), 5.55 (s, 2H), 2.73 (s, 3H), 2.10 (s, 3H). Mass Spectrum (LCMS, ESI pos.) Calcd. For C$_{23}$H$_{22}$N$_3$O$_4$S: 436.5 (M + H), Found 436.2. |
| 96 | 5-(2-methanesulfonyl-phenyl)-2-(4-methoxy-phenoxymethyl)-1H-benzoimidazole<br>$^1$H NMR (400 MHz, CD$_3$OD) δ (ppm): 8.21 (dd, 1H, J = 8.0 Hz, J = 1.2 Hz), 7.88 (d, 1H, J = 2.4 Hz), 7.85 (d, 1H, J = 8.8 Hz), 7.66 (td, 1H, J = 8.2 Hz, J = 1.2 Hz), 7.71 (t, 1H, J = 8.4 Hz, J = 1.2 Hz), 7.62 (dd, 1H, J = 8.0 Hz, J = 1.6 Hz), 7.49 (dd, 1H, J = 7.2 Hz, J = 1.2 Hz), 7.29-7.25 (m, 1H), 6.74-6.71 (m, 2H), 7.66 (ddd, 1H, J = 8.4 Hz, J = 2.4 Hz, J = 0.8 Hz), 5.63 (s, 2H), 3.80 (s, 3H), 2.77 (s, 3H). Mass Spectrum (LCMS, ESI pos.) Calcd. For C$_{22}$H$_{21}$N$_2$O$_4$S: 409.5 (M + H), Found 409.2. |
| 97 | 5-(2-methanesulfonyl-phenyl)-2-(3-methoxy-phenoxymethyl)-1H-benzoimidazole<br>$^1$H NMR (400 MHz, CD$_3$OD) δ (ppm): 8.19 (dd, 1H, J = 8.0 Hz, J = 1.2 Hz), 7.34 (td, 1H, J = 8.2 Hz, J = 1.2 Hz), 7.33-7.65 (m, 2H), 7.64 (td, 1H, J = 8.6 Hz, J = 1.2 Hz), 7.48 (dd, 1H, J = 7.6 Hz, J = 1.2 Hz), 7.33 (d, 1H, J = 8.4 Hz), 7.02 (dt, 2H, J = 9.6 Hz, J = 3.2 Hz), 6.86 (dt, 2H, J = 9.2 Hz, J = 3.2 Hz), 5.31 (s, 2H), 3.74 (s, 3H), 2.65 (s, 3H). Mass Spectrum (LCMS, ESI pos.) Calcd. For C$_{22}$H$_{21}$N$_2$O$_4$S: 409.5 (M + H), Found 409.2. |

EXAMPLE 4

5-(2-methanesulfonyl-phenyl)-2-(4-trifluoromethyl-phenoxymethyl)-1H-benzoimidazole (Cpd 98)

A. (4-trifluoromethyl-phenoxy)-acetonitrile

A mixture of 4-trifluoromethyl-phenol (25.0 g, 0.154 mol), bromoacetonitrile (12.9 mL, 0.185 mol), sodium carbonate (32.7 g, 0.308 mol), and sodium iodide (23.1 g, 0.154 mol) in 214 mL of DMF was heated at 100° C. for 2 hours. The reaction was cooled, and partitioned between water and EtOAc. The organic layers were washed with water and brine, dried with Na$_2$SO$_4$, filtered and the filtrate was concentrated. The residue was purified by chromatography (silica, hexanes: EtOAc, 4:1) to afford the title compound as a colorless oil (29.8 g, 96%). $^1$H NMR (400 MHz, CD$_3$Cl) δ (ppm): 7.63 (d, 2H), 7.07 (d, 2H), 4.83 (s, 2H).

B. 2-(4-trifluoromethyl-phenoxy)-acetimidic acid ethyl ester HCl

To a solution of 2M HCl in ethyl ether (92 mL) was added dropwise a solution of (4-trifluoromethyl-phenoxy)-acetonitrile (29.8 g, 0.148 mol) in ethanol (9.5 mL, 0.163 mol) at 0° C. The reaction mixture was warmed to 25° C. and stirred for 12 hours. Ethyl ether was added to precipitate the product, which was filtered and washed with ethyl ether. The collected white solid was air-dried to provide 2-(4-trifluoromethyl-phenoxy)-acetimidic acid ethyl ester hydrochloride (35.07 g, 83%) as a white solid. $^1$H NMR (400 MHz, CD$_3$Cl) δ (ppm): 7.60 (d, 2H, J=8.8 Hz), 7.18 (d, 2H, J=8.4 Hz), 5.01 (s, 2H), 4.87 (q, 2H, J=7.1 Hz), 1.25 (t, 3H, J=7.0 Hz).

C. 5-bromo-2-(4-trifluoromethyl-phenoxymethyl)-1H-benzoimidazole

A mixture of 4-bromo-phenylene-diamine (19.2 g, 0.103 mol) and 2-(4-trifluoromethyl-phenoxy)-acetimidic acid ethyl ester hydrochloride (35.0 g, 0.123 mol) in EtOH (377 mL) was stirred at room temperature for 12 hours. The reaction was concentrated to give a brown solid, which was partitioned between EtOAc and water. The organic fraction(s) were washed with brine, dried over Na$_2$SO$_4$, and the filtrate was concentrated to afford the title compound as a brown solid (100%). $^1$H NMR (400 MHz, CD$_3$OD) δ (ppm): 7.74 (s, 1H), 7.62 (d, 2H, J=8.0 Hz), 7.50 (d, 1H, J=8.8 Hz), 7.39 (dd, 1H, J=8.4 Hz, J=1.6 Hz), 7.23 (d, 2H, J=8.4 Hz), 5.41 (s, 2H). Mass Spectrum (LCMS, ESI pos.) Calcd. For C$_{15}$H$_{11}$BrF$_3$N$_2$O: 372.2 (M+H), Found 372.9.

D. 5-(2-methanesulfonyl-phenyl)-2-(4-trifluoromethyl-phenoxymethyl)-1H-benzoimidazole A mixture of 5-bromo-2-(4-trifluoromethyl-phenoxymethyl)-1H-benzoimidazole (0.100 g, 0.269 mmol), (2-methylsulfonylphenyl)boronic acid (0.081 g, 0.404 mmol), sodium carbonate (0.228 g, 2.16 mmol), tetrabutylammonium bromide (0.087 g, 0.269 mmol) and 1,1'-[bis(di-tert-butylphosphino)ferrocene]-palladium dichloride (0.035 g, 0.0538 mmol) in DME (2 mL) and H$_2$O (0.5 mL) was heated at 90° C. for 12 hours. The reaction mixture was concentrated under reduced pressure to provide a residue, which was purified by chromatography (silica, hexanes:EtOAc, 1:1) to afford the title compound as an off-white solid. $^1$H NMR (400 MHz, CD$_3$OD) δ (ppm): 8.19 (dd, 1H, J=7.6 Hz, J=1.2 Hz), 7.76-7.71 (m, 2H), 7.66-7.62 (m, 4H), 7.48 (dd, 1H, J=7.6 Hz, J=1.2 Hz), 7.34 (dd, 1H, J=8.4 Hz, J=1.2 Hz), 7.26 (d, 2H, 8.8 Hz), 5.45 (s, 2H), 2.64 (s, 3H). Mass Spectrum (LCMS, ESI pos.) Calcd. For $C_{24}H_{21}F_3N_3O_3S$: 488.5 (M+MeCN+H), Found 488.2.

Using the procedures described in Example 4, and reagents, starting materials and conditions known to those skilled in the art, the following compounds representative of the present invention were prepared:

| Cpd | Name and Data |
|---|---|
| 99 | 5-(3-methanesulfonyl-phenyl)-2-(4-trifluoromethyl-phenoxymethyl)-1H-benzoimidazole<br>$^1$H NMR (400 MHz, CD$_3$OD) δ (ppm): 8.21 (t, 1H, J = 1.8 Hz), 8.01 (ddd, 1H, J = 7.6 Hz, J = 1.6 Hz, J = 0.8 Hz), 7.92 (ddd, 1H, J = 7.8 Hz, J = 1.6 Hz, J = 0.8 Hz), 7.88 (s, 1H), 7.71 (t, 2H, J = 7.6 Hz), 7.64-7.59 (m, 3H), 7.25 (d, 2H, J = 11.6 Hz), 5.45 (s, 2H), 3.19 (s, 3H). Mass Spectrum (LCMS, ESI pos.) Calcd. For $C_{24}H_{20}F_3N_3O_3S$: 488.5 (M + MeCN + H), Found 488.3. |
| 100 | 5-(4-methanesulfonyl-phenyl)-2-(4-trifluoromethyl-phenoxymethyl)-1H-benzoimidazole<br>$^1$H NMR (400 MHz, CD$_3$OD) δ (ppm): 8.02 (d, 2H, J = 8.0 Hz), 7.93-7.90 (m, 3H), 7.70 (d, 1H, J = 8.0 Hz), 7.64-7.62 (m, 3H), 7.25 (d, 2H, J = 8.8 Hz), 5.45 (s, 2H), 3.16 (s, 3H). Mass Spectrum (LCMS, ESI pos.) Calcd. For $C_{24}H_{20}F_3N_3O_3S$: 488.5 (M + MeCN + H), Found 488.3. |
| 101 | N-{2-[2-(4-trifluoromethyl-phenoxymethyl)-1H-benzoimidazol-5-yl]-phenyl}-methanesulfonamide<br>$^1$H NMR (400 MHz, CD$_3$OD) δ (ppm): 7.68-7.61 (m, 4H), 7.53 (d, 1H, J = 9.2 Hz), 7.40-7.28 (m, 4H), 7.23 (d, 2H, J = 8.8 Hz), 5.44 (s, 2H), 2.72 (s, 3H). Mass Spectrum (LCMS, ESI pos.) Calcd. For $C_{24}H_{22}F_3N_4O_3S$: 503.5 (M + MeCN + H), Found 503.3. |
| 102 | N-{3-[2-(4-trifluoromethyl-phenoxymethyl)-1H-benzoimidazol-5-yl]-phenyl}-methanesulfonamide<br>$^1$H NMR (400 MHz, CD$_3$OD) δ (ppm): 7.65-7.62 (m, 5H), 7.53 (dd, 1H, J = 8.4 Hz, J = 1.2 Hz), 7.34 (dt, 2H, J = 8.8 Hz, J = 2.0 Hz), 7.24 (d, 2H, J = 8.8 Hz), 5.43 (s, 2H), 2.99 (s, 3H). Mass Spectrum (LCMS, ESI pos.) Calcd. For $C_{22}H_{19}F_3N_3O_3S$: 462.5 (M + H), Found 462.3. |
| 103 | N-{4-[2-(4-trifluoromethyl-phenoxymethyl)-1H-benzoimidazol-5-yl]-phenyl}-methanesulfonamide<br>$^1$H NMR (400 MHz, CD$_3$OD) δ (ppm): 7.63-7.61 (m, 3H), 7.55-7.52 (m, 2H), 7.45-7.39 (m, 2H), 7.26-7.22 (m, 4H), 5.42 (s, 2H), 3.00 (s, 3H). Mass Spectrum (LCMS, ESI pos.) Calcd. For $C_{24}H_{22}F_3N_4O_3S$: 503.5 (M + MeCN + H), Found 503.3. |
| 104 | 3-[2-(4-trifluoromethyl-phenoxymethyl)-1H-benzoimidazol-5-yl]-benzenesulfonamide<br>$^1$H NMR (400 MHz, CD$_3$OD) δ (ppm): 8.18 (t, 1H, J = 1.8 Hz), 7.90-7.86 (m, 3H), 7.75 (d, 1H, J = 8.4 Hz), 7.68-7.60 (m, 4H), 7.27 (d, 2H, J = 8.4 Hz), 5.54 (s, 2H). Mass Spectrum (LCMS, ESI pos.) Calcd. For $C_{23}H_{20}F_3N_4O_3S$: 489.4 (M + MeCN + H), Found 489.2. |
| 105 | 4-[2-(4-trifluoromethyl-phenoxymethyl)-1H-benzoimidazol-5-yl]-benzenesulfonamide<br>$^1$H NMR (400 MHz, CD$_3$OD) δ (ppm): 8.02-8.00 (m, 3H), 7.89-7.85 (m, 4H), 7.70 (d, 2H, J = 8.8 Hz), 7.31 (d, 2H, J = 8.0 Hz), 5.67 (s, 2H). Mass Spectrum (LCMS, ESI pos.) Calcd. For $C_{23}H_{20}F_3N_4O_3S$: 489.4 (M + MeCN + H), Found 489.2. |
| 106 | N,N-dimethyl-2-[2-(4-trifluoromethyl-phenoxymethyl)-1H-benzoimidazol-5-yl]-benzenesulfonamide<br>$^1$H NMR (400 MHz, CD$_3$OD) δ (ppm): 8.07 (dd, 1H, J = 7.6 Hz, J = 1.2 Hz), 7.68-7.55 (m, 7H), 7.41 (dd, 1H, J = 8.0 Hz, J = 1.2 Hz), 7.25 (d, 2H, J = 8.8 Hz), 5.45 (s, 2H), 2.31 (s, 6H). Mass Spectrum (LCMS, ESI pos.) Calcd. For $C_{25}H_{24}F_3N_4O_3S$: 517.5 (M + MeCN + H), Found 517.3. |
| 107 | 5-o-tolyl-2-(4-trifluoromethyl-phenoxymethyl)-1H-benzoimidazole<br>$^1$H NMR (400 MHz, CD$_3$OD) δ (ppm): 7.61 (d, 1H, J = 8.4 Hz), 7.26-7.19 (m, 7H), 7.16-7.10 (m, 2H), 5.41 (s, 2H), 2.24 (s, 3H). Mass Spectrum (LCMS, ESI pos.) Calcd. For $C_{24}H_{21}F_3N_3O$: 424.4 (M + MeCN + H), Found 424.3. |
| 108 | 5-m-tolyl-2-(4-trifluoromethyl-phenoxymethyl)-1H-benzoimidazole<br>$^1$H NMR (400 MHz, CD$_3$OD) δ (ppm): 7.60 (d, 2H, J = 8.8 Hz), 7.51 (dd, 1H, J = 8.8 Hz, J = 1.6 Hz), 7.44-7.40 (m, 2H), 7.29 (t, 1H, J = 7.6 Hz), 7.22-7.17 (m, 4H), 7.12 (d, 1H, J = 7.6 Hz), 5.41 (s, 2H), 2.41 (s, 3H). Mass Spectrum (LCMS, ESI pos.) Calcd. For $C_{24}H_{21}F_3N_3O$: 424.4 (M + MeCN + H), Found 424.3. |
| 109 | 5-p-tolyl-2-(4-trifluoromethyl-phenoxymethyl)-1H-benzoimidazole<br>$^1$H NMR (400 MHz, CD$_3$OD) δ (ppm): 7.63 (d, 2H, J = 8.8 Hz), 7.54-7.52 (m, 3H), 7.26-7.23 (m, 6H), 5.42 (s, 2H), 2.37 (s, 3H). Mass Spectrum (LCMS, ESI pos.) Calcd. For $C_{22}H_{17}F_3N_2O$: 382.4 (M + H), Found 383.2. |
| 110 | 1-{2-[2-(4-trifluoromethyl-phenoxymethyl)-1H-benzoimidazol-5-yl]-phenyl}-ethanol<br>$^1$H NMR (400 MHz, CD$_3$OD) δ (ppm): 7.67-7.62 (m, 4H), 7.50 (s, 1H), 7.40 (t, 1H, J = 7.4 Hz), 7.30-7.20 (m, 5H), 7.26-7.23 (m, 6H), 5.45 (s, 2H), 4.94 (q, 1H, J = 6.4 Hz), 1.31 (d, 3H, J = 6.4 Hz). Mass Spectrum (LCMS, ESI pos.) Calcd. For $C_{25}H_{23}F_3N_3O_2$: 454.4 (M + MeCN + H), Found 454.2. |
| 111 | 1-{3-[2-(4-trifluoromethyl-phenoxymethyl)-1H-benzoimidazol-5-yl]-phenyl}-ethanol |

| Cpd | Name and Data |
|---|---|
| | $^1$H NMR (400 MHz, CD$_3$OD) δ (ppm): 7.80 (s, 1H), 7.67-7.62 (m, 4H), 7.54 (t, 2H, J = 8.4 Hz), 7.41 (t, 1H, J = 7.6 Hz), 7.34 (d, 1H, J = 8.0 Hz), 7.25 (d, 2H, J = 8.8 Hz), 5.44 (s, 2H), 4.91 (q, 1H, J = 6.5 Hz), 1.50 (d, 3H, J = 6.8 Hz). Mass Spectrum (LCMS, ESI pos.) Calcd. For C$_{25}$H$_{23}$F$_3$N$_3$O$_2$: 454.4 (M + MeCN + H), Found 454.2. |
| 112 | 1-{4-[2-(4-trifluoromethyl-phenoxymethyl)-1H-benzoimidazol-5-yl]-phenyl}-ethanol<br>$^1$H NMR (400 MHz, CD$_3$OD) δ (ppm): 7.77 (s, 1H), 7.63-7.61 (m, 5H), 7.54 (dd, 1H, J = 8.4 Hz, J = 1.6 Hz), 7.45 (d, 2H, J = 8.0 Hz), 7.24 (d, 2H, J = 8.8 Hz), 5.42 (s, 2H), 4.87 (q, 1H, J = 6.6 Hz), 1.48 (d, 3H, J = 6.4 Hz). Mass Spectrum (LCMS, ESI pos.) Calcd. For C$_{25}$H$_{23}$F$_3$N$_3$O$_2$: 454.4 (M + MeCN + H), Found 454.3. |
| 113 | N-{2-[2-(4-trifluoromethyl-phenoxymethyl)-1H-benzoimidazol-5-yl]-phenyl}-acetamide<br>$^1$H NMR (400 MHz, CD$_3$OD) δ (ppm): 7.63 (d, 2H, J = 8.4 Hz), 7.58 (dd, 1H, J = 8.0 Hz, J = 1.2 Hz), 7.26 (dd, 1H, J = 8.0 Hz, J = 1.2 Hz), 7.41-7.27 (m, 5H), 7.24 (d, 2H, J = 8.4 Hz), 5.44 (s, 2H), 1.94 (s, 3H). Mass Spectrum (LCMS, ESI pos.) Calcd. For C$_{23}$H$_{19}$F$_3$N$_3$O$_2$: 426.4 (M + H), Found 426.3. |
| 114 | N-{3-[2-(4-trifluoromethyl-phenoxymethyl)-1H-benzoimidazol-5-yl]-phenyl}-acetamide<br>$^1$H NMR (400 MHz, CD$_3$OD) δ (ppm): 7.88 (s, 1H), 7.81 (t, 1H, J = 2.0 Hz), 7.54 (d, 2H, J = 8.8 Hz), 7.56-7.52 (m, 2H), 7.40-7.32 (m, 3H), 7.25 (d, 2H, J = 8.8 Hz), 5.44 (s, 2H), 2.16 (s, 3H). Mass Spectrum (LCMS, ESI pos.) Calcd. For C$_{25}$H$_{22}$F$_3$N$_4$O$_2$: 467.4 (M + MeCN + H), Found 467.3. |
| 115 | N-{4-[2-(4-trifluoromethyl-phenoxymethyl)-1H-benzoimidazol-5-yl]-phenyl}-acetamide<br>$^1$H NMR (400 MHz, CD$_3$OD) δ (ppm): 7.66-7.60 (m, 7H), 7.57-7.54 (m, 2H), 7.25 (d, 2H, J = 8.8 Hz), 5.44 (s, 2H), 2.14 (s, 3H). Mass Spectrum (LCMS, ESI pos.) Calcd. For C$_{23}$H$_{19}$F$_3$N$_3$O$_2$: 426.4 (M + H), Found 426.3. |
| 116 | {2-[2-(4-trifluoromethyl-phenoxymethyl)-1H-benzoimidazol-5-yl]-phenyl}-methanol<br>$^1$H NMR (400 MHz, CD$_3$OD) δ (ppm): 7.63-7.57 (m, 5H), 7.37 (dd, 1H, J = 8.2 Hz, J = 1.6 Hz), 7.32 (dd, 1H, J = 8.2 Hz, J = 1.6 Hz), 7.28-7.25 (m, 2H), 7.23 (d, 2H, J = 8.4 Hz), 5.43 (s, 2H), 4.54 (s, 2H). Mass Spectrum (LCMS, ESI pos.) Calcd. For C$_{22}$H$_{18}$F$_3$N$_2$O$_2$: 399.4 (M + H), Found 399.2. |
| 117 | {3-[2-(4-trifluoromethyl-phenoxymethyl)-1H-benzoimidazol-5-yl]-phenyl}-methanol<br>$^1$H NMR (400 MHz, CD$_3$OD) δ (ppm): 7.79 (s, 1H), 7.65-7.61 (m, 4H), 7.55 (dd, 2H, J = 8.8 Hz, J = 1.6 Hz), 7.41 (t, 1H, J = 7.6 Hz), 7.32 (d, 1H, J = 8.0 Hz), 7.23 (d, 2H, J = 8.4 Hz), 5.41 (s, 2H), 4.68 (s, 2H). Mass Spectrum (LCMS, ESI pos.) Calcd. For C$_{22}$H$_{18}$F$_3$N$_2$O$_2$: 399.4 (M + H), Found 399.2. |
| 118 | {4-[2-(4-trifluoromethyl-phenoxymethyl)-1H-benzoimidazol-5-yl]-phenyl}-methanol<br>$^1$H NMR (400 MHz, CD$_3$OD) δ (ppm): 7.77 (s, 1H), 7.64-7.61 (m, 5H), 7.54 (dd, 1H, J = 8.4 Hz, J = 1.6 Hz), 7.43 (d, 2H, J = 8.0 Hz), 7.23 (d, 2H, J = 8.4 Hz), 5.41 (s, 2H), 4.65 (s, 2H). Mass Spectrum (LCMS, ESI pos.) Calcd. For C$_{22}$H$_{18}$F$_3$N$_2$O$_2$: 399.4 (M + H), Found 399.2. |
| 119 | 2-[2-(4-trifluoromethyl-phenoxymethyl)-1H-benzoimidazol-5-yl]-phenol<br>$^1$H NMR (400 MHz, CD$_3$OD) δ (ppm): 7.77 (s, 1H), 7.62-7.58 (m, 3H), 7.47 (dd, 1H, J = 8.8 Hz, J = 1.6 Hz), 7.29 (dd, 1H, J = 8.0 Hz, J = 1.6 Hz), 7.22 (d, 2H, J = 8.4 Hz), 7.17-7.13 (m, 1H), 6.92-6.88 (m, 2H), 5.39 (s, 2H). Mass Spectrum (LCMS, ESI pos.) Calcd. For C$_{21}$H$_{16}$F$_3$N$_2$O$_2$: 385.4 (M + H), Found 385.2. |
| 120 | 3-[2-(4-trifluoromethyl-phenoxymethyl)-1H-benzoimidazol-5-yl]-phenol<br>$^1$H NMR (400 MHz, CD$_3$OD) δ (ppm): 7.63 (d, 3H, J = 9.2 Hz), 7.51 (dd, 1H, J = 8.4 Hz, J = 1.2 Hz), 7.27-7.23 (m, 3H), 7.12-7.10 (m, 1H), 7.07 (t, 1H, J = 2.2 Hz), 7.76 (ddd, 1H, J = 8.2 Hz, J = 2.4 Hz, J = 0.8 Hz), 5.43 (s, 2H). Mass Spectrum (LCMS, ESI pos.) Calcd. For C$_{21}$H$_{16}$F$_3$N$_2$O$_2$: 385.4 (M + H), Found 385.2. |
| 121 | 4-[2-(4-trifluoromethyl-phenoxymethyl)-1H-benzoimidazol-5-yl]-phenol<br>$^1$H NMR (400 MHz, CD$_3$OD) δ (ppm): 7.63 (d, 3H, J = 8.4 Hz), 7.48 (dt, 3H, J = 9.2 Hz, J = 2.4 Hz), 7.23 (d, 2H, J = 8.4 Hz), 7.86 (dt, 2H, J = 8.4 Hz, J = 2.0 Hz), 5.41 (s, 2H). Mass Spectrum (LCMS, ESI pos.) Calcd. For C$_{21}$H$_{16}$F$_3$N$_2$O$_2$: 385.4 (M + H), Found 385.2. |
| 122 | 2-[2-(4-trifluoromethyl-phenoxymethyl)-1H-benzoimidazol-5-yl]-phenylamine<br>$^1$H NMR (400 MHz, CD$_3$OD) δ (ppm): 7.66-7.61 (m, 4H), 7.32 (dd, 1H, J = 8.4 Hz, J = 1.2 Hz), 7.23 (d, 2H, J = 8.4 Hz), 7.12-7.07 (m, 2H), 6.83 (d, 1H, J = 7.2 Hz), 7.77 (td, 1H, J = 8.0 Hz, J = 1.2 Hz), 5.43 (s, 2H). Mass Spectrum (LCMS, ESI pos.) Calcd. For C$_{21}$H$_{17}$F$_3$N$_3$O: 384.4 (M + H), Found 384.2. |
| 123 | 3-[2-(4-trifluoromethyl-phenoxymethyl)-1H-benzoimidazol-5-yl]-phenylamine<br>$^1$H NMR (400 MHz, CD$_3$OD) δ (ppm): 7.74 (s, 1H), 7.63-7.60 (m, 3H), 7.50 (dd, 1H, J = 8.4 Hz, J = 1.2 Hz), 7.22 (d, 2H, J = 8.4 Hz), 7.17 (t, 1H, J = 7.8 Hz), 7.03 (t, 1H, J = 2.0 Hz), 6.98 (ddd, 1H, J = 7.4 Hz, J = 1.6 Hz, J = 0.8 Hz), 6.71 (ddd, 1H, J = 8.2 Hz, J = 2.4 Hz, J = 1.2 Hz), 5.43 (s, 2H). Mass Spectrum (LCMS, ESI pos.) Calcd. For C$_{21}$H$_{17}$F$_3$N$_3$O: 384.4 (M + H), Found 384.2. |
| 124 | 4-[2-(4-trifluoromethyl-phenoxymethyl)-1H-benzoimidazol-5-yl]-phenylamine<br>$^1$H NMR (400 MHz, CD$_3$OD) δ (ppm): 7.64-7.61 (m, 3H), 7.46 (dd, 1H, J = 8.8 Hz, J = 1.6 Hz), 7.41 (dt, 2H, J = 8.8 Hz, J = 2.0 Hz), 7.23 (d, 2H, J = 8.4 Hz), 6.81 (dt, 2H, J = 8.8 Hz, J = 2.0 Hz), 6.65-6.58 (m, 1H), 5.40 (s, 2H). Mass |

-continued

| Cpd | Name and Data |
|---|---|
| | Spectrum (LCMS, ESI pos.) Calcd. For $C_{21}H_{17}F_3N_3O$: 384.4 (M + H), Found 384.2. |
| 125 | N-methyl-4-[2-(4-trifluoromethyl-phenoxymethyl)-1H-benzoimidazol-5-yl]-benzenesulfonamide<br>$^1$H NMR (400 MHz, $CD_3OD$) δ (ppm): 7.94-7.86 (m, 5H), 7.72-7.62 (m, 4H), 7.25 (d, 2H, J = 8.8 Hz), 5.46 (s, 2H), 2.56 (s, 3H). Mass Spectrum (LCMS, ESI pos.) Calcd. For $C_{22}H_{19}F_3N_3O_3S$: 462.5 (M + H), Found 462.2. |
| 126 | 5-phenyl-2-(4-trifluoromethyl-phenoxymethyl)-1H-benzoimidazole<br>$^1$H NMR (400 MHz, $CD_3OD$) δ (ppm): 7.65-7.51 (m, 4H), 7.43-7.29 (m, 7H), 7.21 (d, 1H, J = 9.2 Hz), 5.38 (s, 2H). Mass Spectrum (LCMS, ESI pos.) Calcd. For $C_{23}H_{19}F_3N_3O$: 410.4 (M + MeCN + H), Found 410.2. |
| 127 | 2-[2-(4-trifluoromethyl-phenoxymethyl)-1H-benzoimidazol-5-yl]-benzoic acid methyl ester<br>$^1$H NMR (400 MHz, $CD_3OD$) δ (ppm): 7.75 (dd, 1H, J = 7.2 Hz, J = 0.8 Hz), 7.63-7.59 (m, 3H), 7.56 (dt, 1H, J = 8.4 Hz, J = 1.2 Hz), 7.50 (s, 1H), 7.45-7.40 (m, 2H), 7.23 (d, 2H, J = 8.4 Hz), 7.19 (dd, 1H, J = 8.4 Hz, J = 1.2 Hz), 5.42 (s, 2H), 3.57 (s, 3H). Mass Spectrum (LCMS, ESI pos.) Calcd. For $C_{21}H_{17}F_3N_3O$: 468.4 (M + MeCN + H), Found 468.2. |
| 128 | N,N-dimethyl-3-[2-(4-trifluoromethyl-phenoxymethyl)-1H-benzoimidazol-5-yl]-benzenesulfonamide<br>$^1$H NMR (400 MHz, $CD_3OD$) δ (ppm): 8.00 (t, 1H, J = 1.6 Hz), 7.97 (dt, 1H, J = 7.6 Hz, J = 1.6 Hz), 7.85 (s, 1H), 7.75 (dt, 1H, J = 7.6 Hz, J = 1.6 Hz), 7.71 (d, 2H, J = 7.2 Hz), 7.63 (d, 2H, J = 8.4 Hz), 7.58 (dd, 1H, J = 8.0 Hz, J = 1.6 Hz), 7.24 (d, 2H, J = 8.4 Hz), 5.44 (s, 2H), 2.73 (s, 6H). Mass Spectrum (LCMS, ESI pos.) Calcd. For $C_{25}H_{24}F_3N_4O_3S$: 517.5 (M + MeCN + H), Found 517.3. |
| 129 | N,N-dimethyl-4-[2-(4-trifluoromethyl-phenoxymethyl)-1H-benzoimidazol-5-yl]-benzenesulfonamide<br>$^1$H NMR (400 MHz, $CD_3OD$) δ (ppm): 7.90-7.82 (m, 6H), 7.70-7.59 (m, 3H), 7.24 (d, 2H, J = 8.8 Hz), 5.44 (s, 2H), 2.71 (s, 6H). Mass Spectrum (LCMS, ESI pos.) Calcd. For $C_{23}H_{21}F_3N_3O_3S$: 476.5 (M + H), Found 476.2. |
| 130 | 3-[2-(4-trifluoromethyl-phenoxymethyl)-1H-benzoimidazol-5-yl]-benzoic acid methyl ester<br>$^1$H NMR (400 MHz, $CD_3OD$) δ (ppm): 8.29 (t, 1H, J = 2.0 Hz), 7.04 (dt, 1H, J = 8.0 Hz, J = 1.6 Hz), 7.99 (dt, 1H, J = 8.0 Hz, J = 1.4 Hz), 7.91 (dt, 1H, J = 8.0 Hz, J = 1.4 Hz), 7.83 (d, 1H, J = 1.6 Hz), 7.69 (d, 1H, J = 8.4 Hz), 7.64 (d, 2H, J = 8.8 Hz), 7.60-7.55 (m, 2H), 7.25 (d, 1H, J = 9.2 Hz), 5.45 (s, 2H), 3.90 (s, 3H). Mass Spectrum (LCMS, ESI pos.) Calcd. For $C_{25}H_{21}F_3N_3O_3$: 468.4 (M + MeCN + H), Found 468.3. |
| 131 | 4-[2-(4-trifluoromethyl-phenoxymethyl)-1H-benzoimidazol-5-yl]-benzoic acid methyl ester<br>$^1$H NMR (400 MHz, $CD_3OD$) δ (ppm): 8.09 (dt, 2H, J = 8.8 Hz, J = 2.0 Hz), 7.87 (s, 1H), 7.78 (dt, 2H, J = 8.8 Hz, J = 2.0 Hz), 7.68 (s, 1H), 7.65-7.60 (m, 3H), 7.25 (d, 2H, J = 8.8 Hz), 5.44 (s, 2H), 3.31 (s, 3H). Mass Spectrum (LCMS, ESI pos.) Calcd. For $C_{23}H_{18}F_3N_2O_3$: 427.4 (M + H), Found 427.2. |

EXAMPLE 5

4-trifluoromethyl-2-[2-(4-trifluoromethyl-phenoxymethyl)-1H-benzoimidazol-5-yl]-benzenesulfonamide (Cpd 132)

A. 2-bromo-N-tert-butyl-4-trifluoromethyl-benzenesulfonamide

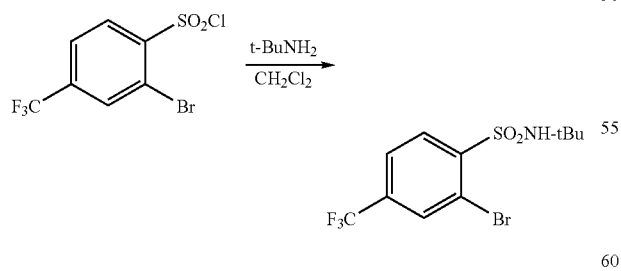

To a solution of 2-bromo-4-(trifluoromethyl)benzenesulfonyl chloride (10 g, 0.031 mol) in $CH_2Cl_2$ (100 mL) was added t-butylamine (8.0 mL, 0.076 mol) at 0° C. The reaction mixture was allowed to warm to room temperature, and stirred for 30 min. A white precipitate formed and was filtered, and the filtrate was concentrated in vacuo to afford the title compound as a yellow oil (11 g, 100%).

B. N-tert-butyl-2-(4,4,5,5-tetramethyl-[1,3,2]dioxaborolan-2-yl)-4-trifluoromethyl-benzenesulfonamide

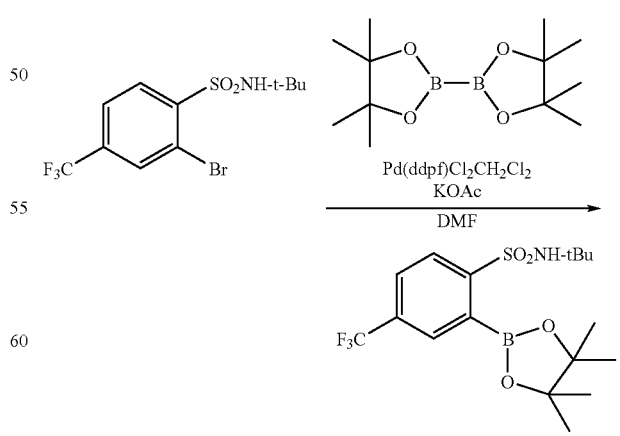

A mixture of 2-bromo-N-tert-butyl-4-trifluoromethyl-benzenesulfonamide (1.16 g, 3.22 mmol), dichloro[1,1'-bis (diphenylphosphino)ferrocene]palladium (II) dichloromethane adduct (0.26 g, 0.322 mmol), potassium acetate (0.95 g, 9.66 mmol), and bis(pinacolato)diboron (1.64 g, 6.44 mmol) in DMF (10 mL) was heated at 80° C. with stirring for 14 hours. The reaction mixture was then concentrated in vacuo. The residue was purified by chromatography (silica, hexanes: EtOAc, 4:1) to afford the title compound as a yellow solid (0.89 g, 68%).

C. 4-trifluoromethyl-2-[2-(4-trifluoromethyl-phenoxymethyl)-1H-benzoimidazol-5-yl]-benzenesulfonamide

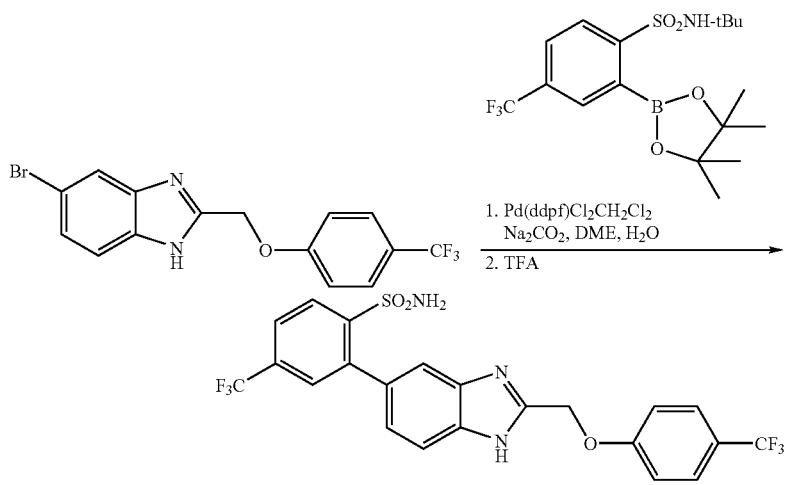

A mixture of 5-bromo-2-(4-trifluoromethyl-phenoxymethyl)-1H-benzoimidazole (0.100 g, 0.269 mmol, from Example 1.1), N-tert-butyl-2-(4,4,5,5-tetramethyl-[1,3,2]dioxaborolan-2-yl)-4-trifluoromethyl-benzenesulfonamide (0.165 g, 0.404 mmol), sodium carbonate (0.171 g, 1.61 mmol), and 1,1'-[bis(di-tert-butylphosphino)ferrocene]-palladium dichloride (0.035 g, 0.0538 mmol) in DME (2 mL) and $H_2O$ (0.5 mL) was heated at 80° C. for 12 hours. The reaction mixture was concentrated under reduced pressure to provide a residue, which was purified by chromatography (silica, hexanes:EtOAc, 1:1) to afford the product as a off-white solid. The obtained material was dissolved in TFA (2 mL) and the resulting solution was heated to 60° C. for 3 hours. The reaction mixture was concentrated in vacuo to provide a residue which was purified by chromatography (silica, hexanes: EtOAc, 1:1) to afford the title compound as a brown solid (0.101 g, 73%). $^1$H NMR (400 MHz, $CD_3OD$) δ (ppm): 0.33 (d, 1H, J=8.0 Hz), 7.89 (dd, 1H, J=8.0 Hz, J=1.2 Hz), 7.82 (d, 1H, J=0.8 Hz), 7.76 (d, 1H, J=8.8 Hz), 7.69-7.65 (m, 3H), 7.50 (dd, 1H, J=8.8 Hz, J=1.6 Hz), 7.28 (d, 2H, J=8.8 Hz), 5.62 (s, 2H). Mass Spectrum (LCMS, ESI pos.) Calcd. For $C_{22}H_{16}F_6N_3O_3S$: 516.4 (M+H), Found 516.3.

Following the reaction of Example 5, starting from different sulfonyl chlorides, the corresponding compounds were prepared:

| Cpd | Name and Data |
| --- | --- |
| 133 | 5-trifluoromethyl-2-[2-(4-trifluoromethyl-phenoxymethyl)-1H-benzoimidazol-5-yl]-benzenesulfonamide<br>$^1$H NMR (400 MHz, $CD_3OD$) δ (ppm): 8.43 (d, 1H, J = 1.2 Hz), 7.95 (dd, 1H, J = 8.0 Hz, J = 1.2 Hz), 7.81 (d, 1H, J = 1.2 Hz), 7.75 (d, 1H, J = 8.0 Hz), 7.66 (d, 2H, J = 8.0 Hz), 7.62 (d, 1H, J = 7.6 Hz), 7.49 (dd, 1H, J = 8.0 Hz, J = 1.6 Hz), 7.28 (d, 2H, J = 8.4 Hz), 5.60 (s, 2H). Mass Spectrum (LCMS, ESI pos.) Calcd. For $C_{22}H_{16}F_6N_3O_3S$: 516.4 (M + H), Found 516.2. |
| 134 | 4-fluoro-2-[2-(4-trifluoromethyl-phenoxymethyl)-1H-benzoimidazol-5-yl]-benzenesulfonamide<br>$^1$H NMR (400 MHz, $CD_3OD$) δ (ppm): 8.19 (dd, 1H, J = 8.8 Hz, J = 5.6 Hz), 7.84 (s, 1), 7.79 (d, 1H, J = 8.8 Hz), 7.69 (d, 2H, J = 8.8 Hz), 7.56 (d, 1H, J = 8.8 Hz), 7.35 (dd, 1H, J = 8.0 Hz, J = 2.8 Hz), 7.30 (d, 2H, J = 8.0 Hz), 7.09 (dd, 1H, J = 9.2 Hz, J = 2.8 Hz), 5.67 (s, 2H). Mass Spectrum (LCMS, ESI pos.) Calcd. For $C_{23}H_{19}F_4N_4O_3S$: 507.4 (M + MeCN + H), Found 507.3. |
| 135 | 2,4-difluoro-6-[2-(4-trifluoromethyl-phenoxymethyl)-1H-benzoimidazol-5-yl]-benzenesulfonamide<br>$^1$H NMR (400 MHz, $CD_3OD$) δ (ppm): 7.64-7.61 (m, 4H), 7.33 (dd, 1H, J = 8.8 Hz, J = 1.2 Hz), 7.26-7.20 (m, 3H), 6.99 (ddd, 1H, J = 8.8 Hz, J = 2.8 Hz, J = 1.2 Hz), 5.49 (s, 2H). Mass Spectrum (LCMS, ESI pos.) Calcd. For $C_{23}H_{18}F_5N_4O_3S$: 525.4 (M + H), Found 525.2. |

EXAMPLE 6

2-[2-(4-trifluoromethyl-benzylamino)-1H-benzoimidazol-5-yl]-benzenesulfonamide (Cpd 136)

A. (5-bromo-1H-benzoimidazol-2-yl)-(4-trifluoromethyl-benzyl)-amine

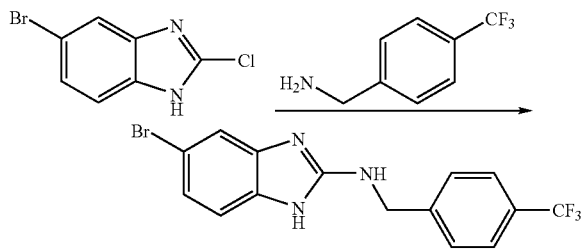

A mixture of 5-bromo-2-chloro-1H-benzoimidazole (0.100 g, 0.432 mmol) and 4-trifluoromethyl-benzylamine (0.8 mL) was heated in a microwave apparatus at 200° C. for 1 hour. The reaction mixture was cooled, and purified by chromatography (silica, hexanes: EtOAc, 1:1) to afford the title product as a white solid (0.101 g, 63%).

B. 2-[2-(4-trifluoromethyl-benzylamino)-1H-benzoimidazol-5-yl]-benzenesulfonamide

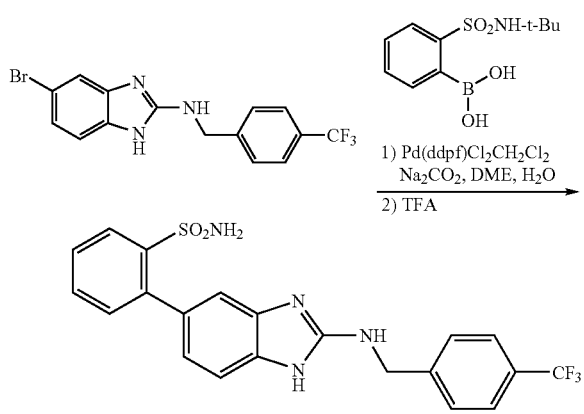

A mixture of (5-bromo-1H-benzoimidazol-2-yl)-(4-trifluoromethyl-benzyl)-amine (0.142 g, 0.384 mmol), 2-(tert-butylamino)sulfonylphenylboronic acid (0.146 g, 0.576 mmol), sodium carbonate (0.241 g, 2.30 mmol), and 1,1'-[bis(di-tert-butylphosphino)ferrocene]-palladium dichloride (0.025 g, 0.0384 mmol) in DME (2 mL) and $H_2O$ (0.5 mL) was heated at 80° C. for 12 hours. The reaction mixture was concentrated under reduced pressure. The residue was purified by chromatography (silica, hexanes:EtOAc, 1:1) to afford the product as an off-white solid. The resulting product was dissolved in trifluoroacetic acid (3 mL) and heated to 60° C. for 2 hours. The reaction mixture was concentrated and the residue was purified by chromatography (silica, hexanes: EtOAc, 1:2) to afford the title compound as an off-white solid (0.043 g, 73%). $^1$H NMR (400 MHz, $CD_3OD$) δ (ppm): 8.12 (dd, 1H, J=8.0 Hz, J=1.2 Hz), 7.71 (d, 2H, J=8.0 Hz), 7.64-7.60 (m, 3H), 7.55 (td, 1H, J=8.4 Hz, J=1.6 Hz), 7.47 (d, 1H, J=1.2 Hz), 7.41 (d, 1H, 8.8 Hz), 7.36 (dd, 1H, J=8.8 Hz, J=1.6 Hz), 7.31 (dd, 1H, J=8.0 Hz, J=1.6 Hz), 5.00 (s, 2H). Mass Spectrum (LCMS, ESI pos.) Calcd. For $C_{23}H_{21}F_3N_5O_2S$: 488.5 (M+MeCN+H), Found 488.2.

Using the procedures described in Example 6, the following compounds were prepared:

| Cpd | Name and Data |
|---|---|
| 137 | 2-{2-[methyl-(4-trifluoromethyl-benzyl)-amino]-1H-benzoimidazol-5-yl}-benzenesulfonamide<br>$^1$H NMR (400 MHz, $CD_3OD$) δ (ppm): 8.12 (dd, 1H, J = 8.0 Hz, J = 1.2 Hz), 7.72 (d, 2H, J = 8.4 Hz), 7.55 (td, 1H, J = 8.2 Hz, J = 1.6 Hz), 7.58-7.51 (m, 4H), 7.44 (d, 1H, 8.0 Hz), 7.36 (dd, 1H, J = 8.0 Hz, J = 1.2 Hz), 7.33 (dd, 1H, J = 8.8 Hz, J = 1.6 Hz), 4.96 (s, 2H), 3.32 (s, 3H). Mass Spectrum (LCMS, ESI pos.) Calcd. For $C_{24}H_{23}F_3N_5O_2S$: 502.5 (M + MeCN + H), Found 502.3. |
| 138 | 2-[2-(4-trifluoromethyl-benzyloxy)-1H-benzoimidazol-5-yl]-benzenesulfonamide<br>$^1$H NMR (400 MHz, $CD_3OD$) δ (ppm): 8.08 (dd, 1H, J = 8.4 Hz, J = 1.2 Hz), 7.62-7.59 (m, 3H), 7.57 (dd, 1H, J = 7.6 Hz, J = 1.2 Hz), 7.53-7.50 (m, 3H), 7.30 (dd, 1H, J = 8.0 Hz, J = 1.2 Hz), 7.15-7.13 (m, 2H), 5.16 (s, 2H). Mass Spectrum (LCMS, ESI pos.) Calcd. For $C_{23}H_{20}F_3N_4O_3S$: 489.4 (M + MeCN + H), Found 489.2. |

EXAMPLE 7

2-{2-[difluoro-(4-trifluoromethyl-phenoxy)-methyl]-1H-benzoimidazol-5-yl}-benzenesulfonamide (Cpd 139)

A. 5-bromo-2-(chloro-difluoro-methyl)-1H-benzoimidazole

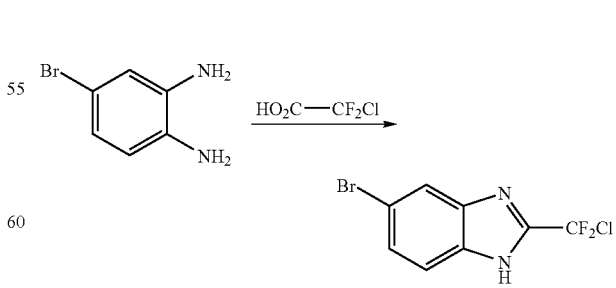

A mixture of 4-bromo-phenylene-diamine (1.00 g, 5.35 mmol), chlorodifluoroacetic acid (3.0 mL, 35.4 mmol), and a drop of water was heated to 80° C. for 14 hours. The crude product was purified by chromatography (silica, hexanes: EtOAc, 4:1) to afford the title compound as a colorless oil (0.63 g, 42%).

B. 5-bromo-2-(chloro-difluoro-methyl)-benzoimidazole-1-carboxylic acid tert-butyl ester

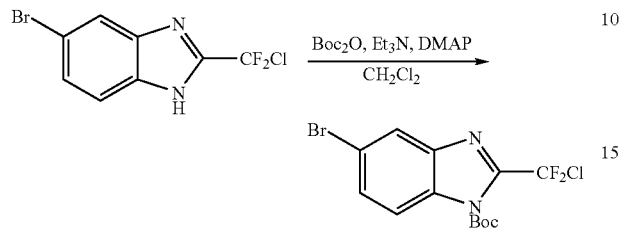

A mixture of 5-bromo-2-(chloro-difluoro-methyl)-1H-benzoimidazole (0.754 g, 2.68 mmol), Boc$_2$O (1.170 g, 5.36 mmol), Et$_3$N (2.2 mL, 8.04 mmol), and DMAP (0.07 g, 0.268 mmol) in CH$_2$Cl$_2$ (8 mL) was stirred for 1 hour. The reaction mixture was concentrated, and the residue was purified by chromatography (silica, hexanes: EtOAc, 8:1) to afford the title compound as a colorless oil (1.002 g, 98%).

C. 5-bromo-2-[difluoro-(4-trifluoromethyl-phenoxy)-methyl]-1H-benzoimidazole

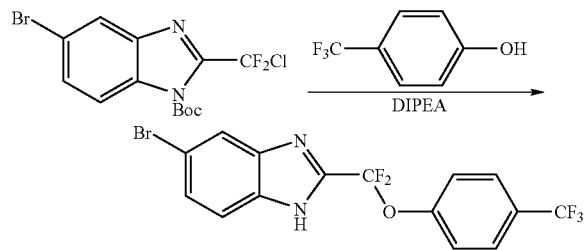

A mixture of 5-bromo-2-(chloro-difluoro-methyl)-benzoimidazole-1-carboxylic acid tert-butyl ester (1.00 g, 2.62 mmol), 4-trifluoromethyl-phenol (0.42 g, 3.93 mmol), and N,N-diisopropylethylamine (0.6 mL, 3.44 mmol) was heated to 85° C. for 14 hours. The crude product was purified by chromatography (silica, hexanes: EtOAc, 4:1) to afford the title compound as a yellow oil (0.58 g, 54%).

D. 2-[2-{difluoro-(4-trifluoromethyl-phenoxy)-methyl]-1H-benzoimidazol-5-yl}-benzenesulfonamide

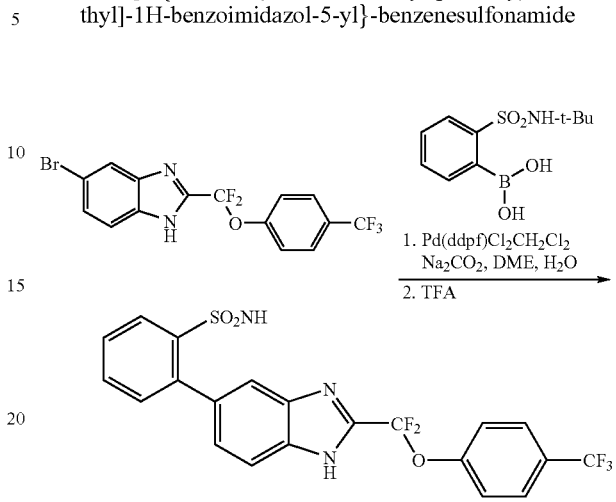

A mixture of 5-bromo-2-[difluoro-(4-trifluoromethyl-phenoxy)-methyl]-1H-benzoimidazole (0.050 g, 0.123 mmol), 2-(tert-butylamino)sulfonylphenylboronic acid (0.047 g, 0.185 mmol), sodium carbonate (0.078 g, 0.738 mmol), and 1,1'-[bis(di-tert-butylphosphino)ferrocene]-palladium dichloride (0.008 g, 0.0123 mmol) in DME (2 mL) and H$_2$O (0.5 mL) was heated at 80° C. for 12 hours. The reaction mixture was concentrated under reduced pressure, and the residue was purified by chromatography (silica, hexanes:EtOAc, 1:1) to afford the product as a off-white solid. The resulting product was dissolved in trifluoroacetic acid (1 mL) and heated to 60° C. for 2 hours. Concentration of the reaction mixture provided the crude material, which was purified by chromatography (silica, hexanes: EtOAc, 1:2) to afford the title compound as an off-white solid (0.043 g, 73%). $^1$H NMR (400 MHz, CD$_3$OD) δ (ppm): 8.14 (dd, 1H, J=8.0 Hz, J=1.2 Hz), 7.79-7.76 (m, 3H), 7.72 (d, 1H, J=9.2 Hz), 7.64 (td, 1H, J=8.2 Hz, J=1.2 Hz), 7.58-7.54 (m, 3H), 7.44-7.40 (m, 2H). Mass Spectrum (LCMS, ESI pos.) Calcd. For C$_{23}$H$_{18}$F$_5$N$_4$O$_3$S: 525.4 (M+MeCN+H), Found 525.2.

Using the procedures described in Example 7, and reagents, starting materials and conditions known to those skilled in the art, the following compounds representative of the present invention were prepared:

| Cpd | Name and Data |
| --- | --- |
| 140 | 2-{2-[difluoro-(4-trifluoromethyl-phenoxy)-methyl]-1H-benzoimidazol-5-yl}-N-methyl-benzenesulfonamide<br>$^1$H NMR (400 MHz, CD$_3$OD) δ (ppm): 8.06 (dd, 1H, J = 7.6 Hz, J = 1.2 Hz), 7.76-7.69 (m, 4H), 7.66 (td, 1H, J = 8.2 Hz, J = 1.2 Hz), 7.58 (dd, 1H, J = 7.6 Hz, J = 1.6 Hz), 7.54 (d, 2H, J = 8.8 Hz), 7.44 (dd, 1H, J = 7.2 Hz, J = 1.2 Hz), 7.34 (dd, 1H, J = 8.4 Hz, J = 1.6 Hz), 2.33 (s, 3H). Mass Spectrum (LCMS, ESI pos.) Calcd. For C$_{22}$H$_{17}$F$_5$N$_3$O$_3$S: 498.5 (M + H), Found 498.1. |
| 141 | 2-{2-[difluoro-(4-trifluoromethyl-phenoxy)-methyl]-1H-benzoimidazol-5-yl}-N,N-dimethyl-benzenesulfonamide<br>$^1$H NMR (400 MHz, CD$_3$OD) δ (ppm): 8.08 (dd, 1H, J = 8.4 Hz, J = 1.2 Hz), 7.78 (d, 2H, J = 8.8 Hz), 7.73 (d, 2H, J = 8.8 Hz), 7.68 (td, 1H, J = 8.2 Hz, J = 1.6 Hz), 7.60 (td, 1H, J = 8.6 Hz, J = 1.2 Hz), 7.56 (d, 2H, J = 8.4 Hz), 7.43 (dd, 1H, J = 7.6 Hz, J = 1.2 Hz), 7.39 (dd, 1H, J = 8.4 Hz, J = 1.2 Hz), 2.33 (s, 6H). Mass Spectrum (LCMS, ESI pos.) Calcd. For C$_{23}$H$_{19}$F$_5$N$_3$O$_3$S: 512.5 (M + H), Found 512.1. |

EXAMPLE 8

2-{2-[2-(4-trifluoromethyl-phenoxymethyl)-1H-benzoimidazol-5-yl]-benzenesulfonyl}-ethanol (Cpd 142)

A. 5-bromo-2-(4-trifluoromethyl-phenoxymethyl)-benzoimidazole-1-carboxylic acid tert-butyl ester

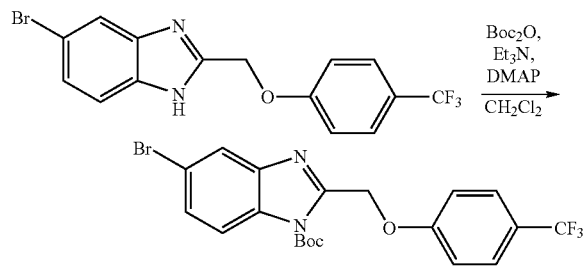

A mixture of 5-bromo-2-(4-trifluoromethyl-phenoxymethyl)-1H-benzoimidazole (1.00 g, 2.69 mmol), $Boc_2O$ (0.706 g, 3.23 mmol), $Et_3N$ (1.1 mL, 8.07 mmol), and DMAP (0.03 g, 0.269 mmol) in $CH_2Cl_2$ (20 mL) was stirred for 1 hour. The reaction mixture was concentrated, and the residue was purified by chromatography (silica, hexanes: EtOAc, 6:1) to afford the title compound as a pale yellow oil (1.23 g, 97%).

B. 5-(4,4,5,5-tetramethyl-[1,3,2]dioxaborolan-2-yl)-2-(4-trifluoromethyl-phenoxymethyl)-benzoimidazole-1-carboxylic acid tert-butyl ester

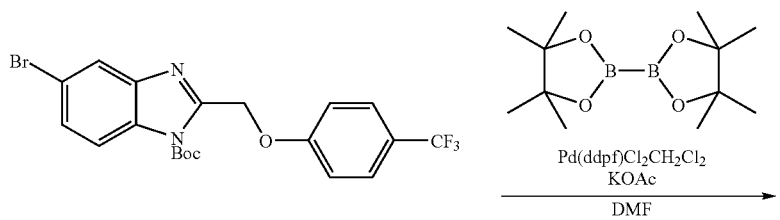

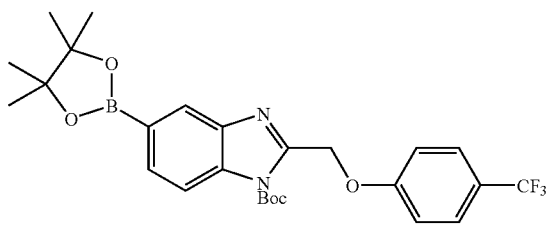

A mixture of 5-bromo-2-(4-trifluoromethyl-phenoxymethyl)-benzoimidazole-1-carboxylic acid tert-butyl ester (0.300 g, 0.637 mmol), dichloro[1,1'-bis(diphenylphosphino)ferrocene]palladium (II) dichloromethane adduct (0.052 g, 0.0637 mmol), potassium acetate (0.187 g, 1.91 mmol), and bis(pinacolato)diboron (0.323 g, 1.27 mmol) in 4 mL of DMF was heated to 90° C. and stirred for 12 hours. The reaction mixture was then concentrated in vacuo, and the residue was purified by chromatography (silica, hexanes: EtOAc, 4:1) to afford the title compound as a brown solid (0.241 g, 73%).

C. 2-{2-[2-(4-trifluoromethyl-phenoxymethyl)-1H-benzoimidazol-5-yl]-benzenesulfonyl}-ethanol

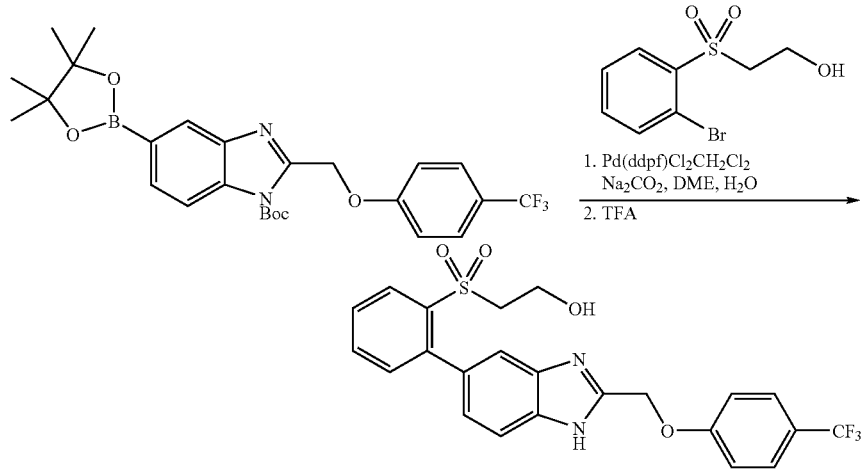

A mixture of 5-(4,4,5,5-tetramethyl-[1,3,2]dioxaborolan-2-yl)-2-(4-trifluoromethyl-phenoxymethyl)-benzoimidazole-1-carboxylic acid tert-butyl ester (0.046 g, 0.0887 mmol), 2-bromophenylsulfonylethanol (0.036 g, 0.133 mmol), sodium carbonate (0.056 g, 0.532 mmol), and 1,1'-[bis(di-tert-butylphosphino)ferrocene]-palladium dichloride (0.006 g, 0.00887 mmol) in DME (2 mL) and H$_2$O (0.5 mL) was heated at 80° C. for 12 hours. The reaction mixture was concentrated under reduced pressure, and the residue was purified by chromatography (silica, EtOAc) to afford the title compound as a light brown solid (0.025 g, 59%). $^1$H NMR (400 MHz, CD$_3$OD) δ (ppm): 8.17 (dd, 1H, J=8.0 Hz, J=1.2 Hz), 7.76-7.61 (m, 6H), 7.46 (dd, 1H, J=7.6 Hz, J=1.2 Hz), 7.34 (d, 1H, J=7.6 Hz), 7.26 (d, 2H, J=8.8 Hz), 5.46 (s, 2H), 3.63 (t, 2H, J=6.6 Hz), 2.91 (t, 2H, J=12.8 Hz). Mass Spectrum (LCMS, ESI pos.) Calcd. For C$_{25}$H$_{23}$F$_3$N$_3$O$_4$S: 518.5 (M+MeCN+H), Found 518.2.

EXAMPLE 9

1-{2-[2-(4-trifluoromethyl-phenoxymethyl)-1H-benzoimidazol-5-yl]-phenyl}-ethanol (Cpd 143)

A. 2-[2-(4-trifluoromethyl-phenoxymethyl)-1H-benzoimidazol-5-yl]-benzaldehyde

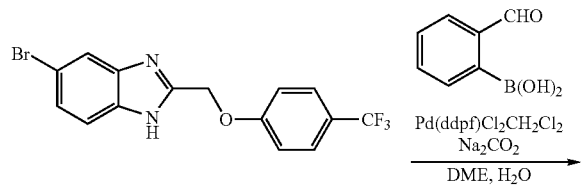

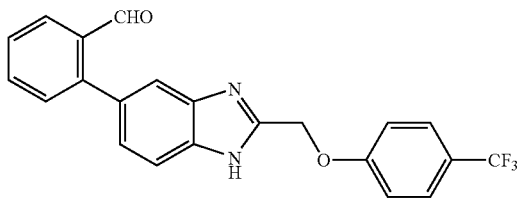

A mixture of 5-bromo-2-(4-trifluoromethyl-phenoxymethyl)-1H-benzoimidazole (0.700 g, 1.89 mmol), 2-formylphenylboronic acid (0.424 g, 2.83 mmol), sodium carbonate (1.200 g, 11.3 mmol), and 1,1'-[bis(di-tert-butylphosphino)ferrocene]-palladium dichloride (0.123 g, 0.189 mmol) in DME (14 mL) and H$_2$O (3.5 mL) was heated at 90° C. for 12 hours. The reaction mixture was concentrated under reduced pressure, and the residue was purified by chromatography (silica, hexanes: EtOAc, 1:1) to afford the product as a yellow oil (0.568 g, 76%).

B. 1-{2-[2-(4-trifluoromethyl-phenoxymethyl)-1H-benzoimidazol-5-yl]-phenyl}-propan-1-ol

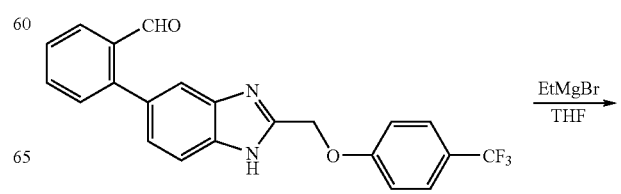

-continued

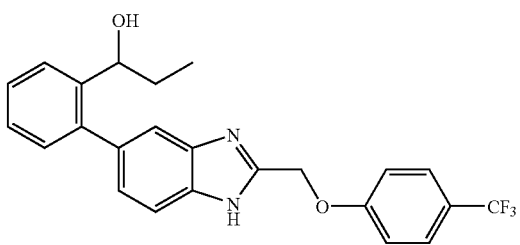

To a solution of 2-[2-(4-trifluoromethyl-phenoxymethyl)-1H-benzoimidazol-5-yl]-benzaldehyde (0.080 g, 0.224 mmol) in THF (6 mL) at −78° C. was added dropwise ethylmagnesium chloride (0.22 mL, 0.673 mmol, 1.0 M solution in THF). After stirring 15 min, the reaction mixture was quenched with brine. The mixture was concentrated, and the residue was purified by chromatography (silica, hexanes: EtOAc, 1:2) to afford the title compound as a off-white solid (0.084 g, 91%). $^1$H NMR (400 MHz, CD$_3$OD) δ (ppm): 7.64-7.59 (m, 4H), 7.39 (td, 1H, J=8.4 Hz, J=1.6 Hz), 7.29 (td, 1H, J=8.0 Hz, J=1.2 Hz), 7.26-7.20 (m, 5H), 5.45 (s, 2H), 4.67 (t, 1H, J=6.6 Hz), 1.68-1.63 (m, 2H), 0.71 (t, 2H, J=7.6 Hz). Mass Spectrum (LCMS, ESI pos.) Calcd. For C$_{24}$H$_{22}$F$_3$N$_2$O$_2$: 427.4 (M+H), Found 427.2.

Using the procedures described in Example 9, Compounds 144 and 145 were prepared from isopropylmagnesium chloride (2.0 M solution in Et$_2$O) and tert-butylmagnesium chloride (1.0 M solution in THF), respectively.

EXAMPLE 10

2-hydroxy-1-{2-[2-(4-trifluoromethyl-phenoxymethyl)-1H-benzoimidazol-5-yl]-phenyl}-propan-1-one (Cpd 146)

A. 1-{2-[2-(4-trifluoromethyl-phenoxymethyl)-1H-benzoimidazol-5-yl]-phenyl}-propan-1-one

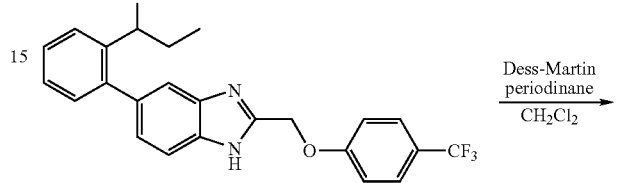

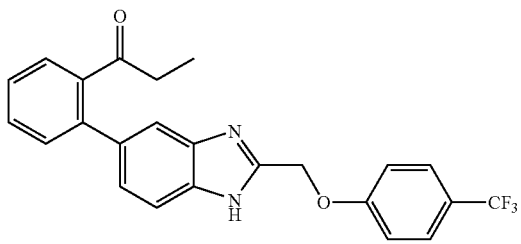

To a solution of 1-{2-[2-(4-trifluoromethyl-phenoxymethyl)-1H-benzoimidazol-5-yl]-phenyl}-propan-1-ol (0.100 g, 0.235 mmol, Example 9, Compound 143) in CH$_2$Cl$_2$ (3 mL) was added Dess-Martin periodinane (0.159 g, 0.375 mmol). After stirring at rt for 2 hours, The reaction mixture was concentrated, and the residue was purified by chromatography (silica, hexanes: EtOAc, 2:1) to afford the title compound as a white solid (0.087 g, 87%).

| Cpd | Name and Data |
|-----|---------------|
| 144 | 2-methyl-1-{2-[2-(4-trifluoromethyl-phenoxymethyl)-1H-benzoimidazol-5-yl]-phenyl}-propan-1-ol $^1$H NMR (400 MHz, CD$_3$OD) δ (ppm): 7.64-7.61 (m, 3H), 7.58 (d, 1H, J = 7.6 Hz), 7.51 (s, 1H), 7.39 (td, 1H, J = 8.0 Hz, J = 1.2 Hz), 7.29 (td, 1H, J = 8.2 Hz, J = 1.2 Hz), 7.26-7.20 (m, 4H), 5.45 (s, 2H), 4.41 (d, 1H, J = 8.0 Hz), 1.89-1.83 (m, 1H), 0.87 (d, 3H, J = 6.8 Hz), 0.51 (d, 3H, J = 6.4 Hz). Mass Spectrum (LCMS, ESI pos.) Calcd. For C$_{25}$H$_{24}$F$_3$N$_2$O$_2$: 441.5 (M + H), Found 441.1. |
| 145 | 2,2-dimethyl-1-{2-[2-(4-trifluoromethyl-phenoxymethyl)-1H-benzoimidazol-5-yl]-phenyl}-propan-1-ol $^1$H NMR (400 MHz, CD$_3$OD) δ (ppm): 9.88 (s, 1H), 7.94 (d, 1H, J = 8.0 Hz), 7.72-7.60 (m, 5H), 7.54 (d, 1H, J = 2.0 Hz), 7.32 (dd, 1H, J = 8.4 Hz, J = 1.2 Hz), 7.26 (d, 2H, J = 8.4 Hz), 5.24 (s, 2H), 1.20 (s, 9H). Mass Spectrum (LCMS, ESI pos.) Calcd. For C$_{26}$H$_{25}$F$_3$N$_2$O$_2$: 454.5 (M), Found 454.1. |

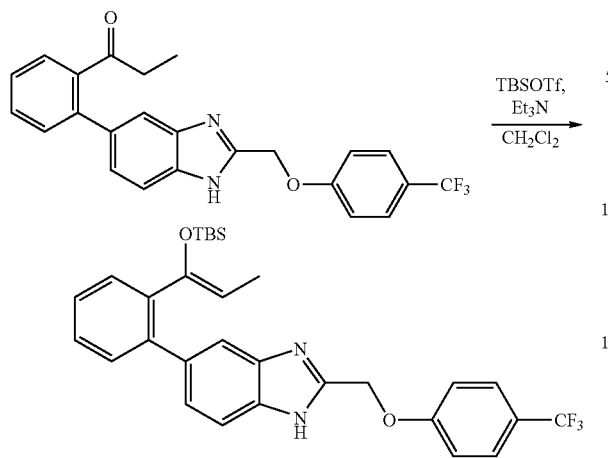

B. 5-{2-[1-(tert-butyl-dimethyl-silanyloxy)-propenyl]-phenyl}-2-(4-trifluoromethyl-phenoxymethyl)-1H-benzoimidazole To a solution of 1-{2-[2-(4-trifluoromethyl-phenoxymethyl)-1H-benzoimidazol-5-yl]-phenyl}-propan-1-one (0.073 g, 0.172 mmol) in CH$_2$Cl$_2$ (4 mL)) at 0° C. was added tert-butyldimethylsilyl trifluoromethanesulfonate (TBSOTf) (0.109 g, 0.413 mmol) and triethylamine (0.07 mL, 0.516 mmol). After stirring for 2 hours, the reaction mixture was concentrated, and the residue was purified by chromatography (silica, hexanes: EtOAc, 4:1) to afford the title compound as a yellow oil (0.065 g, 86%).

C. 5-{2-[2-(tert-butyl-dimethyl-silanyloxy)-3-methyl-oxiranyl]-phenyl}-2-(4-trifluoromethyl-phenoxymethyl)-1H-benzoimidazole

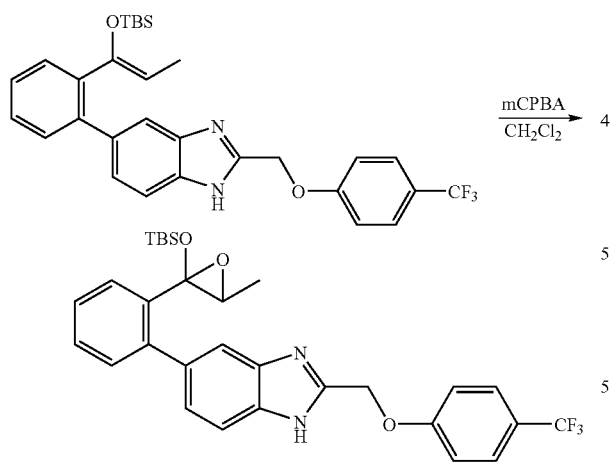

A solution of 5-{2-[1-(tert-butyl-dimethyl-silanyloxy)-propenyl]-phenyl}-2-(4-trifluoromethyl-phenoxymethyl)-1H-benzoimidazole (0.052 g, 0.0965 mmol) in CH$_2$Cl$_2$ (4 mL) at rt was added m-chloroperoxybenzoic acid (77% max, 0.035 g, 0.154 mmol). After stirring for 2 hours, the reaction mixture was concentrated, and the residue was purified by chromatography (silica, hexanes: EtOAc, 2:1) to afford the title compound as a yellow oil (0.050 g, 94%).

D. 2-hydroxy-1-{2-[2-(4-trifluoromethyl-phenoxymethyl)-1H-benzoimidazol-5-yl]-phenyl}-propan-1-one

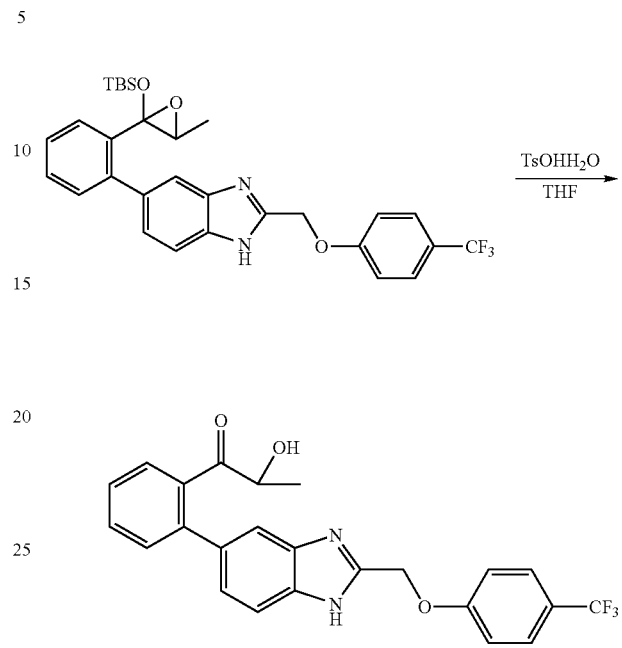

A mixture of 5-{2-[2-(tert-butyl-dimethyl-silanyloxy)-3-methyl-oxiranyl]-phenyl}-2-(4-trifluoromethyl-phenoxymethyl)-1H-benzoimidazole (0.040 g, 0.0721 mmol) and toluenesulfonic acid monohydrate (0.016 g, 0.0865 mmol) in THF (2 mL) was heated to 80° C. for 4 hours. The reaction mixture was then concentrated, and the residue was purified by chromatography (silica, hexanes: EtOAc, 1:2) to afford the title compound as a brown oil (0.028 g, 89%). $^1$H NMR (400 MHz, CD$_3$OD) δ (ppm): 7.66-7.56 (m, 4H), 7.53-7.45 (m, 4H), 7.26-7.22 (m, 3H), 5.43 (s, 2H), 4.12-4.03 (m, 1H), 1.03 (d, 3H, J=7.2 Hz). Mass Spectrum (LCMS, ESI pos.) Calcd. For C$_{26}$H$_{23}$F$_3$N$_3$O$_3$: 482.4 (M+MeCN+H), Found 482.3.

Using the procedures described in Example 10, Compound 147 was prepared from Compound 144 (Example 8).

| Cpd | Name and Data |
|---|---|
| 147 | 2-hydroxy-2-methyl-1-{2-[2-(4-trifluoromethyl-phenoxymethyl)-1H-benzoimidazol-5-yl]-phenyl}-propan-1-one<br>$^1$H NMR (400 MHz, CD$_3$OD) δ (ppm): 7.64-7.62 (m, 3H), 7.53-7.45 (m, 3H), 7.42-7.41 (m, 2H), 7.29 (dd, 1H, J = 6.4 Hz, 1.6 Hz), 7.24 (d, 2H, J = 8.4 Hz). Mass Spectrum (LCMS, ESI pos.)<br>Calcd. For C$_{25}$H$_{22}$F$_3$N$_2$O$_3$:<br>455.5 (M + H), Found 455.3. |

EXAMPLE 11

N,N-dimethyl-2-hydroxy-2-{2-[2-(4-trifluoromethyl-phenoxymethyl)-1H-benzoimidazol-5-yl]-phenyl}-acetamide (Cpd 148)

A. 2,2,2-tris-methylsulfanyl-1-{2-[2-(4-trifluoromethyl-phenoxymethyl)-1H-benzoimidazol-5-yl]-phenyl}-ethanol

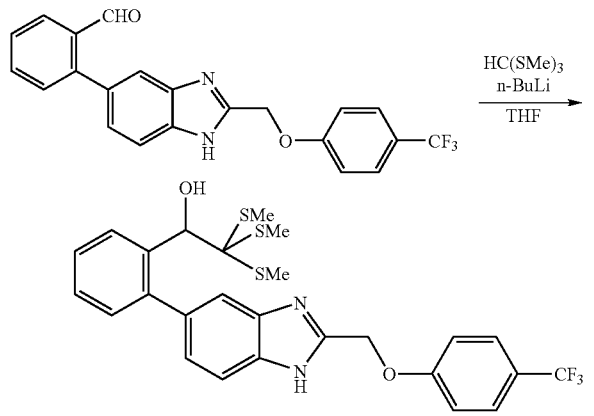

To a solution of tris(methylthio)methane (0.640 g, 4.15 mmol) in THF (12 mL) at −78° C. was added n-butyllithium (1.6 mL, 4.15 mmol). After stirring for 30 min, 2-[2-(4-trifluoromethyl-phenoxymethyl)-1H-benzoimidazol-5-yl]-benzaldehyde (0.274 g, 0.691 mmol, Example 9, Step A) in THF (2 mL) was carefully added to the reaction mixture at −78° C. After 20 min, the reaction was quenched by addition of methanol. The reaction mixture was purified by chromatography (silica, hexanes: EtOAc, 2:1) to afford the title compound as a yellow oil (0.836 g, 94%).

B. hydroxy-{2-[2-(4-trifluoromethyl-phenoxymethyl)-1H-benzoimidazol-5-yl]-phenyl}-acetic acid methyl ester

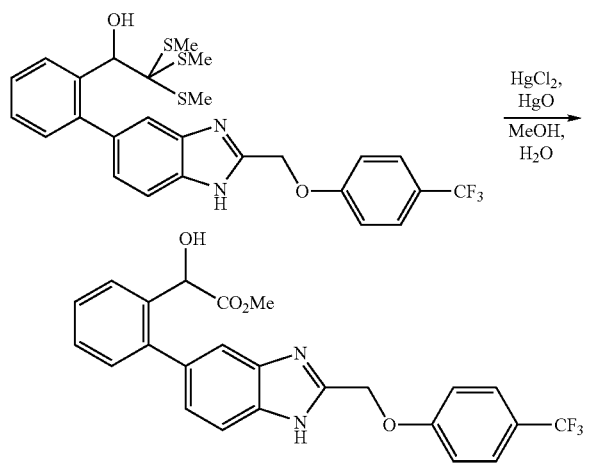

To a solution of 2,2,2-tris-methylsulfanyl-1-{2-[2-(4-trifluoromethyl-phenoxymethyl)-1H-benzoimidazol-5-yl]-phenyl}-ethanol (0.482 g, 0.875 mmol) in a mixed solvent (16 mL, MeOH: $H_2O$=9:1) at rt was added mercuric chloride (0.855 g, 3.15 mmol) and mercuric oxide (0.303 g, 1.40 mmol). The reaction mixture was stirred for 12 hours. The solid was removed by filtration, and the collected filtrate was concentrated under reduced pressure. The residue was purified by chromatography (silica, hexanes: EtOAc, 1:1) to afford the title compound as a white solid (0.312 g, 78%). $^1$H NMR (400 MHz, $CD_3OD$) δ (ppm): 7.71 (s, 1H), 7.62 (d, 2H, J=8.4 Hz), 7.50-7.46 (m, 1H), 7.7.41-7.36 (m, 2H), 7.34-7.31 (m, 2H), 7.25 (d, 2H, J=8.8 Hz), 5.49 (s, 2H), 5.27 (s, 1H), 3.62 (s, 3H). Mass Spectrum (LCMS, ESI pos.) Calcd. For $C_{24}H_{20}F_3N_2O_4$: 457.4 (M+H), Found 457.3.

C. hydroxy-{2-[2-(4-trifluoromethyl-phenoxymethyl)-1H-benzoimidazol-5-yl]-phenyl}-acetic acid

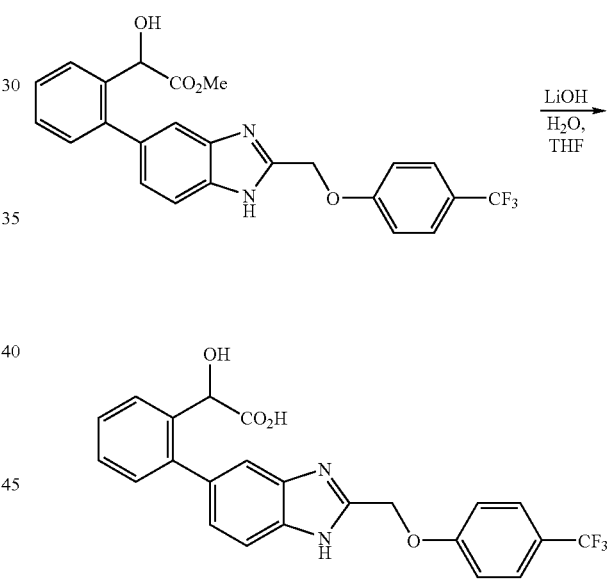

To a solution of hydroxy-{2-[2-(4-trifluoromethyl-phenoxymethyl)-1H-benzoimidazol-5-yl]-phenyl}-acetic acid methyl ester (0.312 g, 0.684 mmol) in mixed solvent (14 mL, MeOH: $H_2O$=3:1) at rt was added lithium hydroxide (LiOH) (0.098 g, 4.10 mmol). After stirring for 12 hours, the reaction mixture was diluted with EtOAc and acidified with aqueous 3N HCl. The organic layer was washed with brine, dried over $Na_2SO_4$, filtered, and the filtrate was concentrated under reduced pressure to afford the title compound as a white solid (0.296 g, 98%).

119

D. N,N-dimethyl-2-hydroxy-2-{2-[2-(4-trifluoromethyl-phenoxymethyl)-1H-benzoimidazol-5-yl]-phenyl}-acetamide (Cpd 148)

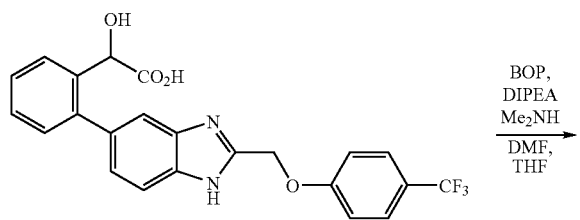

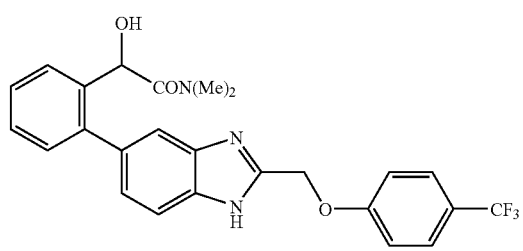

To a solution of hydroxy-{2-[2-(4-trifluoromethyl-phenoxymethyl)-1H-benzoimidazol-5-yl]-phenyl}-acetic acid (0.030 g, 0.0678 mmol) in DMF (0.5 mL) was added (benzotriazo-1-yloxy)tris(dimethylamino)phosphonium hexafluorophosphate (BOP) (0.033 g, 0.0745 mmol), diisopropylethylamine (DIPEA) (0.05 mL, 0.272 mmol), and dimethylamine (0.05 mL, 0.102 mmol, 2.0M solution in THF). After stirring for 12 hours, the crude product was purified by chromatography (silica, $CH_2Cl_2$: MeOH, 5:1) to afford the title compound as a white solid (0.028 g, 83%). $^1$H NMR (400 MHz, $CD_3OD$) δ (ppm): 7.71-7.67 (m, 2H), 7.63 (d, 2H, J=8.4 Hz), 7.41-7.37 (m, 5H), 7.25 (d, 2H, J=8.8 Hz), 5.46 (s, 2H), 5.24 (s, 1H), 2.85 (s, 3H), 2.36 (s, 3H). Mass Spectrum (LCMS, ESI pos.) Calcd. For $C_{25}H_{23}F_3N_3O_3$: 470.5 (M+H), Found 470.3.

Using the procedures described in Example 11, Compound 149 was prepared from N,O-dimethyl hydroxylamine hydrochloride.

| Cpd | Name and Data |
|---|---|
| 149 | 2-hydroxy-N-methoxy-N-methyl-2-{2-[2-(4-trifluoromethyl-phenoxymethyl)-1H-benzoimidazol-5-yl]-phenyl}-acetamide<br>$^1$H NMR (400 MHz, $CD_3OD$) δ (ppm): 7.70-7.64 (m, 4H), 7.46-7.36 (m, 5H), 7.29-7.26 (m, 2H), 5.47 (s, 2H), 5.44 (s, 1H), 3.05 (s, 3H), 2.94 (s, 3H). Mass Spectrum (LCMS, ESI pos.) Calcd. For $C_{25}H_{23}F_3N_3O_4$: 486.5 (M + H), Found 486.3. |

120

EXAMPLE 12

2-hydroxy-1-{2-[2-(4-trifluoromethyl-phenoxymethyl)-1H-benzoimidazol-5-yl]-phenyl}-ethanone (Cpd 151)

1-{2-[2-(4-trifluoromethyl-phenoxymethyl)-1H-benzoimidazol-5-yl]-phenyl}-ethane-1,2-diol (Cpd 150)

A. 1-{2-[2-(4-trifluoromethyl-phenoxymethyl)-1H-benzoimidazol-5-yl]-phenyl}-ethanone

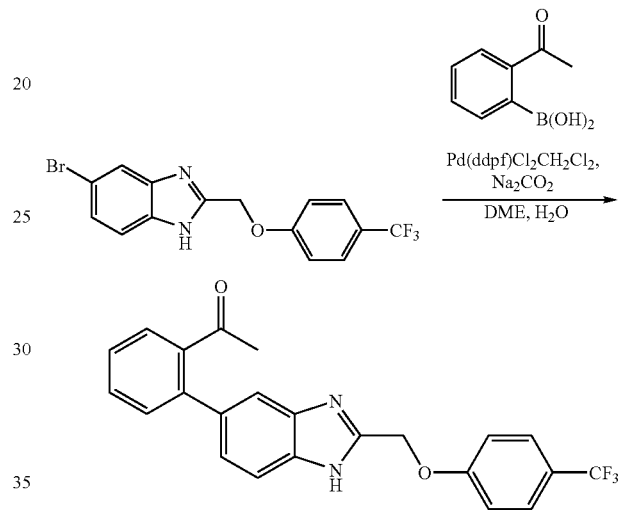

A mixture of 5-bromo-2-(4-trifluoromethyl-phenoxymethyl)-1H-benzoimidazole (0.450 g, 1.21 mmol), 2-acetylphenylboronic acid (0.298 g, 1.82 mmol), sodium carbonate (0.771 g, 7.26 mmol), and 1,1'-[bis(di-tert-butylphosphino)ferrocene]-palladium dichloride (0.079 g, 0.121 mmol) in DME (10 mL) and $H_2O$ (2.5 mL) was heated at 90° C. for 12 hours. The reaction mixture was concentrated under reduced pressure, and the residue was purified by chromatography (silica, hexanes: EtOAc, 1:1) to afford the product as a yellow oil (0.433 g, 87%).

B. 5-{2-[1-(tert-butyl-dimethyl-silanyloxy)-vinyl]-phenyl}-2-(4-trifluoromethyl-phenoxymethyl)-1H-benzoimidazole

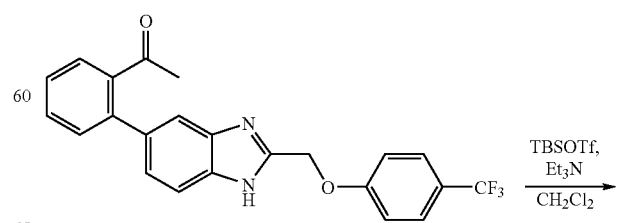

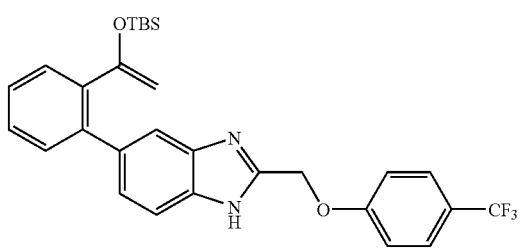

To a solution of 1-{2-[2-(4-trifluoromethyl-phenoxymethyl)-1H-benzoimidazol-5-yl]-phenyl}-ethanone (0.215 g, 0.524 mmol) in CH$_2$Cl$_2$ (8 mL) at 0° C. was added tert-butyldimethylsilyl trifluoromethanesulfonate (TBSOTf) (0.304 g, 1.15 mmol) and triethylamine (0.29 mL, 2.10 mmol). After stirring 2 h, the reaction mixture was concentrated, and the residue was purified by chromatography (silica, hexanes: EtOAc, 2:1) to afford the title compound as a yellow oil (0.242 g, 88%).

C. 5-{2-[2-(tert-butyl-dimethyl-silanyloxy)-oxiranyl]-phenyl}-2-(4-trifluoromethyl-phenoxymethyl)-1H-benzoimidazole

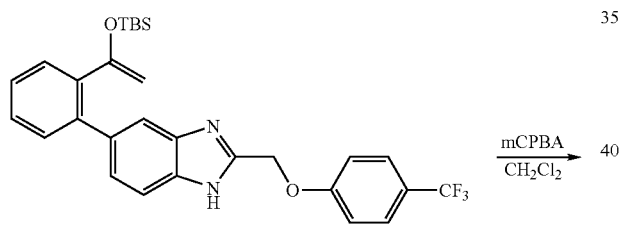

To a solution of 5-{2-[1-(tert-butyl-dimethyl-silanyloxy)-vinyl]-phenyl}-2-(4-trifluoromethyl-phenoxymethyl)-1H-benzoimidazole (0.126 g, 0.240 mmol) in CH$_2$Cl$_2$ (5 mL) at rt was added m-chloroperoxybenzoic acid (77% max, 0.161 g, 0.720 mmol). After stirring 1 hour, the reaction mixture was concentrated, and the residue was purified by chromatography (silica, hexanes: EtOAc, 2:1) to afford the title compound as a colorless oil (0.115 g, 94%).

D. 2-hydroxy-1-{2-[2-(4-trifluoromethyl-phenoxymethyl)-1H-benzoimidazol-5-yl]-phenyl}-ethanone (Cpd 151)

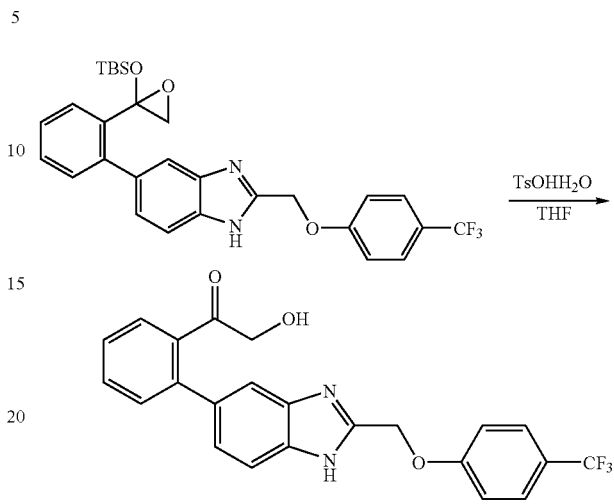

A reaction mixture of 5-{2-[2-(tert-butyl-dimethyl-silanyloxy)-oxiranyl]-phenyl}-2-(4-trifluoromethyl-phenoxymethyl)-1H-benzoimidazole (0.072 g, 0.134 mmol) and toluenesulfonic acid monohydrate (0.031 g, 0.161 mmol) in THF (2 mL) was heated to 80° C. and stirred for 2 hours. The reaction mixture was concentrated and the residue was purified by chromatography (silica, hexanes: EtOAc, 1:2) to afford the title compound as a brown oil (0.053 g, 92%). $^1$H NMR (400 MHz, CD$_3$OD) δ (ppm): 7.64 (d, 2H, J=9.2 Hz), 7.62-7.56 (m, 2H), 7.54-7.46 (m, 4H), 7.26-7.23 (m, 3H), 5.45 (s, 2H), 4.06 (s, 2H). Mass Spectrum (LCMS, ESI pos.) Calcd. For C$_{23}$H$_{18}$F$_3$N$_2$O$_3$: 427.4 (M+H), Found 427.0.

E. 1-{2-[2-(4-trifluoromethyl-phenoxymethyl)-1H-benzoimidazol-5-yl]-phenyl}-ethane-1,2-diol (Cpd 150)

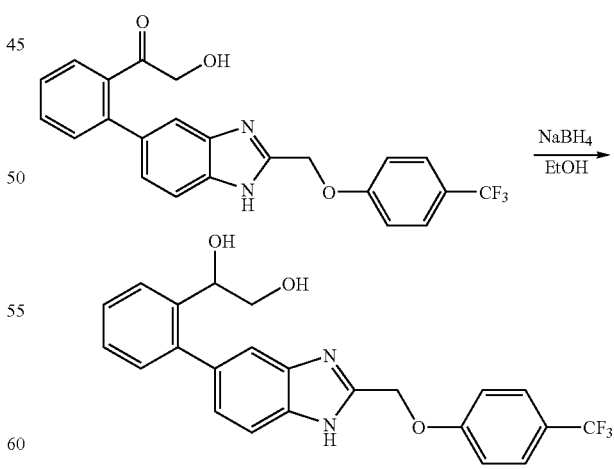

A solution of 2-hydroxy-1-{2-[2-(4-trifluoromethyl-phenoxymethyl)-1H-benzoimidazol-5-yl]-phenyl}-ethanone (0.082 g, 0.192 mmol) in ethanol (6 mL) was added sodium borohydride (0.029 g, 0.769 mmol) at 0° C. After stirring for 20 min, the reaction was quenched by water. EtOAc was added to dilute and the organic layer was washed with brine, dried over Na$_2$SO$_4$, and concentrated under reduced pressure to provide a residue, which was purified by chromatography (silica, CH$_2$Cl$_2$: MeOH, 10:1) to afford the title compound as a pale yellow oil (0.075 g, 91%). $^1$H NMR (400 MHz, CD$_3$OD) δ (ppm): 7.64-7.61 (m, 4H), 7.40 (dt, 1H, J=8.4 Hz, J=1.6 Hz), 7.32 (dt, 1H, J=8.2 Hz, J=1.6 Hz), 7.26-7.23 (m, 5H), 5.45 (s, 2H), 4.86 (dd, 1H, J=6.8 Hz, J=1.2 Hz), 3.58-3.55 (m, 1H), 1.60-1.57 (m, 1H). Mass Spectrum (LCMS, ESI pos.) Calcd. For C$_{23}$H$_{20}$F$_3$N$_2$O$_3$: 429.4 (M+H), Found 429.1.

EXAMPLE 13

N-(2-hydroxy-ethyl)-2-[2-(4-trifluoromethyl-phenoxymethyl)-1H-benzoimidazol-5-yl]-benzamide (Cpd 152)

A. 2-[2-(4-trifluoromethyl-phenoxymethyl)-1H-benzoimidazol-5-yl]-benzoic acid methyl ester

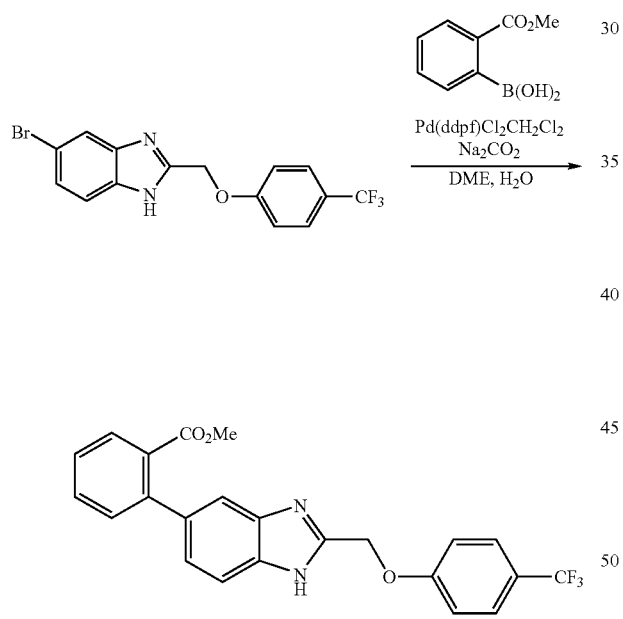

A mixture of 5-bromo-2-(4-trifluoromethyl-phenoxymethyl)-1H-benzoimidazole (0.500 g, 1.35 mmol), (2-methoxycarbonylphenyl)boronic acid (0.290 g, 1.62 mmol), sodium carbonate (0.857 g, 8.10 mmol), and 1,1'-[bis(di-tert-butylphosphino)ferrocene]-palladium dichloride (0.088 g, 0.135 mmol) in DME (10 mL) and H$_2$O (2.5 mL) was heated at 80° C. for 12 hours. The reaction mixture was concentrated under reduced pressure, and the residue was purified by chromatography (silica, hexanes: EtOAc, 1:1) to afford the product as a yellow oil (0.494 g, 86%).

B. 2-[2-(4-trifluoromethyl-phenoxymethyl)-1H-benzoimidazol-5-yl]-benzoic acid

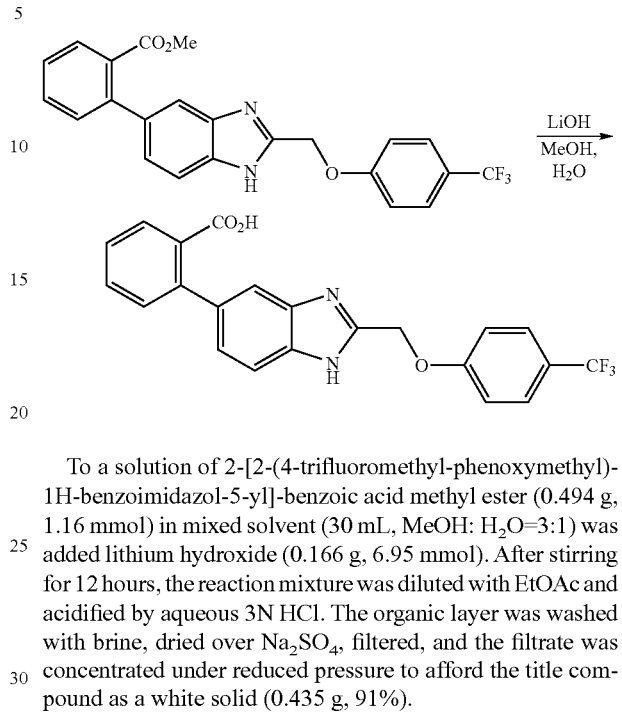

To a solution of 2-[2-(4-trifluoromethyl-phenoxymethyl)-1H-benzoimidazol-5-yl]-benzoic acid methyl ester (0.494 g, 1.16 mmol) in mixed solvent (30 mL, MeOH: H$_2$O=3:1) was added lithium hydroxide (0.166 g, 6.95 mmol). After stirring for 12 hours, the reaction mixture was diluted with EtOAc and acidified by aqueous 3N HCl. The organic layer was washed with brine, dried over Na$_2$SO$_4$, filtered, and the filtrate was concentrated under reduced pressure to afford the title compound as a white solid (0.435 g, 91%).

C. N-(2-hydroxy-ethyl)-2-[2-(4-trifluoromethyl-phenoxymethyl)-1H-benzoimidazol-5-yl]-benzamide

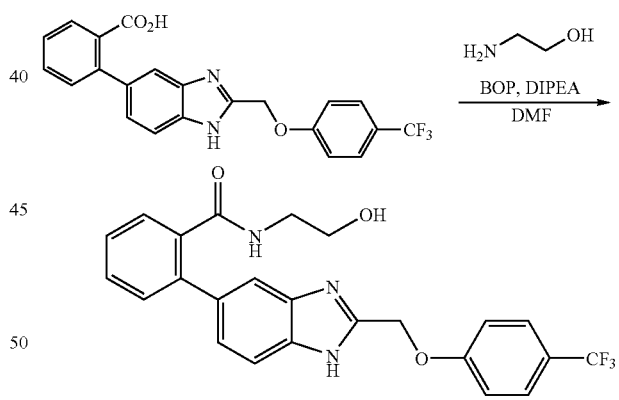

A mixture of 2-[2-(4-trifluoromethyl-phenoxymethyl)-1H-benzoimidazol-5-yl]-benzoic acid (0.050 g, 0.121 mmol), BOP (0.059 g, 0.133 mmol), DIPEA (0.07 mL, 0.363 mmol) and ethanolamine (0.011 g, 0.182 mmol) in DMF (0.5 mL) was stirred at rt for 12 hours. The crude product was purified by chromatography (silica, CH$_2$Cl$_2$: MeOH, 5:1) to afford the title compound as a brown oil (0.043 g, 78%). $^1$H NMR (400 MHz, CD$_3$OD) δ (ppm): 7.64-7.59 (m, 3H), 7.54-7.46 (m, 4H), 7.41 (td, 1H, J=8.2 Hz, J=1.6 Hz), 7.35 (dd, 1H, J=8.0 Hz, J=1.6 Hz), 7.15 (d, 2H, J=8.0 Hz), 5.42 (s, 2H), 5.24 (s, 1H), 3.91 (t, 2H, J=6.0 Hz), 3.24 (t, 2H, J=6.2 Hz). Mass Spectrum (LCMS, ESI pos.) Calcd. For C$_{24}$H$_{21}$F$_3$N$_3$O$_3$: 456.4 (M+H), Found 456.2.

Using the procedures described in Example 13, Compounds 153-155 were prepared from 1-amino-2-methyl-propan-2-ol, dl-1-amino-2-propanol, and 2-(methylamino)ethanol (Procedure C).

heated to 70° C. for 2 hours. The solvent was evaporated to provide a residue, which was purified by chromatography (silica, hexanes: EtOAc, 1:1) to afford the title compound as a yellow oil (0.150 g, 92%).

| Cpd | Name and Data |
|---|---|
| 153 | N-(2-hydroxy-2-methyl-propyl)-2-[2-(4-trifluoromethyl-phenoxymethyl)-1H-benzoimidazol-5-yl]-benzamide<br>$^1$H NMR (400 MHz, CD$_3$OD) δ (ppm): 7.63-7.60 (m, 3H), 7.54-7.40 (m, 5H), 7.34 (dd, 1H, J = 8.0 Hz, J = 1.6 Hz), 7.22 (d, 2H, J = 8.4 Hz), 5.42 (s, 2H), 3.11 (s, 2H), 0.88 (s, 6H). Mass Spectrum (LCMS, ESI pos.) Calcd. For C$_{26}$H$_{25}$F$_3$N$_3$O$_3$: 484.5 (M + H), Found 484.3. |
| 154 | N-(2-hydroxy-propyl)-2-[2-(4-trifluoromethyl-phenoxymethyl)-1H-benzoimidazol-5-yl]-benzamide<br>$^1$H NMR (400 MHz, CD$_3$OD) δ (ppm): 7.63-7.61 (m, 3H), 7.53-7.39 (m, 5H), 7.35 (dd, 1H, J = 8.0 Hz, J = 1.6 Hz), 7.23 (d, 2H, J = 8.4 Hz), 5.42 (s, 2H), 3.60 (hex, 1H, J = 2.4 Hz), 3.16 (dd, 1H, J = 13.2 Hz, J = 6.4 Hz), 3.03 (dd, 1H, J = 13.2 Hz, J = 6.0 Hz), 0.79 (d, 3H, J = 6.4 Hz). Mass Spectrum (LCMS, ESI pos.) Calcd. For C$_{25}$H$_{23}$F$_3$N$_3$O$_3$: 471.5 (M + 2H), Found 471.3. |
| 155 | N-(2-hydroxy-ethyl)-N-methyl-2-[2-(4-trifluoromethyl-phenoxymethyl)-1H-benzoimidazol-5-yl]-benzamide<br>$^1$H NMR (400 MHz, CD$_3$OD) δ (ppm): 7.64-7.62 (m, 3H), 7.54-7.36 (m, 6H), 7.24 (d, 2H, J = 8.8 Hz), 5.43 (s, 2H), 3.42-3.36 (m, 2H), 3.28-3.18 (m, 2H), 2.60 (s, 3H). Mass Spectrum (LCMS, ESI pos.) Calcd. For C$_{25}$H$_{23}$F$_3$N$_3$O$_3$: 470.5 (M + H), Found 470.3. |

EXAMPLE 14

2-{2-[1-(4-trifluoromethyl-phenoxy)-ethyl]-1H-benzoimidazol-5-yl}-benzenesulfonamide (Cpd 156)

A. N-tert-butyl-2-[2-(1-chloro-ethyl)-1H-benzoimidazol-5-yl]-benzenesulfonamide

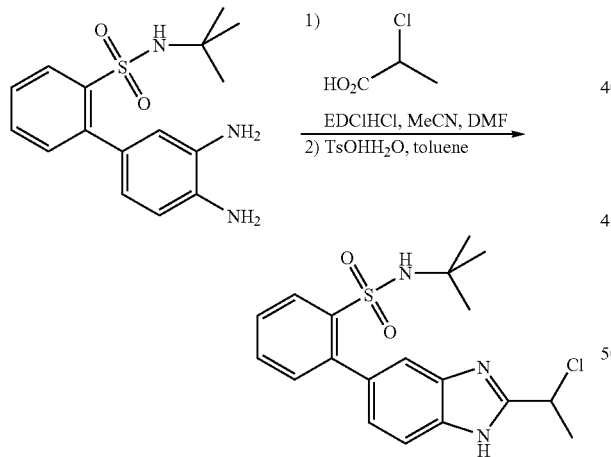

A mixture of 3',4'-diamino-biphenyl-2-sulfonic acid tert-butylamide (0.250 g, 0.783 mmol, Example 1 Step C) and N-ethyl-N'-(3-dimethylaminopropyl)carbodiimide hydrochloride (0.120 g, 0.602 mmol) in MeCN (4 mL) was stirred at rt for 20 min. To this mixture was added dropwise a solution of 2-chloropropionic acid (0.064 g, 0.602 mmol) in DMF (1 mL), and the reaction was stirred for 12 hours. The reaction mixture was concentrated, and the residue, was purified by chromatography (silica, hexanes: EtOAc, 2:1) to afford the product as yellow oil (0.170 g, 53%). It was then dissolved in toluene (4 mL), to which toluenesulfonic acid monohydrate (0.118 g, 0.622 mmol) was added. The reaction mixture was heated to 70° C. for 2 hours. The solvent was evaporated to provide a residue, which was purified by chromatography (silica, hexanes: EtOAc, 1:1) to afford the title compound as a yellow oil (0.150 g, 92%).

B. 2-{2-[1-(4-trifluoromethyl-phenoxy)-ethyl]-1H-benzoimidazol-5-yl}-benzenesulfonamide

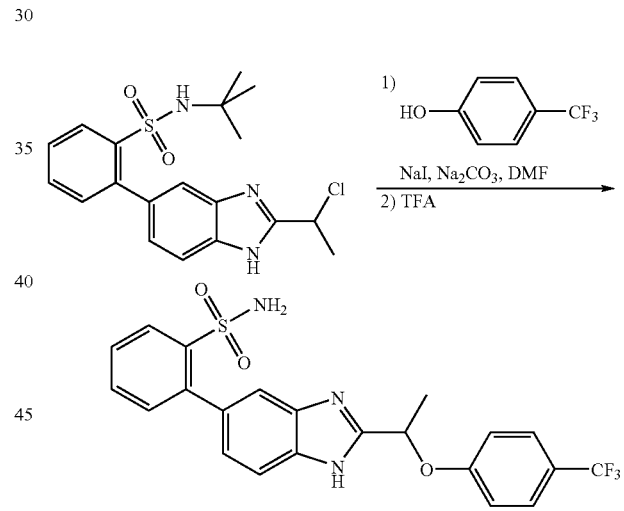

A mixture of N-tert-butyl-2-[2-(1-chloro-ethyl)-1H-benzoimidazol-5-yl]-benzenesulfonamide (0.042 g, 0.107 mmol), 4-trifluoromethyl-phenol (0.069 g, 0.428 mmol), Na$_2$CO$_3$ (0.045 g, 0.428 mmol), and NaI (0.064 g, 0.428 mmol) in DMF at rt (2 mL) was stirred for 24 hours. The reaction mixture was purified by chromatography (silica, hexanes: EtOAc, 1:1) to afford the protected product. This material dissolved in 1,2-dichloroethane (1 mL) and TFA (1 mL), was heated to 60° C. for 2 hours, and then cooled. The solvent was evaporated and the resulting crude material was purified by chromatography (silica, EtOAc: hexanes, 2:1) afforded the title compound as a pale yellow oil (0.033, 67%).
$^1$H NMR (400 MHz, CD$_3$OD) δ (ppm): 8.14 (dd, 1H, J=8.0 Hz, J=1.2 Hz), 7.70 (dd, 1H, J=1.6 Hz, J=0.8 Hz), 7.67-7.58 (m, 4H), 7.55 (td, 1H, J=8.6 Hz, J=1.6 Hz), 7.39 (td, 2H, J=9.0 Hz, J=1.6 Hz), 7.20 (d, 2H, J=8.8 Hz), 5.91 (q, 1H), 1.87 (d, 3H, J=6.8 Hz). Mass Spectrum (LCMS, ESI pos.) Calcd. For C$_{24}$H$_{22}$F$_3$N$_4$O$_3$S: 503.5 (M+MeCN+H), Found 503.2.

Using the procedures described in Example 14, Compound 157 was prepared from 2-chlorobutyric acid.

| Cpd | Name and Data |
|---|---|
| 157 | 2-{2-[1-(4-trifluoromethyl-phenoxy)-propyl]-1H-benzoimidazol-5-yl}-benzenesulfonamide<br>$^1$H NMR (400 MHz, CD$_3$OD) δ (ppm): 8.11 (dd, 1H, J = 7.6 Hz, J = 1.2 Hz), 7.66-7.50 (m, 6H), 7.37 (dd, 1H, J = 7.6 Hz, J = 1.2 Hz), 7.30 (d, 1H, J = 8.4 Hz), 7.15 (d, 2H, J = 8.8 Hz), 5.54 (t, 1H), 2.29-2.15 (m, 2H), 1.08 (t, 3H, J = 7.4 Hz). Mass Spectrum (LCMS, ESI pos.) Calcd. For C$_{25}$H$_{24}$F$_3$N$_4$O$_3$S:<br>517.5 (M + MeCN + H), Found 517.2. |

EXAMPLE 15

5-(2-trifluoromethanesulfonyl-phenyl)-2-(4-trifluoromethyl-phenoxymethyl)-1H-benzoimidazole (Cpd 158)

A. [2-tert-butoxycarbonylamino-4-(4,4,5,5-tetramethyl-[1,3,2]dioxaborolan-2-yl)-phenyl]-carbamic acid tert-butyl ester A mixture of (4-bromo-2-tert-butoxycarbonylamino-phenyl)-carbamic acid tert-butyl ester (2.00 g, 8.73 mmol), dichloro[1,1'-bis(diphenylphosphino)ferrocene]palladium (II) dichloromethane adduct (0.71 g, 0.873 mmol), potassium acetate (1.71 g, 17.5 mmol), and bis(pinacolato)diboron (3.33 g, 13.1 mmol) in DMF (12 mL) was heated at 80° C. for 12 hours. The reaction mixture was then concentrated in vacuo, and the residue was purified by chromatography (silica, hexanes: EtOAc, 2:1) to afford the title compound as an off-white solid (1.88 g, 84%).

B. (4-tert-butoxycarbonylamino-2'-trifluoromethanesulfonyl-biphenyl-3-yl)-carbamic acid tert-butyl ester

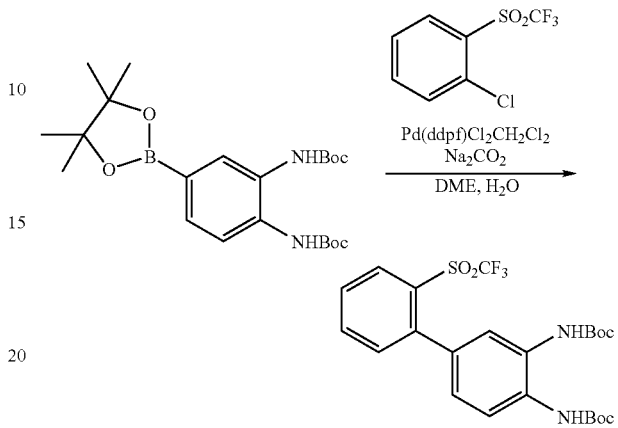

A mixture of [2-tert-butoxycarbonylamino-4-(4,4,5,5-tetramethyl-[1,3,2]dioxaborolan-2-yl)-phenyl]-carbamic acid tert-butyl ester (0.213 g, 0.490 mmol), 1-chloro-2-trifluoromethanesulfonyl-benzene (0.100 g, 0.409 mmol), sodium carbonate (0.260 g, 2.45 mmol), and 1,1'-[bis(di-tert-butylphosphino)ferrocene]-palladium dichloride (0.027 g, 0.0409 mmol) in DME (2 mL) and H$_2$O (0.5 mL) was heated at 90° C. for 12 hours. The reaction mixture was concentrated under reduced pressure, and the residue was purified by chromatography (silica, hexanes: EtOAc, 1:1) to afford the title compound as a yellow solid (0.158 g, 75%).

C. 2'-trifluoromethanesulfonyl-biphenyl-3,4-diamine

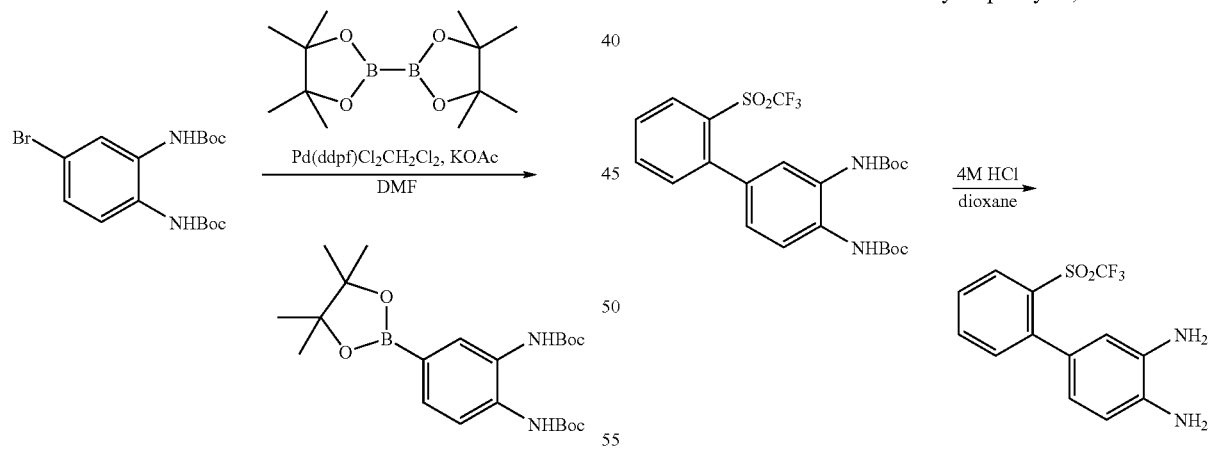

A solution of (4-tert-butoxycarbonylamino-2'-trifluoromethanesulfonyl-biphenyl-3-yl)-carbamic acid tert-butyl ester (0.072 g, 0.228 mmol) in 4M HCl in dioxane (3 mL) was stirred at room temperature for 2 h. The reaction mixture was concentrated under reduced pressure. The residue was dissolved in EtOAc, and the solution was washed with saturated sodium bicarbonate and water (pH=7). The organic layer was dried over Na$_2$SO$_4$, filtered, and the filtrate was concentrated in vacuo to provide the title compound as a yellow oil (0.043 g, 98%).

D. 5-(2-trifluoromethanesulfonyl-phenyl)-2-(4-trif-luoromethyl-phenoxymethyl)-1H-benzoimidazole

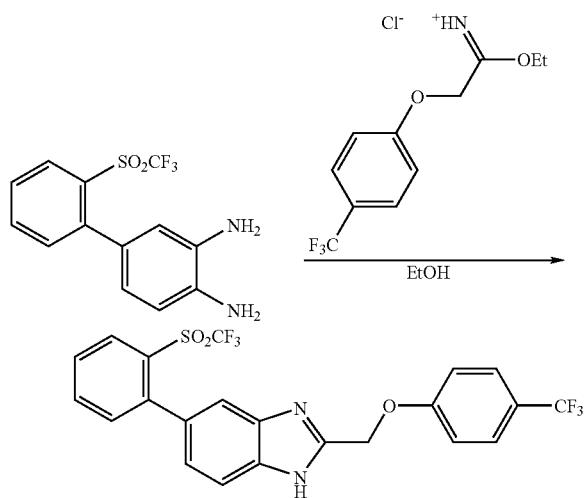

A mixture of 2'-trifluoromethanesulfonyl-biphenyl-3,4-diamine (0.042 g, 0.133 mmol) and 2-(4-trifluoromethyl-phenoxy)-acetimidic acid ethyl ester hydrochloride (0.045 g, 0.159 mmol, Example 1.1) in EtOH (4 mL) was stirred at room temperature for 12 hours. The reaction was concentrated to give a residue, which was purified by chromatography (silica, hexanes: EtOAc, 1:2) to afford the product as brown oil (0.065 g, 98%). $^1$H NMR (400 MHz, CD$_3$OD) δ (ppm): 8.25 (d, 1H, J=7.6 Hz), 7.92 (td, 1H, J=8.4 Hz, J=1.6 Hz), 7.77 (td, 1H, J=8.4 Hz, J=1.2 Hz), 7.65-7.54 (m, 3H), 7.27-7.20 (m, 4H), 7.14 (d, 1H, J=8.4 Hz), 5.45 (s, 2H). Mass Spectrum (LCMS, ESI pos.) Calcd. For C$_{22}$H$_{15}$F$_6$N$_2$O$_3$S: 501.4 (M+H), Found 501.2.

EXAMPLE 16

2-methyl-1-{2-[2-(4-trifluoromethyl-phenoxymethyl)-1H-benzoimidazol-5-yl]-benzenesulfonyl}-propan-2-ol (Cpd 159)

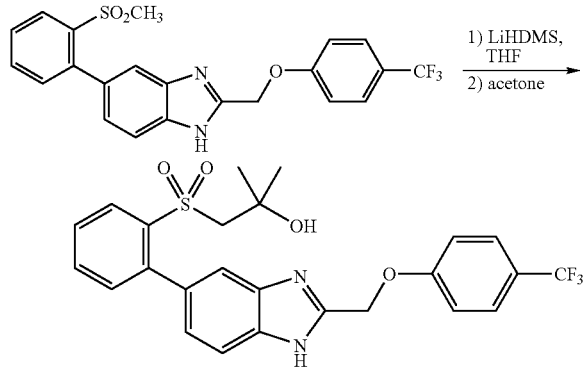

To a solution of 5-(2-methanesulfonyl-phenyl)-2-(4-trifluoromethyl-phenoxymethyl)-1H-benzoimidazole (0.030 g, 0.0671 mmol) in THF (3 mL) was added lithium bis(trimethylsilyl)amide (0.20 mL, 0.201 mmol, 1.0 M solution in THF) at –78° C. After stirring for 30 min, acetone (0.2 mL) was added. The mixture was further stirred another 30 min. followed by an addition of MeOH to quench the reaction. Solvent evaporation provided a residue, which was purified by chromatography (silica, hexanes: EtOAc, 1:2) to afford the title compound as a white solid (0.030 g, 88%). $^1$H NMR (400 MHz, CD$_3$OD) δ (ppm): 8.19 (dd, 1H, J=8.0 Hz, J=1.2 Hz), 7.75-7.70 (m, 2H), 7.66-7.62 (m, 4H), 7.46 (dd, 1H, J=8.0 Hz, J=1.2 Hz), 7.35 (d, 1H, J=7.6 Hz), 7.25 (d, 2H, J=8.8 Hz), 5.46 (s, 2H), 2.92 (s, 2H), 1.08 (s, 6H). Mass Spectrum (LCMS, ESI pos.) Calcd. For C$_{25}$H$_{24}$F$_3$N$_2$O$_4$S: 505.5 (M+H), Found 505.3.

Using the procedures described in Example 16, Compound 160 was prepared from acetaldehyde in replacement of acetone.

| Cpd | Name and Data |
|---|---|
| 160 | 1-{2-[2-(4-trifluoromethyl-phenoxymethyl)-1H-benzoimidazol-5-yl]-benzenesulfonyl}-propan-2-ol<br>$^1$H NMR (400 MHz, CD$_3$OD) δ (ppm): 8.18 (dd, 1H, J = 7.6 Hz, J = 1.2 Hz), 7.75-7.71 (m, 2H), 7.67-7.61 (m, 4H), 7.47 (dd, 1H, J = 7.6 Hz, J = 1.2 Hz), 7.34 (dd, 1H, J = 8.0 Hz, J = 1.6 Hz), 7.25 (d, 2H, J = 8.4 Hz), 5.46 (s, 2H), 3.98-3.90 (m, 1H), 2.89 (dd, 1H, J = 14.4 Hz, J = 7.2 Hz), 2.73 (dd, 1H, J = 14.4 Hz, J = 4.4 Hz), 0.97 (d, 3H, J = 6.4 Hz). Mass Spectrum (LCMS, ESI pos.) Calcd. For C$_{24}$H$_{22}$F$_3$N$_2$O$_4$S: 491.5.5 (M + H), Found 491.2. |

EXAMPLE 17

2-{2-[2-(4-trifluoromethanesulfonyl-phenoxymethyl)-1H-benzoimidazol-5-yl]-benzenesulfonyl}-ethanol (Cpd 161)

A. [4-tert-butoxycarbonylamino-2'-(2-hydroxyethanesulfonyl)-biphenyl-3-yl]-carbamic acid tert-butyl ester

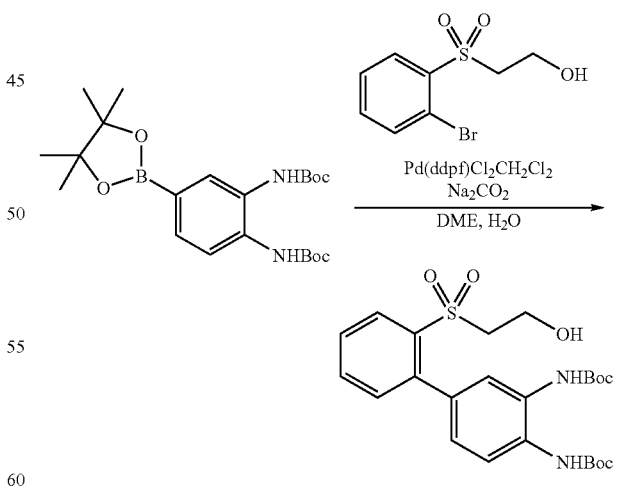

A mixture of [2-tert-butoxycarbonylamino-4-(4,4,5,5-tetramethyl-[1,3,2]dioxaborolan-2-yl)-phenyl]-carbamic acid tert-butyl ester (0.300 g, 0.691 mmol, Example 15, Step A), 2-bromophenylsulfonylethanol (0.153 g, 0.576 mmol), sodium carbonate (0.439 g, 4.15 mmol), and 1,1'-[bis(di-tert-butylphosphino)ferrocene]-palladium dichloride (0.153 g, 0.0576 mmol) in DME (6 mL) and H$_2$O (1.5 mL) was heated at 100° C. for 12 hours. The reaction mixture was concentrated under reduced pressure to provide a residue, which was purified by chromatography (silica, hexanes:EtOAc, 1:1) to afford the title compound as a yellow oil (0.233 g, 82%).

B. 2-(3',4'-diamino-biphenyl-2-sulfonyl)-ethanol

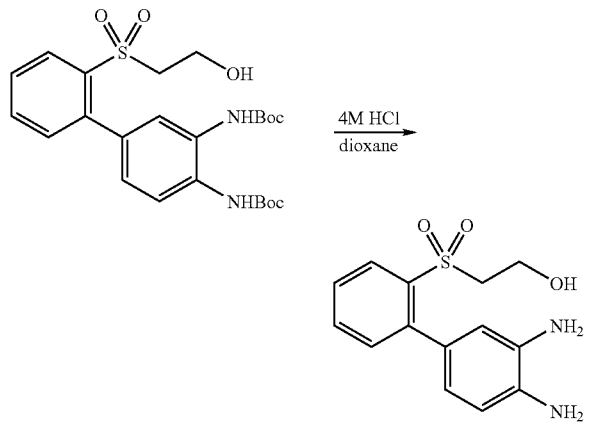

[4-tert-butoxycarbonylamino-2'-(2-hydroxy-ethanesulfonyl)-biphenyl-3-yl]-carbamic acid tert-butyl ester (0.233 g, 0.476 mmol) in a solution of 4M HCl in dioxane (6 mL) was stirred at room temperature for 2 hours. The reaction mixture was concentrated under reduced pressure. The residue was dissolved in EtOAc, and the solution was washed with saturated sodium bicarbonate and water (pH=7). The organic layer was dried over Na$_2$SO$_4$, filtered, and the filtrate was concentrated in vacuo to provide the title compound as a yellow oil (0.136 g, 98%).

C. 2-[2-(2-bromomethyl-1H-benzoimidazol-5-yl)-benzenesulfonyl]-ethanol

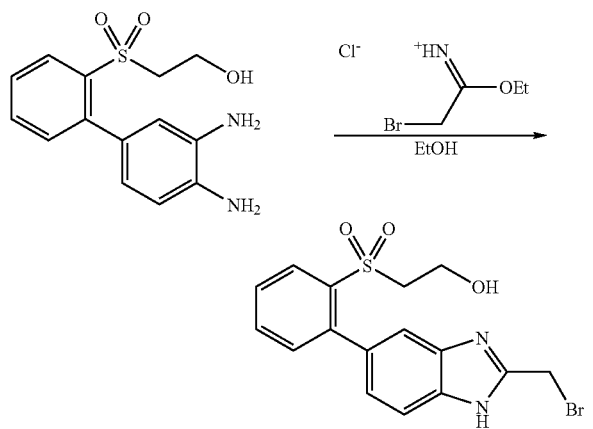

A mixture of 2-(3',4'-diamino-biphenyl-2-sulfonyl)-ethanol (0.140 g, 0.479 mmol) and 2-bromoacetimidic acid ethyl ester hydrochloride salt (0.116 g, 0.575 mmol) in anhydrous ethanol (100%, 6 mL) was stirred at room temperature for 12 hours. The reaction mixture was concentrated under reduced pressure and extracted with ethyl acetate and brine. The organic layer was dried over Na$_2$SO$_4$, filtered, and the filtrate was concentrated in vacuo to provide 2-bromomethyl-5-(2-methanesulfonyl-phenyl)-1H-benzoimidazole as yellow oil (0.178 g, 94%).

D. 2-bromomethyl-5-[2-(2-hydroxy-ethanesulfonyl)-phenyl]-benzoimidazole-1-carboxylic acid tert-butyl ester

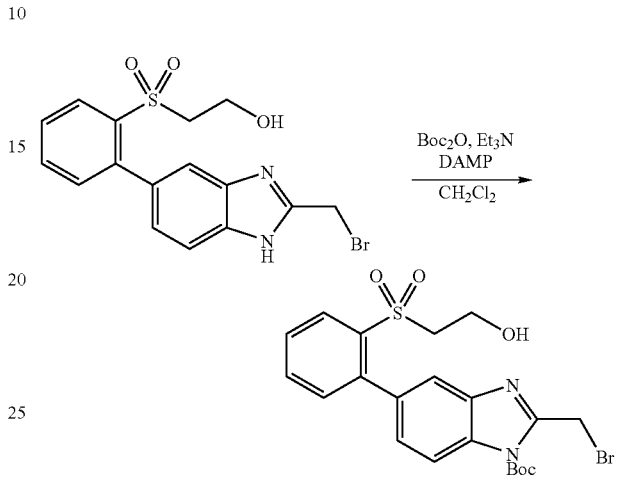

A mixture of 2-[2-(2-bromomethyl-1H-benzoimidazol-5-yl)-benzenesulfonyl]-ethanol (0.124 g, 0.314 mmol), Boc$_2$O (0.151 g, 0.690 mmol), Et$_3$N (0.131 mL, 0.942 mmol), and DMAP (0.004 g, 0.0314 mmol) in CH$_2$Cl$_2$ was stirred at rt for 2 hours. The reaction mixture was concentrated under reduced pressure and the residue was purified by chromatography (silica, EtOAc: hexanes, 1:2) to afford the title compound as a yellow oil (0.123 g, 79%).

E. 2-{2-[2-(4-trifluoromethanesulfonyl-phenoxymethyl)-1H-benzoimidazol-5-yl]-benzenesulfonyl}-ethanol

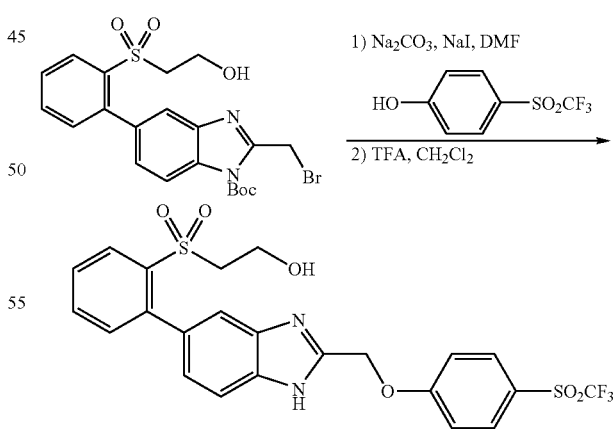

A mixture of 2-bromomethyl-5-[2-(2-hydroxy-ethanesulfonyl)-phenyl]-benzoimidazole-1-carboxylic acid tert-butyl ester (0.030 g, 0.0606 mmol), 4-trifluoromethanesulfonyl-phenol (0.027 g, 0.121 mmol), Na$_2$CO$_3$ (0.026 g, 0.242 mmol), and NaI (0.036 g, 0.242 mmol) in DMF (1 mL) was stirred for 12 hours at room temperature. The reaction mixture was concentrated under reduced pressure and the resulting residue was dissolved in CH$_2$Cl$_2$ (1 mL) followed by an addition of TFA (0.3 mL) and the mixture was stirred at rt for 3 hours. The reaction mixture was concentrated, and the residue was purified by chromatography (silica, CH$_2$Cl$_2$: MeOH, 5:1) to afford the title compound as a white solid. $^1$H NMR (400 MHz, CD$_3$OD) δ (ppm): 8.17 (dd, 1H, J=8.0 Hz, J=1.2 Hz), 8.03 (d, 2H, J=8.8 Hz), 7.76-7.62 (m, 4H), 7.48-7.45 (m, 3H), 7.35 (d, 1H, J=8.4 Hz), 5.57 (s, 2H), 3.63 (t, 2H, J=6.4 Hz), 2.91 (t, 2H, J=6.6 Hz). Mass Spectrum (LCMS, ESI pos.) Calcd. For C$_{25}$H$_{23}$F$_3$N$_3$O$_6$S$_2$: 582.5 (M+MeCN+H), Found 582.2.

Using the procedures described in Example 17, Compound 162 was prepared from 4-methanesulfonyl-phenol (Procedure E).

| Cpd | Name and Data |
|---|---|
| 162 | 2-{2-[2-(4-methanesulfonyl-phenoxymethyl)-1H-benzoimidazol-5-yl]-benzenesulfonyl}-ethanol<br>$^1$H NMR (400 MHz, CD$_3$OD) δ (ppm): 8.17 (dd, 1H, J = 8.4 Hz, J = 1.2 Hz), 7.93 (td, 2H, J = 8.8 Hz, J = 2.6 Hz), 7.76-7.62 (m, 4H), 7.46 (dd, 1H, J = 7.6 Hz, J = 1.2 Hz), 7.35-7.30 (m, 3H), 5.50 (s, 2H), 3.62 (t, 2H, J = 6.6 Hz), 3.09 (s, 3H), 2.91 (t, 2H, J = 6.2 Hz). Mass Spectrum (LCMS, ESI pos.) Calcd. For C$_{25}$H$_{26}$N$_3$O$_6$S$_2$: 528.6 (M + MeCN + H), Found 528.2. |

EXAMPLE 18

2-[2-(4-cyclopropyl-phenoxymethyl)-1H-benzoimidazol-5-yl]-benzenesulfonamide (Cpd 163)

A. acetic acid 4-cyclopropyl-phenyl ester

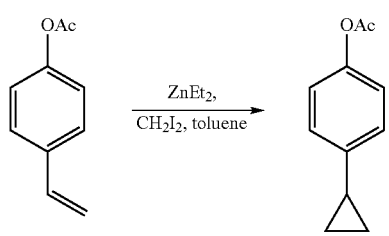

To a solution of diethylzinc (200 mL, 0.220 mol, 1.1 M in toluene) in toluene (270 mL) was added 4-acetoxystyrene (16.8 mL, 0.110 mol) and subsequently diiodomethane (23.0 mL, 0.286 mol). After the reaction mixture was stirred at rt for 5 hours, it was heated at reflux for 12 hours. The reaction was quenched with aqueous 2N HCl. The organic layer was separated and washed with brine, dried over Na$_2$SO$_4$, filtered, and the filtrate was concentrated under reduced pressure to afford the title compound as a brown oil (16.1 g, 83%).

B. 4-cyclopropyl-phenol

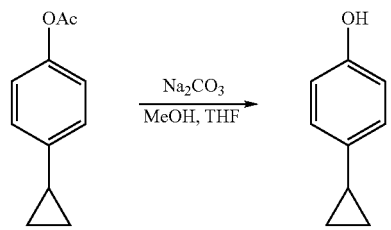

To a solution of acetic acid 4-cyclopropyl-phenyl ester (16.1 g, 0.0914 mol) in mixed solvent (40 mL, MeOH:THF=1:1) was added sodium acetate (19.4 g, 0.183 mol). The reaction mixture was stirred two hours. Solvent was evaporated under reduced pressure to provide a crude mixture, to which was then added Et$_2$O. The solid was filtered and the filtrate was concentrated to afford the title compound as a yellow oil (12.1 g, 99%).

C. (4-cyclopropyl-phenoxy)-acetic acid methyl ester

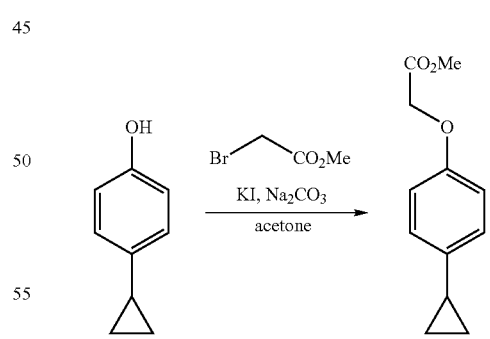

To a solution of 4-cyclopropyl-phenol (1.00 g, 7.46 mmol) in acetone (20 mL) was added potassium iodide (2.47 g, 16.4 mmol), sodium carbonate (2.34 g, 16.4 mmol), and methyl bromoacetate (0.63 mL, 6.78 mmol), and the reaction mixture was stirred 12 hours. After filtering off the solid, the filtrate was concentrated. The residue was purified by chromatography (silica, hexanes: EtOAc=4:1) to afford the title compound as a yellow oil (1.29 g, 84%).

D. (4-cyclopropyl-phenoxy)-acetic acid

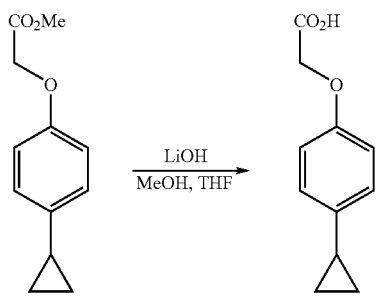

To a solution of (4-cyclopropyl-phenoxy)-acetic acid methyl ester (1.29 g, 6.27 mmol) in mixed solvent (10 mL, MeOH: THF=1:1) was added 1N lithium hydroxide solution (5 mL). After stirring for 6 hours, the reaction mixture was acidified with aqueous 2N HCl and subsequently extracted with EtOAc. The separated organic layer was washed with brine, dried over $Na_2SO_4$, filtered, and the filtrate was concentrated under reduced pressure to afford the title compound as a yellow oil (1.18 g, 98%).

E. 5-bromo-2-(4-cyclopropyl-phenoxymethyl)-1H-benzoimidazole

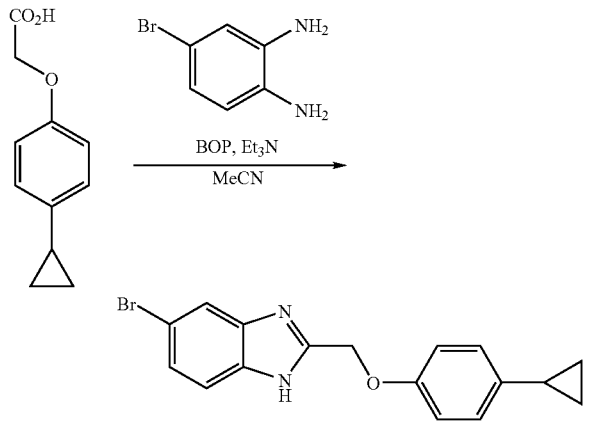

To a solution of 4-bromo-benzene-1,2-diamine (0.759 g, 4.06 mmol), BOP (1.381 g, 3.12 mmol), and triethylamine (0.44 mL, 3.12 mmol) in acetonitrile (18 mL) were added dropwise over 2 hours a solution of 4-cyclopropyl-phenoxy)-acetic acid (0.600 g, 3.12 mmol) in acetonitrile (5 mL). The reaction mixture was stirred for 12 hours followed by heating at 80° C. for another 8 hours. The reaction mixture was concentrated under reduced pressure to provide a residue, which was purified by chromatography (silica, hexanes: EtOAc=1:1) to afford the title compound as a yellow solid (0.825 g, 77%).

F. 2-[2-(4-cyclopropyl-phenoxymethyl)-1H-benzoimidazol-5-yl]-benzenesulfonamide

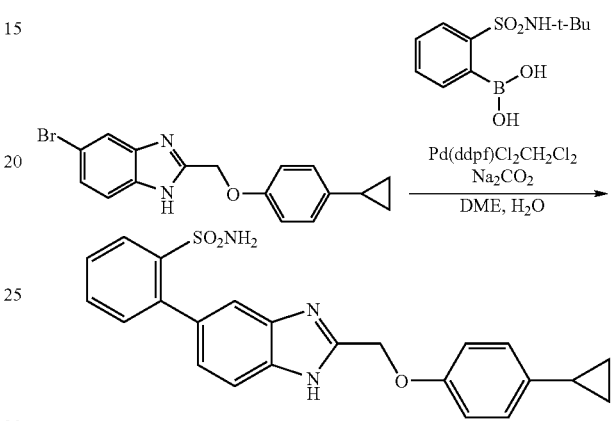

A mixture of 5-bromo-2-(4-cyclopropyl-phenoxymethyl)-1H-benzoimidazole (0.030 g, 0.0874 mmol), 2-(tert-butylamino)sulfonylphenylboronic acid (0.029 g, 0.114 mmol), sodium carbonate (0.079 g, 0.524 mmol), and 1,1'-[bis(di-tert-butylphosphino)ferrocene]-palladium dichloride (0.006 g, 0.00874 mmol) in DME (2 mL) and $H_2O$ (0.5 mL) was heated at 90° C. for 12 hours. The reaction mixture was concentrated under reduced pressure to provide a residue, which was purified by chromatography (silica, hexanes:EtOAc, 1:1) to afford the product. It was then dissolved in trifluoroacetic acid (3 mL) and heated to 60° C. for 2 hours. The reaction mixture was concentrated and the residue was purified by chromatography (silica, hexanes: EtOAc, 1:2) to afford the title compound as a light brown solid. $^1$H NMR (400 MHz, $CD_3OD$) δ (ppm): 8.14 (dd, 1H, J=8.0 Hz, J=1.2 Hz), 7.77 (s, 1H), 7.73 (d, 1H, J=9.2 Hz), 7.65 (td, 1H, J=8.2 Hz, J=1.6 Hz), 7.50 (td, 1H, J=8.4 Hz, J=1.6 Hz), 7.51 (dd, 1H, J=8.8 Hz, J=1.2 Hz), 7.41 (dd, 1H, J=6.0 Hz, J=1.2 Hz), 7.08-6.99 (m, 4H), 5.50 (s, 2H), 1.90-1.84 (m, 1H), 0.92-0.90 (m, 2H), 0.62-0.58 (m, 2H). Mass Spectrum (LCMS, ESI pos.) Calcd. For $C_{23}H_{22}N_3O_3S$: 420.5 (M+H), Found 420.4.

Using the procedures described in Example 18, and reagents, starting materials and conditions known to those skilled in the art, the following compounds representative of the present invention were prepared:

| Cpd | Name and Data |
|---|---|
| 164 | 2-{2-[2-(4-cyclopropyl-phenoxymethyl)-1H-benzoimidazol-5-yl]-phenyl}-propan-2-ol<br>$^1$H NMR (400 MHz, $CD_3OD$) δ (ppm): 7.81 (dd, 1H, J = 8.0 Hz, J = 1.2 Hz), 7.54 (d, 1H, J = 8.0 Hz), 7.43 (s, 1H), 7.34 (td, 1H, J = 8.6 Hz, J = 1.6 Hz), 7.20 (td, 1H, J = 8.2 Hz, J = 1.2 Hz), 7.15 (dd, 1H, J = 8.4 Hz, J = 1.6 Hz), 7.05 (dd, 1H, J = 7.2 Hz, J = 1.6 Hz), 7.03-6.95 (m, 4H), 5.30 (s, 2H), 1.87-1.81 (m, 1H), 1.32 (s, 6H), |

-continued

| Cpd | Name and Data |
|---|---|
| | 0.90-0.87 (m, 2H), 0.60-0.56 (m, 2H). Mass Spectrum (LCMS, ESI pos.) Calcd. For $C_{26}H_{27}N_2O_2$: 399.5 (M + H), Found 399.5. |
| 165 | 2-[2-(4-cyclopropyl-phenoxymethyl)-1H-benzoimidazol-5-yl]-N-methyl-benzenesulfonamide<br>$^1$H NMR (400 MHz, $CD_3OD$) δ (ppm): 8.05 (dd, 1H, J = 8.0 Hz, J = 1.2 Hz), 7.66-7.60 (m, 4H), 7.55 (td, 1H, J = 8.4 Hz, J = 1.6 Hz), 7.40 (dd, 1H, J = 7.6 Hz, J = 1.2 Hz), 7.30 (dd, 1H, J = 8.4 Hz, J = 1.6 Hz), 7.02-6.94 (m, 4H), 5.31 (s, 2H), 2.34 (s, 3H), 1.87-1.80 (m, 1H), 0.90-0.85 (m, 2H), 0.59-0.55 (m, 2H). Mass Spectrum (LCMS, ESI pos.) Calcd. For $C_{24}H_{24}N_3O_3S$: 433.5 (M + H), Found 434.4. |
| 166 | 2-[2-(4-cyclopropyl-phenoxymethyl)-1H-benzoimidazol-5-yl]-N,N-dimethyl-benzenesulfonamide<br>$^1$H NMR (400 MHz, $CD_3OD$) δ (ppm): 8.07 (dd, 1H, J = 8.0 Hz, J = 1.2 Hz), 7.65 (td, 1H, J = 8.8 Hz, J = 1.2 Hz), 7.61-7.54 (m, 3H), 7.40 (dd, 1H, J = 7.2 Hz, J = 1.2 Hz), 7.25 (dd, 1H, J = 8.8 Hz, J = 1.6 Hz), 7.03-6.94 (m, 4H), 5.31 (s, 2H), 2.30 (s, 6H), 1.87-1.82 (m, 1H), 0.91-0.86 (m, 2H), 0.60-0.56 (m, 2H). Mass Spectrum (LCMS, ESI pos.) Calcd. For $C_{25}H_{26}N_3O_3S$: 448.6 (M + H), Found 448.5. |
| 167 | 2-(4-cyclopropyl-phenoxymethyl)-5-(2-methanesulfonyl-phenyl)-1H-benzoimidazole<br>$^1$H NMR (400 MHz, $CD_3OD$) δ (ppm): 8.18 (dd, 1H, J = 8.4 Hz, J = 1.2 Hz), 7.72 (td, 1H, J = 8.2 Hz, J = 1.2 Hz), 7.69-7.61 (m, 3H), 7.46 (dd, 1H, J = 8.0 Hz, J = 1.2 Hz), 7.32 (dd, 1H, J = 8.4 Hz, J = 1.6 Hz), 7.03-6.95 (m, 4H), 5.32 (s, 2H), 2.64 (s, 3H), 1.88-1.81 (m, 1H), 0.91-0.86 (m, 2H), 0.60-0.56 (m, 2H). Mass Spectrum (LCMS, ESI pos.) Calcd. For $C_{24}H_{23}N_2O_3S$: 419.5 (M + H), Found 419.4. |
| 168 | N-{2-[2-(4-cyclopropyl-phenoxymethyl)-1H-benzoimidazol-5-yl]-phenyl}-methanesulfonamide<br>$^1$H NMR (400 MHz, $CD_3OD$) δ (ppm): 7.67-7.63 (m, 2H), 7.54-7.51 (m, 1H), 7.40-7.36 (m, 2H), 7.33-7.28 (m, 2H), 7.02-6.94 (m, 4H), 5.31 (s, 2H), 2.70 (s, 3H), 1.87-1.80 (m, 1H), 0.90-0.85 (m, 2H), 0.59-0.55 (m, 2H). Mass Spectrum (LCMS, ESI pos.) Calcd. For $C_{24}H_{24}N_3O_3S$: 433.5 (M + H), Found 434.4. |

BIOLOGICAL EXAMPLES

EXAMPLE 1

Human TRPV1 (TRPV1) Binding Assay

Compounds of the present invention were tested for their ability to inhibit the binding of [$^3$H] RTX to hTRPV1 receptors in a [$^3$H] RTX binding assay as previously described (See, PCT International Application WO02/33411A1 and Elfrida G. R. et al., J. Pharmacol. Exp. Ther., 2002, 300(1): 9-17.)

HEK293 cells were transfected with hTRPV1 vanilloid receptors and washed with Hank's balanced Salt Solution, dissociated with cell dissociation buffer (Sigma), and then centrifuged at 1000×g for 5 min. Cell pellets were homogenized in cold 20 mM HEPES buffer (pH=7.4), containing 5.8 mM NaCl, 320 mM sucrose, 2 mM $MgCl_2$, 0.75 $CaCl_2$ and 5 mM KCl and centrifuged at 1000×g for 15 min. The resultant supernatant was then centrifuged at 40,000×g for 15 min. The pelleted membranes were stored in a freezer at −80° C.

Approximately 120 μg protein/mL from membranes were incubated with indicated concentrations of [$^3$H]RTX in 0.5 mL of the HEPES buffer (pH 7.4) containing 0.25 mg/mL fatty acid-free bovine serum albumin at 37° C. for 60 min. The reaction mixture was then cooled to 4° C., and 0.1 mg of $α_1$-acid glycoprotein was added to each sample, which was then incubated at 4° C. for 15 min. The samples were centrifuged at 18,500×g for 15 min. The tip of the microcentrifuge tube containing the pellet was cut off. Bound radioactivity was quantified by scintillation counting. Non-specific binding was measured in the presence of 200 nM unlabeled RTX.

Alternatively, a binding assay using rat tissue was used. Rat spinal cord was homogenized twice with a Polytron and centrifuged at 3000 rpm for 10 min in 20 mM HEPES buffer (pH=7.4), containing 5.8 mM NaCl 5.8, 320 mM sucrose, 2 mM $MgCl_2$, 0.75 mM $CaCl_2$ 0.75 and 5 mM KCl. The supernatant was then centrifuged at 40,000×g for 15 min. The pellet was saved in a tube, and 10 mL of assay buffer were added into the tube. The pellet and buffer were mixed with a Polytron. The assay contained 120 μg/mL membrane protein and 0.3-0.6 nM [$^3$H]-RTX (Perkin-Elmer, Boston) in a total volume of 0.5 mL HEPES buffer. Following incubation for 60 min at 37° C., the samples were cooled on ice, and 0.1 mg of $α_1$-acid glycoprotein were added into the samples. After centrifugation at 18,500×g for 15 min, the supernatant was aspirated and the tips of tubes were cut off and placed into 6 mL vials.

Data were calculated according to the equation: % inhibition=100%×[(total binding−binding)/(total binding−non specific binding)]. $K_i$ values were calculated using a Prism program.

Compound 1 was tested and found to provide a $K_i$ value of 2.7 nM.

EXAMPLE 2

Human TRPV1 (hTRPV1) Functional Assay

The functional activity of the test compounds was determined by measuring changes in intracellular calcium concentration using a $Ca^{++}$-sensitive fluorescent dye and FLIPR™ technology. Increases in $Ca^{++}$ concentration were readily detected upon challenge with capsaicin.

HEK293 cells expressing hTRPV1 were grown on poly-D-lysine coated 384 well black-walled plates (BD 354663) and 1 day later loaded with Calcium 3 Dye for 35 min at 37° C., 5% $CO_2$ and then for 25 min at room temperature, and subsequently tested for agonist-induced increases in intracellular $Ca^{2+}$ levels using FLIPR™ technology. Cells were challenged with test compounds (at varying concentrations) and intracellular $Ca^{2+}$ was measured for 5 min prior to the addition of capsaicin to all wells to achieve a final concentration of 0.030 μM eliciting ~80% maximal response.

$EC_{50}$ or $IC_{50}$ values were determined from concentration-response studies, which were generated using the average of quadruplicate wells for each data point. For those compounds tested, $IC_{50}$ and percent inhibition values are shown in Table 1. The symbol "a" represents percent inhibition obtained at a test concentration of 0.5 μm; the symbol "b" represents percent inhibition obtained at a test concentration of 0.2 μm; the symbol "c" represents an $IC_{50}$ value (nM) derived from a variety of test concentrations. The term "NA" means that the result is not applicable for a particular compound.

TABLE 1

| Cpd | Data | |
|---|---|---|
| 1 | [a]100; [c]3 | |
| 2 | [a]99; [c]10 | |
| 3 | [a]43 | |
| 4 | [a]67 | |
| 5 | [a]71 | |
| 6 | [a]87; [c]102 | |
| 7 | [c]13 | |
| 8 | [c]6.6 | |
| 9 | [c]110 | |
| 10 | [c]120 | |
| 11 | [c]38 | |
| 12 | [c]18 | |
| 13 | [c]61 | |
| 14 | [c]110 | 40281189 |
| 15 | [c]25 | |
| 16 | [a]99; [c]10 | |
| 17 | [a]100; [c]1 | |
| 18 | [a]97; [c]71 | |
| 19 | [a]100; [c]8 | |
| 20 | [a]100; [c]20 | |
| 21 | [a]99; [c]14 | |
| 22 | [a]100; [c]4 | |
| 23 | [a]100; [c]19 | |
| 24 | [a]92; [c]156 | |
| 25 | [a]100; [c]13 | |
| 26 | [a]87; [c]177 | |
| 27 | [a]98; [c]12 | |
| 28 | [a]98; [c]8.9 | |
| 29 | [a]98; [c]22 | |
| 30 | [a]99; [c]13 | |
| 31 | [a]97; [c]10.6 | |
| 32 | [b]100; [c]6 | |
| 33 | [a]100; [c]44 | |
| 34 | [a]100; [c]13 | |
| 35 | [a]97; [c]16 | |
| 36 | [a]98; [c]32 | |
| 37 | [a]50 | |
| 38 | [a]13 | |
| 39 | [a]5 | |
| 40 | [a]100; [c]8.6 | |
| 41 | [b]98; [c]4.9 | |
| 42 | [b]93; [c]75 | |
| 43 | [b]87; [c]123 | |
| 44 | [b]12 | |
| 45 | [b]2 | |
| 46 | [b]5 | |
| 47 | [b]46 | |
| 48 | [b]41 | 40323608 |
| 49 | [b]89; [c]106 | |
| 50 | [b]81; [c]91 | |
| 51 | [b]100; [c]7.8 | |
| 52 | [b]99; [c]35 | 40323634 |
| 53 | [b]17 | |
| 54 | [b]4 | |
| 55 | [b]20 | 40339312 |
| 56 | [b]31 | |
| 57 | [b]14 | |
| 58 | [b]22 | 40451151 |
| 59 | [b]87; [c]18 | 40572285 |
| 60 | [b]49 | |
| 61 | [b]77; [c]66 | |
| 62 | [b]24 | 40572376 |
| 63 | [b]37 | |
| 64 | [b]58 | 40575457 |

TABLE 1-continued

| Cpd | Data | |
|---|---|---|
| 65 | [b]91; [c]58 | |
| 66 | [b]85; [c]81 | 40572233 |
| 67 | [b]70 | 40572220 |
| 68 | [b]59 | 40575392 |
| 69 | [b]21 | |
| 70 | [b]33 | |
| 71 | [b]43 | |
| 72 | [b]96; [c]30 | 40572311 |
| 73 | [b]33 | |
| 74 | [b]60 | 40575340 |
| 75 | [b]93; [c]68 | |
| 76 | [b]96; [c]31 | |
| 77 | [b]100; [c]3 | 40575483 |
| 78 | [b]98; [c]3 | |
| 79 | [b]61 | |
| 80 | [b]99; [c]14 | |
| 81 | [b]96; [c]85 | |
| 82 | [b]99; [c]7 | |
| 83 | [b]51 | |
| 84 | [b]96; [c]54 | |
| 85 | [b]12 | |
| 86 | [b]97; [c]4.9 | |
| 87 | [b]96; [c]14 | |
| 88 | [b]36 | |
| 89 | [b]90; [c]52 | |
| 90 | [b]31 | |
| 91 | [b]99; [c]21 | |
| 92 | [b]76; [c]86 | |
| 93 | [b]11 | |
| 94 | [b]1 | |
| 95 | [b]1 | |
| 96 | [b]6 | |
| 97 | [b]42 | |
| 98 | [a]94; [c]2.1 | |
| 99 | [a]14 | |
| 100 | [a]13 | |
| 101 | [a]94; [c]10 | |
| 102 | [a]8 | |
| 103 | [a]7 | |
| 104 | [a]8 | |
| 105 | [a]7 | |
| 106 | [a]94; [c]3 | |
| 107 | [a]16 | |
| 108 | [a]10 | |
| 109 | [a]3 | |
| 110 | [a]98; [c]58 | |
| 111 | [a]18 | |
| 112 | [a]1 | |
| 113 | [a]42 | |
| 114 | [a]6 | |
| 115 | [a]14 | |
| 116 | [a]99; [c]8.1 | |
| 117 | [a]13 | |
| 118 | [a]2 | |
| 119 | [a]14 | |
| 120 | [a]15 | |
| 121 | [a]9 | |
| 122 | [a]21 | |
| 123 | [a]7 | |
| 124 | [a]12 | |
| 125 | [a]11 | |
| 126 | [a]4 | |
| 127 | [a]85; [c]24.3 | |
| 128 | [a]13 | |
| 129 | [a]8 | |
| 130 | [a]11 | |
| 131 | [a]5 | |
| 132 | [a]100; [c]85 | |
| 133 | [a]92; [c]105 | |
| 134 | [a]98; [c]16 | |
| 135 | [a]100; [c]47 | |
| 136 | [a]99; [c]68 | |
| 137 | [a]37 | |
| 138 | [a]18 | |
| 139 | [a]99; [c]21 | |
| 140 | [a]101; [c]17 | |
| 141 | [a]99; [c]83 | |

TABLE 1-continued

| Cpd | Data |
|---|---|
| 142 | [b]97; [c]8 |
| 143 | [b]96; [c]13 |
| 144 | [b]82; [c]114 |
| 145 | [b]12 |
| 146 | [b]72 |
| 147 | [b]98; [c]7 |
| 148 | [b]89; [c]58 |
| 149 | [b]89; [c]46 |
| 150 | [b]99; [c]16 |
| 151 | [b]33 |
| 152 | [b]38 |
| 153 | [b]31 |
| 154 | [b]68 |
| 155 | [b]21 |
| 156 | [b]76; [c]78 |
| 157 | [b]20 |
| 158 | [b]13 |
| 159 | [b]90; [c]22 |
| 160 | [b]90; [c]12.5 |
| 161 | [b]63 |
| 162 | [b]4 |
| 163 | [b]98; [c]3 |
| 164 | [b]97; [c]25 |
| 165 | [b]98; [c]6 |
| 166 | [b]98; [c]7 |
| 167 | [b]98; [c]7 |
| 168 | [b]97; [c]24 |

EXAMPLE 3

Chemically-Induced Models of Inflammatory Pain

Compounds of the present invention were tested in animal models of inflammation and inflammatory pain. To assess the ability of test compounds to reverse thermal hyperalgesia, baseline response latencies on a radiant heat (RH) paw stimulator were obtained before an intraplantar injection of 100 μL (1 μg/μL) CFA (1:1 CFA:saline) in male Sprague-Dawley rats. Only withdrawal responses that were quick hind paw movements (with or without licking of the hind paw) were recorded. Paw movements associated with locomotion or a shifting of weight were not considered a withdrawal response. The stimulus intensity that produced 10-15 sec baseline withdrawal latencies was used and a maximum cut-off of 20 sec was imposed. Hypersensitivity was evaluated 24 h after CFA. Only rats that exhibited at least a 25% reduction in response latency from baseline (i.e. hyperalgesia) were included in further analysis.

Following the post-inflammogen latency assessment, rats were orally dosed (2.5 mL/kg) with test compound (10 mg/kg) or vehicle (20% hydroxypropyl beta cyclodextran). To determine the time of peak effect, latencies were redetermined 30, 60, 100, 180 and 300 min after compound administration.

Data are presented as the maximal percent reversal of hypersensitivity obtained during the 300 min test, which was calculated for each animal according to the formula:

% reversal=100%×(treatment response−post-inflammogen response)/(pre-inflammogen response−post-inflammogen response)

TABLE 2

| Cpd | % Reversal |
|---|---|
| 1 | 85 |
| 2 | 80 |

TABLE 2-continued

| Cpd | % Reversal |
|---|---|
| 16 | 70 |
| 17 | 100 |
| 21 | 100 |
| 86 | 100 |
| 98 | 30 |
| 101 | 22 |

Throughout this application, various publications are cited. The disclosure of these publications is hereby incorporated by reference into this application to describe more fully the state of the art to which this invention pertains.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

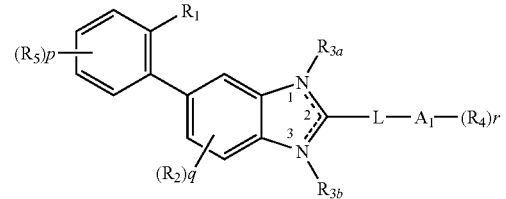

or a stereoisomeric, tautomeric or salt form thereof, wherein:
the dashed lines between positions 1, 2 and 3 in Formula (I) indicate the positions of a tautomeric double bond,
wherein when a double bond is formed between positions 1 and 2, then $R_{3b}$ is present, and
wherein, when a double bond is formed between positions 2 and 3, then $R_{3a}$ is present;
p is 0, 1 or 2;
q is 0, 1 or 2;
r is 0, 1, 2 or 3;
L is —X—$C_{1-3}$alkyl- or —$C_{1-3}$alkyl-Y—, wherein each instance of alkyl is optionally perfluorinated;
X and Y are each O, S, SO, $SO_2$ or $NR_6$;
$A_1$ is selected from the group consisting of indanyl, 1,2,3,4-tetrahydro-naphthalenyl, phenyl, naphthyl, benzo[1,3]dioxolyl, pyridinyl and quinolinyl;
$R_1$ is $C_{1-6}$alkylsulfonyl, $C_{1-6}$alkylsulfonylamino, aminosulfonyl or $(C_{1-4}alkyl)_{1-2}$aminosulfonyl,
wherein each instance of alkyl is optionally substituted with one, two or three substituents independently selected from the group consisting of $C_{1-8}$alkoxy, amino, $(C_{1-4}alkyl)_{1-2}$amino, $C_{1-6}$alkylcarbonylamino, $C_{1-6}$alkoxycarbonylamino, aminocarbonylamino, $(C_{1-6}alkyl)_{1-2}$aminocarbonylamino, $C_{1-6}$alkylsulfonylamino, halogen, oxo and hydroxy, and
wherein, each instance of alkyl and alkoxy is optionally perfluorinated;
$R_2$ is each selected from the group consisting of halogen, $C_{1-4}$alkyl, $C_{1-4}$alkoxy, $C_{1-4}$alkylsulfonyl, nitro, $(C_{1-4}alkyl)_{1-2}$amino and cyano, wherein each instance of alkyl and alkoxy is optionally perfluorinated;

$R_{3a}$ and $R_{3b}$ are each selected from the group consisting of hydrogen and $C_{1-4}$alkyl;

$R_4$ is each halogen, nitro, cyano, $C_{1-6}$alkyl, $C_{1-6}$alkoxy, halo$C_{1-6}$alkyl, halo$C_{1-6}$alkoxy, $C_{1-6}$alkoxy-$C_{1-6}$alkyl, $C_{1-6}$alkylthio, halo$C_{1-6}$alkylthio, $C_{1-6}$alkylsulfonyl, halo$C_{1-6}$alkylsulfonyl, $C_{3-8}$cycloalkyl, $C_{3-8}$cycloalkyl-$C_{1-4}$alkyl, $C_{3-8}$cycloalkyl-$C_{1-4}$alkoxy, $C_{3-8}$cycloalkyloxy, amino, $(C_{1-6}$alkyl$)_{1-2}$amino, $(C_{3-8}$cycloalkyl$)_{1-2}$amino, $(C_{3-8}$cycloalkyl-$C_{1-4}$alkyl$)_{1-2}$amino, cyano, $C_{1-6}$alkylcarbonyl, $C_{1-6}$alkoxy-carbonyl, $C_{1-6}$alkoxycarbonyl-$C_{1-6}$alkyl, aminocarbonyl, $(C_{1-6}$alkyl$)_{1-2}$aminocarbonyl, $C_{1-6}$alkylcarbonylamino, $C_{1-6}$alkoxycarbonylamino, aminocarbonylamino, $(C_{1-6}$alkyl$)_{1-2}$aminocarbonylamino, $C_{1-6}$alkylsulfonylamino, aminosulfonyl or $(C_{1-4}$alkyl$)_{1-2}$aminosulfonyl, wherein each instance of alkyl and alkoxy is optionally perfluorinated;

$R_5$ is selected from the group consisting of halogen, hydroxy, $C_{1-4}$alkyl, halo$C_{1-4}$alkyl, hydroxy$C_{1-4}$alkyl, $C_{1-4}$alkoxy, $C_{1-4}$alkylsulfonyl, nitro, $C_{1-6}$alkylcarbonyl, $C_{1-6}$alkoxycarbonyl, amino, $(C_{1-4}$alkyl$)_{1-2}$amino, $C_{1-6}$alkylcarbonylamino, $C_{1-6}$alkylsulfonylamino, aminosulfonyl, $(C_{1-6}$alkyl$)_{1-2}$aminosulfonyl, and cyano, wherein each instance of alkyl and alkoxy is optionally perfluorinated; and $R_6$ is one substituent selected from the group consisting of hydrogen and optionally perfluorinated $C_{1-4}$alkyl.

2. The compound of claim 1, wherein a double bond is formed between positions 1 and 2 and $R_{3b}$ is present;

p is 0, 1 or 2;

q is 0;

r is 0, 1, 2 or 3;

L is —X—$C_{1-3}$alkyl- or —$C_{1-3}$alkyl-Y—, wherein each instance of alkyl is optionally perfluorinated;

X and Y are each O, S, SO$_2$ or NR$_6$;

$A_1$ is selected from the group consisting of indanyl, 1,2,3,4-tetrahydro-naphthalenyl, phenyl, naphthyl, benzo[1,3]dioxolyl, pyridinyl and quinolinyl;

$R_1$ is $C_{1-6}$alkylsulfonyl, amino, $C_{1-6}$alkylsulfonylamino, aminosulfonyl or $(C_{1-4}$alkyl$)_{1-2}$aminosulfonyl, wherein each instance of alkyl is optionally substituted with one, two or three substituents independently selected from the group consisting of halogen and hydroxy;

$R_{3b}$ is selected from the group consisting of hydrogen and $C_{1-4}$alkyl;

$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl, cyano, $C_{1-6}$alkylcarbonyl, $C_{1-6}$alkoxy-carbonyl-$C_{1-6}$alkyl and $C_{1-6}$alkylcarbonylamino;

$R_5$ is selected from the group consisting of halogen, hydroxy, $C_{1-4}$alkyl, halo$C_{1-4}$alkyl, hydroxy$C_{1-4}$alkyl, $C_{1-4}$alkylsulfonyl, $C_{1-6}$alkoxycarbonyl, amino, $C_{1-6}$alkylcarbonylamino, $C_{1-6}$alkylsulfonylamino, aminosulfonyl and $(C_{1-6}$alkyl$)_{1-2}$aminosulfonyl; and $R_6$ is one substituent selected from the group consisting of hydrogen and $C_{1-4}$alkyl.

3. The compound of claim 1, wherein a double bond is formed between positions 1 and 2 and $R_{3b}$ is present;

p is 0, 1 or 2;

q is 0;

r is 0, 1, 2 or 3;

L is —X—$C_{1-3}$alkyl- or —$C_{1-3}$alkyl-Y—, wherein each instance of alkyl is optionally perfluorinated;

X and Y are each O, S or NH;

$A_1$ is selected from the group consisting of indanyl, 1,2,3,4-tetrahydro-naphthalenyl, phenyl, naphthyl, benzo[1,3]dioxolyl and quinolinyl;

$R_1$ is $C_{1-6}$alkyl, $C_{1-6}$alkylsulfonyl, $C_{1-6}$alkylsulfonylamino, aminosulfonyl or $(C_{1-4}$alkyl$)_{1-2}$aminosulfonyl, wherein each instance of alkyl is optionally substituted with one, two or three substituents independently selected from the group consisting of halogen and hydroxy;

$R_{3b}$ is selected from the group consisting of hydrogen and $C_{1-4}$alkyl;

$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl, cyano or $C_{1-6}$alkylcarbonyl; and $R_5$ is selected from the group consisting of halogen and halo$C_{1-4}$alkyl.

4. The compound of claim 1, wherein a double bond is formed between positions 1 and 2 and $R_{3b}$ is present;

p is 0, 1 or 2;

q is 0;

r is 1 or 2;

L is —X—$C_{1-3}$alkyl- or —$C_{1-3}$alkyl-Y—, wherein each instance of alkyl is optionally perfluorinated;

X and Y are each O or S;

$A_1$ is selected from the group consisting of indanyl, 1,2,3,4-tetrahydro-naphthalenyl, phenyl and naphthyl;

$R_1$ is $C_{1-6}$alkylsulfonyl, $C_{1-6}$alkylsulfonylamino, aminosulfonyl or $(C_{1-4}$alkyl$)_{1-2}$aminosulfonyl, wherein each instance of alkyl is optionally substituted with one hydroxy substituent;

$R_{3b}$ is selected from the group consisting of hydrogen and $C_{1-4}$alkyl;

$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl or $C_{1-6}$alkylcarbonyl; and $R_5$ is halogen.

5. The compound of claim 1, wherein a double bond is formed between positions 1 and 2 and $R_{3b}$ is present;

p is 0;

q is 0;

r is 1;

L is —X—$C_{1-3}$alkyl- or —$C_{1-3}$alkyl-Y—;

X and Y are each O or S;

$A_1$ is phenyl;

$R_1$ is $C_{1-6}$alkylsulfonyl, $C_{1-6}$alkylsulfonylamino, aminosulfonyl or $(C_{1-4}$alkyl$)_{1-2}$aminosulfonyl, wherein each instance of alkyl is optionally substituted with one hydroxy substituent;

$R_{3b}$ is selected from the group consisting of hydrogen and $C_{1-4}$alkyl;

$R_4$ is halogen, $C_{1-6}$alkyl, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl or $C_{3-8}$cycloalkyl.

6. The compound of claim 1, wherein $R_4$ is cyclopropyl.

7. The compound of claim 1, wherein a double bond is formed between positions 1 and 2 and $R_{3b}$ is present;

p is 0;

q is 0;

r is 1;

L is —$C_{1-3}$alkyl-O—;

$A_1$ is phenyl;

145

R$_1$ is C$_{1-6}$alkylsulfonyl, C$_{1-6}$alkylsulfonylamino, aminosulfonyl or C$_{1-4}$alkylaminosulfonyl,
wherein each instance of alkyl is optionally substituted with one hydroxy substituent;
R$_{3b}$ is hydrogen; and
R$_4$ is haloC$_{1-6}$alkyl, haloC$_{1-6}$alkoxy or haloC$_{1-6}$alkylsulfonyl.

8. The compound of claim 1, wherein
a double bond is formed between positions 1 and 2 and R$_{3b}$ is present;
p is 0;
q is 0;
r is 1;
L is —CH$_2$—O—;
A$_1$ is phenyl;
R$_1$ is methylsulfonyl, methylsulfonylamino, aminosulfonyl or methylaminosulfonyl,
wherein isopropyl is optionally substituted with one hydroxy substituent;
R$_{3b}$ is hydrogen; and
R$_4$ is trifluoromethyl, trifluoromethoxy or trifluoromethylsulfonyl.

9. A compound of Formula (Ia):

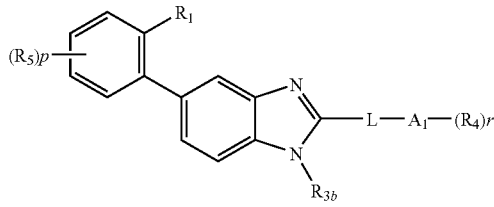

(Ia)

or a stereoisomeric, tautomeric or salt form thereof, wherein:
p is 0, 1 or 2;
r is 0, 1, 2 or 3;
L is —X—C$_{1-3}$alkyl- or —C$_{1-3}$alkyl-Y—, wherein each instance of alkyl is optionally perfluorinated;
X and Y are each O, S, SO, SO$_2$ or NR$_6$;
A$_1$ is selected from the group consisting of indanyl, 1,2,3,4-tetrahydro-naphthalenyl, phenyl, naphthyl, benzo[1,3]dioxolyl, pyridinyl and quinolinyl;
R$_1$ is C$_{1-6}$alkylsulfonyl, C$_{1-6}$alkylsulfonylamino, aminosulfonyl or (C$_{1-4}$alkyl)$_{1-2}$aminosulfonyl,
wherein each instance of alkyl is optionally substituted with one, two or three substituents independently selected from the group consisting of C$_{1-8}$alkoxy, amino, (C$_{1-4}$alkyl)$_{1-2}$amino, C$_{1-6}$alkylcarbonylamino, C$_{1-6}$alkoxycarbonylamino, aminocarbonylamino, (C$_{1-6}$alkyl)$_{1-2}$aminocarbonylamino, C$_{1-6}$alkylsulfonylamino, halogen, oxo and hydroxy;
R$_{3b}$ is selected from the group consisting of hydrogen and C$_{1-4}$alkyl;
R$_4$ is each halogen, nitro, cyano, C$_{1-6}$alkyl, C$_{1-6}$alkoxy, haloC$_{1-6}$alkyl, haloC$_{1-6}$alkoxy, C$_{1-6}$alkoxy-C$_{1-6}$alkyl, C$_{1-6}$alkylthio, haloC$_{1-6}$alkylthio, C$_{1-6}$alkylsulfonyl, haloC$_{1-6}$alkylsulfonyl, C$_{3-8}$cycloalkyl, C$_{3-8}$cycloalkyl-C$_{1-4}$alkyl, C$_{3-8}$cycloalkyl-C$_{1-4}$alkoxy, C$_{3-8}$cycloalkyloxy, amino, (C$_{1-6}$alkyl)$_{1-2}$amino, (C$_{3-8}$cycloalkyl)$_{1-2}$amino, (C$_{3-8}$cycloalkyl-C$_{1-4}$alkyl)$_{1-2}$amino, cyano, C$_{1-6}$alkylcarbonyl, C$_{1-6}$alkoxy-carbonyl, C$_{1-6}$alkoxycarbonyl-C$_{1-6}$alkyl, aminocarbonyl, (C$_{1-6}$alkyl)$_{1-2}$aminocarbonyl, C$_{1-6}$alkylcarbonylamino, C$_{1-6}$alkoxycarbonylamino, aminocarbonylamino, (C$_{1-6}$alkyl)$_{1-2}$aminocarbonylamino, C$_{1-6}$alkylsulfonylamino, aminosulfonyl or (C$_{1-4}$alkyl)$_{1-2}$aminosulfonyl;
R$_5$ is selected from the group consisting of halogen, hydroxy, C$_{1-4}$alkyl, haloC$_{1-4}$alkyl, hydroxyC$_{1-4}$alkyl, C$_{1-4}$alkoxy, C$_{1-4}$alkylsulfonyl, nitro, C$_{1-6}$alkylcarbonyl, C$_{1-6}$alkoxycarbonyl, amino, (C$_{1-4}$alkyl)$_{1-2}$amino, C$_{1-6}$alkylcarbonylamino, C$_{1-6}$alkylsulfonylamino, aminosulfonyl, (C$_{1-6}$alkyl)$_{1-2}$aminosulfonyl and cyano; and
R$_6$ is one substituent selected from the group consisting of hydrogen and C$_{1-4}$alkyl.

10. The compound of claim 9, wherein
p is 0, 1 or 2;
r is 0, 1, 2 or 3;
L is —X—C$_{1-3}$alkyl- or —C$_{1-3}$alkyl-Y—, wherein each instance of alkyl is optionally perfluorinated;
X and Y are each O, S, SO$_2$ or NR$_6$;
A$_1$ is selected from the group consisting of indanyl, 1,2,3,4-tetrahydro-naphthalenyl, phenyl, naphthyl, benzo[1,3]dioxolyl, pyridinyl and quinolinyl;
R$_1$ is C$_{1-6}$alkylsulfonyl, C$_{1-6}$alkylsulfonylamino, aminosulfonyl or (C$_{1-4}$alkyl)$_{1-2}$aminosulfonyl,
wherein each instance of alkyl is optionally substituted with one, two or three substituents independently selected from the group consisting of halogen and hydroxy;
R$_{3b}$ is selected from the group consisting of hydrogen and C$_{1-4}$alkyl;
R$_4$ is each halogen, C$_{1-6}$alkyl, C$_{1-6}$alkoxy, haloC$_{1-6}$alkyl, haloC$_{1-6}$alkoxy, haloC$_{1-6}$alkylthio, C$_{1-6}$alkylsulfonyl, haloC$_{1-6}$alkylsulfonyl, C$_{3-8}$cycloalkyl, cyano, C$_{1-6}$alkylcarbonyl, C$_{1-6}$alkoxy-carbonyl-C$_{1-6}$alkyl and C$_{1-6}$alkylcarbonylamino;
R$_5$ is selected from the group consisting of halogen, hydroxy, C$_{1-4}$alkyl, haloC$_{1-4}$alkyl, hydroxyC$_{1-4}$alkyl, C$_{1-4}$alkylsulfonyl, C$_{1-6}$alkoxycarbonyl, amino, C$_{1-6}$alkylcarbonylamino, C$_{1-6}$alkylsulfonylamino, aminosulfonyl and (C$_{1-6}$alkyl)$_{1-2}$aminosulfonyl; and
R$_6$ is one substituent selected from the group consisting of hydrogen and C$_{1-4}$alkyl.

11. The compound of claim 9, wherein
p is 0, 1 or 2;
r is 0, 1, 2 or 3;
L is —X—C$_{1-3}$alkyl- or —C$_{1-3}$alkyl-Y—, wherein each instance of alkyl is optionally perfluorinated;
X and Y are each O, S or NH;
A$_1$ is selected from the group consisting of indanyl, 1,2,3,4-tetrahydro-naphthalenyl, phenyl, naphthyl, benzo[1,3]dioxolyl and quinolinyl;
R$_1$ is C$_{1-6}$alkylsulfonyl, C$_{1-6}$alkylsulfonylamino, aminosulfonyl or (C$_{1-4}$alkyl)$_{1-2}$aminosulfonyl,
wherein each instance of alkyl is optionally substituted with one, two or three substituents independently selected from the group consisting of halogen and hydroxy;
R$_{3b}$ is selected from the group consisting of hydrogen and C$_{1-4}$alkyl;
R$_4$ is each halogen, C$_{1-6}$alkyl, C$_{1-6}$alkoxy, haloC$_{1-6}$alkyl, haloC$_{1-6}$alkoxy, haloC$_{1-6}$alkylthio, C$_{1-6}$alkylsulfonyl, haloC$_{1-6}$alkylsulfonyl, C$_{3-8}$cycloalkyl, cyano or C$_{1-6}$alkylcarbonyl; and
R$_5$ is selected from the group consisting of halogen and haloC$_{1-4}$alkyl.

12. The compound of claim 9, wherein
p is 0, 1 or 2;
r is 1 or 2;
L is —X—C$_{1-3}$alkyl- or —C$_{1-3}$alkyl-Y—, wherein each instance of alkyl is optionally perfluorinated;

X and Y are each O or S;

$A_1$ is selected from the group consisting of indanyl, 1,2,3,4-tetrahydro-naphthalenyl, phenyl and naphthyl;

$R_1$ is $C_{1-6}$alkylsulfonyl, $C_{1-6}$alkylsulfonylamino, aminosulfonyl or $(C_{1-4}$alkyl$)_{1-2}$aminosulfonyl, wherein each instance of alkyl is optionally substituted with one hydroxy substituent;

$R_{3b}$ is selected from the group consisting of hydrogen and $C_{1-4}$alkyl;

$R_4$ is each halogen, $C_{1-6}$alkyl, $C_{1-6}$alkoxy, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl, $C_{3-8}$cycloalkyl or $C_{1-6}$alkylcarbonyl; and $R_5$ is halogen.

13. The compound of claim 9, wherein p is 0;

r is 1;

L is —X—$C_{1-3}$alkyl- or —$C_{1-3}$alkyl-Y—;

X and Y are each O or S;

$A_1$ is phenyl;

$R_1$ is $C_{1-6}$alkylsulfonyl, $C_{1-6}$alkylsulfonylamino, aminosulfonyl or $(C_{1-4}$alkyl$)_{1-2}$aminosulfonyl, wherein each instance of alkyl is optionally substituted with one hydroxy substituent;

$R_{3b}$ is selected from the group consisting of hydrogen and $C_{1-4}$alkyl; and $R_4$ is halogen, $C_{1-6}$alkyl, halo$C_{1-6}$alkyl, halo$C_{1-6}$alkoxy, halo$C_{1-6}$alkylthio, $C_{1-6}$alkylsulfonyl, halo$C_{1-6}$alkylsulfonyl or $C_{3-8}$cycloalkyl.

14. The compound of claim 9, wherein $R_4$ is cyclopropyl.

15. The compound of claim 9, wherein p is 0;

r is 1;

L is —$C_{1-3}$alkyl-O—;

$A_1$ is phenyl;

$R_1$ is $C_{1-6}$alkylsulfonyl, $C_{1-6}$alkylsulfonylamino, aminosulfonyl or $C_{1-4}$alkylaminosulfonyl, wherein each instance of alkyl is optionally substituted with one hydroxy substituent;

$R_{3b}$ is hydrogen; and $R_4$ is halo$C_{1-6}$alkyl, halo$C_{1-6}$alkoxy or halo$C_{1-6}$alkylsulfonyl.

16. The compound of claim 9, wherein p is 0;

r is 1;

L is —$CH_2$—O—;

$A_1$ is phenyl;

$R_1$ is methylsulfonyl, methylsulfonylamino, aminosulfonyl or methylaminosulfonyl, wherein isopropyl is optionally substituted with one hydroxy substituent;

$R_{3b}$ is hydrogen; and $R_4$ is trifluoromethyl, trifluoromethoxy or trifluoromethylsulfonyl.

17. A compound selected from the group consisting of:

2-[2-(4-trifluoromethyl-phenoxymethyl)-1H-benzoimidazol-5-yl]-benzenesulfonamide, 2-[2-(4-trifluoromethanesulfonyl-phenoxymethyl)-1H-benzoimidazol-5-yl]-benzenesulfonamide, 2-[2-(2-fluoro-phenoxymethyl)-1H-benzoimidazol-5-yl]-benzenesulfonamide, 2-[2-(3-fluoro-phenoxymethyl)-1H-benzoimidazol-5-yl]-benzenesulfonamide, 2-[2-(4-fluoro-phenoxymethyl)-1H-benzoimidazol-5-yl]-benzenesulfonamide, 2-[2-(3-chloro-phenoxymethyl)-1H-benzoimidazol-5-yl]-benzenesulfonamide, 2-[2-(4-chloro-phenoxymethyl)-1H-benzoimidazol-5-yl]-benzenesulfonamide, 2-[2-(4-bromo-phenoxymethyl)-1H-benzoimidazol-5-yl]-benzenesulfonamide, 2-[2-(2,4-difluoro-phenoxymethyl)-1H-benzoimidazol-5-yl]-benzenesulfonamide, 2-[2-(3,4-difluoro-phenoxymethyl)-1H-benzoimidazol-5-yl]-benzenesulfonamide, 2-[2-(3-chloro-4-fluoro-phenoxymethyl)-1H-benzoimidazol-5-yl]-benzenesulfonamide, 2-[2-(4-fluoro-3-trifluoromethyl-phenoxymethyl)-1H-benzoimidazol-5-yl]-benzenesulfonamide, 2-[2-(3-trifluoromethyl-phenoxymethyl)-1H-benzoimidazol-5-yl]-benzenesulfonamide, 2-[2-(2,3,4-trifluoro-phenoxymethyl)-1H-benzoimidazol-5-yl]-benzenesulfonamide, 2-[2-(3-trifluoromethoxy-phenoxymethyl)-1H-benzoimidazol-5-yl]-benzenesulfonamide, 2-[2-(4-trifluoromethoxy-phenoxymethyl)-1H-benzoimidazol-5-yl]-benzenesulfonamide, N-methyl-2-[2-(4-trifluoromethyl-phenoxymethyl)-1H-benzoimidazol-5-yl]-benzenesulfonamide, 2-[2-(4-chloro-phenoxymethyl)-1H-benzoimidazol-5-yl]-N-methyl-benzenesulfonamide, 2-[2-(4-methanesulfonyl-phenoxymethyl)-1H-benzoimidazol-5-yl]-N-methyl-benzenesulfonamide, N-methyl-2-[2-(4-trifluoromethanesulfonyl-phenoxymethyl)-1H-benzoimidazol-5 yl]-benzenesulfonamide, 2-(2-phenoxymethyl-1H-benzoimidazol-5-yl)-benzenesulfonamide, 2-(2-p-tolyloxymethyl-1H-benzoimidazol-5-yl)-benzenesulfonamide, 2-[2-(4-isopropyl-phenoxymethyl)-1H-benzoimidazol-5-yl]-benzenesulfonamide, 2-[2-(3,4-dichloro-phenoxymethyl)-1H-benzoimidazol-5-yl]-benzenesulfonamide, 2-[2-(4-chloro-3-trifluoromethyl-phenoxymethyl)-1H-benzoimidazol-5-yl]-benzenesulfonamide, 2-[2-(3,5-bis-trifluoromethyl-phenoxymethyl)-1H-benzoimidazol-5-yl]-benzenesulfonamide, 2-[2-(4-tert-butyl-phenoxymethyl)-1H-benzoimidazol-5-yl]-benzenesulfonamide, 2-[2-(4-ethoxy-phenoxymethyl)-1H-benzoimidazol-5-yl]-benzenesulfonamide, 2-[2-(4-trifluoromethylsulfanyl-phenoxymethyl)-1H-benzoimidazol-5-yl]-benzenesulfonamide, 2-[2-(4-acetyl-phenoxymethyl)-1H-benzoimidazol-5-yl]-benzenesulfonamide, 2-[2-(naphthalen-2-yloxymethyl)-1H-benzoimidazol-5-yl]-benzenesulfonamide, 2-[2-(quinolin-6-yloxymethyl)-1H-benzoimidazol-5-yl]-benzenesulfonamide, 2-[2-(pyridin-4-yloxymethyl)-1H-benzoimidazol-5-yl]-benzenesulfonamide, 2-[2-(5-trifluoromethyl-pyridin-2-yloxymethyl)-1H-benzoimidazol-5-yl]-benzenesulfonamide, 2-[1-methyl-2-(4-trifluoromethyl-phenoxymethyl)-1H-benzoimidazol-5-yl]-benzenesulfonamide, 2-[2-(4-trifluoromethyl-phenylsulfanylmethyl)-1H-benzoimidazol-5-yl]-benzenesulfonamide, 2-[2-(4-chloro-phenylsulfanylmethyl)-1H-benzoimidazol-5-yl]-benzenesulfonamide, 2-[2-(4-trifluoromethoxy-phenylsulfanylmethyl)-1H-benzoimidazol-5-yl]-benzenesulfonamide, 2-[2-(4-trifluoromethyl-benzenesulfonylmethyl)-1H-benzoimidazol-5-yl]-benzenesulfonamide, 2-[2-(4-chloro-benzenesulfonylmethyl)-1H-benzoimidazol-5-yl]-benzenesulfonamide,
2-[2-(4-trifluoromethoxy-benzenesulfonylmethyl)-1H-benzoimidazol-5-yl]-benzenesulfonamide,
2-{2-[(4-trifluoromethyl-phenylamino)-methyl]-1H-benzoimidazol-5-yl}-benzenesulfonamide,
2-{2-[(4-trifluoromethoxy-phenylamino)-methyl]-1H-benzoimidazol-5-yl}-benzenesulfonamide,
2-[2-(4-isopropyl-phenoxymethyl)-1H-benzoimidazol-5-yl]-N-methyl-benzenesulfonamide,
N-methyl-2-[2-(3-trifluoromethyl-phenoxymethyl)-1H-benzoimidazol-5-yl]-benzenesulfonamide,
5-(2-methanesulfonyl-phenyl)-2-phenoxymethyl-1H-benzoimidazole,
2-(2-fluoro-phenoxymethyl)-5-(2-methanesulfonyl-phenyl)-1H-benzoimidazole,
2-(3-fluoro-phenoxymethyl)-5-(2-methanesulfonyl-phenyl)-1H-benzoimidazole,
2-(4-fluoro-phenoxymethyl)-5-(2-methanesulfonyl-phenyl)-1H-benzoimidazole,
2-(2-chloro-phenoxymethyl)-5-(2-methanesulfonyl-phenyl)-1H-benzoimidazole,
2-(3-chloro-phenoxymethyl)-5-(2-methanesulfonyl-phenyl)-1H-benzoimidazole,
2-(4-chloro-phenoxymethyl)-5-(2-methanesulfonyl-phenyl)-1H-benzoimidazole,
2-(3-bromo-phenoxymethyl)-5-(2-methanesulfonyl-phenyl)-1H-benzoimidazole,
2-(4-bromo-phenoxymethyl)-5-(2-methanesulfonyl-phenyl)-1H-benzoimidazole,
2-(2,4-difluoro-phenoxymethyl)-5-(2-methanesulfonyl-phenyl)-1H-benzoimidazole,
2-(3,4-difluoro-phenoxymethyl)-5-(2-methanesulfonyl-phenyl)-1H-benzoimidazole,
2-(2,4-dichloro-phenoxymethyl)-5-(2-methanesulfonyl-phenyl)-1H-benzoimidazole,
2-(3,4-dichloro-phenoxymethyl)-5-(2-methanesulfonyl-phenyl)-1H-benzoimidazole,
2-(4-chloro-2-fluoro-phenoxymethyl)-5-(2-methanesulfonyl-phenyl)-1H-benzoimidazole,
2-(3-chloro-4-fluoro-phenoxymethyl)-5-(2-methanesulfonyl-phenyl)-1H-benzoimidazole,
5-(2-methanesulfonyl-phenyl)-2-(3,4,5-trifluoro-phenoxymethyl)-1H-benzoimidazole,
5-(2-methanesulfonyl-phenyl)-2-(2,4,5-trifluoro-phenoxymethyl)-1H-benzoimidazole,
5-(2-methanesulfonyl-phenyl)-2-(2,3,4-trifluoro-phenoxymethyl)-1H-benzoimidazole,
2-(2-fluoro-3-trifluoromethyl-phenoxymethyl)-5-(2-methanesulfonyl-phenyl)-1H-benzoimidazole,
2-(4-fluoro-3-trifluoromethyl-phenoxymethyl)-5-(2-methanesulfonyl-phenyl)-1H-benzoimidazole,
2-(3,5-bis-trifluoromethyl-phenoxymethyl)-5-(2-methanesulfonyl-phenyl)-1H-benzoimidazole,
5-(2-methanesulfonyl-phenyl)-2-(2-trifluoromethyl-phenoxymethyl)-1H-benzoimidazole,
5-(2-methanesulfonyl-phenyl)-2-(3-trifluoromethyl-phenoxymethyl)-1H-benzoimidazole,
5-(2-methanesulfonyl-phenyl)-2-p-tolyloxymethyl-1H-benzoimidazole,
2-(4-isopropyl-phenoxymethyl)-5-(2-methanesulfonyl-phenyl)-1H-benzoimidazole,
2-(4-tert-butyl-phenoxymethyl)-5-(2-methanesulfonyl-phenyl)-1H-benzoimidazole,
1-{4-[5-(2-methanesulfonyl-phenyl)-1H-benzoimidazol-2-ylmethoxy]-phenyl}-ethanone,
5-(2-methanesulfonyl-phenyl)-2-(naphthalen-2-yloxymethyl)-1H-benzoimidazole,
2-(4-ethoxy-phenoxymethyl)-5-(2-methanesulfonyl-phenyl)-1H-benzoimidazole,
5-(2-methanesulfonyl-phenyl)-2-(4-trifluoromethanesulfide-phenoxymethyl)-1H-benzoimidazole,
4-[5-(2-methanesulfonyl-phenyl)-1H-benzoimidazol-2-ylmethoxy]-benzonitrile,
5-(2-methanesulfonyl-phenyl)-2-(4-trifluoromethoxy-phenoxymethyl)-1H-benzoimidazole,
2-(4-methanesulfonyl-phenoxymethyl)-5-(2-methanesulfonyl-phenyl)-1H-benzoimidazole,
5-(2-methanesulfonyl-phenyl)-2-(4-trifluoromethanesulfonyl-phenoxymethyl)-1H-benzoimidazole,
5-(2-methanesulfonyl-phenyl)-2-(5,6,7,8-tetrahydro-naphthalen-2-yloxymethyl)-1H-benzoimidazole,
3-{4-[5-(2-methanesulfonyl-phenyl)-1H-benzoimidazol-2-ylmethoxy]-phenyl}-propionic acid methyl ester,
2-(2,4-dimethyl-phenoxymethyl)-5-(2-methanesulfonyl-phenyl)-1H-benzoimidazole,
2-(3,5-dimethyl-phenoxymethyl)-5-(2-methanesulfonyl-phenyl)-1H-benzoimidazole,
2-(indan-5-yloxymethyl)-5-(2-methanesulfonyl-phenyl)-1H-benzoimidazole,
2-(benzo[1,3]dioxol-5-yloxymethyl)-5-(2-methanesulfonyl-phenyl)-1H-benzoimidazole,
2-(3,5-dichloro-phenoxymethyl)-5-(2-methanesulfonyl-phenyl)-1H-benzoimidazole,
N-{3-[5-(2-methanesulfonyl-phenyl)-1H-benzoimidazol-2-ylmethoxy]-phenyl}-acetamide,
N-{4-[5-(2-methanesulfonyl-phenyl)-1H-benzoimidazol-2-ylmethoxy]-phenyl}-acetamide,
5-(2-methanesulfonyl-phenyl)-2-(4-methoxy-phenoxymethyl)-1H-benzoimidazole,
5-(2-methanesulfonyl-phenyl)-2-(3-methoxy-phenoxymethyl)-1H-benzoimidazole,
5-(2-methanesulfonyl-phenyl)-2-(4-trifluoromethyl-phenoxymethyl)-1H-benzoimidazole,
5-(3-methanesulfonyl-phenyl)-2-(4-trifluoromethyl-phenoxymethyl)-1H-benzoimidazole,
5-(4-methanesulfonyl-phenyl)-2-(4-trifluoromethyl-phenoxymethyl)-1H-benzoimidazole,
N-{2-[2-(4-trifluoromethyl-phenoxymethyl)-1H-benzoimidazol-5-yl]-phenyl}-methanesulfonamide,
N-{3-[2-(4-trifluoromethyl-phenoxymethyl)-1H-benzoimidazol-5-yl]-phenyl}-methanesulfonamide,
N-{4-[2-(4-trifluoromethyl-phenoxymethyl)-1H-benzoimidazol-5-yl]-phenyl}-methanesulfonamide,
3-[2-(4-trifluoromethyl-phenoxymethyl)-1H-benzoimidazol-5-yl]-benzenesulfonamide,
4-[2-(4-trifluoromethyl-phenoxymethyl)-1H-benzoimidazol-5-yl]-benzenesulfonamide,
N,N-dimethyl-2-[2-(4-trifluoromethyl-phenoxymethyl)-1H-benzoimidazol-5-yl]-benzenesulfonamide,
N-methyl-4-[2-(4-trifluoromethyl-phenoxymethyl)-1H-benzoimidazol-5-yl]-benzenesulfonamide,
N,N-dimethyl-3-[2-(4-trifluoromethyl-phenoxymethyl)-1H-benzoimidazol-5-yl]-benzenesulfonamide
N,N-dimethyl-4-[2-(4-trifluoromethyl-phenoxymethyl)-1H-benzoimidazol-5-yl]-benzenesulfonamide
4-trifluoromethyl-2-[2-(4-trifluoromethyl-phenoxymethyl)-1H-benzoimidazol-5-yl]-benzenesulfonamide,
5-trifluoromethyl-2-[2-(4-trifluoromethyl-phenoxymethyl)-1H-benzoimidazol-5-yl]-benzenesulfonamide,
4-fluoro-2-[2-(4-trifluoromethyl-phenoxymethyl)-1H-benzoimidazol-5-yl]-benzenesulfonamide, 2,4-difluoro-6-[2-(4-trifluoromethyl-phenoxymethyl)-1H-benzoimidazol-5-yl]-benzenesulfonamide,
2-[2-(4-trifluoromethyl-benzylamino)-1H-benzoimidazol-5-yl]-benzenesulfonamide,
2-{2-[methyl-(4-trifluoromethyl-benzyl)-amino]-1H-benzoimidazol-5-yl}-benzenesulfonamide,
2-[2-(4-trifluoromethyl-benzyloxy)-1H-benzoimidazol-5-yl]-benzenesulfonamide,
2-{2-[difluoro-(4-trifluoromethyl-phenoxy)-methyl]-1H-benzoimidazol-5-yl}-benzenesulfonamide,
2-{2-[difluoro-(4-trifluoromethyl-phenoxy)-methyl]-1H-benzoimidazol-5-yl}-N-methyl-benzenesulfonamide,
2-{2-[difluoro-(4-trifluoromethyl-phenoxy)-methyl]-1H-benzoimidazol-5-yl}-N,N-dimethyl-benzenesulfonamide,
2-{2-[2-(4-trifluoromethyl-phenoxymethyl)-1H-benzoimidazol-5-yl]-benzenesulfonyl}-ethanol,
2-{2-[1-(4-trifluoromethyl-phenoxy)-ethyl]-1H-benzoimidazol-5-yl}-benzenesulfonamide,
2-{2-[1-(4-trifluoromethyl-phenoxy)-propyl]-1H-benzoimidazol-5-yl}-benzenesulfonamide,
5-(2-trifluoromethanesulfonyl-phenyl)-2-(4-trifluoromethyl-phenoxymethyl)-H-benzoimidazole,
2-methyl-1-{2-[2-(4-trifluoromethyl-phenoxymethyl)-1H-benzoimidazol-5-yl]-benzenesulfonyl}-propan-2-ol,
1-{2-[2-(4-trifluoromethyl-phenoxymethyl)-1H-benzoimidazol-5-yl]-benzenesulfonyl}-propan-2-ol,
2-{2-[2-(4-trifluoromethanesulfonyl-phenoxymethyl)-1H-benzoimidazol-5-yl]-benzenesulfonyl}-ethanol,
2-{2-[2-(4-methanesulfonyl-phenoxymethyl)-1H-benzoimidazol-5-yl]-benzenesulfonyl}-ethanol,
2-[2-(4-cyclopropyl-phenoxymethyl)-1H-benzoimidazol-5-yl]-benzenesulfonamide,
2-[2-(4-cyclopropyl-phenoxymethyl)-1H-benzoimidazol-5-yl]-N-methyl-benzenesulfonamide,
2-[2-(4-cyclopropyl-phenoxymethyl)-1H-benzoimidazol-5-yl]-N,N-dimethyl-benzenesulfonamide,
2-(4-cyclopropyl-phenoxymethyl)-5-(2-methanesulfonyl-phenyl)-1H-benzoimidazole, and
N-{2-[2-(4-cyclopropyl-phenoxymethyl)-1H-benzoimidazol-5-yl]-phenyl}-methanesulfonamide.

18. The compound of claim 17, selected from the group consisting of

2-[2-(4-trifluoromethyl-phenoxymethyl)-1H-benzoimidazol-5-yl]-benzenesulfonamide,
2-[2-(4-trifluoromethanesulfonyl-phenoxymethyl)-1H-benzoimidazol-5-yl]-benzenesulfonamide,
2-[2-(3-fluoro-phenoxymethyl)-1H-benzoimidazol-5-yl]-benzenesulfonamide,
2-[2-(4-fluoro-phenoxymethyl)-1H-benzoimidazol-5-yl]-benzenesulfonamide,
2-[2-(3-chloro-phenoxymethyl)-1H-benzoimidazol-5-yl]-benzenesulfonamide,
2-[2-(4-chloro-phenoxymethyl)-1H-benzoimidazol-5-yl]-benzenesulfonamide,
2-[2-(4-bromo-phenoxymethyl)-1H-benzoimidazol-5-yl]-benzenesulfonamide,
2-[2-(2,4-difluoro-phenoxymethyl)-1H-benzoimidazol-5-yl]-benzenesulfonamide,
2-[2-(3,4-difluoro-phenoxymethyl)-1H-benzoimidazol-5-yl]-benzenesulfonamide,
2-[2-(3-chloro-4-fluoro-phenoxymethyl)-1H-benzoimidazol-5-yl]-benzenesulfonamide,
2-[2-(4-fluoro-3-trifluoromethyl-phenoxymethyl)-1H-benzoimidazol-5-yl]-benzenesulfonamide,
2-[2-(3-trifluoromethyl-phenoxymethyl)-1H-benzoimidazol-5-yl]-benzenesulfonamide,
2-[2-(2,3,4-trifluoro-phenoxymethyl)-1H-benzoimidazol-5-yl]-benzenesulfonamide,
2-[2-(3-trifluoromethoxy-phenoxymethyl)-1H-benzoimidazol-5-yl]-benzenesulfonamide,
2-[2-(4-trifluoromethoxy-phenoxymethyl)-1H-benzoimidazol-5-yl]-benzenesulfonamide,
N-methyl-2-[2-(4-trifluoromethyl-phenoxymethyl)-1H-benzoimidazol-5-yl]-benzenesulfonamide,
2-[2-(4-chloro-phenoxymethyl)-1H-benzoimidazol-5-yl]-N-methyl-benzenesulfonamide,
2-[2-(4-methanesulfonyl-phenoxymethyl)-1H-benzoimidazol-5-yl]-N-methyl-benzenesulfonamide,
N-methyl-2-[2-(4-trifluoromethanesulfonyl-phenoxymethyl)-1H-benzoimidazol-5 yl]-benzenesulfonamide,
2-(2-phenoxymethyl-1H-benzoimidazol-5-yl)-benzenesulfonamide,
2-(2-p-tolyloxymethyl-1H-benzoimidazol-5-yl)-benzenesulfonamide,
2-[2-(4-isopropyl-phenoxymethyl)-1H-benzoimidazol-5-yl]-benzenesulfonamide,
2-[2-(3,4-dichloro-phenoxymethyl)-1H-benzoimidazol-5-yl]-benzenesulfonamide,
2-[2-(4-chloro-3-trifluoromethyl-phenoxymethyl)-1H-benzoimidazol-5-yl]-benzenesulfonamide,
2-[2-(3,5-bis-trifluoromethyl-phenoxymethyl)-1H-benzoimidazol-5-yl]-benzenesulfonamide,
2-[2-(4-tert-butyl-phenoxymethyl)-1H-benzoimidazol-5-yl]-benzenesulfonamide,
2-[2-(4-ethoxy-phenoxymethyl)-1H-benzoimidazol-5-yl]-benzenesulfonamide,
2-[2-(4-trifluoromethylsulfanyl-phenoxymethyl)-1H-benzoimidazol-5-yl]-benzenesulfonamide,
2-[2-(4-acetyl-phenoxymethyl)-1H-benzoimidazol-5-yl]-benzenesulfonamide,
2-[2-(naphthalen-2-yloxymethyl)-1H-benzoimidazol-5-yl]-benzenesulfonamide,
2-[2-(quinolin-6-yloxymethyl)-1H-benzoimidazol-5-yl]-benzenesulfonamide,
2-[1-methyl-2-(4-trifluoromethyl-phenoxymethyl)-1H-benzoimidazol-5-yl]-benzenesulfonamide,
2-[2-(4-trifluoromethyl-phenylsulfanylmethyl)-1H-benzoimidazol-5-yl]-benzenesulfonamide,
2-[2-(4-chloro-phenylsulfanylmethyl)-1H-benzoimidazol-5-yl]-benzenesulfonamide,
2-[2-(4-trifluoromethoxy-phenylsulfanylmethyl)-1H-benzoimidazol-5-yl]-benzenesulfonamide,
2-[2-(4-isopropyl-phenoxymethyl)-1H-benzoimidazol-5-yl]-N-methyl-benzenesulfonamide,
N-methyl-2-[2-(3-trifluoromethyl-phenoxymethyl)-1H-benzoimidazol-5-yl]-benzenesulfonamide,
2-(4-chloro-phenoxymethyl)-5-(2-methanesulfonyl-phenyl)-1H-benzoimidazole,
2-(4-bromo-phenoxymethyl)-5-(2-methanesulfonyl-phenyl)-1H-benzoimidazole,
2-(2,4-dichloro-phenoxymethyl)-5-(2-methanesulfonyl-phenyl)-1H-benzoimidazole,
2-(3,4-dichloro-phenoxymethyl)-5-(2-methanesulfonyl-phenyl)-1H-benzoimidazole,
2-(4-chloro-2-fluoro-phenoxymethyl)-5-(2-methanesulfonyl-phenyl)-1H-benzoimidazole,
2-(3-chloro-4-fluoro-phenoxymethyl)-5-(2-methanesulfonyl-phenyl)-1H-benzoimidazole,
5-(2-methanesulfonyl-phenyl)-2-(3,4,5-trifluoro-phenoxymethyl)-1H-benzoimidazole, 2-(4-fluoro-3-trifluoromethyl-phenoxymethyl)-5-(2-methanesulfonyl-phenyl)-1H-benzoimidazole,
5-(2-methanesulfonyl-phenyl)-2-(2-trifluoromethyl-phenoxymethyl)-1H-benzoimidazole,
5-(2-methanesulfonyl-phenyl)-2-(3-trifluoromethyl-phenoxymethyl)-1H-benzoimidazole,
5-(2-methanesulfonyl-phenyl)-2-p-tolyloxymethyl-1H-benzoimidazole,
2-(4-isopropyl-phenoxymethyl)-5-(2-methanesulfonyl-phenyl)-1H-benzoimidazole,
2-(4-tert-butyl-phenoxymethyl)-5-(2-methanesulfonyl-phenyl)-1H-benzoimidazole,
2-(4-ethoxy-phenoxymethyl)-5-(2-methanesulfonyl-phenyl)-1H-benzoimidazole,
5-(2-methanesulfonyl-phenyl)-2-(4-trifluoromethanesulfide-phenoxymethyl)-1H-benzoimidazole,
4-[5-(2-methanesulfonyl-phenyl)-1H-benzoimidazol-2-ylmethoxy]-benzonitrile,
5-(2-methanesulfonyl-phenyl)-2-(4-trifluoromethoxy-phenoxymethyl)-1H-benzoimidazole,
5-(2-methanesulfonyl-phenyl)-2-(4-trifluoromethanesulfonyl-phenoxymethyl)-1H-benzoimidazole,
5-(2-methanesulfonyl-phenyl)-2-(5,6,7,8-tetrahydro-naphthalen-2-yloxymethyl)-1H-benzoimidazole,
2-(2,4-dimethyl-phenoxymethyl)-5-(2-methanesulfonyl-phenyl)-1H-benzoimidazole,
2-(indan-5-yloxymethyl)-5-(2-methanesulfonyl-phenyl)-1H-benzoimidazole,
2-(benzo[1,3]dioxol-5-yloxymethyl)-5-(2-methanesulfonyl-phenyl)-1H-benzoimidazole,
5-(2-methanesulfonyl-phenyl)-2-(4-trifluoromethyl-phenoxymethyl)-1H-benzoimidazole,
N-{2-[2-(4-trifluoromethyl-phenoxymethyl)-1H-benzoimidazol-5-yl]-phenyl}-methanesulfonamide,
N,N-dimethyl-2-[2-(4-trifluoromethyl-phenoxymethyl)-1H-benzoimidazol-5-yl]-benzenesulfonamide,
4-trifluoromethyl-2-[2-(4-trifluoromethyl-phenoxymethyl)-1H-benzoimidazol-5-yl]-benzenesulfonamide,
5-trifluoromethyl-2-[2-(4-trifluoromethyl-phenoxymethyl)-1H-benzoimidazol-5-yl]-benzenesulfonamide,
4-fluoro-2-[2-(4-trifluoromethyl-phenoxymethyl)-1H-benzoimidazol-5-yl]-benzenesulfonamide,
2,4-difluoro-6-[2-(4-trifluoromethyl-phenoxymethyl)-1H-benzoimidazol-5-yl]-benzenesulfonamide,
2-[2-(4-trifluoromethyl-benzylamino)-1H-benzoimidazol-5-yl]-benzenesulfonamide,
2-{2-[difluoro-(4-trifluoromethyl-phenoxy)-methyl]-1H-benzoimidazol-5-yl}-benzenesulfonamide,
2-{2-[difluoro-(4-trifluoromethyl-phenoxy)-methyl]-1H-benzoimidazol-5-yl}-N-methyl-benzenesulfonamide,
2-{2-[difluoro-(4-trifluoromethyl-phenoxy)-methyl]-1H-benzoimidazol-5-yl}-N,N-dimethyl-benzenesulfonamide,
2-{2-[2-(4-trifluoromethyl-phenoxymethyl)-1H-benzoimidazol-5-yl]-benzenesulfonyl}-ethanol,
2-{2-[1-(4-trifluoromethyl-phenoxy)-ethyl]-1H-benzoimidazol-5-yl}-benzenesulfonamide,
2-methyl-1-{2-[2-(4-trifluoromethyl-phenoxymethyl)-1H-benzoimidazol-5-yl]-benzenesulfonyl}-propan-2-ol,
1-{2-[2-(4-trifluoromethyl-phenoxymethyl)-1H-benzoimidazol-5-yl]-benzenesulfonyl}-propan-2-ol,
2-{2-[2-(4-trifluoromethanesulfonyl-phenoxymethyl)-1H-benzoimidazol-5-yl]-benzenesulfonyl}-ethanol,
2-[2-(4-cyclopropyl-phenoxymethyl)-1H-benzoimidazol-5-yl]-benzenesulfonamide,
2-[2-(4-cyclopropyl-phenoxymethyl)-1H-benzoimidazol-5-yl]-N-methyl-benzenesulfonamide,
2-[2-(4-cyclopropyl-phenoxymethyl)-1H-benzoimidazol-5-yl]-N,N-dimethyl-benzenesulfonamide,
2-(4-cyclopropyl-phenoxymethyl)-5-(2-methanesulfonyl-phenyl)-1H-benzoimidazole, and
N-{2-[2-(4-cyclopropyl-phenoxymethyl)-1H-benzoimidazol-5-yl]-phenyl}-methanesulfonamide.

19. The compound of claim 18, selected from the group consisting of
2-[2-(4-trifluoromethyl-phenoxymethyl)-1H-benzoimidazol-5-yl]-benzenesulfonamide,
2-[2-(4-trifluoromethanesulfonyl-phenoxymethyl)-1H-benzoimidazol-5-yl]-benzenesulfonamide,
2-[2-(4-chloro-phenoxymethyl)-1H-benzoimidazol-5-yl]-benzenesulfonamide,
2-[2-(4-bromo-phenoxymethyl)-1H-benzoimidazol-5-yl]-benzenesulfonamide,
2-[2-(3-chloro-4-fluoro-phenoxymethyl)-1H-benzoimidazol-5-yl]-benzenesulfonamide,
2-[2-(4-fluoro-3-trifluoromethyl-phenoxymethyl)-1H-benzoimidazol-5-yl]-benzenesulfonamide,
2-[2-(3-trifluoromethoxy-phenoxymethyl)-1H-benzoimidazol-5-yl]-benzenesulfonamide,
2-[2-(4-trifluoromethoxy-phenoxymethyl)-1H-benzoimidazol-5-yl]-benzenesulfonamide,
N-methyl-2-[2-(4-trifluoromethyl-phenoxymethyl)-1H-benzoimidazol-5-yl]-benzenesulfonamide,
2-[2-(4-methanesulfonyl-phenoxymethyl)-1H-benzoimidazol-5-yl]-N-methyl-benzenesulfonamide,
N-methyl-2-[2-(4-trifluoromethanesulfonyl-phenoxymethyl)-1H-benzoimidazol-5 yl]-benzenesulfonamide,
2-(2-p-tolyloxymethyl-1H-benzoimidazol-5-yl)-benzenesulfonamide,
2-[2-(4-isopropyl-phenoxymethyl)-1H-benzoimidazol-5-yl]-benzenesulfonamide,
2-[2-(3,4-dichloro-phenoxymethyl)-1H-benzoimidazol-5-yl]-benzenesulfonamide,
2-[2-(4-chloro-3-trifluoromethyl-phenoxymethyl)-1H-benzoimidazol-5-yl]-benzenesulfonamide,
2-[2-(3,5-bis-trifluoromethyl-phenoxymethyl)-1H-benzoimidazol-5-yl]-benzenesulfonamide,
2-[2-(4-tert-butyl-phenoxymethyl)-1H-benzoimidazol-5-yl]-benzenesulfonamide,
2-[2-(4-ethoxy-phenoxymethyl)-1H-benzoimidazol-5-yl]-benzenesulfonamide,
2-[2-(4-trifluoromethylsulfanyl-phenoxymethyl)-1H-benzoimidazol-5-yl]-benzenesulfonamide,
2-[2-(4-acetyl-phenoxymethyl)-1H-benzoimidazol-5-yl]-benzenesulfonamide,
2-[2-(naphthalen-2-yloxymethyl)-1H-benzoimidazol-5-yl]-benzenesulfonamide,
2-[1-methyl-2-(4-trifluoromethyl-phenoxymethyl)-1H-benzoimidazol-5-yl]-benzenesulfonamide,
2-[2-(4-trifluoromethyl-phenylsulfanylmethyl)-1H-benzoimidazol-5-yl]-benzenesulfonamide,
2-[2-(4-isopropyl-phenoxymethyl)-1H-benzoimidazol-5-yl]-N-methyl-benzenesulfonamide,
N-methyl-2-[2-(3-trifluoromethyl-phenoxymethyl)-1H-benzoimidazol-5-yl]-benzenesulfonamide,
2-(4-chloro-phenoxymethyl)-5-(2-methanesulfonyl-phenyl)-1H-benzoimidazole,
2-(4-fluoro-3-trifluoromethyl-phenoxymethyl)-5-(2-methanesulfonyl-phenyl)-1H-benzoimidazole,
5-(2-methanesulfonyl-phenyl)-2-p-tolyloxymethyl-1H-benzoimidazole, 2-(4-isopropyl-phenoxymethyl)-5-(2-methanesulfonyl-phenyl)-1H-benzoimidazole,
2-(4-tert-butyl-phenoxymethyl)-5-(2-methanesulfonyl-phenyl)-1H-benzoimidazole,
5-(2-methanesulfonyl-phenyl)-2-(4-trifluoromethane-sulfide-phenoxymethyl)-1H-benzoimidazole,
5-(2-methanesulfonyl-phenyl)-2-(4-trifluoromethane-sulfonyl-phenoxymethyl)-1H-benzoimidazole,
5-(2-methanesulfonyl-phenyl)-2-(5,6,7,8-tetrahydro-naphthalen-2-yloxymethyl)-1H-benzoimidazole,
2-(indan-5-yloxymethyl)-5-(2-methanesulfonyl-phenyl)-1H-benzoimidazole,
5-(2-methanesulfonyl-phenyl)-2-(4-trifluoromethyl-phenoxymethyl)-1H-benzoimidazole,
N-{2-[2-(4-trifluoromethyl-phenoxymethyl)-1H-benzoimidazol-5-yl]-phenyl}-methanesulfonamide,
N,N-dimethyl-2-[2-(4-trifluoromethyl-phenoxymethyl)-1H-benzoimidazol-5-yl]-benzenesulfonamide,
4-fluoro-2-[2-(4-trifluoromethyl-phenoxymethyl)-1H-benzoimidazol-5-yl]-benzenesulfonamide,
2,4-difluoro-6-[2-(4-trifluoromethyl-phenoxymethyl)-1H-benzoimidazol-5-yl]-benzenesulfonamide,
2-{2-[difluoro-(4-trifluoromethyl-phenoxy)-methyl]-1H-benzoimidazol-5-yl}-benzenesulfonamide,
2-{2-[difluoro-(4-trifluoromethyl-phenoxy)-methyl]-1H-benzoimidazol-5-yl}-N-methyl-benzenesulfonamide,
2-{2-[2-(4-trifluoromethyl-phenoxymethyl)-1H-benzoimidazol-5-yl]-benzenesulfonyl}-ethanol,
2-methyl-1-{2-[2-(4-trifluoromethyl-phenoxymethyl)-1H-benzoimidazol-5-yl]-benzenesulfonyl}-propan-2-ol,
1-{2-[2-(4-trifluoromethyl-phenoxymethyl)-1H-benzoimidazol-5-yl]-benzenesulfonyl}-propan-2-ol,
2-[2-(4-cyclopropyl-phenoxymethyl)-1H-benzoimidazol-5-yl]-benzenesulfonamide,
2-[2-(4-cyclopropyl-phenoxymethyl)-1H-benzoimidazol-5-yl]-N-methyl-benzenesulfonamide,
2-[2-(4-cyclopropyl-phenoxymethyl)-1H-benzoimidazol-5-yl]-N,N-dimethyl-benzenesulfonamide,
2-(4-cyclopropyl-phenoxymethyl)-5-(2-methanesulfonyl-phenyl)-1H-benzoimidazole, and
N-{2-[2-(4-cyclopropyl-phenoxymethyl)-1H-benzoimidazol-5-yl]-phenyl}-methanesulfonamide.

20. The compound of claim 19, selected from the group consisting of
2-[2-(4-trifluoromethyl-phenoxymethyl)-1H-benzoimidazol-5-yl]-benzenesulfonamide,
2-[2-(4-trifluoromethanesulfonyl-phenoxymethyl)-1H-benzoimidazol-5-yl]-benzenesulfonamide,
2-[2-(4-bromo-phenoxymethyl)-1H-benzoimidazol-5-yl]-benzenesulfonamide,
2-[2-(4-trifluoromethoxy-phenoxymethyl)-1H-benzoimidazol-5-yl]-benzenesulfonamide,
N-methyl-2-[2-(4-trifluoromethyl-phenoxymethyl)-1H-benzoimidazol-5-yl]-benzenesulfonamide,
2-[2-(4-methanesulfonyl-phenoxymethyl)-1H-benzoimidazol-5-yl]-N-methyl-benzenesulfonamide,
2-[2-(4-isopropyl-phenoxymethyl)-1H-benzoimidazol-5-yl]-benzenesulfonamide,
2-[2-(4-tert-butyl-phenoxymethyl)-1H-benzoimidazol-5-yl]-benzenesulfonamide,
2-[1-methyl-2-(4-trifluoromethyl-phenoxymethyl)-1H-benzoimidazol-5-yl]-benzenesulfonamide,
2-[2-(4-trifluoromethyl-phenylsulfanylmethyl)-1H-benzoimidazol-5-yl]-benzenesulfonamide,
2-[2-(4-isopropyl-phenoxymethyl)-1H-benzoimidazol-5-yl]-N-methyl-benzenesulfonamide,
2-(4-isopropyl-phenoxymethyl)-5-(2-methanesulfonyl-phenyl)-1H-benzoimidazole,
2-(4-tert-butyl-phenoxymethyl)-5-(2-methanesulfonyl-phenyl)-1H-benzoimidazole,
5-(2-methanesulfonyl-phenyl)-2-(4-trifluoromethane-sulfide-phenoxymethyl)-1H-benzoimidazole,
5-(2-methanesulfonyl-phenyl)-2-(4-trifluoromethane-sulfonyl-phenoxymethyl)-1H-benzoimidazole,
5-(2-methanesulfonyl-phenyl)-2-(4-trifluoromethyl-phenoxymethyl)-1H-benzoimidazole,
N-{2-[2-(4-trifluoromethyl-phenoxymethyl)-1H-benzoimidazol-5-yl]-phenyl}-methanesulfonamide,
N,N-dimethyl-2-[2-(4-trifluoromethyl-phenoxymethyl)-1H-benzoimidazol-5-yl]-benzenesulfonamide,
2-[2-(4-cyclopropyl-phenoxymethyl)-1H-benzoimidazol-5-yl]-N-methyl-benzenesulfonamide,
2-[2-(4-cyclopropyl-phenoxymethyl)-1H-benzoimidazol-5-yl]-N,N-dimethyl-benzenesulfonamide, and
2-(4-cyclopropyl-phenoxymethyl)-5-(2-methanesulfonyl-phenyl)-1H-benzoimidazole.

21. The compound of claim 20, selected from the group consisting of
2-[2-(4-trifluoromethyl-phenoxymethyl)-1H-benzoimidazol-5-yl]-benzenesulfonamide,
2-[2-(4-trifluoromethanesulfonyl-phenoxymethyl)-1H-benzoimidazol-5-yl]-benzenesulfonamide,
2-[2-(4-trifluoromethoxy-phenoxymethyl)-1H-benzoimidazol-5-yl]-benzenesulfonamide,
N-methyl-2-[2-(4-trifluoromethyl-phenoxymethyl)-1H-benzoimidazol-5-yl]-benzenesulfonamide,
5-(2-methanesulfonyl-phenyl)-2-(4-trifluoromethane-sulfonyl-phenoxymethyl)-1H-benzoimidazole,
5-(2-methanesulfonyl-phenyl)-2-(4-trifluoromethyl-phenoxymethyl)-1H-benzoimidazole, and
N-{2-[2-(4-trifluoromethyl-phenoxymethyl)-1H-benzoimidazol-5-yl]-phenyl}-methanesulfonamide.

22. A salt of the compound of claim 1 selected from the group consisting of acetate, adipate, benzenesulfonate, benzoate, bicarbonate, bisulfate, bitartrate, borate, bromide, calcium, camsylate, carbonate, chloride, choline, clavulanate, citrate, dihydrochloride, diphosphate, dipotassium, disodium, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate, potassium, salicylate, sodium, stearate, sulfate, succinate, tartrate, tromethane, tosylate, trichloroacetate and trifluoroacetate.

23. The salt of claim 22, wherein the salt is selected from the group consisting of disodium, hydrochloride, phosphate, diphosphate and sodium.

24. A pharmaceutical composition comprising the compound of claim 1 and one or more pharmaceutically acceptable carriers, excipients or diluents.

25. A method for treating a TRPV1 ion channel mediated disease selected from chronic or acute pain due to a disease that causes inflammatory pain, burning pain or post-operative pain in a subject in need thereof comprising administering to the subject an effective amount of the compound of claim 1.

26. The method of claim 25, wherein the effective amount of the compound is in a range of from about 0.001 mg/kg/day to about 300 mg/kg/day.

27. A process for preparing the compound of claim 1 comprising the steps of:
Step A. reacting a Compound III-1 with bromoacetonitrile in a solvent such as DMF with sodium carbonate and an equivalent of sodium iodide to provide a Compound III-2:

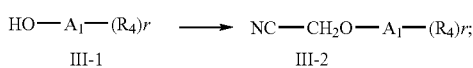

Step B. reacting Compound III-2 with 2N HCl and 1.1 equivalents of ethanol to provide a Compound III-3:

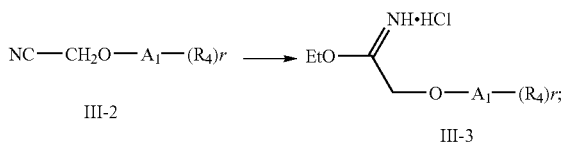

Step C. reacting Compound III-3 with a Compound I-1 in ethanol to provide a compound III-4:

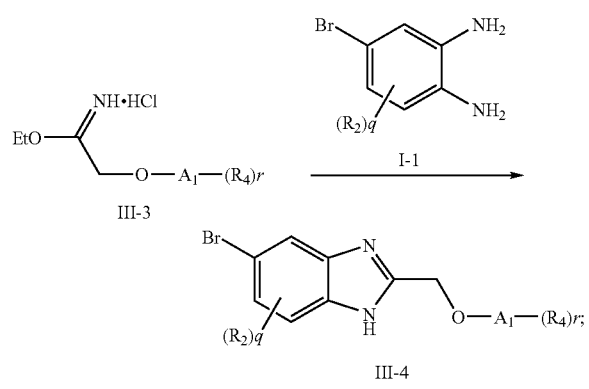

Step D. reacting Compound III-4 with a boronic acid or boronate ester Compound I-3 in sodium carbonate and a catalytic amount of a palladium catalyst in a solvent at a temperature of at least about 100° C. to give a Compound III-5:

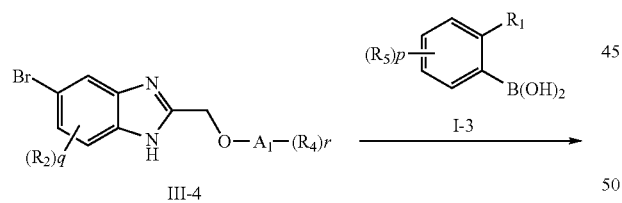

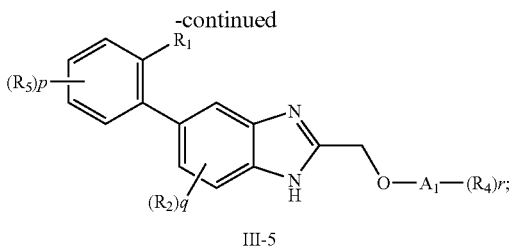

wherein the palladium catalyst is selected from the group consisting of a dichloro[1,1'-bis(diphenylphosphino) ferrocene]palladium (II) dichloromethane adduct, palladium tetrakistriphenylphosphine and 1,1'-[bis(di-tert-butylphosphino)ferrocene]-palladium dichloride, and wherein the solvent is a mixture of dioxane or dimethoxyethane and water or ethanol;

Step E. reacting Compound III-5 with $R_3X$ to provide a Compound III-6a and Compound III-6b as a tautomeric mixture:

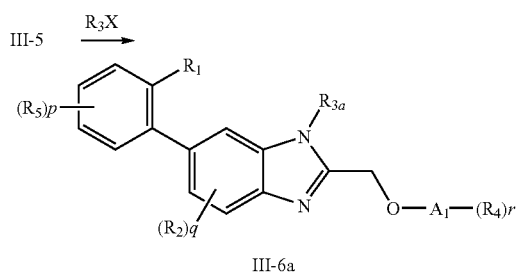

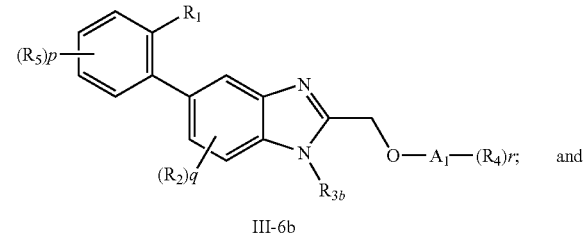

Step F. separating each isomer from the tautomeric mixture to provide a substantially pure Compound III-6a and a substantially pure Compound III-6b.

\* \* \* \* \*